United States Patent
Yan et al.

(10) Patent No.: US 10,196,647 B1
(45) Date of Patent: Feb. 5, 2019

(54) ENHANCEMENT OF NITROGEN USE EFFICIENCY IN WHEAT AND OTHER PLANTS

(71) Applicant: THE BOARD OF REGENTS FOR OKLAHOMA STATE UNIVERSITY, Stillwater, OK (U

(72) Inventors: Liuling Yan, Stillwater, OK (US); Hailin Zhang, Stillwater, OK (US); Brett Carver, Stillwater, OK (US); Genqiao Li, Stillwater, OK (US); Lei Lei, Stillwater, OK (US)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 155 days.

(21) Appl. No.: 15/049,546

(22) Filed: Feb. 22, 2016

Related U.S. Application Data

(63) Continuation-in-part of application No. 13/892,403, filed on May 13, 2013, which is a continuation of application No. 13/841,201, filed on Mar. 15, 2013, which is a continuation-in-part of application No. 13/157,057, filed on Jun. 9, 2011, now abandoned.

(60) Provisional application No. 61/352,979, filed on Jun. 9, 2010, provisional application No. 61/367,671, filed on Jul. 26, 2010.

(51) Int. Cl.
*C12N 15/82* (2006.01)
*C07K 14/415* (2006.01)

(52) U.S. Cl.
CPC ........ *C12N 15/8243* (2013.01); *C07K 14/415* (2013.01); *C12N 15/8261* (2013.01)

(58) Field of Classification Search
None
See application file for complete search history.

(56) References Cited

PUBLICATIONS

Chen et al (2009) Theoretical and Applied Genetics 118: p. 881-889.*

* cited by examiner

*Primary Examiner* — Matthew R Keogh
(74) *Attorney, Agent, or Firm* — Crowe & Dunlevy; Terry L. Watt

(57) ABSTRACT

Genes associated with nitrogen utilization efficiency (NUE) in plants are provided. The gene $VRN1^N$ was identified as TaNUE1 in chromosome 5A of the wheat cultivar Jagger and is encompassed by quantitative trait locus Qnue.osu-5A. $VRN1^N$ is regulated by nitrogen is associated with enhanced NUE by plants which contain the gene. In addition, the gene ANR1 from wheat cultivar Jagger has also been identified as involved in nitrogen metabolism. Methods for genetically engineering plants to contain and express one or both of $VRN1^N$ and ANR1 are also provided, as are genetically modified plants that have been transformed with one or both of the genes, and plants that have been bred conventionally and selected for the presence of one or both genes.

5 Claims, 42 Drawing Sheets

Specification includes a Sequence Listing.

FIG. 3A

AAACCTTGGACCTAACCCTCTGTAGAAACCTTTCCATCCATCTTCAGCGATCAATCTTCTAACTACCTCAC
TGGCTTTTGGCTTGTTTTGATTAACCTAGATGAAAAAACAGAAAAAAAATATTAATGTGGCTGATATAAAA
CCATAATTCGCAGGATGCATGTACAGTTAAGAAATAGAAAAAAATGCAAATTCTGATGACATAAAGAAAA
CATCAGCTGCACGGAGCATTTTCTTAAAGCATCACCAGAAAAATTGAACACTGGGGGTTGAACGCTACAGT
CTAGAAGTGTGATTGTAATTAACTAAAAGTCTACACTCGACACTATCAACACAGATAAAACATGTAATGTT
AAGAAAGTTGTGAA       (SEQ ID NO: 1)

FIG. 3B

AAACCTTGGACCTAACCCTCTGTAGAAACCTTTCCATCCATCTTCAGCAATCAATCTTCTAACTACCTCAC
TGGCTTTTGGCTTGTTTTGATTAACCTAGATGAAAAAACAGAAAAAAAATATTAATGTGGCTGATATAAAA
CCATAATTCGCAGGATGCATGTACAGTTAAGAAATAGAAAAAAATGCAAATTCTTGATGACATAAAGAAA
ACATCAGCTGCACGGAGCATTTTCTTAAAGCATCACCAGAAAAATTGAACACTGGGGGTTGAACGCTACAG
TCTAGAAGTGTGATTGTAATTAACTAAAAGTCTACACTCGACACTATCAACACAGATAAAACATGTAATGT
TAAGAAAGTTGTGAA      (SEQ ID NO: 2)

FIG. 4A

TGCAGCATCCTCCTTCCAGATTAGTGTAGGTCTTGCTGGGACTACCAATAAGACGGTTAAGATGCCGAAAA
ACTTCACCCTTAGGGCCCCAGGTCCGGGGTACACATGTGGGCGTGCTCTTGTTGGCAGGCCTACCAAGTAT
TACTCGTCAGACGGGCGCAGGGTAACCCAAGCTCTCAGTAAGTTGCCCACTTATTGCTCTTCACTGCTTGC
TCTATATTGCTTTAATACTTTGCGCAAATGCATTAGCAAGCTACACTAATTGAGCTAAACACATCTTAGTA
CCACTTTTGTACGTTTCTGCTCCTTAATTGTGAATGAATTTTATGTTATAATATGTGTAGGATTAGTGAAA
GACTGAAAGGAGTGAAACCATTGAAATCGGAAGTGATTCATTTTCGAGAGGAGATGAGTTCATCACCTAGG
ATCGATGTTAGCTCATATTTATTTGAAAATAAGCCACCACTAAGCCTGATAATATCTTAACTAGTTTTGTT
CACTTGCAAATAATGGATTTCAAATGCAGGAAACATC       (SEQ ID NO: 3)

FIG. 4B

TGCAGCATCCTCCTTCCAGATTAGTGTAGGTCTTGCTGGGACTACCAATAAGACGGTTAAGATGCCGAAAA
ACTTCACCCTTAGGGCCCCAGGTCCGGGGTACACATGTGGGCGTGCTCTTGTTGGCAGGCCTACCAAGTAT
TACTCGTCAGACGGGCGCAGGGTAACCCAAGCTCTCAGTAAGTTGCCCACTTATTGCTCTTCACTGCTTGC
TCTATATTGCTTTAATACTTTGCGCAAATGCATTAGCAAGCTACACTAATTGAGCTAAACACATCTTAGTA
CCACTTTTGTACGTTTCTGCTCCTTAATTGTGAATGAATTTTATGTTATAATATGTGTAGGATTAGTGAAA
GACTGAAAGGAGTGAAACCATTGAAATCGGAAGTGATTCATTTTCGAGAGGAGATGAGTTCATCACCTAGG
ATCAATGTTAGCTCATATTTATTTGAAAATAAGCCACCACTAAGCCTGATAATATCTTAACTAGTTTTGTT
CACTTGCAAATAATGGATTTCAAATGCAGGAAACATC       (SEQ ID NO: 4)

FIG. 5A

```
CGAGATGCCGACGCTGACGAAGCTGTACAGCATGAAGGAGGCCGCCCTCCACAACACCCCCGACGACTGCT
GGATCGTCGTCGACGGCAAGGTAGCGCCTCCCTCATACCCCTCGCCGCCGATCTGGCTTCAGCAATACTGC
CCCTAACATCGGTAGGTAGGTAGGTAGGGTCTAGGGTGTATGGACGCGTTTCGTTGTTGCTAGTTGGGCTT
CGACCCCCGCCCTTAGCCTGTTCGACCGAATGCCTGGGAGATCCCGCGCTCGCTTTGTTAGTGAGAAGGCT
GCAGGAATCGAAACCGAACGTCTCTGCGAGTGGCGTGGCCTGCTAGTCACCTCGTGGGGCAGTTGTGCTGG
GGTATCCTCTGTTGAAGGCAACCACAGCAGATGCCTCTGTTGAGGGCTTTGAATCAAATAGAATTTGTGTC
AGCAGAGAGTAGATACGCATTACAATACTACCTGGCAAATATGTTCCACTACTCTGATTCTGTGGCGAGCT
CATGCCCTGTTGATGAATACAATGCAGATTTATGATGTGACCGCGTATTTGGATGACCATCCTGGGGGTGC
TGATGTGCTGCTTGCCGTGACTGGTACTACTTCTCAGTTCTCACCTCTTGTTTTCATGTTCTTGTTCAGCA
CATTTTAGTTTCTCATAGGCTGTCTGCTCATACATGATAATCTGTTTCAAGGTATGGATGGCACCGAGGAA
TTTGAAGATGCGGGCCACAGCAAGGATGCCAAGGAGTTGATGAAAGATTACTTCATTGGGGAGTTGGACTT
GGACGAAACACCTGACATGCCTGAGATGGAGGTTTTCAGGAAAGAGCAGGACAAGGACTTCGCCAGCAAGC
TGGCGGCTTACGCTGTGCAGTACTGGGCCATTCCGGTAGCAGCAGTTGGGATATCAGCCGTGCTTGCTATA
TTGTATGCTCGAAGGAAGTGATGATCGGTTATAGGTTGATTGAAGGACCATTTTGGGGTAACCAACACATT
TATAGCTGGTTATGGATGGAGAGATTATGTACTTCTGTCCAAAGGGGAAGACACATTGCTGTATTGAGCCC
TTAGGTACTTGAGTCAAATATTTGTCCACAAAATTGGTGGTACTATTTTGTCAATATGTCATTCAATGGAT
AGATTCATTTCAAGACCTGAACCATGTGTGTGATGTAAACCCTCTTACGCCTTGAGGCAGCTGCTGGCGCA
GATTTCTTCCGTGCCATTATTGCTTCTATTTTTGTTATTTTCGTGGGATGTGCCACGGTACTGCTATTTCT
GAATATTGTGATTTTTCAATCCCTCACTTGCTCCTGAATAACCCTGAAGACTTTTGTGTAACTTGTTCTTT
TGTAACTTTCAAGATGCAAATTGGGATTTGTTGGCCCCTCCTTTTGAGTCGACATTTGTTGAAAGCTTCCC
GTGCAAGCATTTCATCCATATATTTTCCTATTCGTTTTTCTTCCCCTTGTGTCACCTCACAAGGTGTAGAT
AGTTGGGCAGTAGACTTCAGAAAGATAGCAGGTAGCTTTTGCCGCCCCCTCTCTTGATATTTCTAAACTGG
GGTTGCTTCGCCATCACTACGTAATACTAGTTGAAGAAATTTTATCATGTGCTACTGCTGTGCTTAGTAAC
CTAGCACCTGGGTTCGACACAGCCTCTTGGCATTGCATTGTGCAGATAAGGCTTGCCTCAATGCCTTGTAT
AATCCTTCCCCAGGTGTCACCTGGAAATGTACACCTTACCTGATAGTATTATGCAGGGGTATCACTTGGAA
TTGATGGTGTTGCTTGAAGGCAGAGCAAAAACCAACATGTGGAAGGTGGTGCTGAGCTTCTCAACC
(SEQ ID NO: 5)
```

FIG. 5B

```
CGAGATGCCGACGCTGACGAAGCTGTACAGCATGAAGGAGGCCGCCCTCCACAACACCCCCGACGACTGCT
GGATCGTCGTCGACGGCAAGGTAGCGCCTCCCTCATACCCCTCGCCGCCGATCTGGCTTCAGCAATACTGC
CCCTAACATCGGTAGGTAGGTAGGTAGGGTCTAGGGTGTATGGACGCGTTTCGTTGTTGCTAGTTGGGCTT
CGACCCCCGCCCTTAGCCTGTTCGACCGAATGCCTGGGAGATCCCGCGCTCGCTTTGTTAGTGAGAAGGCT
GCAGGAATCGAAACCGAACGTCTCTGCGAGTGGCGTGGCCTGCTAGTCACCTCGTGGGGCAGTTGTGCTGG
GGTATCCTCTGTTGAAGGCAACCACAGCAGATGCCTCTGTTGAGGGCTTTGAATCAAATAGAATTTGTGTC
AGCAGAGAGTAGATACGCATTACAATACTACCTGGCAAATATGTTCCACTACTCTGATTCTGTGGCGAGCT
CATGCCCTGTTGATGAATACAATGCAGATTTATGATGTGACCGCGTATTTGGATGACCATCCTGGGGGTGC
TGATGTGCTGCTTGCCGTGACTGGTACTACTTCTCAGTTCTCACCTCTTGTTTTCATGTTCTTGTTCAGCA
CATTTTAGTTTCTCATAGGCTGTCTGCTCATACATGATAATCTGTTTCAAGGTATGGATGGCACCGAGGAA
TTTGAAGATGCGGGCCACAGCAAGGATGCCAAGGAGTTGATGAAAGATTACTTCATTGGGGAGTTGGACTT
GGACGAAACACCTGACATGCCTGAGATGGAGGTTTTCAGGAAAGAGCAGGACAAGGACTTCGCCAGCAAGC
TGGCGGCTTACGCTGTGCAGTACTGGGCCATTCCGGTAGCAGCAGTTGGGATATCAGCCGTGCTTGCTATA
TTGTATGCTCGAAGGAAGTGATGATCGGTTATAGGTTGATTGAAGGACCATTTTGGGGTAACCAACACATT
TATAGCTGGTTATGGATGGAGAGATTATGTACTTCTGTCCAAAGGGGAAGACACATTGCTGTATTGAGCCC
TTAGGTACTTGAGTCAAATATTTGTCCACAAAATTGGTGGTACTATTTTATCAATATGTCATTCAATGGAT
```

FIG. 5B (con't)

```
AGATTCATTTCAAGACCTGAACCATGTGTGTGATGTAAACCCTCTTACGCCTTGAGGCAGCTGCTGGCGCA
GATTTCTTCCGTGCCATTATTGCTTCTATTTTTGTTATTTTCGTGGGATGTGCCACGGTACTGCTATTTCT
GAATATTGTGATTTTTCAATCCCTCACTTGCTCCTGAATAACCCTGAAGACTTTTGTGTAACTTGTTCTTT
TGTAACTTTCAAGATGCAAATTGGGATTTGTTGGCCCCTCCTTTTGAGTCGACATTTGTTGAAAGCTTCCC
GTGCAAGCATTTCGTCCATATATTTTCCTATTCGTTTTTCTTCCCCTTGTGTCACCTCACAAGGTGTAGAT
AGTTGGGCAGTAGACTTCAGAAAGATAGCAGGTAGCTTTTGCCGCCCCTCTCTTGATATTTCTAAACTGG
GGTTGCTTCGCCATCACTACGTAATACTAGTTGAAGAAATTTTATCATGTGCTACTGCTGTGCTTAGTAAC
CTAGCACCTGGGTTCGACACAGCCTCTTGGCATTGCATTGTGCAGATAAGGCTTGCCTCAATGCCTTGTAT
AATCCTTCCCCAGGTGTCACCTGGAAATGTACACCTTACCTGATAGTATTATGCAGGGGTATCACTTGGAA
TTGATGGTGTTGCTTGAAGGCAGAGCAAAAACCAACATGTGGAAGGTGGTGCTGAGCTTCTCAACC
(SEQ ID NO: 6)
```

FIG. 6A

```
GAGGTCGGAGGTCGGAGATGGGTCGCGGCAAGGTGGTGCTGCAGCGGATCGAGAACAAGATCAGCCGCCAG
GTGACGTTCGCCAAGCGCCGCAACGGCCTGCTCAAGAAGGCCTACGAGCTCTCCCTCCTCTGCGACGCCGA
GGTCGCGCTCGTCCTCTTCTCCCACGCTGGCCGCCTCTACCAGTTCTCCTCCTCCTCCAAGTAATTACTCC
TTCCGATCTCCCCCAGTGCCGTACCATATCGATCCCTCCATTTCCTTTTCTCTTTGTGGTTTTGCCGAGTC
GATCCTTTTGATTTGCTCTCCCCGTTCAAACATTTTGTCCATACGCGACGTTCGATCTGAATTTTCTTGCG
TCTTAGGGCGTCCGTGCATGAACTTATGGGGGGCTGGGTCCGTACGTTCTTTCCCTCTTGTTTGCTGTTCT
GTTGGCCACTGTGTCAAAGAGGCTAGCAAGAAACAAACAAAGGAAAAAGTGATGAGCTCACCCGCAGCAG
CAGATCGACGGACATACTATGCAGTAGGAGTATATGTCATGCGTATGTTTGTCTCATTCACAGTAGAGGAT
TAAAAAGGGGTTTTAATCTAAAAAAAACAAGAAGAAAAGATGTTTTTATTTGATGTACGCCTGACCACACC
TGTATTGAGGATACATGTATGCACATAATTAGAGCTTTGATCACCTGCTGAGATTAATTTGCACCAATATG
GCATGCATCCTTGTGAAACTCATACGGGCACTAATTGTTTTTCTACAAATTTTATCTAGCTTTGTCTTATG
GTCTGGGTAGTATGATGATCCACTTCTGAGAATTAATTTGAATTATGTAATTTTAAATACTTTTCTGCAGA
CCCAAGTTCAATCTATTTTTTTTCTCAAAACAAAGGTTCAGTCTAATTTGACACCTTTAAGGCGTAGGATT
GAATTATATATGCTTGTTTAATGTTATTTGTCAAAGAACTAAGAAAGGATATATACCGCTTTCAGTTAACT
GAATTGCATTAATTTTCTAGTCAAAGTACCGAAATAATACTATTGAAAAAATGAAACAGTTAAGTGCTTT
AATTCAACTGTGGCCTTACATGATGTGACAGGGCAAGTGCTGCATCATATGTACTAGGTACAAATGAAGTG
CTATTTGTACTTCCTTGGAGCAAAAGAAAACAAGTAATAAACTAGCTAATGTTAGGTTCGTACCTACTCCC
TCCGTCCCATAATGTAAGACCTTTTTTAACACGGTCTTATATTATGGGATGAAAGGAGTACGCAATAATTT
AAGCAGCTCTATAGGGTAGCATTACCTAATGATATCAGAACTTTATGTATGTTCGAGTCAAATATAGCTAG
GTTTTAATCTGTCAAAATTATAAAGCCACTGAGTTTGCTCAAAAAGTTTGTAAAAGCGCTGATACATGAAA
TGTGAAACCAGACTTGGTAAAATTGCATGCTAATATTTTGTAGGGCCAATCATGATTACTACTTGTCAGTT
CTATACAAACATGCCACTGGTGGCTAGCTTAAACTTTGTAGCAATTTTGGCTGAAATAGCTTTTTTGGTGA
AAATTAACAACTGTACTTCTCACAGTAGTAGCTCAATAAACATTCTTACAGTGGCATAGTTCTCCCAAAAG
TTTAATTAGTCAAAGGAAACAGATATGTCTTCTTTTTTATATAATGGAAAGTTCTTTTTAGGTACATCGTC
AAGTCTTCACTAGATTGTGATGTTTACACAACTTTGAAGCCATGTGTCAATGGCTATAAAGTGACCAAAAA
TTAGCTCAAAAGACTAAGACAACATATAGAATTTGTTAGAAGTTGAACATACAGAAAGTTTATTATGCGAG
AGACCTTCATTGTCCAATAATTATCGAATTCTGTCATGTAAATAGTGATACTTAGTTTCTAATCCCTCCCC
CTCCCCCAGTGAATCTGAATTTATGTTATTTACCTATGCGTGTACTTGCACAACTTAATCTCGAATTTTCA
ACTCATCGCAGCATGCTTAAGACCCTCGAGAAGTACCAGAGGTACATTTTCGCTTCCCAAGATGCTGCCGT
GCCGACTACCGATGAGATGCAGGTCTGAGGCTTTTATTCCCAATGCGCATATTATGAAGATTCTACAAATT
TTCCTCAGATACAACATCTTTGAATTTTTAACTAGCAGGTTATCAGAGAAATTTGTTTTCCTTCGTAGAAC
AATGTATCTATAATGCCCTAAATAACATATATAAATTGATTTTGTGAAGAGATAAAACATTCAGTCATAC
ATTTAAAATATTTCATTCTGTATGACGTACGTTATATGAAGCATTGCCTATTCGTAAATGTTACCTAGTTC
ACACATGATTGCTAAAAGGTATTTCTCTGCTGGTAAAGGTGTTATATTTCCGTGTTTAGAACATGGATTTC
TGTTGCTTGTCATATAGGCAGTGAACTAATTATTTTGTTTGACTTTTTTATGTAAAATTACTGCCTTGTAA
ACATGCCCACATGGTTTGAAGCAAAAGATAAACCTTTGATAAATTTTTAGCAGTTACAAAATATTAAATGG
GAATGTAAGTTCATGGCAATTAGAATGTTGGAAAGTACAGCTAGAGCATTGGCCCAGTGCATTTCATGCAT
ACGCGCAGCATAATTCACGTACGTGGCTATCTATGTGAAATACAGCATCGAGTAACTGGGCACTGGGGAGA
CCTATATCTGCGCATGTTCCTTGAATTATCGCTAATGTACATGCATTTTGTGGTTGGTTATAACTTATAAG
TAGACTAACAGCTTGGTTGGCCACCACATGCAGTATTGTAGCAGATAGCAGCTTCAGACTGATTGGCCATA
TGCCATATACCTGCTGATGAGTTTATTACAACAGTGGAATGTATTAAAATTGATAAATACAATATGGCTAT
ATGTTATATGGTATAAATGTGGTAGTTGTTTATTAAAAGGCATGGGGTAAAATGTTCAATTTATGTTTAG
TAGAGCCTAAGCTATGGTACGCCTTCTTCATGGTCACGGTCATATTTTCCAAATGACATGTCCAAAAGAAT
AGATTTGGACTTACTAGATCCTTTACTATTCATGCGAGAATTTATTGTTTATGAGGATTCACACACAGAGA
GTTGCCAGTATGTAATTTTTAGGATTCATGGTACAATTTAATCATAATCTTAATTGCTAGAACGTGTACTA
ATTTCTTTAGAAGATGGCAAGTGGGAACCTATAAACACACGAAGCAAGAACCATATGAACTCAACACAAGC
AATCAACTAAGCCATAGCAAAGCGCAAACAAGAGAACATTGATAGATGATTGGTTTCCCTAACGCTAGATC
```

FIG. 6A (con't)

GTAGTGTAGATGAACAATCCAAGTGCTAGAAGTTGCGAGAGAGTGACAATATGACTCGTTTGATCTCTTGA
TGTTGTGTAGAAAGGGAGCCGCAGTTGGGTTCATCTTCTTTTTTCCGATAAACTTGGGTTCATCTTCATAG
TCATGATTATGGCATGCTCATGTCAAATCTTATGACATATAGTAAAACAAAGGTCTTCTGCGCACAATAAG
GATATCGAAGTATAACAAAAGGTTCACACGAATTGCTCTAGGATTTTTCAGTGATGTGGTACTCCAAGTTT
TTATTCTAGGAAGTATTCCTAGATTTATGGTATAAGTTGGTATATATTAACTCTTCAGTCATAATCATCTC
CAAGGTGATACTTTGACCATTTGTTTTTTTCTTCTTTTTGCGACTGAACTATCAATTTCTATAAAAATA
TGTTGATACACATAAAACATTTTACTCATTATGGAATTATGTTCTGCGATAATTCAAATATCTGTGTCAAA
TGTTTGTAATTTTATTTTTATTTTTACTGATAATCAGATTAAGAGTGCTTGCTGTTTTTTTTTTGAAATG
ACCTATACTATGTGACTCATATGAAGGGGTACTCCTAGCTTGTAATCTTACAAAGTCGTCCGGGATTTATG
TTTAAAATTTTTAAATATTACCTCTTGTGTCATAATGTAGGTTGTCTCCAGCACGTGATACTTTGACAATC
AGTTTCCATAACAATATGCTGGTTCAAATGAAACATGGTACACTTTATAGATTATGTTTCACGACAACGTA
AATTTTGTTTCACGTTTTGTAAGTTTCTTTTTTTTTATGATGAAACCAAGAATGTTTGACGGACACAACTT
TGGAATTGTCCTACAATGTTACTCACATGAAGTATTTGATTTTTGCGGGACAAAAAGGCATTTTTCTTAAG
CTTTTATTTTTGCAGGACAAAATGGCATTTTTCTTAAGTTTACTTGATTTAGCATTTTCCCCATATCTCCT
TCTTTACACTAACTGCAGAATACACTAACTGCAGAACAACTATCTGGAGTATATGGAGCTGAAGTCAAGAG
TTGAGGTTTTACAACGCTCACAAAGGTGATGTTTCTATATTCCTCTCAGATAATTGCTCATTAATTTCAGC
AGGTTACCGCAACATTTGCTATGTTTGCTAAAGTAAGTACTGTTGATGGTGCCACAGGAATCTCCTAGGCG
AGGATTTGGCTCCACTGAGTACAATCGAGCTTGAACAGCTTGAGGGTCAAGTAGGCAAGACCTTGAGGCAA
ATAAGGTCAAGAAAGGTAAACTACATAGCAATAAAAAAAGTTAAGAGTATAAGTAGAAATTAGGTTAATCT
GCTAAAATCCATTCGTCTTATCGAGCAACGCTTGCTGCTAGTTTCACTAACTAGTGTCCATGATTTAACCT
GTACCACAGACTCAAGTACTGCTGGATGAAATGTGCGACCTGAAGAGAAAGGTAGCACTAAAAATACTTTC
CATTTCTGTTGCTAAATGATGGACGATGTCCTATTCCGTAGCTTCAAGCACAATCTTGTTTTGCAGGAGCA
AATATTGCAGGATGCAAATATGACCCTGAAAAGAAAGGTAACATGACCCAAATCATTTTTCCTAGCTAGAA
AGGTCTGCATTTGTACGCACGTAGCTAGGGAGGGACCATCCTCAAGGAGAAGCTGTCTCATTTCACTTGGG
CCAGTGACAAGTGATTGGAAAGTTGATGACTCGGCAAGCCCACTAGTAGTTAGTTAGTAGGCAGGGGACCC
CTGGTTGGCACCACAGTATAAACACAGGTGGCTTTCAGGTACCACCAATTGCAGCTACCTGCCGTGTTTAT
GTGTGTTTGTGCACTGCAAGCATTCTTCTTCTTCCTGGCTTTCAGAAAATCACTCTTCTTGTTTTTACCCT
CTACTGAAAACGGCTTCATCCATTGGTGTATGTAATGCTCTTGATCACTCCCGTTTCACTTCAGCTGGGCG
AGATCGAGCTGGAGGCGACACCTGATCCCCCGCAGCAGCCGCAGCAGCAGCAGATGTGGCAGGGCGACCGG
GGCGTGCCGCCCCACACGCCTCCGCAGCCAGAGCACTTCTTCCAGGCCCTAGAACGCTATCCTTCCCTGCA
GCCAGTGTAAGACTTCTAACTCTTTTTTTCCTTTTCCTGCTGCTAAACTCATGGCACAGAGACTAATGATC
ACCGACGTTCGTCTCTGCAGATTTCGTGGCATGGATGTGAACCAGCCGCCGCCTGCATGGATGGCATAGCT
ACG     (SEQ ID NO: 7)

FIG. 6B

GAGGTCGGAGGTCGGAGATGGGTCGCGGCAAGGTGGTGCTGCAGCGGATCGAGAACAAGATCAGCCGCCAG
GTGACGTTCGCCAAGCGCCGCAACGGCCTGCTCAAGAAGGCCTACGAGCTCTCCCTCCTCTGCGACGCCGA
GGTCGCGCTCGTCCTCTTCTCCCACGCTGGCCGCCTCTACCAGTTCTCCTCCTCCTCCAAGTAATTACTCC
TTCCGATCTCCCCCAGTGCCGTACCATATCGATCCCTCCATTTCCTTTTCTCTTTGTGGTTTTGCCGAGTC
GATCCTTTTGATTTGCTCTCCCCGTTCAAACATTTTGTCCATACGCGACGTTCGATCTGAATTTTCTTGCG
TCTTAGGGCGTCCGTGCATGAACTTATGGGGGCTGGGTCCGTACGTTCTTTCCCTCTTGTTTGCTGTTCT
GTTGGCCACTGTGTCAAAAGAGGCTAGCAAGAAACAAACAAAGGAAAAAGTGATGAGCTCACCCGCAGCAG
CAGATCGACGGACATACTATGCAGTAGGAGTATATGTCATGCGTATGTTTGTCTCATTCACGGTAGAGGAT
TAAAAAGGGGTTTTAATCTAAAAAAAACAAGAAGAAAAGATGTTTTTATTTGATGTACGCCTGACCACACC
TGTATTGAGGATACATGTATGCACATAATTAGAGCTTTGATCACCTGCTGAGATTAATTTGCACCAATATG
GCATGCATCCTTGTGAAACTCATACGGGCACTAATTGTTTTTCTACAAATTTTATCTAGCTTTGTCTTATG
GTCTGGGTAGTATGATGATCCACTTCTGAGAATTAATTTGAATTATGTAATTTTAAATACTTTTCTGCAGA
CCCAAGTTCAATCTATTTTTTTTCTCAAAACAAAGGTTCAGTCTAATTTGACACCTTTAAGGCGTAGGATT
GAATTATATATGCTTGTTTAATGTTATTTGTCAAAGAACTAAGAAAGGATATATACCGCTTTGAGTTAACT

FIG. 6B (con't)

```
GAATTGCATTAATTTTCTAGTCAAAGTACCGAAATAATACTATTGAACAAAATGAAACAGTTAAGTGCTTT
AATTCAACTGTGGCCTTACATGATGTGACAGGGCAAGTGCTGCATCATATGTACTAGGTACAAATGAAGTG
CTATTTGTACTTCCTTGGAGCAAAAGAAAACAAGTAATAAACTAGCTAATGTTAGGTTCGTACCTACTCCC
TCCGTCCCATAATGTAAGACCTTTTTTAACACGGTCTTATATTATGGGATGAAAGGAGTACGCAATAATTT
AAGCAGCTCTATAGGGTAGCATTACCTAATGATATCAGAACTTTATGTATGTTCGAGTCAAATATAGCTAG
GTTTTAATCTGTCAAAATTATAAAGCCACTGAGTTTGCTCAAAAAGTTTGTAAAAGCGCTGATACATGAAA
TGTGAAACCAGACTTGGTAAAATTGCATGCTAATATTTTGTAGGGCCAATCATGATTACTACTTGTCAGTT
CTATACAAACATGCCACTGGTGGCTAGCTTAAACTTTGTAGCAATTTTGGCTGAAATAGCTTTTTTGGTGA
AAATTAACAACTGTACTTCTCACAGTAGTAGCTCAATAAACATTCTTACAGTGGCATAGTTCTCCCAAAAG
TTTAATTAGTCAAAGGAAACAGATATGTCTTCTTTTTTATATAATGGAAAGTTCTTTTTAGGTACATCGTC
AAGTCTTCACTAGATTGTGATGTTTACACAACTTTGAAGCCATGTGTCAATGGCTATAAAGTGACCAAAAA
TTAGCTCATAAGACTAAGACAACATATAGAATTTGTTAGAAGTTGAACATACAGAAAGTTTATTATGCGAG
AGACCTTCATTGTCCAATAATTATCGAATTCTGTCATGTAAATAGTGATACTTAGTTTCTAATCCCTCCCC
CTCCCCAGTGAATCTGAATTTATGTTATTTACCTATGCGTGTACTTGCACAACTTAATCTCGAATTTTCAA
CTCATCGCAGCATGCTTAAGACCCTCGAGAAGTACCAGAGGTACATTTCGCTTCCCAAGATGCTGCCGTG
CCGACTACCGATGAGATGCAGGTCTGAGGCTTTTATTCCCAATGCGCATATTATGAAGATTCTACAAATTT
TCCTCAGATACAACATCTTTGAATTTTTAACTAGCAGGTTATCAGAGAAATTTGTTTTCCTTCGTAGAACA
ATGTATCTATAATGCCCTAAATAACATATATAAATTGATTTTGTGAAGAGATAAAACATTCAGTCATACA
TTTAAAATATTTCATTCTGTATGACGTACGTTATATGAAGCATTGCCTATTCGTAAATGTTACCTAGTTCA
CACATGATTGCTAAAAGGTATTTCTCTGCTGGTAAAGGTGTTATATTTCCGTGTTTAGAACATGGATTTCT
GTTGCTTGTCATATAGGCAGTGAACTAATTATTTTGTTTGACTTTTTTATGTAAAATTACTGCCTTGTAAA
CATGCCCACATGGTTTGAAGCAAAAGATAAACCTTTGATAAATTTTTAGCAGTTACAAAATATTAAATGGG
AATGTAAGTTCATGGCAATTAGAATGTTGGAAAGTACAGCTAGAGCATTGGCCCAGTGCATTTCATGCATA
CGCGCAGCATAATTCACGTACGTGGCTATCTATGTGAAATACAGCATCGAGTAACTGGGCACTGGGGAGAC
CTATATCTGCGCATGTTCCTTGAATTATCGCTAATGTACATGCATTTTGTGGTTGGTTATAACTTATAAGT
AGACTAACAGCTTGGTTGGCCACCACATGCAGTATTGTAGCAGATAGCAGCTTCAGACTGATTGGCCATAT
GCCATATACCTGCTGATGAGTTTATTACAACAGTGGAATGTATTAAAATTGATAAATACAATATGGCTATA
TGTTATATGGTATAAATGTGGTAGTTGTTTATTAAAAAGGCATGGGGTAAAATGTTCAATTTATGTTTAGT
AGAGCCTAAGCTATGGTACGCCTTCTTCATGGTCACGGTCATATTTTCCAAATGACATGTCCAAAAGAATA
GATTTGGACTTACTAGATCCTTTACTATTCATGCGAGAATTTATTGTTTACGAGGATTCACACACAGAGAG
TTGCCAGTATGTAATTTTTAGGATTCATGGTACAATTTAATCATAATCTTAATTGCTAGAACGTGTACTAA
TTTCTTTAGAAGATGGCAAGTGGGAACCTATAAACACACGAAGCAAGAACCATATGAACTCAACACAAGCA
ATCAACTAAGCCATAGCAAAGCGCAAACAAGAGAACATTGATAGATGATTGGTTTCCCTAACGCTAGATCG
TAGTGTAGATGAACAATCCAAGTGCTAGAAGTTGCGAGAGAGTGACAATATGACTCGTTTGATCTCTTGAT
GTTGTGTAGAAAGGGAGCCGCAGTTGGGTTCATCTTCTTTTTTCCGATAAACTTGGGTTCATCTTCATGGT
CATGATTATGGCATGCTCATGTCAAACCTTATGACATATAGTAAAACAAAGGTCTTCTGCGCACAATAAGG
ATATCGAAGTATAACAAAAGGTTCACATGAATTGCTCTAGGATTTTTCAGTGATGTGGTACTCCAAGTTTT
TATTCTAGGAAGTATTCCTAGATTTATGGTATAAGTTGGTATATATTAACTCTTCAGTCATAATCATCTCC
AAGGTGATACTTTGACCATTTGTTTTTTTTCTTCTTTTTGCGACTGAACTATCAATTTCTATAAAAAATAT
GTTGATACACATAAAACATTTTACTCATTATGGAATTATGTTCTGCGATAATTCAAATATCTGTGTCAAAT
GTTTGTAATTTTATTTTTATTTTTACTGATAATCAGATTAAGAGTGCTTGCTGTTTTTTTTTTGAAATGA
CCTATACTATGTGACTCATATGAAGGGGTACTCCTAGCTTGTAATCTTACAAAGTCGTCCGGGATTTATGT
TTAAAATTTTTAAATATTACCTCTTGTGTCATAATGTAGGTTGTCTCCAGCACGTGATACTTTGACAATCA
GTTTCCATAACAATATGCTGGTTCAAATGAAACATGGTACACTTTATAGATTATGTTTCACGACAACGTAA
ATTTTGTTTCACGTTTTGTAAGTTTCTTTTTTTTATGATGAAACCAAGAATGTTTGACGGACACAACTTT
GGAATTGTCCTACAATGTTACTCACATGAAGTATTTGATTTTTGCGGGACAAAAAGGCATTTTTCTTAAGC
TTTTATTTTTGCAGGACAAAATGGCATTTTTCTTAAGTTTACTTGATTTAGCATTTTCCCCATATCTCCTT
CTTTACACTAACTGCAGAATACACTAACTGCAGAACAACTATCTGGAGTATATGGAGCTGAAGGCAAGAGT
TGAGGTTTTACAACGCTCACAAAGGTGATGTTTCTATATTCCTCTCAGATAATTGCTCATTAATTTCAGCA
```

FIG. 6B (con't)

```
GGTTACCGCAACATTTGCTATGTTTGCTAAAGTAAGTACTGTTGATGGTGCCACAGGAATCTCCTAGGCGA
GGATTTGGCTCCACTGAGTACAATCGAGCTTGAACAGCTTGAGGGTCAAGTAGGCAAGACCTTGAGGCAAA
TAAGGTCAAGAAAGGTAAACTACATAGCAATAAAAAAAGTTAAGAGTATAAGTAGAAATTAGGTTAATCTG
CTAAAATCCATTCGTCTTATCGAGCAACGCTTGCTGCTAGTTTCACTAACTAGTGTCCATGATTTAACCTG
TACCACAGACTCAAGTACTGCTGGATGAAATGTGCGACCTGAAGAGAAAGGTAGCACTAAAAATACTTTCC
ATTTCTGTTGCTAAATGATGGACGATGTCCTATTCCGTAGCTTCAAGCACAATCTTGTTTTGCAGGAGCAA
ATATTGCAGGATGCAAATATGACCCTGAAAAGAAAGGTAACATGACCCAAATCATTTTTCCTAGCTAGAAA
GGTCTGCATTTGTACGCACGTAGCTAGGGAGGGACCATCCTCAAGGAGAAGCTGTCTCATTTCACTTGGGC
CAGTGACAAGTGATTGGAAAGTTGATGACTCGGCAAGCCCACTAGTAGTTAGTTAGTAGGCAGGGGACCCC
TGGTTGGCACCACAGTATAAACACAGGTGGCTTTCAGGTACCACCAATTGCAGCTACCTGCCGTGTTTATG
TGTGTTTGTGCACTGCAAGCATTCTTCTTCTTCCTGGCTTTCAGAAAATCACTCTTCTTGTTTTTACCCTC
TACTGAAAACGGCTTCATCCATTGGTGTATGTAATGCTCTTGATCACTCCCGTTTCACTTCAGCTGGGCGA
GATCGAGCTGGAGGCGACACCTGATCCCCCGCAGCAGCCGCAGCAGCAGCAGATGTGGCAGGGCGACCGGG
GCGTGCCGCCCCACACGCCTCCGCAGCCAGAGCACTTCTTCCAGGCCCTAGAACGCTATCCTTCCCTGCAG
CCAGTGTAAGACTTCTAACTCTTTTTTTCCTTTTCCTGCTGCTAAACTCATGGCACAGAGACTAATGATCA
CCGACGTTCGTCTCTGCAGATTTCGTGGCATGGATGTGAACCAGCCGCCGCCTGCATGGATGGCATAGCTA
CG      (SEQ ID NO: 8)
```

FIG. 7A

```
GAAAGGAAAAATTCTGCTCGTTTTTTTGCTCTGTGGTGTGTGTTTGTGGCGAGAGAAAATGATTTGGGGAA
AGCAAAATCCGGAGATTCGCACGTACGATCGTTCGACACGTCGACGCCCGGCGGGCCCGGGGTGGGGCATC
GTGTGGCTGCAGGACCGCGGGGCCCCGCAAAGCGGGCCGGGCCAATGGGTGCTCGACAGCGGCTATGCTCC
AGACCAGCCCGGTATTGCATACCGCGCTCGGGGCCAGATCCCTTTAAAAACCCCTCCCCCCCTGCCGGAAT
CCTCGTTTTGGCCTGGCCATCCTCCCTCTCCTCCCCTCTCTTCCACCTCACGTCCTCACCCAACCACCTGA
TAGCCATGGCTCCGCCGCCTCGCCTCCGCCTGCGCCAGTCGGAGTAGCCGTCGCGGTCTGCCGGTGTTGGA
GGGTAGGGGCGTAGGGTTGGCCCGGTTCTCGAGCGGAGATGGGGCGGGGGAAGGTGCAGCTGAAGCGGATC
GAGAACAAGATCAACCGGCAGGTGACCTTCTCCAAGCGCCGCTCGGGGCTTCTCAAGAAGGCGCACGAGAT
CTCCGTGCTCTGCGACGCCGAGGTCGGCCTCATCATCTTCTCCACCAAGGGAAAGCTCTACGAGTTCTCCA
CCGAGTCATGGTAAATTAAGCACGCGCTGTCTTTAAATTTGTTCCCCAATACGCCTTCGATTTCGATTTCC
TGCGCACCGTTCTGGTCCTGCGAGACGACCCGGCCGACCCCAGGGCCTTCTCCATTTCCGCGCTGCTGTTT
GGTAGATTCCGTTTGCCCGCTCGCTGTTTCCATCCGATTCTGCCGTGGCTGCTTGCTCGTTTTTCTTAGAA
TCGATGGGGGAGCTGGCGTTCCGCGCGGCCGCGATTTCTTGCTATGGGGGGTAGGGCGCGCGATGGGTCGC
CGGGCTATTTTATGCTCCGCCAGCGCCGGGAAGGTTGTTCATCTGGCGTATTTTGGGGAAATTTTGGTCCC
GGACGCGCCAGGTGGCACCCCAAGTGGAAGGGTTAAGACGGTAATCTCTTGATATTTCTATCGGGCTGGGG
TTATTTACGTAAAAAATATATATGGGGTTAAAGTGACATCGCAATTTAGCATGCTACCTCATCTTCTCATT
TGGAATCTTAACTAGACGCTACAATACCTTGTTGTCTCCCTCATCAAATCTGTGCTTGCTGCTTGAACAAA
TGAACCTCGTCATCTCGGTTATTTCCAGAATTTTGTTCCACAGGCTTTGCTATCATTCATATTGGTAGCTC
CGGCCATGCGGCCATTTTGTTGCTTGCTTGGAGATACTGTCTACGGCACGCACGGAGAAAAGAGTCACTTG
ACCAGCTAATGCATGGAATTATTGTCTGCAGCTGATGAAACTCCGGCATGAAGAGTCAAACCAAAAGTAG
AGAGTTCCTTCCAAATATAAAATAAGAGTTTCTGCATACTTTTTTTCCCTTTCAACCATCATAGTTTGCCC
GTGATATTTGTTGGTGCTGGCGATGGTTCTTCACAAAGTAAAGGAGTCAATAAAATCACGGAGACTGATCC
ATTATTTCCCCCACACGCTGACATTAGTCCATGTTAGTTTCCCATTTCTGTCTGCTTCCATAATTCCCGTC
CGGCGAAGTACTAGATCAGCCTCCACGGTTTGAAAGTAAGATATATCATACCGTCGAAAGGATCGCTACTG
CTTAGTAAATATCCATTGTTGTTTGTAATCTTGCTGAGAAAGCAACATTACCATCAGCTTCATGGCAAGGA
CCTGTATGTTGAGGTGCTAAATCTCTTCTAGTTTTGTACCACTGAGGGTATGCGCGGCGCTAACGGAAAAG
GGTAGGTAAAGTTTTATTGGCTTGCCTTCAGCTTCCTTGGTTGTTTGACGCATAGGTGCTTGCATGCATGT
ATCAAGCTGGTCACGTGATGAAAACGCGTAAGAATCAAAGTCGGTTAAATTAAGATATAAATAGATGCAGT
CATATTTTAAGCTAGTGCTGCACTGTGAACTTCAGTATCTCAGATCAAAGTACTGAATAAAATTACCCCCT
GTTTCCGTGCTGTTCATTTGGAAAAGACTGCCATGAACATCCGAATTGGTAACCATGCATTAATCAGCTTG
CCGGCTTTATTTTCTTCTCTGTCGTTCCTTGTCATTTGGTTTGCTTTGCCTACCTCTGCACGATAGGCACG
TGTAAGTAGCTCACGGGGACAAGTAACTGCTATGCTTTGTCTAGAGCCTATGAGACAGCACGCTGATGCAC
CACGATATTCCATGGTTTAGGATCGGAACTAAAATCTTGAGATCTTACAATATTCTAAAAAGGCATCTATA
GCCTGCATATAACCGACTCAGGCACAAAATCAGCATTGATCGAGCAGGCATCATATGCATACACTAAAATG
CAGCTAATGATGTAGCCTGCTGATTTTCTGGACCTGGCTTGGATAATGGTTAATGTACCCAATTGTTATTC
ACTCTATATCCTCCATCTCCTTATCGGTCGATTAATTTACCACACATAGCAAAGGTCCAAAGCTGACATTG
CAACCAACTTTACTCATCTCTAGACTAGTAAACACGAAGTAAGCTGTTAGGGACTGTGTGATGGGTCTATG
TTACATGCATTTGTTGTCGGTCTAGTACTTAACCAAGTCTGGGAACCAGTTATCCTCTACACCTATTGTGT
CCCTAAACCTATATACTTGAGAGTAAAACAGAAGTTATTCCTAGGAATATCTGACTAAGCTATGGGATAGT
CAACTTCCATTTTTGCTCCTGCCACATCTTTACTTAGTCCACAAACGACATATAGATGATCAGCTAGAACC
GTTATTTAGAGTTTATATCTGCTCATTACATGTATTAATTCCATGAAATAGAAGAAAAACTGAATAGGCAC
ACAATATAGTTGAAGCTCGGCAGATGACTTCATAAGTGTCATATCTATTAACCATTTCACATATTGTTACA
TTTTTGCTGCAGTGATATTTGTTAGCTCCCAGTTACAAGTTAACTAATATATGGAGATCCTGGGCACGTA
CATGTAAGCAGATCCTATCGACTTTCGCGTATCCGCTGATGGAATCACACCTCAGGATTTCATGGCATAGT
CTTGATATGTCACGAACTGGTTGTTACTTTATTTATTTATTTTACATTGTGTTTGCCCACCCAGATGATAG
AAATGTTATGTATTTAAAATGTAATCTCACAGTCATTGTTGTTGGTATCGACTGTATGCCAAAAAGGGTTT
TACCATGAAGTCTATTAATGAATAATTATTTATGTTACAACTTGATTGCTTTACATTAGTTAAAATTAGTT
ATTTTGTACCTTTGTGCCCCCCTTCTTGTTCAACCATTTATCTTACCAAACTATGCATCAACAAACATGCA
CAGTCACTATTCATAAATTTCATATTCTCAAAATTTAAATATTAAGAACAAAAGTTATGTTTCTACTTTTT
```

FIG. 7A (con't)

CCAACTGACAATTCTCTGAACTCAAATTTTATAATTTGAAATTTTAATATTAACATTTTATTTTAAAACTT
TTTGAATTTCTTTTTTATTATAAAAAAGTTTGGATGGCATAAATTTATGTATGAACTATTATGAAACCACA
AGCAATAACGAAAGTGTGTTTTTAAGCAAAACCTTATGACCCATCACTCAAATAGTTTGCGTTTGATTTTC
AAATTGACGCGCATTAAAGACATATACATGCAGTCTTCATATCACATGTGTGCTTTTCCTGCTTAAGGTAG
TAGGACTATCTCTTTTTTGAGAAACACCGATTACAACGTAGATGCACACACAAGTGCACATTACCACCACA
CGTACACACTCACACAATGTTTAGTAAGGACTAAAATTGTGGAGCTTCAAGATCTCTGGAACGTCAGGAAT
GTCGCCTCCCACGGAACGAATAATCCGCACAGTGTGTCAAACCATTGGTTCGATCTTCCTTGGTGGGCTGT
GAGTCAAGGTACTAAAAAAGCGGTAGGCGCTAATCTGAATTTTGCCTATGCCTAGTGCAATGACCGCCTAG
GCGCACTTATGCCTTCGTATGACAAAGAAGGAGATTTTACAACAATGAAATCAATGGTGCGGAGCCTAGAG
GGAGGTATCGGTGGTGAGTTGGAGTGAGAAATCCCTCCTCTGATTCAACCTTTCTTGACAACATAGCCCAA
ACAAGACCGTCCATTTTCTTTGCATCCCCCTTTTCCCGTCTCTTTGTATCGTTAGGTCTCTTTCATTCGTC
ATTTGTATGTAGCGATAATGGTGGTGTCTGCAGCTTCTTCCCTGCATTCGCTTCTCCTTTCCTACCGTCGC
CGGAAAAAGATCTCATCGGTCATGGAGAACATAGTCGGGCGCCTAAACCTTGGCCTATGGCAAAAGTGAGG
CGGTAGTCTGCTTAGCGCCTAAGTGGCTTCTTTTCATTGTCCTTTTTTCCATGTTGGGAGTACAACCGCAC
TCCTAACCCACTAATCATAGATTGGTTATCATCTAGTACTTTCTGTACCACTTTTATCTTACAAACGCGAG
GGTATTGTGGTGGAGAGCCATGTATTACAACTTTGATAATCAAAATTCAAAATTCAAGTCTCTGAAGATCC
TTTGAAAAATGTGTTTTGTCAAGGGCAAAAAATATATCTTTGTTTGCCATACCAAGATACTCCCTCCGTAA
AGAAATATAAGAGCGTTTAGGTCACTACTTGAGTGATCTGAACGCTCTTATATTTGTTTACCAGGGAGTAC
AAAAGACCATATTCTTGCCACTAATTTTTACTAGTGGTTATGCCCGGGCATATGAGGGTCGGGAAGGAAGGC
GCAAGGGACATCTAGTAAAAATTAGTGAGAGAATAACCGCAAGGGACATTGTGCACTAATGTTTACCAGGG
AGTACAAAAGACCACATTGTGCCCGGGCATATGAGGGTCGGGAAGGAAGGCGCAAGGGACATCTATAAGAT
GGCTAAGATCGTGAGGAAGGCGAGGGATGTCAAACAAGTCAAATGCATCAAGGATAGAGCAGATCAACTCC
TGGTGAAGGACAAGGAGATCAAGCATAGATGACAGGAGTACTCCGACAAGCTATTCAATGGAGAGATGAAT
CTAGGGGTCTGAGATTAGGGAGGCTTTACAAAGAATAATGTTATAGGAGTCATTGGGCACCACTTAAGAGT
AATGGCAAGCGTGACCAAAAATCAGTTTGTTTTCATGCCTGAGAGGTTGATCATGGAAGTCATTTTCTTGG
TATGAAAACTTATGGAGAAATACAGGGAGCAAAAAGAAGACTTGCATATGATGTTCATTGACTTGAAAAAG
TCCTGCAATAAGATACTGCAAAATGTCATGTGGTGGTCCTTGGAGAAACACAAAGTCCCAATAAAGTACAT
TACTCTCATCAAGGACATGTACAATGATCTCATGACAAGTGTTCAAAAAAGTGATGGCGACACTGATGACC
TTCCGCATAAAATAGGACAGCACCAAGGGTCAACTTCGAGCCCTTATCTTTTTGCCTTGATGATGGATGAG
GTCACAAGGGATATGCAAGGAGATATTCCATGGTGTATTCTCTTTACTATTGATGTGGTGCTAGTCAATGA
TAGTAGCTCGAGGCATAATGGAAAGTTAGAGCTATGGAGACAAACTTTGGATCAAAGTTTTTAGGCTTAGT
AGAACTAAAATTGAGTACATGAGGTGCGGTTTCAGTGCTACTTGGCACGAGGAGGTTAGCCTCAATGGGTA
GGTGGTACCTCAGAAGGGCACCTTTTGATATTTGGGATCAGTGTTGGAAAAGGATGCCGATATTGATGAAG
ATGTGAGCCATTAAATCAAAGTCGGATGGAGGAAATGATGCCAAGTTTCTGGTGTTCTCTCTTGACAAGAT
AGTGCCACGAAAGCTAAAAGGCAGGTTCGATAGGACGGCGCCCCGCAATGTATGGCGCTGAGTATTGGCCG
ACTAAAATGAGACATATTCAACAATTGGGTGTAGCAGAAATGCGCATCTTGAGATGGATGTGTGGTCACCC
AAGAAAGGATCGAGTCCAAAATGATGATATACATGTAGAGTCGGGGTAGCACCGATTGAAGGGAAGCTTGT
CGAACATCGTCTGAGATGGCTTGGATATATACAAAGTAGGCCTTTAGAAACTTTCGTGCATAGCAGGCGGT
TAATACATGCTAATAATGTAAGAGAGGTTGGGCTAGACCAAACTTGACATGGAAGGAGTCCGTGAAGAGAG
ATCTGAAGCACTAAAGTATCACACGGAACTAGTCATGGACAGGGGTGTGTGGAAGTTAGCTATCCACACGC
CAGAACCATTACTTGGTTTTGAGATCTTATGGATTTCAGCTCTACCCTATCCAACTTATTTGGGACTAAAC
GCTTTGTTGTTGTATCTCTTGCCTTGGTCTTAGCAACTTACCATGTGCATGTCTTTTCTCAAAAAGGAAAA
TTGAATGCCAAGTATTTCCTGAAGTTGTACATTGTACAATTTGATGTCCTTGCTCCACGGTACATCAGATT
TCCCATCTCATGATGATGCAACAACTAGGTCTTAGAGCAACTCTAGCAGAGTCTTCATGGCTTCCGTCGCT
ATATTTCTTTTATCTCGCTCCATACACAGGTCTCGTGGCCTCCATATTTGGAGGTTGGAGAGGTCCAGTAA
GGAGCTCGCCCCAAAACCAACCGCTAAAGTTTTAAGCTTCCTCCTCGCGCCTCCTGTCGGATTTGAAGCAA
CCCGCGCCCTCGGATTCTTATGGCGGTCCATTGGATGACCGCCATGCGGCATCATCTTCTTGCTTGCATGT
GAGCAGACTGGAGGTGTGCGAGTAGGTCGCTGCAGCATTTCTCATAGGGAGGCGCGCCCTTCGACTACCCG
CCATTAGCTGCCACCCGCGTCCCCAAGTGCCTCCCTAATGGCGCCTGCGGTGGCCTGTAAAAGGCCGGCGC
CCTCCGCTCTCTAGCTTCAATGCTATCTTCGACGCCTCTTATTCCAATCTCACACGCCTCCAATCCACCAT
CCCCTTTGTCGTCCACAGCGCATCCAGAGGAGCTCCCTCTCGCCTTCAATTTTTGGCATAAGGTGGAGGAG

FIG. 7A (con't)

```
TAGCCCGCGGATCCTTTGCCCCCCTTTAGGGACCAGACGGACCTAGTCCTGGAGGGGGGCTGCGCAGAGCA
ACTTGTAGCACCCAAGATTCTATCCCGATCACGTGATGAATTCATGATCGGAGCAGAATCGCATTTCGAGC
GCATAGCGAGGTGGATATCATTACAACATACCATGCACTAAATAGATGAGAATACCAGATAAAGGTTTACA
CTCGCCACAAGCTACAACATGAATACATCAATACACAACAATCATCATACAGGAGAGCAGGATCCGACTAT
GGATGAAATCAAACAAAAGAAGAACGACATCTACCCTGCTAATCCCGGGCTCCTGAACTGGAACCCATCC
TATGATCGACGAAGAAGCAGAAGAAGAACTCCAAAAGCAAACATGCATCGCTCTCACGTCAAGCATTGCTT
TATCTATACCTGCACCTGTTGTAGTAATCTATGAGCCATGGGACCCAGCAATCTCATTACCAAGGGTAGC
AAAACTAGCAAAGATTAATGGGTATGGAAGGGTTAAGTGGTGAGGAGGCTGGAAGCATTAAGCATTTGTAT
GGTGGCTAACTTACGAGTACAAGAGTAAGAAGAGTAAACTACACATAGCGGTCGCAAACTATTAATGATCA
AGAAGTGATCCTGAACTACTTATGAGTCAGTCATAACCCCACCGTGTTCACTTCCCGAACTCCTTGGAAAA
GAGACGATCACGTAACGCACGCGGTTGGTGTATTTTAATTGGGTTCAGTGTCAAGTTCTCTAAAATCGGAT
ATTATAAATTTTTAAGTCGCCACATAACCGCGGGCACGGCTTCCGAAAAGATTTAGCCCTGCAGGGGTGCA
CCAAGTAGTCCATTATAAATTACCACATGCATCCGATGGAACATCCTCACACCATGATAACACGATGCTTA
CAATAAGGAACCCCGGTGGACAAGCCACTCGTCAAAGGCAAAACTAAACCAGCAAGACCACCCGGTGTGTC
GTCACCCCGATAAGAGCCGCGCCTATTTCTAGGGTTGCCTAACCCTTGGGATCCCTTGGACCACCTTACT
ATGTGCATGTTTCTTTTCACACGGGCATTTATCTGCTTTGGCATCAAAGCTTTCATTTGAAAATTTGCTA
CTACCACCTATATTTGTACTGACAATACCTTTGCATGGACCCACACATTAGGTTTTAAAATGGTTCTCACA
TTCGTGTTGTCTTACTTATCTAGGCATGGCTCTTGCCCAGATAATTGTTGTTGGTCACACCCTTCTATATT
ATCGGTTTGTGAGTCTAGCTGATTGGATACGTGAGTTGTTGCACACTCTTGAACTGATTTTGACTTGATGA
CCATTGTAACCATTTGCGGGTTATAGGCTAGCACATAGTTCAACACTATAACTAATTGTTGGTTCATTCCT
ACTATAGGTTATAGGGTAGCGTTTGACAATTTTCCATGTGTTGTGGGTACTTGTGACAATTGAGGACACGA
TGTTTGTGGTGACAGAGAACACGTTGACCTCCACAAATAGTTAGGATGCTGGGTAAAGCCTACGGGAAAAC
AGGGAGAAGGTATAGGAGGAGAATAACATGAGTAGTAAAAAAGTTAATGACTTAAATACAACATCAAGGAA
CGTTTCTTAAACTGAAGCTCTAGCACTATAGTTAAATAATTTGAATCTGGCAGAAATTATACTAACCTTGC
CTAGCACAATTCCACCCCTAAACTTCTGTTTTGCAAATTTCGTTAAGTCTATAGACAGAAGAAAAGGGTCA
CTCTATTTTCCCAACAAAACTTGAACAACACCAGAACCTTAATTTGAAGTCAGTTTCGTGCTCTTTCTATC
ATTTACACGTCACAGTGAAATGCTTTGCAAACTATTTGACCAGATGCTGTATACCACATTTGAATCTCATT
TGCATATACTGACATGAAACAACGCATTACAGAAAAGCTTCTGATATGTCAAAATGTATCATATATCAATT
CTTGAGATTGTGCATATACTGGACATTAATCTTGTTTACATGTACTTCCAATGACTAGATATTTCTTTCTC
TTATGCAGTATGGACAAAATTCTTGAACGGTATGAGCGCTATTCTTATGCAGAAAAGGTTCTCGTTTCAAG
TGAATCTGAAATTCAGGTAAAAATGAAAAACAAGCGGTTTGCTTTCCTTTAGCTATGAAATAAATTGTTGC
CGATATCAGATGTTCTGAAATTTATTTGTAGGCCACTATATTTTGAATGATTTCCATGCGCTATGAAGTTA
ATTGACTTGCAACTATGGATTGTTGGTCTATTTGATTCTCTTGTAACCTATTATCAGTTTTTCTTCGATGA
ATGCTTAGGCATGGTCGAATAATGTAACCAAATACCACTTGACCAATTTACTTTCATGGCTACTGAACTAG
ACTAGCGTGCTGATTCGTACATACTGCCTTTGGAAGAACTACAAAAATGTGATCTGACTTTAAGAGTTACT
AAATTAGTACGTAGTAAACTGCAATGCATGGCCAGATCAGCAATTCTGGATTAGCCGGCTGAGTTTTTGAA
GGGCTTAGCAACAAAAATTGACAAGCTTATATATTATAATGGCTTTAAAATACTTGTGTGCATCAGTGAAA
ATCACAATATTTTGATTGCAATAACAAAATGCTATCCTAGATTATTAAGACTTGTTACTAGATTGGTCATT
GATCTTAAGTTCTTAGGATAAACTGTTGAATCTCCAGTCCTTCGGATTGTATTATGCTACTAATGGCCATT
AAGGATAGCCCCATGACATTAGTTCTCATCTCCAATTTTTCTGTATTGTTTGCGATATTGCTGCAGTTTCT
TATTACAGCTTGTCTAAGGCTAACCATCTAGGATAAAAAGTAGATCCTGCAGACTTAGAAGATCCAGTTAG
GCTCAATATTCTTATTTTTGTAACTCGGAACTCCAGGACCTCGCTTCAATTTTTTGGCCAATTTTTGCACA
AACCAAGTTGTAGCTCCAACTGAGGGATCCAACCAGTTCTATCTGATTGCTGACAAACAGATTCAGCATGT
ACGTATGACGAGGACTATTTAAACATGTAATTACTAACCCAAAAAATATTCCAAATTTTATTTAAATATTT
ACCTCCGCTGCAGCATTTTTAATATTACGAAATATGATTTTTACATCTGATAGTAACACTTGTTGCAGTGA
CATAATTGATTTGAAGTTATGAAAATTCAAGTTCACTGCACAGAACAATCCTTCCTGATTTATGCCCCGG
GGTAAAGGAGGAGGGTTGTGATAGGCTTGGCGAGCCAACGTAAAAACTCAGCCACTCTTATGGAGATGAAA
CCCAAAAGCCAAAGAGCTAGCTATGGACAGGGGTGCGTGGAAGCTTGCTATCCATGTGCCAGAGCCATGAG
TTGGTTGCGAGATCTTATGGGTTTCACCTCTAGCCTACCCCAACTTGTTTGGGACTAAAGGCTTTGTTGTT
GTTGTTGGTGGTGGTGGTGTCAATGTTGTTAAAGTCTCTTTGTTCATTTCTGAACTAACTTAGCCTATTTG
TAGCATTTCTGTCATTGTTCCTTCCTGTCCCACCCAAAGTTAGCAATGCGATTGTTATTTGTTTGTGCAGG
GAAACTGGTGTCACGAATATAGGAAACTGAAGGCGAAGGTTGAGACAATACAGAAATGTCAAAAGTAATTT
```

FIG. 7A (con't)

```
GTAACGATTTTGGTTGATTGCCAGTATATTGTATACACTCTGAAGATAAATGGGACTGAATTTCTACATCC
TGCATCTGCAGGCATCTCATGGGAGAGGATCTTGAATCTTTGAATCTCAAGGAGTTGCAGCAACTGGAGCA
GCAGCTGGAAAGCTCACTGAAACATATCAGATCCAGGAAGGTACTGATTTAAATGATTTGATACAGCAGCA
CAATATATAAAAAAACAAGAAAAACACTTGCAGAGAAGTTCAGCAAAGTATATCTGAAATCAGATTCTAGA
CTGAGATGTTCAAAATATGTATATGCATTTTAGTCATATGCTCTTCATAGTTAAAAAAAATGACTAATTTTT
TTCATTTTTTGTACTTGCAGAACCAACTTATGCACGAATCCATTTCTGAGCTTCAGAAGAAGGTAAGCTGT
CAACCTTGCATACCTTATTCGGTATTCGAACTGGTCAACTTGTCATGAAGCCTTAGCTTGTTTCAAGATTT
GTGACATTATAACATGTATGCAAGTAACTGGTCTACATGCACGTAACCTCATTACATCGTTCTTGCTGCAG
GAGAGGTCACTGCAGGAGGAGAATAAAGTTCTCCAGAAGGAAGTAAGCCCGTTATATCACCTTATGGTCCA
ACCGGTCTAAATTGTTCCGTATAGCAAATTTTATTGACAGAGGTCCGTGTCCCTTCCCCACAGCTCGTGGA
GAAGCAGAAGGCCCATGCGGCGCAGCAAGATCAAACTCAGCCTCAAACCAGCTCTTCATCTTCTTCCTTCA
TGCTGAGGGATGCTCCCCCTGCCGCAAATACCAGGTGATGATGTACATCACAAGTCTAATCTTATTCAGAG
TTCAAGTAACCATCTTTTGAATTGGTCGGGTTGTTCCTTGCAGCCCACTTTTGGTCTCTATGCAGTTCTGT
CGGGCCACATTTAAGTAACATAATACTAATATGCTTGTGTTCGCTTTGGTTGTGCAGCATTCATCCAGCGG
CAACAGGCGAGAGGGCAGAGGATGCGGCAGTGCAGCCGCAGGCCCCACCCCGGACGGGGCTTCCACCGTGG
ATGGTGAGCCACATCAACGGGTGAAGGGCATCCAGCCCATACAGGCGTACTATTCAGTAGAGGGT
(SEQ ID NO: 9)
```

FIG. 7B

```
GAAAGGAAAAATTCTGCTCGTTTTTTTGCTCTGTGGTGTGTGTTTGTGGCGAGAGAAAATGATTTGGGGAA
AGCAAAATCCGGAGATTCGCACGTACGATCGTTCGACACGTCGACGCCCGGCGGGCCCGGGGTGGGGCATC
GTGTGGCTGCAGGACCGCGGGGCCCCGCAAAGCGGGCCGGGCCAATGGGTGCTCGACAGCGGCTATGCTCC
AGACCAGCCCGGTATTGCATACCGCGCTCGGGGCCAGATCCCTTTAAAAACCCCTCCCCCCCTGCCGGAAT
CCTCGTTTTGGCCTGGCCATCCTCCCTCTCCTCCCCTCTCTTCCACCTCACGTCCTCACCCAACCACCTGA
TAGCCATGGCTCCGCCGCCTCGCCTCCGCCTGCGCCAGTCGGAGTAGCCGTCGCGGTCTGCCGGTGTTGGA
GGGTAGGGGCGTAGGGTTGGCCCGGTTCTCGAGCGGAGATGGGGCGGGGGAAGGTGCAGCTGAAGCGGATC
GAGAACAAGATCAACCGGCAGGTGACCTTCTCCAAGCGCCGCTCGGGGCTTCTCAAGAAGGCGCACGAGAT
CTCCGTGCTCTGCGACGCCGAGGTCGGCCTCATCATCTTCTCCACCAAGGGAAAGCTCTACGAGTTCTCCA
CCGAGTCATGGTAAATTAAGCACGCGCTGTCTTTAAATTTGTTCCCCAATACGCCTTCGATTTCGATTTCC
TGCGCACCGTTCTGGTCCTGCGAGACGACCCGGCCGACCCCAGGGCCTTCTCCATTTCCGCGCTGCTGTTT
GGTAGATTCCGTTTGCCCGCTCGCTGTTTCCATCCGATTCTGCCGTGGCTGCTTGCTCGTTTTTCTTAGAA
TCGATGGGGGAGCTGGCGTTCCGCGCGGCCGCGATTTCTTGCTATGGGGGTAGGGCGCGCGATGGGTCGC
CGGGCTATTTTATGCTCCGCCAGCGCCGGGAAGGTTGTTCATCTGGCGTATTTTGGGGAAATTTTGGTCCC
GGACGCGCCAGGTGGCACCCCAAGTGGAAGGGTTAAGACGGTAATCTCTTGATATTTCTATCGGGCTGGGG
TTATTTACGTAAAAAATATATATGGGGTTAAAGTGACATCGCAATTTAGCATGCTACCTCATCTTCTCATT
TGGAATCTTAACTAGACGCTACAATACCTTGTTGTCTCCCTCATCAAATCTGTGCTTGCTGCTTGAACAAA
TGAACCTCGTCATCTCGGTTATTTCCAGAATTTTGTTCCACAGGCTTTGCTATCATTCATATTGGTAGCTC
CGGCCATGCGGCCATTTTGTTGCTTGCTTGGAGATACTGTCTACGGCACGACGAGAAAAGAGTCACTTG
ACCAGCTAATGCATGGAATTATTGTCTGCAGCTGATGAAACTCCGGCATGAAGAGTCAAACCAAAAGTAG
AGAGTTCCTTCCAAATATAAAATAAGAGTTTCTGCATACTTTTTTTCCCTTTCAACCATCATAGTTTGCCC
GTGATATTTGTTGGTGCTGGCGATGGTTCTTCACAAAGTAAAGGAGTCAATAAAATCACGGAGACTGATCC
ATATTTCCCCCACACGCTGACATTAGTCCATGTTAGTTTCCCATTTCTGTCTGCTTCCATAATTCCCGTCC
GGCGAAGTACTAGATCAGCCTCCACGGTTTGAAAGTAAGAAATATCATACCGTCGAAAGGATCGCTACTGC
TTAGTAAATATCCATTGTTGTTTGTAATCTTGCTGAGAAAGCAACATTACCATCAGCTTCATGGCAAGGAC
CTGTATGTTGAGGTGCTAAATCTCTTCTAGTTTTGTACCACTGAGGGTATGCGCGGCGCTAACGGAAAAGG
GTAAGTAAAGTTTTATTGGCTTGCCTTCAGCTTCCTTGGTTGTTTGACGCATAGGTGCTTGCATGCATGTA
TCAAGCTGGTCACGTGATGAAAACGCGTAAGAATCAAAGTCGGTTAAATTAAGATATAAATAGATGCAGTC
ATATTTTAAGCTAGTGCTGCACTGTGAACTTCAGTATCTCAGATCAAAGTACTGAATAAAATTACCCCCTG
TTTCCGTGCTGTTCATTTGGAAAAGACTGCCATGAACATCCGAATTGGTAACCATGCATTAATCAGCTTGC
CGGCTTTATTTTCTTCTCTGTCGTTCCTTGTCATTTGGTTTGCTTTGCCTACCTCTGCACGATAGGCACGT
GTAAGTAGCTCACGGGACAAGTAACTGCTATGCTTTGTCTAGAGCCTATGAGACAGCACGCTGATGCACC
```

FIG. 7B (con't)

```
ACGATATTCCATGGTTTAGGATCGGAACTAAAATCTTGAGATCTTACAATATTCTAAAAAGGCATCTATAG
CCTGCATATAACCGACTCAGGCACAAAATCAGCATTGATCGAGCAGGCATCATATGCATACACTAAAATGC
AGCTAATGATGTAGCCTGCTGATTTTCTGGACCTGGCTTGGATAATGGTTAATGTACCCAATTGTTATTCA
CTCTATATCCTCCATCTCCTTATCGGTCGATTAATTTACCACACATAGCAAAGGTCCAAAGCTGACATTGC
AACCAACTTTACTCATCTCTAGACTAGTAAACACGAAGTAAGCTGTTAGGGACTGTGTGATGGGTCTATGT
TACATGCATTTGTTGTCGGTCTAGTACTTAACCAAGTCTGGGAACCAGTTATCCTCTACACCTATTGTGTC
CCTAAACCTATATACTTGAGAGTAAAACAGAAGTTATTCCTAGGAATATCTGACTAAGCTATGGGATAGTC
AACTTCCATTTTTGCTCCTGCCACATCTTTACTTAGTCCACAAACGACATATAGATGATCAGCTAGAACCG
TTATTTAGAGTTTATATCTGCTCATTACATGTATTAATTCCATGAAATAGAAGAAAAACTGAATAGGCACA
CAATATAGTTGAAGCTCGGCAGATGACTTCATAAGTGTCATATCTATTAACCATTTGACATATTGTTACAT
TTTTGCTGCAGTGATATTTTGTTAGCTCCCAGTTACAAGTTAACTAATATATGGAGATCCTGGGCACGTAC
ATGTAAGCAGATCCTATCGACTTTCGTGGATCCGCTGATGGAATCACACCTCAGGATTTCATGGCATAGTC
TTGATATGTCACGAACTGGTTGTTACTTTATTTATTTATTTTACATTGTGTTTGCCCACCCAGATGATAGA
AATGTTATGTATTTAAAATATAATCTCACAGTCATTGTTGTTGGTATGGACCGTATGCCAAAAAGGGTTTT
ACCATGAAGTCTATTAATGAATAATTATTTATGTTACAACTTGATTGCTTTACATTAGTTAAAATTAGTTA
TTTTGTACCTTTGTGCCCCCCTTCTTGTTCAACCATTTATCTTACCAAACTATGCATCAACAAACATGCAC
AGTCACTATTCATAAATTTCATATTCTCAAAATTTAAATATTAAGAACAAAAGTTATGTTTCTACTTTTTC
CAACTGACAATTCTCTGAACTCAAATTTTATAATTTGAAATTTTAATATTAACATTTTATTTTAAAACTTT
TTGAATTTCTTTTTTATTATAAAAAAGTTTGGATGGCATAAATTTATGTATGAACTATTATGAAACCACAA
GCAATAACGAAAGTGTGTTTTAAGCAAAACCTTATGACCCATCACTCAAATAGTTTGCGTTTGATTTTCA
AATTGACGCGCATTAAAGACATATACATGCAGTCTTCATATCACATGTGTGCTTTTCCTGCTTAAGGTAGT
AGGACTATCTCTTTTTTGAGAAACACCGATTACAACGTAGATGCACACACAAGTGCACATTACCACCACAC
GTACACACTCACACAATGTTTAGTAAGGACTAAAATTGTGGAGCTTCAAGATCTCTGGAACGTCAGGAATG
TCGCCTCCCACGGAACGAATAATCCGCACAGTGTGTCAAACCATTGGTTCGATCTTCCTTGGTGGGCTGTG
AGTCAAGGTACTAAAAAAGCGGTAGGCGCTAATCTGAATTTTGCCTATGCCTAGTGCAATGACCGCCTAGG
CGCACTTATGCCTTCGTATGACAAAGAAGGAGATTTTACAACAATGAAATCAATGGTGCGGAGCCTAGAGG
GAGGTATCGGTGGTGAGTTGGAGTGAGAAATCCCTCCTCTGATTCAACCTTTCTTGACAACATAGCCCAAA
CAAGACCGTCCATTTCTTTGCATCCCCCTTTTCCCGTCTCTTTGTATCGTTAGGTCTCTTTCATTCGTCA
TTTGTATGTAGCGATAATGGTGGTGTCTGCAGCTTCTTCCCTGCATTCGCTTCTCCTTTCCTACCGTCGCC
GGAAAAAGATCTCATCGGTCATGGAGAACATAGTCGGGCGCCTAAACCTTGGCCTATGGCAAAAGTGAGGC
GGTAGTCTGCTTAGCGCCTAAGTGGCTCCTTTTCATTGTCCTTTTTTTCCATGTTGGGAGTACAACCGCACT
CCTAACCCACTAACCATAGATTGGTTATCATCTAGTACTTTCTGTACCACGTTTATCTTACAAACGCGAGG
GTATTGTGGTGGAGAGCCATGTATTACAACTTTGATAATCAAAATTCAAAATTCAAGTCTCTGAAGATCCT
TTGAAAAATGTGTTTTGTCAAGGGCAAAAAATATATCTTTGTTTGCCATACCAAGATACTCCCTCCGTAAA
GAAATATAAGAGCGTTTAGGTCACTACTTGAGTGATCTGAACGCTCTTATATTTGTTACCAGGGAGTACA
AAAGACCATATTCTTGCACTAATTTTTACTAGTGGTTATGCCCGGGCATATGAGGGTCGGGAAGGAAGGCG
CAAGGGACATCTAGTAAAAATTAGTGAGAGAATAACCGCAAGGGACATTGTGCACTAATGTTTACCAGGGA
GTACAAAAGACCACATTGTGCCCGGGCATATGAGGGTCGGGAAGGAAGGCGCAAGGGACATCTATAAGATG
GCTAAGATCGTGAGGAAGGCGAGGGATGTCAAACAAGTCAAATGCATCAAGGATAGAGCAGATCAACTCCT
GGTGAAGGACAATGAGATCAAGCATAGATGACAGGAGTACTCCGACAAGCTATTCAATGGAGAGATGAATC
TAGGGGTCTGAGATTAGGGAGGCTTTACAAAGAATAATGTTATAGGAGTCATTGGGCACCACTTAAGAGTA
ATGGCAAGCGTGACCAAAAATCAGTTTGTTTTCATGCCTGAGAGGTTGATCATGGAAGTCATTTTCTTGGT
ATGAAAACTTATGGAGAAATACAGGGAGCAAAAAGAAGACTTGCATATGATGTTCATTGACTTGAAAAAGT
CCTGCAATAAGATACTGCAAAATGTCATGTGGTGGTCCTTGGAGAAACACAAAGTCCCAATAAAGTACATT
ACTCTCATCAAGGACATGTACGATGATCTCATGACAAGTGTTCAAAAAAGTGATGGCGACACTGATGACCT
TCCGCATAAAATAGGACAGCACCAAGGGTCAACTTCGAGCCCTTATCTTTTTGCCTTGATGATGGATGAGG
TCACAAGGGATATGCAAGGAGATATTCCATGGTGTATTCTCTTTACGATTGATGTGGTGCTAGTCAATGAT
AGTAGCTCGAGGCATAATGGAAAGTTAGAGCTATGGAGACAAACTTTGGATCAAAGTTTTTAGGCTTAGTA
GAACTAAAATTGAGTACATGAGGTGCGGTTTGAGTACTACTTGGCACGAGGAGGTTAGCCTCAATGGGTAG
GTGGTACCTCAGAAGGGCACCTTTTGATATTTGGGATCAGTGTTGGAAAAGGATGCCGATATTGATGAAGA
```

FIG. 7B (con't)

```
TGTGAGCCATTAAATCAAAGTCGGATGGAGGAAATGATGCCAAGTTTCTGGTGTTCTCTCTTGACAAGATA
GTGCCACGAAAGCTAAAAGGCAGGTTCGATAGGACGGCGCCCCGCAATGTTTGGCGCTGAGTATTGGCCGA
CTAAAATGAGACATATTCAACAATTGGGTGTAGCAGAAATGCGCATCTTGAGATGGATGTGTGGTCACCCA
AGAAAGGATCGAGTCCAAAATGATGATATACATGTAGAGTCGGGGTAGCACCGATTGAAGGGAAGCTTGTC
GAACATCGTCTGAGATGGCTTGGATATATACAAAGTAGGCCTTTAGAAACTTTCGTGCATAGCAGGCGGTT
AATACATGCTAATAATGTAAGAGAGGTTGGGCTAGACCAAACTTGACATGGAAGGAGTCCGTGAAGAGAGA
TCTGAAGCACTAAAGTATCACACGGAACTAGTCATGGACAGGGGTGTGTGGAAGTTAGCTATCCACACGCC
AGAACCATTACTTGGTTTTGAGATCTTATGGATTTCAGCTCTACCCTATCCAACTTATTTGGGACTAAACG
CTTTGTTGTTGTATCTCTTGCCTTGGTCTTAGCAACTTACCATGTGCATGTCTTTTCTCAAAAAGGAAAAT
TGAATGCCAAGTATTTCCTGAAGTTGTACATTGTACAATTTGATGTCCTTGCTCCACGGTACATCAGATTT
CCCATCTCATGATGATGCAACAACTAGGTCTTAGAGCAACTCTAGCAGAGTCTTCATGGCTTCCGTCGCTA
TATTTCTTTTATCTCGCTCCATACACAGGTCTCGTGGCCTCCATATTTGGAGGTTGGAGAGGTCCAGTAAG
GAGCTCGCCCCAAAACTAACCGCTAAAGTTTTAAGCTTCCTCCTCGCGCCTCCTGTCGGATTTGAAGCAAC
CCGCGCCCTCGGATTCCTATGGCGGTCCATTGGATGACCGCCATGCGGCATCATCTTCTTGCTTGCATGTG
AGCAGACTGGAGGTGTGCGAGTAGGTCGCTGCAGCATTTCTCATAGGGAGGCGCGCCCTTCGACTACCCGC
CATTAGCTGCCACCCGCGTCCCCAAGTGCCTCCCTAATGGCGCCTGCGGTGGCCTGTAAAAGGCCGGCGCC
CTCCGCTCTCTAGCTTCAATGCTATCTTCGACGCCTCTTATTCCAATCTCACACGCCTCCAATCCACCATC
CCCTTTGTCGTCCACAGCGCATCCAGAGGAGCTCCCTCTCGCCTTCAATTTTTGGCATAAGGTGGAGGAGT
AGCCCGCGGATCCTTTGCCCCCCTTTAGGGACCAGACGGACCTAGTCCTGGAGGGGGCTGCGCAGAGCAA
CTTGTAGCACCCAAGATTCTATCCCGATCACGTGATGAATTCATGATCGGAGCAGAATCGCATTTCGAGCG
CATAGCGAGGTGGATATCATTACAACATACCATGCACTAAATAGATGAGAATACCAGATAAAGGTTTACAC
TCGCCACAAGCTACAACATGAATACATCAATACACAACAATCATCATACAGGAGAGCAGGATCCGACTATG
GATGAAATCAAACAAAAGAAGAAAGACATCTACCCTGCTAATCCCGGGCTCCTGAACTGGAACCCATCCT
ATGATCGACGAAGAAGCAGAAGAAGAACTCCAAAAGCAAACATGCATCGCTCTCACGTCAAGCATTGCTTT
ATCTATACCTGCACCTGTTGTAGTAATCTATGAGCCATGGGGACCCAGCAATCTCATTACCAAGGGTAGCA
AAACTAGCAAAGATTAATGGGTATGGAAGGGTTAAGTGGTGAGGAGGCTGGAAGCATTAAGCATTTGTATG
GTGGCTAACTTACGAGTACAAGAGTAAGAAGAGTAAACTACACATAGCGGTCGCAAACTATTAATGATCAA
GAAGTGATCCTGAACTACTTATGAGTCAGTCATAACCCCACCGTGTTCACTTCCCGAACTCCTTGGAAAAG
AGACGATCACGTAACGCACGCGGTTGGTGTATTTTAATTGGGTTCAGTGTCAAGTTCTCTAAAATCGGATA
TTATAAATTTTTAAGTCGCCACATAACCGCGGGCACGGCTTCCGAAAAGATTTAGCCCTGCAGGGGTGCAC
CAAGTAGTCCATTATAAATTACCACATGCATCGGATGGAACATCCTCACACCATGATAACACGATGCTTAC
AATAAGGAACCCCGGTGGACAAGCCACTCGTCAAAGGCAAAACTAAACCAGCAAGACCACCCGGTGTGTCG
TCACCCCGATAAGAGCCGCGCCCTATTTTCTAGGGTTGCCTAACCCTTGGGATCCCCTTGGACCACCTTACTA
TGTGCATGTTTTCTTTTCACACGGGCATTTATCTGCTTTGGCATCAAAGCTTTCATTTGAAAATTTGCTAC
TACCACCTATATTTGTACTGACAATACCTTTGCATGGACCCACACATTAGGTTTTAAAATGGTTCTCACAT
TCGTGTTGTCTTACTTATCTAGGCATGGCTCTTGCCCAGATAATTGTTGTTGGTCACACCCTTCTATATTA
TCGGTTTGTGAGTCTAGCTGATTGGATACGTGAGTTGTTGCACACTCTTGAACTGATTTTGACTTGATGAC
CATTGTAACCATTTGCGGGTTATAGGCTAGCACATAGTTCAACACTATAACTAATTGTTGGTTCATTCCTA
CTATAGGTTATAGGGTAGCGTTTGACAATTTTCCATGTGTTGTGGGTACTTGTGACAATTGAGGACACGAT
GTTTGTGGTGACAGAGAACACGTTGACCTCCACAAATAGTTAGGATGCTGGGTAAAGCCTACGGGAAAACA
GGGAGAAGGTATAGGAGGAGAATAACATGAGTAGTAAAAAGTTAATGACTTAAATACAACATCAAGGAAC
GTTTCTTAAACTGAAGCTCTAGCACTATAGTTAAATAATTTGAATCTGGCAGAAATTATACTAACCTTGCC
TAGCACAATTCCACCCCTAAACTTCTGTTTTGCAAATTTCGGTAAGTCTATAGACGAAGAAAAGGGTCAC
TCTATTTTCCCAACAAAACTTGAACAACACCAGAACCTTAATTTGAAGTCAGTTTCGTGCTCTTTCTATCA
TTTACACGTCACAGTGAAATGCTTTGCAAACTATTTGACCAGATGCTGTATACCACATTTGAATCTCATTT
GCATATACTGACATGAAACAACGCATTACAGAAAAGCTTCTGATATGTCAAAATGTATCATATATCAATTC
TTGAGATTGTGCATATACTGGACATTAATCTTGTTTACATGTACTTCCAATGACTAGATATTTCTTTCTCT
TATGCAGTATGGACAAAATTCTTGAACGGTATGAGCGCTATTCTTATGCAGAAAAGGTTCTCGTTTCAAGT
GAATCTGAAATTCAGGTAAAAATGAAAAACAAGCGGTTTGCTTTCCTTTAGCTATGAAATAAATTGTTGCC
GATATCAGATGTTCTGAAATTTATTTGTAGGCCACTATATTTTGAATGATTTCCATGCGCTATGAAGTTAA
```

FIG. 7B (con't)

```
TTGACTTGCAACTATGGATTGTTGGTCTATTTGATTCTCTTGTAACCTATTATCAGTTTTTCTTCGATGAA
TGCTTAGGCATGGTCGAATAATGTAACCAAATACCACTTGACCAATTTACTTTCATGGCTACTGAACTAGA
CTAGCGTGCTGATTCGTACATACTGCCTTTGGAAGAACTACAAAAATGTGATCTGACTTTAAGAGTTACTA
AATTAGTACGTAGTAAACTGCAATGCATGGCCAGATCAGCAATTCTGGATTAGCCGGCTGAGTTTTTGAAG
GGCTTAGCAACAAAAATTGACAAGCTTATATATTATAATGGCTTTAAAATACTTGTGTGCATCAGTGAAAA
TCACAATATTTTGATTGCAATAACAAAATGCTATCCTAGATTATTAAGACTTGTTACTAGATTGGTCATTG
ATCTTAAGTTCTTAGGATAAACTGTTGAATCTCCAGTCCTTCGGATTGTATTATGCTACTAATGGCCATTA
AGGATAGCCCCATGACATTAGTTCTCATCTCCAATTTTTCTGTATTGTTTGCGATATTGCTGCAGTTTCTT
ATTACAGCTTGTCTAAGGCTAACCATCTAGGATAAAAGTAGATCCTGCAGACTTAGAAGATCCAGTTAGG
CTCAATATTCTTATTTTTGTAACTCGGAACTCCAGGACCTCGCTTCAATTTTTTGGCCAATTTTTGCACAA
ACCAAGTTGTAGCTCCAACTGAGGGATCCAACCAGTTCTATCTGATTGCTGACAAACAGATTCAGCATGTA
CGTATGACGAGGACTATTTAAACATGTAATTACTAACCCAAAAAATATTCCAAATTTTATTTAAATATTTA
CCTCCGCTGCAGCATTTTTAATATTACGAAATATGATTTTTACATCTGATAGTAACACTTGTTGCAGTGAC
ATAATTGATTTGAAGTTATGAAAATTCAAGTTCACTGCACAGAACAATCCTTCCTGATTTATGCCCCCGGG
GTAAAGGAGGAGGGTTGTGATAGGCTTGGCGAGCCAACGTAAAAACTCAGCCACTCTTATGGAGATGAAAC
CCAAAAGCCAAAGAGCTAGCTATGGACAGGGGTGCGTGGAAGCTTGCTATCCATGTGCCAGAGCCATGAGT
TGGTTGCGAGATCTTATGGGTTTCACCTCTAGCCTACCCCAACTTGTTTGGGACTAAAGTCTTTGTTGTTG
TTGTTGGTGGTGGTGGTGTCAATGTTGTTAAAGTCTCTTTGTTCATTTCTGAACTAACTTAGCCTATTTGT
AGCATTTCTGTCATTGTTCCTTCCTGTCCCACCCAAAGTTAGTAATGCGATTGTTATTTGTTTGTGCAGGG
AAACTGGTGTCACGAATATAGGAAACTGAAGGCGAAGGTTGAGACAATACAGAAATGTCAAAAGTAATTTG
TAACGATTTTGGTTGATTGCCAGTATATTGTATACACTCTGAAGATAAATGGGACTGAATTTCTACATCCT
GCATCTGCAGGCATCTCATGGGAGAGGATTTTGAATCTTTGAATCTCAAGGAGTTGCAGCAACTGGAGCAG
CAGCTGGAAAGCTCACTGAAACATATCAGATCCAGGAAGGTACTGATTTAAATGATTTGATACAGCAGCAC
AATATATAAAAAAACAAGAAAAACACTTGCAGAAGTTCAGCAAAGTATATCTGAAATCAGATTCTAGAC
TGAGATGTTCAAAATATGTATATGCATTTTAGTCATATGCTCTTCATAGTTAAAAAAAATGACTAATTTTT
TTCATTTTTTGTACTTGCAGAACCAACTTATGCACGAATCCATTTCTGAGCTTCAGAAGAAGGTAAGCTGT
CAACCTTGCATACCTTATTCGGTATTCGAACTGGTCAACTTGTCATGAAGCCTTAGCTTGTTTCAAGATTT
GTGACATTATAACATGTATGCAAGTAACTGGTCTACATGCACGTAACCTCATTACATCGTTCTTGCTGCAG
GAGAGGTCACTGCAGGAGGAGAATAAAGTTCTCCAGAAGGAAGTAAGCCCGTTATATCACCTTTGGTCCAA
CCGGTCTAAATTGTTCCGTATAGCAAATTTTATTGACAGAGGTCCGTGTCCCTTCCCCACAGCTCGTGGAG
AAGCAGAAGGCCCATGTGGCGCAGCAAGATCAAACTCAGCCTCAAACCAGCTCTTCATCTTCTTCCTTCAT
GCTGAGGGATGCTCCCCCTGCCGCAAATACCAGGTGATGATGTACATCACAAGTCTAATCTTATTCAGAGT
TCAAGTAACCATCTTTTGAATTGGTCGGGTTGTTCCTTGCAGCCCACTTTTGGTCTCTATGCAGTTCTGTC
GGGCCACATTTAAGTAACATAATACTAATATGCTTGTGTTCGCTTTGGTTGTGCAGCATTCATCCAGCGGC
AACAGGCGAGAGGGCAGAGGATGCGGCAGTGCAGCCGCAGGCCCCACCCCGGACGGGGCTTCCACCGTGGA
TGGTGAGCCACATCAACGGGTGAAGGGCATCCAGCCCATACAGGCGTACTATTCAGTAGAGGGT
```
(SEQ ID NO: 10)

FIG. 8A

```
CATTCCCACAGGCCACAGCTAGCCATGTCTCGGTCCACGTTAATCATCCTCGCTCTCCTCGCCGTGAGCAG
CGCCGTCGCTGCTCCCCGTGCTCTCGCGGCACGGGAGCTCGCCGGCAACGATGCCATCGCCGTCGACGCTG
CCATGGTGTTGAGGCACGAGAAGTGGATGGCGGAGCACGGGCGCACGTACGCGGACGAGGAGGAGAAGGCG
CGGCGGCTGGAGGTATTCCTCGCCAACGCCAAGTTCATCGACTCGTTTAACGCCCTCACCGTCAGCAGCGG
GGAGCATGGACTGGAGGGCCATGGGCGCCGTCACCGGCGTCAAGGACCAAGGCTCTTGCGGTACGTACAAT
CAACACGACAACACTGGCACGCACGCTACTGCAGATGCATACAAATTAAGCTGCAGAACATTGCAAGCACC
GGAACATTTACCACCTGGATCAAGCTTTTTTAGACTTCTAAAAATGTTAAAAAAGAACTTGCAAGTGGCAA
CACGCGCGTAGGAAAAGTAAAAAATTGACGTGAGATTGTACCGGGATGACTAGAGTCTACAAACAAGTCAT
GCGTGCACTTTTCGGTCAACCCAGACAGCAAGAGGAGTCAGCGTTCACTTTACTTCAATGATTGGAGTATC
ATTCTTAATTTTCCATTTTGGACATGTCCTAAGCTTAATTGCCTCTGTTTCATCATTTAATCAAATAACTT
GGGTGACATGCATATGCAGGCTGCTGCTGGGCGTTCTCGGCGGTGGCGGCGGTGGAAGGGCTGACCAAGAT
CCGCACGGGGCGGCTTATGTCACTGTCGGAGCAGCAGCTGGTGGACTGCGACGTGAACGGCGACGACGAGG
GCTGCGCCGGCGGCCTCATGGACAACGCCTTCGAGTACATGGTCCGCCGCGGCGGCCTCACCACGGAGTCG
TCCTACCCGTACCGCGGCACGGACGGGTCGTGCCGCCGCTCGGCCTCGGCCGCGTCCATCCGTGGGTACGA
GGACGTGCCGGCCAACAACGAGGCGGCGCTGATGGCGGTCGTGGCGCACCAGCCCGTGTCCGTGGCCATCA
ACGGCGGCGACAGTGTGTTCCGGTTCTACGACAGCGGCGTGCTGGGCGGGTCCGGCTGCGGCACGGAGCTC
AACCACGCCATCACGGCGGTCGGGTACGGCACGGCGAGCGACGGCAGCAAGTACTGGATCATGAAGAACTC
GTGGGGCACGTCGTGGGGCGAGCGCGGCTACGTCAGGATCCGCCGCGGGGAGCGCGGCGAGGGCGTCTGCG
GCCTCGCCCAGCTCGCGTCCTCCCTGTCTAG      (SEQ ID NO: 11)
```

FIG. 8B

```
CATTCCCACAGGCCACAGCTAGCCATGTCTCGGTCCACGTTAATCATCCTCGCTCTCCTCGCCGTGAGCAG
CGCCGTCGCCGCTCCCCGTGCTCTCGCGGCACGGGAGCTCGCCGGCAACGATGCCATCGCCGTCGACGCTG
CCATGGTGTCGAGGCACGAGAAGTGGATGGCGGAGCACGGGCGCACGTACGCCGACGAGGAGGAGAAGGCG
CGGCGGCTGGAGGTATTCCTCGCCAACGCCAAGTTCATCGACTCGTTTAGCGCCCTCACCGTCAGCAGCGG
GGAGCATGGACTGGAGGGCCATGGGCGCCGTCACCGGCGTCAAGGACCAAGGCTCTTGCGGTACGTACAAT
CAACACGACAACACTGGCACGCACGCTACTGCAGATGCATACAAATTAAGCTGCAGAACATTGCAAGCACC
GGAACATTTACCACCTGGATCAAGCTTTTTTAGACTTCTAAAAATGTTAAAAAAGAACTTGCAAGTGGCAA
CACGCGCGTAGGAAAAGTAAAAAATTGACGTGAGATTGTACCGGGATGACCAGAGTCTACAAACAAGTCAT
GCGTGCACTTTTCGGTCAACCCAGACAGCAAGAGGAGTCAGCGTTCACTTTACTTCAATGATTGGAGTATC
ATTCTTAATTTTCCATTTCGGACATGTCCTAAGCTTAATTGCCTCCGTTTCATCATGTACTAATCCAATAA
CTTTGGGTGACATGCATATGCAGGCTGTTGCTGGGCGTTCTCGGCGGTGGCGGCGGTGGAAGGGCTGACCA
AGATCCGCACGGGGCGGTTGGTGTCGCTGTCGGAGCAGCAGCTGGTGGACTGCGACGTGAACGGCGACGAC
GAGGGCTGCGCCGGCGGCCTCATGGACAACGCCTTCGAGTACATGGTCCGCCGCGGCGGCCTCACCACGGA
GTCGTCCTACCCGTACCGCGGCACGGACGGGTCGTGCCGCCGCTCGGCCTCGGCCGCGTCCATCCGGGGGT
ACGAGGACGTGCCGGCCAACAACGAGGCCGCGCTGATGGCGGCCGTGGCGCACCAGCCCGTGTCCGTGGCC
ATCAACGGCGGCGACAGCGTGTTCCGGTTCTACGACAGCGGCGTGCTGGGCGGGTCCGGCTGCGGCACGGA
GCTCAACCACGCCATCACGGCGGTCGGGTACGGCACGGCGAGCGACGGCAGCAAATACTGGATCATGAAGA
ACTCGTGGGGCGCGTCGTGGGGCGAGCGCGGCTACGTCAGGATCCGCCGCGGCGTGCGCGGCGAGGGCGTC
TGCGGCCTCGCCCAGCTCGCGTCCTACCCTGTCTAG      (SEQ ID NO: 12)
```

FIG. 9A

ATCAAGTGGGAAGCGCCATCCAAATTAGCCGAGCTCGCACACTACTGCCGCGTCAGCTCTTGCGGGGAAGA
CGAGCCGCGCCGGAGTGACGTCGTACGGCTTCCCGTTCCCCTCTCGGTTTCCCGACGCCTCTCTTGGCTCA
CCCGCCCGCCCGCCGCCGCCCTGCCACTTCCTCCGCGCGTGAAAGCCCACCGCCTATTCCCCTTCCCTTCG
CTCTCCGACGCCGGGCGCCACCCCGGCGGATCGAGCGGGCGGGCGGTTAGTTAGTTGCGCATCGCTGTTGC
TTGCTTCTTCTACCGTTTGGCGCAGGGAGGAGGAGCGTGGGGGTAACATCGCTGTCCCACTCCCACCCGGG
TGCTGCCCCTCCTGTTCCCTTCTCACTCACTGCGTGTGCTTATCCGCGCCGGGCGAATCCAATCCCCCAC
TCTCCCCCGTCCTTCTCCAGAAAAGTCGCGGCTTTCCCCCCGCCCCCTCATGATTCCCGTCGATTCCTCCT
CCGCCCATTTGCCCCTCCGCGTCGCAGAATCCCCCGCGCCACCGCTGCTGACCGTCGCGCCGTAGGGGGAG
GGGCAGGAGCGAGGAGCCTAGCTCGGGGGTGGTCGTGGTGGCGACCGGCGGCGAGATGTCGTCGTCGCGGT
CCAACAACCGGCCGGCGTGCTCGCGGGGGAGCTCGGCGCGCTCCAAGCACAGCGAGCGGGTGGTGGCGCAG
ACGCCCGTGGACGCGCGCCTGCACGCCGAGTTCGAGGGCTCGCAGCGCCACTTCGACTATTCCTCCTCGGT
CAGCGCGCTCAACCGCTCCGGGGCCAGCACCAGCTCCGCCGTCTCCGCCTACCTCCAGAACATGCAGCGGG
GCCGCTACATCCAGCCCTTCGGCTGCCTGCTCGCGATCCACCCGGAGTCCTTCGC
(SEQ ID NO: 13)

FIG. 9B

ATCAAGTGGGAAGCGCCATCCAAATTAGCCGAGCTCGCACACTACTGCCGCGTCAGCTCTTGCGGGGAAGA
CGAGCCGCGCCGGAGTGACGTCGTACGGCTTCCCGTTCCCCTCTCGGTTTCCCGACGCCTCTCTTGGCTCA
CCCGCCCGCCCGCCGCCGCCCTGCCACTTCCTCCGCGCGTGAAAGCCCACCGCCTATTCCCCTTCCCTTCG
CTCTCCGACGCCGGGCGCCACCCCGGCGGATCGAGCGGGCGGGCGGTTAGTTAGCTGCGCATCGCTGTTGC
TTGCTTCTTCTACCGTTTGGCGCAGGGAGGAGGAGCGTGGGGGTAACATCGCTGTCCCACTCCCACCCGGG
TGCTGCCCCTCCTGTTCCCTTCTCACTCACTGCGTGTGCTTATCCGCGCCGGGCGAATCCAATCCCCCAC
TCTCCCCCGTCCTTCTCCAGAAAAGTCGCGGCTTTCCCCCCGCCCCCTCATGATTCCCGTCGATTCCTCCT
CCGCCCATTTGCCCCTCCGCGTCGCAGAATCCCCCGCGCCACCGCTGCTGACCGTCGCGCCGTAGGGGGAG
GGGCAGGAGCGAGGAGCCTAGCTCGGGGGTGGTCGTGGTGGCGACCGGCGGCGAGATGTCGTCGTCGCGGT
CCAACAACCGGCCGGCGTGCTCGCGGGGGAGCTCGGCGCGCTCCAAGCACAGCGAGCGGGTGGTGGCGCAG
ACGCCCGTGGACGCGCGCCTGCACGCCGAGTTCGAGGGCTCGCAGCGCCACTTCGACTATTCCTCCTCGGT
CAGCGCGCTCAACCGCTCCGGGGCCAGCACCAGCTCCGCCGTCTCCGCCTACCTCCAGAACATGCAGCGGG
GCCGCTACATCCAGCCCTTCGGCTGCCTGCTCGCGATCCACCCGGAGTCCTTCGC
(SEQ ID NO: 14)

FIG. 10A

CTGATCTGCTTGCAGCAACCCGGGTACGACATCATAGCGCAGTTCATGATCGGCTACGCGCTACCCGGCAA
GCCCATCGCCAACCTGCTCTTCAAGATCTACGGCCGGATCAGCACCGTGCACGCGCTCTCCTTCCTCGCCG
ACCTCAAGCTCGGCCACTACATGAAGATCCCGCCACGCTGCATGTACACCGCCCAGGTACGTGACAGAGAT
CGATCTCTCAGCCCCCACAATGCACTAGATGCTCATCACTCGCTGAACTAACCGGCGTGCGCTTGGCCGGT
GCAGCTGGTGGGCACGGTGGTCGCCGGCGTGGTGAACCTGGCGGTGGCGTGGTGGATGCTGGACAGCATCG
ACAACATCTGCGACGTGGAGGCGCTGCACCCGGACAGCCCTGGACGTGCCCCAAGTACCGGGTCACCTTC
GACGCGTCGGTGATCTGGGGCCTCATCGGGCCGGGGCGCCTCTTCGGCCAGCACGGGTTGTACCGGAACCT
GGTGTGGCTGTTCGTGGTCGGCGCCGTGCTGCCGGTGCCGGTGTGGCTGCTGAGCCGGGCGTTCCCGGAGA
AGAAGTGGATCGCGCTCGTCAACGTGCCCGTCATCTCCTACGGCTTCGCCGGGATGCCGCCGGCCACGCCC
ACCAACATCGCCAGCTGGCTCGTCACCGGCACCGTCTTCAACTTCTTCGTCTTCAGGTACCGCAAGGGGTG
GTGGCAGAAGTACAACTACGTGCTATCGGCGGCGCTCGACGCCGGCACCGCCTTCATGGGGGTGCTCATCT
TCTTCGCGCTCCAGAACGCGCACCACGACCTCAAGTGGTGGGGCACCGAGGTCGACCACTGCCCGCTCGCC
ACCTGCCCCACCGCGCCCGGCATCGTCGTCAAGGGCTGCCCGGTCTTCTGAGCACTGAGCTCGCCGGAGCA
TCATCGGACACTGCCCGCCATGTATG      (SEQ ID NO: 15)

FIG. 10B

CTGATCTGCTTGCAGCAACCCGGGTACGACATCATAGCGCAGTTCATGATCGGCTACGCGCTACCCGGCAA
GCCCATCGCCAACATGCTCTTCAAGATCTACGGCCGGATCAGCACCGTGCACGCGCTCTCCTTCCTCGCCG
ACCTCAAGCTCGGCCACTACATGAAGATCCCGCCACGCTGCATGTACACCGCCCAGGTACGTGACAGAGAT
CGATCTCTCAGCCCCCACAATGCACTAGATGCTCATCACTCGCTGAACTAACCGGCGTGCGCTTGGCCGGT
GCAGCTGGTGGGCACGGTGGTCGCCGGCGTGGTGAACCTGGCGGTGGCGTGGTGGATGCTGGACAGCATCG
ACAACATCTGCGACGTGGAGGCGCTGCACCCGGACAGCCCTGGACGTGCCCCAAGTACCGGGTCACCTTC
GACGCGTCGGTGATCTGGGGCCTCATCGGGCCGGGGCGCCTCTTCGGCCAGCACGGGTTGTACCGGAACCT
GGTGTGGCTGTTCGTGGTCGGCGCCGTGCTGCCGGTGCCGGTGTGGCTGCTGAGCCGGGCGTTCCCGGAGA
AGAAGTGGATCGCGCTCGTCAACGTGCCCGTCATCTCCTACGGCTTCGCCGGGATGCCGCCGGCCACGCCC
ACCAACATCGCCAGCTGGCTCGTCACCGGCACCGTCTTCAACTTCTTCGTCTTCAGGTACCGCAAGGGGTG
GTGGCAGAAGTACAACTACGTGCTATCGGCGGCGCTCGACGCCGGCACCGCCTTCATGGGGGTGCTCATCT
TCTTCGCGCTCCAGAACGCGCACCACGACCTCAAGTGGTGGGGCACCGAGGTCGACCACTGCCCGCTCGCC
ACCTGCCCGACCGCGCCCGGCATCGTCGTCAAGGGCTGCCCGGTCTTCTGAGCACTGAGCTCGCCGGAGCA
TCATCGGACACTGCCCGCCATGTAG      (SEQ ID NO: 16)

FIG. 11A

```
GTTCTCACATTTCGTGGTTGTTTGTCCTGGGACTTTCATTCTGCAGTTGGTTTTCTCTGGACATGCCTCTG
GGAGGCTCTTGAAATACAATCCCGAAACAAAGGAGACAACAGTCCTTCACCGCAACCTCCAGTTTCCCAAC
GGAGTGAGCTTAAGCAAGGATGGCTCGTTCTTCGTCTTCTGTGAAGGATCTCGTGGAAGGTCTATACACTC
TTCCCTCCATTTGGTTCAGGATTTCATACATGTATACTTGAAATTAGTCACTGATTATTGTGTCCTTATCC
AAACAGGTTGAGCAGATACTGGCTGAAAGGTGAGAAGGCAGGCACCGTCGATCTCTTCGCCATCCTGCCTG
GGTTCCCGGACAACGTGAGGACCAACGACAAGGGCGAATTCTGGGTGGCCATCCATTGCCGACGCAGCGCA
TACGCCCGGCTCTTGAGTCGCCGCGTCCAGCTCAGAAAGTTCTTGCTCAGCCTCCCGATCCCCGCCAAGTA
TCACTACCTGATGCAAATCGGCGGCAATCTGCACGCGCTCATCATCAAGTACAGCCCTGAAGGCGAGGTGC
TTGACATCTTGGAGGACACTAAAGGGCAGGTGGTGAGAGCTGTGAGCGAAGTGGAGGAGAAGGATGGCAAG
CTCTGGATAGGATCTGTTCTCATGCCCTTCATTGCCGTCTTTGACTACGCCAAGGAATCCTAAGCCGCCCT
TTTGCCGGGATACATGGGTAAGAGAGTATGAAATCCACGAACGCCGTTGCACACTATTGCTTCATCCAAAT
AAATCTAGTGTTGGAAGCAACCTAGAATTGCTTGATGTTTCAGCCTTTTCCTAGTAGCAACTGTAACTCAC
TGACATTTTAGTTTGTCCCTGGGATCTTTCAA        (SEQ ID NO: 17)
```

FIG. 11B

```
CGGCAGCACTTTTCATGATGTTTGTCCTGGGACTTTCATTATGCAGTGGGTTTTCTCTGGAGATGCCTCTG
GGAGGCTCTTGAAATACAATCCCGAAACAAAGGAGACAACAGTCCTTCACCGCAACCTCCAGTTTCCCAAC
GGAGTGAGCTTAAGCAAGGATGGCTCGTTCTTCGTCTTCTGTGAAGGATCTCGTGGAAGGTCTATACACTC
TTCCCTCCATTTGGTTCAGAATTTCATACATGTATACTTGAAATTAGTCACTGATTATTGTGTCCTTATCC
AAACAGGTTGAGCAGATACTGGCTGAAAGGTGAGAAGGCAGGCACCGTCGATCTCTTCGCCATCCTGCCTG
GGTTCCCGGACAACGTGAGGACCAACGACAAGGGCGAATTCTGGGTGGCAATCCATTGCCGACGCAGCGCA
TACGCCCGGCTCTTGAGTCGCCGCGTCCAGCTCAGAAAGTTCTTGCTCAGCCTCCCGATCCCCGCCAAGTA
TCACTACCTGATGCAAATCGGCGGCAATCTGCACGCGCTCATCATCAAGTACAGCCCTGAAGGCGAGGTGC
TTGACATCTTGGAGGACACTAAAGGGCAGGTGGTGAGAGCTGTGAGCGAAGTGGAGGAGAAGGATGGCAAG
CTCTGGATAGGATCTGTTCTCATGCCCTTCATTGCCGTCTTTGACTACGCCAAGGAATCCTAAGCCGCCCT
TTTGCCGGGATACATGGGTAAGAGAGTATGAAATCCACGAACGCCGTTGCACACTATTGCTTCATCCAAAA
TAAATCTAGTGTTGGAAGCAACCTAGAATTGCTTGATGTTTCAGCCTTTTCCTAGTAGCAACTGTAACTCA
CTGACATTTTAGTTTGTCCCTGGGGATCTTTCAA        (SEQ ID NO: 18)
```

FIG. 12A

```
CGCGCCAGGCCGCCGCCCACACTTCCCGCCGAGCCTAAAAGATGCAAGAAGAGAGAGGGGAGAGGCTAGAG
GGTGATGGAGGGGCTCACCGCACCAATAACAATGGATAGCGCTGCTGCGGTGGATTTCCCTCTGGCTGAAT
TTGTCCCCCACCCCACCCGCTCACCCACACTCGCGTGAATTGATTTGCGCCATTCGCCGTTGCCGTCTGTT
TTTAATCTTTTTCAAGCGGGTGCAGGTGAGCTCGGGCCCGACTGAGGGCCTTTTTGATTCATAGGATTGCA
AAAACACAGGAATAGGAAAAACGCAGGATTGAAATGGCATGTCCATTGGATCCCTATAGGATTTGAGTTTG
TTTGATTGTGTTAAGGGAAAAACAAAGGATTTTTTTTCAAGAGGTTTGAGTGGATGCTAGAATTTCTGTGA
AATGTAGTACAAATGAACCCTTAGAAAAAAAATACAGGATTCAATCCTACGAATCAAACGATCAACGTAGAA
AAAATTCCTAAGGATTCTAATCCTTCAAAGATCTTATGAAAATCCTTTGAATCAAAGAGACCTTGAAGTTG
TGGAGCTCAAAATTTATAGTATTCCTCTAGAAGAAGCTCGAAATTACTTCTATACTGATTAACTGATGTGT
GTGCAAAAAGAAAGAACTGATTAACCGATGAAACAACCAGTGTTTGGTACACTTCTGCGGGGGTGAATTG
GTGAGCTGGACAGGGCCCACCCGCAGCAAATTGCTTCTATTATGGTGGCCGCCTCCTCCTCCTCCCTGGC
CAGATCCCAAATTTGAAATCGCCCAACGTCTCCAGACTCCTCTCCGCTCCCATTTCAAAACCTCCAATCT
CGTCCTCTCCCCACCCCCACCCACCGCCGCCGGCCCGCCGCGCCGCTGCTCTGCCCAGATCCCGCCCGCCG
CAAGCCCATCCCTGCCTCCGTCGCAGCCGCAGCGGTACCCGCAGCCGCAGCCGCGATGCTGTCGGACGGTG
GCGACGACGACAGCTCCGCCCCGCGCGGTTCGAGCTGCAGGAGGACCCCTCCTTCTGGAAGGACAACAAC
GTGCAGGTAGTGATTCTTCTCGCCCCCCTCGCCGGGAGCTCCCGCGCCTCCGCCTCCTCGATTCTCCCCTG
GCAGCGGCGTCCCGATCTAGTTTCGCCCGCGGCCGCGCGCTGCGCCGTTGGATCATTTCGTCGAGCACCTA
GGTTCGTCAGGTCCGGTCCGCGCTAACCGCTCCGCCCCGCAGGTCGTGATTCGTGTCCGGCCGCTCAGCAG
CAGCGAGATATCGGTGCAGGGGACAAGAGGTGCGTCAGGCAGGACAGCGGCCAGAGCATTACCTGGACCT
GCCACCCGGAGTCCCGGTTCACCTTTGATCTAGTCGCCGATGAGCACATCACGCAGGTATACTCCTTGTTC
CTGTTCGCCCGTTCCTTTACTTGTTCCGCAGATGTGTAAATACTCTTGTGCTTGTGCTGTATAGGAGAGTC
TTTTCAAGGTTGCTGGGGTGCCCATGGTGGAGAACTGCATGGCTGGCTATAACAGCTGCATGTTTGCCTAT
GGGCAGGTGAGCTACAGCCTCCACCTCCACCTGCTGTTGCAGTGTGCTTACTCTCTTTTATTTGCACTTTG
AATCATTGAGCTTACAAAAGTATCCTGTTTCTTAGACCGGTAGTGGCAAGACCCACACGATGCTTGGGGAC
ATAGAAAATGGCACACGGGGAAACAATGAGAACTGTGGTATGACGCCTCGAGTGTTTGAGCATCTCTTCCT
AAGAATCCAGAAGGCAAGCTCTGATGATATGTTGATTCTGATGCCTAATTTTGTGCTGTAGATGGTGTACT
GTTTCTGAGGTAAACTTTTCAATTGCTGTTTGCAGGAAAAGGAAATACGAAGAGATGAAAAGCTCAGTTTT
ACTTGCAAGTGCTCATTCCTGGAGATATATAATGAGCAGATTCTGGATTTGCTCAATCCAAATGCAACAAA
CTTACAGGTAATTCACTGAAATCTAGTGTCTGCGTATACCTATTTGGTGGTTGCATCTTTGTCGTGACACT
GTTGGGAAAAGTTTACAAAGTTTGCATCTAACTTACAGCTATGCTTTTCTTTTACAGTTAAGGGAGGATGC
GAAAAGGGGTATGCATGTTGAGAATCTGACTGAACATGAGGTTTCTAATGCCCGAGAAGCACTGCAACAAC
TTATCGAGGTCAGTGTCCCAAAAACAGCGTAGTAGGCCTGATTTTGGCAGTACCTGTGTCGATGATTGCAG
AATGATTAATATAACATGCCTACATCAATTTTGCTCAaGGTTCTTCGCACAAACAGTCAAATACACACATA
TAAACTAAGTGTATAAATATAAACATGCTTTTTTCAATCTCCAATTCCTTGTCTCCTTGACTTCTCTTTTG
ATCGTTTTAGCAACTGTCACTGACAATTACAGCCACTTACTTTTCAAAACTATATACTTAAACATTACACA
ATACAGTTTTCTTTTGATGCAGTATGAATAGAAATCCGTAAATATGAATTTTAAATAGGAAAAACAATTAG
CATATTATACTTTACTGACAAGATGGAGTGACTGAACTATTTAGAACATGGACTGCAGTTAAGCTGATCAG
ATCCATCATTTTCGCATGGCATGTTACACTAGTTTTTCCTTTATCTCTAGGGATTGCAGCAAGTTTTTCCC
TCCCTTTATTAGTCACATTATTATCTGTGTTAGTTTCACTAAATCACTAGCTAAATTCTGCATTTTCTCTT
CAGGGGGCAGCAAACAGAAAGGTGGCATCTACCAATATGAACCGAGCAAGTAGCCGTTCTCATAGTGTATT
CACTTGTCTTATAGAGAGCAAGGTATAGTTTTTGTGTAATAGGAAGCAAAACATTCTTGCCTTAACTTTCA
AAGATATTGCTAGACCAGCATATATTTGTCCCTACCTTAATGCATGCATATGTATTGATGCACTTAATCTT
CTAACTGAACTATCAACCTTACAGTGGGAATCTCAAGGTATCAAGCATCATCGATTTCTCATCTTAACCT
TGTTGACCTTGCTGGCTCAGAGAGGTAAGTTCCACATGTAACCTTGCTTTTTTTGTTACGTATGATCTTG
TATTTCAGAGCCACCACAAATATACCTGTTATGCTTCTCAAGTCTCCTATTCTTGCAACTGAACGTGGATG
ATGTGTGATGTGCAGGCAAAAGAGTTCAGGTGCAGAAGGGGAACGCTTGAAGGAAGCTTCGAACATCAACA
```

FIG. 12A (con't)

```
AGTCACTCTCAACCTTAGGGTTAGTTGTGGAGCTTCAATTCTTTACCTCAGATAATACTAAACTGTTCATA
GCTTGACTTGATTCAGTTTAATCATTTCACTGTTTCCCTATGGGATTGTTACAGACATGTTATTACCAGCC
TTATTGCTGTGTCAAACAAAAAGTCACAGCATGTTCCCTACCGAGATTCAAAATTGACATTTCTGCTGCAG
GTAATATGCACAGCTGAAGTGGTAGATTTCTCACGTTATGTTTTTGACATCTCTGATGTTAACTTTGTTTA
TTTATACATTTTCATCTCTTTCCAGGACTCACTTGGAGGTAACTCCAAGACCACTATAATTGCAAATATAA
GCCCATCTAGCTGGTAGACTTCTAAACACGATTTCTTTTTCCTTTTCTGCAAAAGGCTTGCTATAGTTACA
TGCATCTTACTGATATTTTAATTTGTATTTCTAGCTGTGCAGCTGAGACATTGAGCACATTAAAATTCGCG
CAACGGGCTAAGCACATACGGAATAATGTATGTCATGAACATGTCTTATTGACTTGTTTTAATATGCAAA
ACAATAACTAATTGTTGTTTTGTAGGCTATTATAAATGAGGATGCCTCTGGTGATGTGCTGAGCATGCGT
TTAGAGATCCAACATCTCAAGGTATAGATGATGAATTTCAATTTCGGTTTAATGAAAAATATTCTGTGCAC
TGGATTGCAATAAGTTCCAGGTTAACATGTTTCTTCTAATTATGGTCCTTTGTGCTATGATTGACGTTTGT
TGTTAATTAACAGTGGCCTGTGCCTGATATTTTTTGTTGCAGAGCGTTAATATGTTTTGTTGTACACAATC
TAATGCTTTGCTATTACCACAGAAAGAGCTTAGTCGCCTGCAAGGACAATCTGGATTTACTAACAATGGAT
TTGTCTGCGAGTCCCCTAGCGCATTCAAATGGGATCAAGCTAATGGCACATTCAGTCCACTTATGTTTGAT
AAGAGAGCTACACAGGTATTCATATACTGTTTTGTCTATATCGAACATTATCCATGTACTGGTTCTGTTTG
TTGAACTTATGTTTTTAACCGTATGCTTACTTTCTCTTTCTCGTGTTGTGTTCAGAGGGAGAGATTATGATA
TTACACTTGCCGCTGCATTTAGGAGGGAGCAGGAAAAAGAAGCAAAGCTAAAGGCAGCAATTGCTGCAAAG
CAGATTGCCGAAGAGCTGGTATGCATCTCTCTTCACTACATTAGATTTTGTAGATACTCTAGAACACTTTG
TCACTAAAAAAGCAAATATATGCCAGTATAGTATTTTTTTTCTTAATGTCAATTTGTTGTTGCACCACAG
GTGACTCAAAGATCAGAAGAGGTGAGAAGTTTCAGGATGAGGCTTCGCTTTCGTGAAGATCGAATCAAGAG
ATTGGAGCAAGTTGCATCGGGGAAGTTATCCGCTGAAGCACATCTCTTGCAAGAAAAGGAAGACCTCATGA
AGGAAATTGAAGCTCTACGGAACCAACTAGAACGAAATCCAGAAATTACAAGATTTGCTATGGAAAATCTA
CAACTGAAGGAGGAGATTCGAAGGTTAGCTTCGGTATCCAATCACTTCAGTTGCCCCCCTTTTCTACTGCC
TACACTAATATAGTTGGTAGCTTGATGCCTTTTTTTTTGAACTTGTAGGTTGCAGTCATTTGTTGATGAAG
GAGAATTGGAAAGAATGCATCAGCAGATAAATGTTTTAGAACATCAGGTATCCACTTTTGTGAAGGGGAAT
TTTTCAGTGATAAATTTTTTTTGTACTAAAATGAACTTTTTTTTACTCTTATAATTTTCTTAACATCCTGA
ACTTACTTAGTTTGTTTTCCTTTAGCTCCTAGAAGCACTTGACTGGAAACTTATGAATGAGAAGGATCCTG
TTAACAAGGTATGCTATATAATTTGTAGACTTCAATCCTGTTTAGTGAAAATATATGCAAAACTTTTGAAT
TTTCTTTAGCTAGCTGTTACAAATACTTGCATGGCATTATATCTCTTTACCTACCATTTTGCTTAGACGAT
ATCCCATAATGACTTCTACAGGACCTCTCACTATTTGGGGAGGAAGCTGGTGATGAGAAAAACGAGTTTCT
TCTTGTGCAGGTTGGTATTGTAGAACTATATTTGGCATATCGTCTGATGATATCTTCACAGATCTTTTAAA
ACAACCTGTAAATTAATCATAAGTGTACATTGTTGATCAACTCCGATACGGAGGAGGTAGCTGACTTAATA
AGTATCCTATTCTGATTCATTTTTTCTGTAACATCAGTTTGTAATGTTGTTATACAGGCTATCCAAAATG
AGAGAGAAATCGAGTCACTACGTAAAAATTTGAGCGTCTGTCTTCAAGCAAAAGAGAAACTCGAGAGGTAT
ATCACTATTTCTTGTCTGTGTATTCTGTTATTGCATGCTATGGTTGTGTGGTATGATGAGAAAGGAATATC
ACTATTTCTTGTCTGTGTATTCTGTTATTGCATGCTATGGTTGTGTGGTATGATGAGAAAGGAATATTAAT
GTCATCAGCTTTTGCAATCATAATTAGTTCCTTAAATTTACAGTATTTACTTCAGGCCCCATGGTAACACA
ACTCTCACATATGTAAAACCCTTGGTGCCCCACAAACAAGATTAGAGGTGTATAGTATCTAGAAGTAAAAA
AACACTTTGTTGTTAGTGTTTCAAGTCACTGTAACTGCAGAAATTGTTGTGCTGTTTTTGCGCGCTACATT
TCAAGACCTACCATTTGGTTCTTGGTGTTCTTCTTGTTGTTGTTTTTATTCTCCTTAGGAACGAAGCCTA
TAATAGTTGGTGGGAGGTCACCCAGGTTTGAGTTCCCCTCAACCTGAATCTGGGTGCTTATCTCTCCATCA
CTGAAAAGTTTCTTAGTTCCTTCCAGGCAATCTAGTATTTTTTTCTGCTTGGTAGTACTGTGCATATCGAA
TGGATAATATGCTTAGAATAGTTGGTGGGAGGTCACCCAGGTTTTGAGATATCAATTATTTAGTGGTTGGA
GTTAATGATGCATTTGTGCAAGTTCAAGAAAAGGTGTGCTTCTCAGAAGGGGTGATGGCTAGCGTAGGTGT
AGATCAACCACAACAACTCATCTGTGCTGCATTTTGTTTGATTTACTTGCATATGATATCCCAAGAATTAT
AAAAAGGCCCTAAAGAGTATGGCAAGTCATTTCTAAATCATCTTGGTTTGCAAGCTTCACTGATGGTTTTC
ACTGCATACTATTTTGTGTGTCCGGAATTATGTTCCTTTTTTTTGCTTTGTCTTGTCCAGAGATTTATGTG
GTTCATTTCTCACATTGGATGTTGTGCAGGCGTGTTGATGATTTGACTGTGGAGTTGGAGGTAGCGAAGAA
ATGCGACCATGAGAACAAAGAATTTAAGGCTGCACAGCACCAGGAACAGTCCGTCTTGCTTGATGCTCAGA
CAGAACTTAAGACATTGGTAGATGCAATAGCAACTGCAAGTCAAAGAGAAGCAGAAGCTCATGAAACTGCA
ATTGGGTTGGCCAAAGAGAATGAGAAATTGAGAACAGAGCTTACGACCCTGATCGAGGATAACAAGAGACT
```

FIG. 12A (con't)

```
GGTTGATCTCTATGAACAGGCTATTGTCAACATTGAGGTGAAACAACATGGAAATTATCCTTCCATTCCTC
AAACTGAAGATTCGAATGAGCAGCAGAGCAGCCATCCTTCTAATGGAGGGAATAGCCTGCTGGATGACCAA
CCAGAGGGTGCATATGGTTCACGTAGTGATGCTGTAGAAGAGCCTATGATAGTGGATGAAAACTGCAGCCA
CAAGGATGACCCTTCGAGATCTGAATtTTCAGAACTGCAGCTTCAACTGGAAGAGATGCATGAAGAAAATG
ATAAACTTATGAGTTTGTATGAGAAAGCAATGCAAGAAAGGGATGAATTTAAAAGGAAATTTTCTGAGCAA
AGCAATCATGAAACCACAGAAGACGTTCAGTTCAGAGATGCTGAAATGGATGAAGCAATGGATACCATGCA
AAGCAATCCTGAAACTACAGAAGACATTCAGTTCAGAGATGCTGAAATGGATAGTATGCTAAGCAATCTTG
AAAGTTCAGAAGACATTCAGTTCAGAGATGCTGAAACCGATGCTGAGGGTTTCCAAGGAGAGCATGTACAT
GACTCTCCAATTGTAGCTTTCAAAGAAGCGATGCAGCTTGTCCGTGTCAAGCTGGAGCATGTCCAAGACAA
GCTTGTGACTGCCCAGGATGCAGTGCAATATTTCAAGCTACTTGAAATGGCTAGCACCAAGGCAGAAGAAC
TTTCATCAAGCATTCAGCTCTGCTGTCTAGATGTCCAGAAAGAGCAGGAAGACATCAACGCCCTCAAGTCC
GCACTGTCAATATCACACGAGAGAGAAAACGCTTTGGAAGGCAAGTTTTTCTCGCCTGTGGCATCATGCCG
GGACTTGCATTTGAAAACCGAAGCCCTTGCCGGGTCCAAGTTTGGCGTCAATGTTCAATCAATGAATAAAA
AGATGGAGCAGTTGAGTAGGTTGAGAACTCGCAAAACCGAGATTTCCGCTGCACGTGCAGAGGCACGCAGG
TCTGAAACCGAGCTGAGAAACAAAATCGATGGCCTTAAACAGAAATACCGTTCCTTCGAGGCCCAAAGGAA
GGAGACAGAAAGGGTTCTCTTCGCCATCGACAACCTGGAGTGCCCCGCGACTCCGTTGCAGAAGCCCATGA
ATTTCGGCAAGGCGTCGGAGCTGCTGAAGTCCGAGGAGGAGAGGACAAAGCTCTTGTCTGAACTGAAGAAG
TTCCGCGAGCAGCTTAGCGTGGTGCAGAAGGAGATCAAGAGCATGAGGAACTGCGACGACATCGACGGTGA
GATGTCGCGCCTTGAATCGGAGATGGAGGGCTGCTTCCTCTCCCTGCTGGAAGCCGAGACCGAGAAGTTTG
TGCGGGATCACACCTTGGCCGAAGTCTGGGAGGTTCAGCAGAAGGACTTGCCGAGCCTACTGGTCGACTAC
CAGGACAGCGTTTTCCATGTGAAGCTGGAGGAGGAGCAGATCAGGGTGTGCGAGGCGTCGTTGCAGCACCA
GACGACGTCCCTGGACGAGATGAACTCGAAGCTGAGCCAGGCGATGCGGGACCTCGGCGAGCTTCTGGTTG
CCAGAGGTTTGGACGCCTCCACGCCGCACGTCTCCGACAAGGTGAAGGGGGACCTCGACGCCATCGAGGCC
CATGTCGCCGAGGCCAGGCAGCTCTTGCTCGTCGACAACCAATAAGATTTGCTGCGAACCAAAGCAAACCG
GTTCTCGCCATTGACAGACAGGCTGGTCTGTCTCCGCCTTCATTTTGTACAAATTCTTTGTAACGGAACGT
TGGTTCTCTCGGGTGCTGTTATCTGTGATTCGATTCTGTAGTTTGGATGGATGGGTGGATGTAGGTCCTGA
AGTGGACTGTAATAACTGTTCTGCGCGGCCTCTTGTTCTGTTCTCTGGTGGTCTGGCATCGAAGCTTCTTC
CAGAAGGCCGTTGCTAAGCTATGCAACTATAGATTCACCTCCTTCTGGTATGCACTTGGCCGTGCAAGACA
GCAATGATTGGACAATGTCGATTTCAAGAGGGCTTGACTATTTTGTTGTTTATCATAATCTGTGGCAGCGA
GCGTGGTTGCGTGTGTTCGTGAAGAAAAGAATGCCGGTGTTTCAGTTCATCGCAGGAGGTTGCAGGCCGAG
AAACTTGTTTTCCATTATTGTACTACTACATTTGGTGTTAACTTGGGCTGTGTCGTGGCGGTTGAGAAATG.
TGTTCTGCAGGTCCTTGAGGGCATTAGGGCAGGTACAACGGTGTCCAGTCAGCTGTCTGGAAGGGGTGACA
GCTAGGATTTTAGATGATGTGGAGGAGAGAGAACAAAGAAAGAGAAACAACCCGTCTGTAGAATAACCAAC
GATCTGCAGCCCTTAAAATCCGGTGGATACAGATGGCCTTCTACCGTTGTATGGGGTGCCGTCTGCAAAGT
TGTTTGTAACTGCCTCCTTTGTCCCTGGATTAGTCTTCCACTCATCAATATTTGACAGTAAAATAGACGGT
CTAATGTATAGGGTGTCTTAATCTCTGTATATACGTGATGTGGAGCATCGTTACAGACAACGAGTTGTCTG
AACTAATGTAAATGCCCTCATGCTCCATGCTGCCGCCAGGTTCGGTTGTTTGGATTGCTTCTGGAAGCTCC
TTGAGCTATTTTGTCTCTTCAGGGTTGCTTCTTTGCCTCTTTGTGTCCACTTGTTTGGTTGGACTGCTCG
GCTCGCCTATTTGGTCGTTGTTTTC          (SEQ ID NO: 19)
```

FIG. 12B

```
CGCGCCAGGCCGCCGCCCACACTTCCCGCCGAGCCTAAAAGATGCAAGAAGAGAGAGGGGAGAGGCTAGAG
GGTGATGGAGGGGCTCACCGCACCAATAACAATGGATAGCGCTGCTGCGGTGGATTTCCCTCTGGCTGAAT
TTGTCCCCCACCCCACCCGCTCACCCACACTCGCGTGAATTGATTTGCGCCATTCGCCGTTGCCGTCTGTT
TTTAATCTTTTTCAAGCGGGTGCAGGTGAGCTCGGGCCCGACTGAGGGCCTTTTTGATTCATAGGATTGCA
AAAACACAGGAATAGGAAAAACGCAGGATTGAAATGGCATGTCCATTGGATCCCTATAGGATTTGAGTTTG
TTTGATTGTGTTAAGGGAAAAACAAAGGATTTTTTTTCAAGAGGTTTGAGTGGATGCTAGAATTTCTGTGA
AATGTAGTACAAATGAACCCTTAGAAAAAAATACAGGATTCAATCCTACGAATCAAACGATCAACGTAGAA
AAAATTCCTAAGGATTCTAATCCTTCAAAGATCTTATGAAAATCCTTTGAATCAAAGAGACCTTGAAGTTG
TGGAGCTCAAAATTTATAGTATTCCTCTAGAAGAAGCTCGAAATTACTTCTATACTGATTAACTGATGTGT
```

FIG. 12B (con't)

```
GTGCAAAAAGAAAAGAACTGATTAACCGATGAAACAACCAGTGTTTGGTACACTTCTGCGGGGGTGAATTG
GTGAGCTGGACAGGGCCCACCCGCAGCAAATTGCTTCTATTATGGTGGCCGCCTCCTCTCCTCTCCCTGGC
CAGATCCCAAATTTGAAATCGCCCAACGTCTCCAGACTCCTCTCCGCTCCCCATTTCAAAACCTCCAATCT
CGTCCTCTCCCCACCCCCACCCACCGCCGCCGGCCCGCCGCGCCGCTGCTCTGCCCAGATCCCGCCCGCCG
CAAGCCCATCCCTGCCTCCGTCGCAGCCGCAGCGGTACCCGCAGCCGCAGCCGCGATGCTGTCGGACGGTG
GCGACGACGACAGCTCCGCCCCCGCGCGGTTCGAGCTGCAGGAGGACCCCTCCTTCTGGAAGGACAACAAC
GTGCAGGTAGTGATTCTTCTCGCCCCCCTCGCCGGGAGCTCCCGCGCCTCCGCCTCCTCGATTCTCCCCTG
GCAGCGGCGTCCCGATCTAGTTTCGCCCGCGGCCGCGCGCTGCGCCGTTGGATCATTTCGTCGAGCACCTA
GGTTCGTCAGGTCCGGTCCGCGCTAACCGCTCCGCCCCGCAGGTCGTGATTCGTGTCCGGCCGCTCAGCAG
CAGCGAGATATCGGTGCAGGGGGACAAGAGGTGCGTCAGGCAGGACAGCGGCCAGAGCATTACCTGGACCT
GCCACCCGGAGTCCCGGTTCACCTTTGATCTAGTCGCCGATGAGCACATCACGCAGGTATACTCCTTGTTC
CTGTTCGCCCGTTCCTTTACTTGTTCCGCAGATGTGTAAATACTCTTGTGCTTGTGCTGTATAGGAGAGTC
TTTTCAAGGTTGCTGGGGTGCCCATGGTGGAGAACTGCATGGCTGGCTATAACAGCTGCATGTTTGCCTAT
GGGCAGGTGAGCTACAGCCTCCACCTCCACCTGCTGTTGCAGTGTGCTTACTCTCTTTTATTTGCACTTTG
AATCATTGAGCTTACAAAAGTATCCTGTTTCTTAGACCGGTAGTGGCAAGACCCACACGATGCTTGGGGAC
ATAGAAAATGGCACACGGGGAAACAATGAGAACTGTGGTATGACGCCTCGAGTGTTTGAGCATCTCTTCCT
AAGAATCCAGAAGGCAAGCTCTGATGATATGTTGATTCTGATGCCTAATTTTGTGCTGTAGATGGTGTACT
GTTTCTGAGGTAAACTTTTCAATTGCTGTTTGCAGGAAAAGGAAATACGAAGAGATGAAAAGCTCAGTTTT
ACTTGCAAGTGCTCATTCCTGGAGATATATAATGAGCAGATTCTGGATTTGCTCAATCCAAATGCAACAAA
CTTACAGGTAATTCACTGAAATCTAGTGTCTGCGTATACCTATTTGGTGGTTGCATCTTTGTCGTGACACT
GTTGGGAAAAGTTTACAAAGTTTGCATCTAACTTACAGCTATGCTTTTCTTTTACAGTTAAGGGAGGATGC
GAAAAGGGGTATGCATGTTGAGAATCTGACTGAACATGAGGTTTCTAATGCCCGAGAAGCACTGCAACAAC
TTATCGAGGTCAGTGTCCCAAAAACAGCGTAGTAGGCCTGATTTTGGCAGTACCTGTGTCGATGATTGCAG
AATGATTAATATAACATGCCTACATCAATTTTGCTCAaGGTTCTTCGCACAAACAGTCAAATACACACATA
TAAACTAAGTGTATAAATATAAACATGCTTTTTTCAATCTCCAATTCCTTGTCTCCTTGACTTCTCTTTTG
ATCGTTTTAGCAACTGTCACTGACAATTACAGCCACTTACTTTTCAAAACTATATACTTAAACATTACACA
ATACAGTTTCTTTTGATGCAGTATGAATAGAAATCCGTAAATATGAATTTTAAATAGGAAAAACAATTAG
CATATTATACTTTACTGACAAGATGGAGTGACTGAACTATTTAGAACATGGACTGCAGTTAAGCTGATCAG
ATCCATCATTTTCGCATGGCATGTTACACTAGTTTTTCCTTTATCTCTAGGGATTGCAGCAAGTTTTTCCC
TCCCTTTATTAGTCACATTATTATCTGTGTTAGTTTCACTAAATCACTAGCTAAATTCTGCATTTTCTCTT
CAGGGGGCAGCAAACAGAAAGGTGGCATCTACCAATATGAACCGAGCAAGTAGCCGTTCTCATAGTGTATT
CACTTGTCTTATAGAGAGCAAGGTATAGTTTTTGTGTAATAGGAAGCAAAACATTCTTGCCTTAACTTTCA
AAGATATTGCTAGACCAGCATATATTTGTCCCTACCTTAATGCATGCATATGTATTGATGCACTTAATCTT
CTAACTGAACTATCAACCTTACAGTGGGAATCTCAAGGTATCAAGCATCATCGATTTTCTCATCTTAACCT
TGTTGACCTTGCTGGCTCAGAGAGGTAAGTTCCACATGTAACCTTGCTTTTTTTGTTACGTATGATCTTG
TATTTCAGAGCCACCACAAATATACCTGTTATGCTTCTCAAGTCTCCTATTCTTGCAACTGAACGTGGATG
ATGTGTGATGTGCAGGCAAAAGAGTTCAGGTGCAGAAGGGGAACGCTTGAAGGAAGCTTCGAACATCAACA
AGTCACTCTCAACCTTAGGGTTAGTTGTGGAGCTTCAATTCTTTACCTCAGATAATACTAAACTGTTCATA
GCTTGACTTGATTCAGTTTAATCATTTCACTGTTTCCCTATGGGATTGTTACAGACATGTTATTACCAGCC
TTATTGCTGTGTCAAACAAAAAGTCACAGCATGTTCCCTACCGAGATTCAAAATTGACATTTCTGCTGCAG
GTAATATGCACAGCTGAAGTGGTAGATTTCTCACGTTATGTTTTGACATCTCTGATGTTAACTTTGTTTA
TTTATACATTTTCATCTCTTTCCAGGACTCACTTGGAGGTAACTCCAAGACCACTATAATTGCAAATATAA
GCCCATCTAGCTGGTAGACTTCTAAACACGATTTCTTTTTCCTTTTCTGCAAAAGGCTTGCTATAGTTACA
TGCATCTTACTGATATTTTAATTTGTATTTCTAGCTGTGCAGCTGAGACATTGAGCACATTAAAATTCGCG
CAACGGGCTAAGCACATACGGAATAATGTATGTCATGAACATGTCTTATTGACTTGTTTTTAATATGCAAA
ACAATAACTAATTGTTGTTTTGTAGGCTATTATAAATGAGGATGCCTCTGGTGATGTGCTGAGCATGCGT
TTAGAGATCCAACATCTCAAGGTATAGATGATGAATTTCAATTTCGGTTTAATGAAAAATATTCTGTGCAC
TGGATTGCAATAAGTTCCAGGTTAACATGTTTCTTCTAATTATGGTCCTTTGTGCTATGATTGACGTTTGT
TGTTAATTAACAGTGGCCTGTGCCTGATATTTTTGTTGCAGAGCGTTAATATGTTTTGTTGTACACAATC
TAATGCTTTGCTATTACCACAGAAAGAGCTTAGTCGCCTGCAAGGACAATCTGGATTTACTAACAATGGAT
```

FIG. 12B (con't)

TTGTCTGCGAGTCCCCTAGCGCATTCAAATGGGATCAAGCTAATGGCACATTCAGTCCACTTATGTTTGAT
AAGAGAGCTACACAGGTATTCATATACTGTTTTGTCTATATCGAACATTATCCATGTACTGGTTCTGTTTG
TTGAACTTATGTTTTTAACCGTATGCTTACTTTCTCTTTCTCGTGTTGTGTTCAGAGGAGAGATTATGATA
TTACACTTGCCGCTGCATTTAGGAGGGAGCAGGAAAAAGAAGCAAAGCTAAAGGCAGCAATTGCTGCAAAG
CAGATTGCCGAAGAGCTGGTATGCATCTCTCTTCACTACATTAGATTTTGTAGATACTCTAGAACACTTTG
TCACTAAAAAAGCAAATATATGCCAGTATAGTATTTTTTTTCTTAATGTCAATTTGTTGTTGCACCACAG
GTGACTCAAAGATCAGAAGAGGTGAGAAGTTTCAGGATGAGGCTTCGCTTTCGTGAAGATCGAATCAAGAG
ATTGGAGCAAGTTGCATCGGGGAAGTTATCCGCTGAAGCACATCTCTTGCAAGAAAAGGAAGACCTCATGA
AGGAAATTGAAGCTCTACGGAACCAACTAGAACGAAATCCAGAAATTACAAGATTTGCTATGGAAAATCTA
CAACTGAAGGAGGAGATTCGAAGGTTAGCTTCGGTATCCAATCACTTCAGTTGCCCCCCTTTTCTACTGCC
TACACTAATATAGTTGGTAGCTTGATGCCTTTTTTTTTGAACTTGTAGGTTGCAGTCATTTGTTGATGAAG
GAGAATTGGAAAGAATGCATCAGCAGATAAATGTTTAGAACATCAGGTATCCACTTTTGTGAAGGGGAAT
TTTTCAGTGATAAATTTTTTTGTACTAAAATGAACTTTTTTTACTCTTATAATTTCTTAACATCCTGA
ACTTACTTAGTTTGTTTTCCTTTAGCTCCTAGAAGCACTTGACTGGAAACTTATGAATGAGAAGGATCCTG
TTAACAAGGTATGCTATATAATTTGTAGACTTCAATCCTGTTTAGTGAAAATATATGCAAAACTTTTGAAT
TTTCTTTAGCTAGCTGTTACAAATACTTGCATGGCATTATATCTCTTTACCTACCATTTTGCTTAGACGAT
ATCCCATAATGACTTCTACAGGACCTCTCACTATTTGGGGAGGAAGCTGGTGATGAGAAAAACGAGTTTCT
TCTTGTGCAGGTTGGTATTGTAGAACTATATTTGGCATATCGTCTGATGATATCTTCACAGATCTTTTAAA
ACAACCTGTAAATTAATCATAAGTGTACATTGTTGATCAACTCCGATACGGAGGAGGTAGCTGACTTAATA
AGTATCCTATTCTGATTCATTTTTTCTGTAACATCAGTTTGTAATGTTGTTATACAGGCTATCCAAAATG
AGAGAGAAATCGAGTCACTACGTAAAAATTTGAGCGTCTGTCTTCAAGCAAAAGAGAAACTCGAGAGGTAT
ATCACTATTTCTTGTCTGTGTATTCTGTTATTGCATGCTATGGTTGTGTGGTATGATGAGAAAGGAATATC
ACTATTTCTTGTCTGTGTATTCTGTTATTGCATGCTATGGTTGTGTGGTATGATGAGAAAGGAATATTAAT
GTCATCAGCTTTTGCAATCATAATTAGTTCCTTAAATTTACAGTATTTACTTCAGGCCCCATGGTAACACA
ACTCTCACATATGTAAAACCCTTGGTGCCCCACAAACAAGATTAGAGGTGTATAGTATCTAGAAGTAAAAA
AACACTTTGTTGTTAGTGTTTCAAGTCACTGTAACTGCAGAAATTGTTGTGCTGTTTTTGCGCGCTACATT
TCAAGACCTACCATTTGGTTCTTGGTGTTCTTCTTGTTGTTGTTTTTATTCTCCTTAGGAACGAAGCCTA
TAATAGTTGGTGGGAGGTCACCCAGGTTTGAGTTCCCCTCAACCTGAATCTGGGTGCTTATCTCTCCATCA
CTGAAAAGTTTCTTAGTTCCTTCCAGGCAATCTAGTATTTTTTTCTGCTTGGTAGTACTGTGCATATCGAA
TGGATAATATGCTTAGAATAGTTGGTGGGAGGTCACCCAGGTTTTGAGATATCAATTATTTAGTGGTTGGA
GTTAATGATGCATTTGTGCAAGTTCAAGAAAAGGTGTGCTTCTCAGAAGGGGTGATGGCTAGCGTAGGTGT
AGATCAACCACAACAACTCATCTGTGCTGCATTTTGTTTGATTTACTTGCATATGATATCCCAAGAATTAT
AAAAAGGCCCTAAAGAGTATGGCAAGTCATTTCTAAATCATCTTGGTTTGCAAGCTTCACTGATGGTTTTC
ACTGCATACTATTTTGTGTGTCCGGAATTATGTTCCTTTTTTTTGCTTTGTCTTGTCCAGAGATTTATGTG
GTTCATTTCTCACATTGGATGTTGTGCAGGCGTGTTGATGATTTGACTGTGGAGTTGGAGGTAGCGAAGAA
ATGCGACCATGAGAACAAAGAATTTAAGGCTGCACAGCACCAGGAACAGTCCGTCTTGCTTGATGCTCAGA
CAGAACTTAAGACATTGGTAGATGCAATAGCAACTGCAAGTCAAAGAGAAGCAGAAGCTCATGAAACTGCA
ATTGGGTTGGCCAAAGAGAATGAGAAATTGAGAACAGAGCTTACGACCCTGATCGAGGATAACAAGAGACT
GGTTGATCTCTATGAACAGGCTATTGTCAACATTGAGGTGAAACAACATGGAAATTATCCTTCCATTCCTC
AAACTGAAGATTCGAATGAGCAGCAGAGCAGCCATCCTTCTAATGGAGGGAATAGCCTGCTGGATGACCAA
CCAGAGGGTGCATATGGTTCACGTAGTGATGCTGTAGAAGAGCCTATGATAGTGGATGAAAACTGCAGCCA
CAAGGATGACCCTTCGAGATCTGAATtTTCAGAACTGCAGCTTCAACTGGAAGAGATGCATGAAGAAAATG
ATAAACTTATGAGTTTGTATGAGAAAGCAATGCAAGAAAGGGATGAATTTAAAAGGAAATTTTCTGAGCAA
AGCAATCATGAAACCACAGAAGACGTTCAGTTCAGAGATGCTGAAATGGATGAAGCAATGGATACCATGCA
AAGCAATCCTGAAACTACAGAAGACATTCAGTTCAGAGATGCTGAAATGGATAGTATGCTAAGCAATCTTG
AAAGTTCAGAAGACATTCAGTTCAGAGATGCTGAAACCGATGCTGAGGGTTTCCAAGGAGAGCATGTACAT
GACTCTCCAATTGTAGCTTTCAAAGAAGCGATGCAGCTTGTCCGTGTCAAGCTGGAGCATGTCCAAGACAA
GCTTGTGACTGCCCAGGATGCAGTGCAATATTTCAAGCTACTTGAAATGGCTAGCACCAAGGCAGAAGAAC
TTTCATCAAGCATTCAGCTCTGCTGTCTAGATGTCCAGAAAGAGCAGGAAGACATCAACGCCCTCAAGTCC
GCACTGTCAATATCACACGAGAGAGAAAACGCTTTGGAAGGCAAGTTTTTCTCGCCTGTGGCATCATGCCG

FIG. 12B (con't)

```
GGACTTGCATTTGAAAACCGAAGCCCTTGCCGGGTCCAAGTTTGGCGTCAATGTTCAATCAATGAATAAAA
AGATGGAGCAGTTGAGTAGGTTGAGAACTCGCAAAACCGAGATTTCCGCTGCACGTGCAGAGGCACGCAGG
TCTGAAACCGAGCTGAGAAACAAAATCGATGGCCTTAAACAGAAATACCGTTCCTTCGAGGCCCAAAGGAA
GGAGACAGAAAGGGTTCTCTTCGCCATCGACAACCTGGAGTGCCCCGCGACTCCGTTGCAGAAGCCCATGA
ATTTCGGCAAGGCGTCGGAGCTGCTGAAGTCCGAGGAGGAGGACAAAGCTCTTGTCTGAACTGAAGAAG
TTCCGCGAGCAGCTTAGCGTGGTGCAGAAGGAGATCAAGAGCATGAGGAACTGCGACGACATCGACGGTGA
GATGTCGCGCCTTGAATCGGAGATGGAGGGCTGCTTCCTCTCCCTGCTGGAAGCCGAGACCGAGAAGTTTG
TGCGGGATCACACCTTGGCCGAAGTCTGGGAGGTTCAGCAGAAGGACTTGCCGAGCCTACTGGTCGACTAC
CAGGACAGCGTTTTCCATGTGAAGCTGGAGGAGGAGCAGATCAGGGTGTGCGAGGCGTCGTTGCAGCACCA
GACGACGTCCCTGGACGAGATGAACTCGAAGCTGAGCCAGGCGATGCGGGACCTCGGCGAGCTTCTGGTTG
CCAGAGGTTTGGACGCCTCCACGCCGCACGTCTCCGACAAGGTGAAGGGGGACCTCGACGCCATCGAGGCC
CATGTCGCCGAGGCCAGGCAGCTCTTGCTCGTCGACAACCAATAAGATTTGCTGCGAACCAAAGCAAACCG
GTTCTCGCCATTGACAGACAGGCTGGTCTGTCTCCGCCTTCATTTTGTACAAATTCTTTGTAACGGAACGT
TGGTTCTCTCGGGTGCTGTTATCTGTGATTCGATTCTGTAGTTTGGATGGATGGGTGGATGTAGGTCCTGA
AGTGGACTGTAATAACTGTTCTGCGCGGCCTCTTGTTCTGTTCTCTGGTGGTCTGGCATCGAAGCTTCTTC
CAGAAGGCCGTTGCTAAGCTATGCAACTATAGATTCACCTCCTTCTGGTATGCACTTGGCCGTGCAAGACA
GCAATGATTGGACAATGTCGATTTCAAGAGGGCTTGACTATTTTGTTGTTTATCATAATCTGTGGCAGCGA
GCGTGGTTGCGTGTGTTCGTGAAGAAAAGAATGCCGGTGTTTCAGTTCATCGCAGGAGGTTGCAGGCCGAG
AAACTTGTTTTCCATTATTGTACTACTACATTTGGTGTTAACTTGGGCTGTGTCGTGGCGGTTGAGAAATG
TGTTCTGCAGGTCCTTGAGGGCATTAGGGCAGGTACAACGGTGTCCAGTCAGCTGTCTGGAAGGGGTGACA
GCTAGGATTTAGATGATGTGGAGGAGAGAGAACAAAGAAAGAGAAACAACCCGTCTGTAGAATAACCAAC
GATCTGCAGCCCTTAAAATCCGGTGGATACAGATGGCCTTCTACCGTTGTATGGGGTGCCGTCTGCAAAGT
TGTTTGTAACTGCCTCCTTTGTCCCTGGATTAGTCTTCCACTCATCAATATTTGAGAGTGCTATAGACAGT
AAAATAGACGGTCTAATGTATAGGGTGTCTTAATCTCTGTCTATACGTGACGTGGAGCATCGTTACAGACA
ACGAGTTGTCTGAACTAATGTACATGCCCTCATGCTCCATGCTGCCGCCCGGTTCGGTTGTTTGGATTGCT
TCTGGAAGCTCCTTGAGCTATTTTTGTCTCTTCAGGGTTGCTTCTTTGCCTCTTTGTGTCCACTTGTTTGG
TTGGACTGCTCGGCTCGCCTATTTGGTCGTTGTTTTC (SEQ ID NO: 20)
```

FIG. 13A

```
AGAGCTCGGGGCTGGGCGGTTCGGTAAGAGAGGGAGAAGAACAAGGTCAGGGCCTTCTGGATCGCTAGGAG
GGGGATAGAGAGATTTTTCAGGCGAAATTGGTGCGGGACTGTTAAAATGGGGATGACATAGATTAAGAGAA
AGAAGAAGATGAATATGACACATGGACCCGCGTAGTTAGCGACATTAGCGTGTGATCCCGCTCAGGATTTT
CCTTTTCACTATGCGCCAAACATGTATTTAGCAGAAATCAACAGGAATAGACCGGGATTAAAGAGTATAGG
GTGACAGTTTCAGAGATTTATAAGTCAGGGTTTAACTCGAAGTGAGAGTACGAATTCAAGGTTTATTTCAT
ACTTTAGTGGTGCTTGCAATCCTCATGACAACTAAATTTGCCAATGTGGTACAAATTAGTTCATGTATTTA
ATTAACATATCTTGTGCACTCACCAATGTGGTTTCTCAATTGTTCACTTTGTTTCATATCTACTTTATGGC
ATGAAAATTTTGATGTCATTGTAAAAAGAACTCTAGCCGAAGATAGAGATGCAACTCTTCAATCTTAAGG
AGTAAGGGTGTTGTGAGAACCGGGTGAACCGGGTGCTAACTCAATGGCCTGAGTTTGTAGTGGCAAAGCCA
TGCACTCTCTTCGAGTCTATACAGTAGACTCCGTTGGGGTGCGATCCGTGTTAAATTGCACAAATATCTCA
TCACATATTTACATAACATCCGGTTAAGTTTTTTGCCAATGTTCAGGACTAAGGCTGCTAAAGACAATTTG
AATAAAAACCATGAACAAGTAGCAGTTTACTGGTTAGAACGCCAATTTTTTGGCTTCAGCCCCGAGGTGTA
TGGATGTTGAAAAACAAGTTTGACTGAAAACAGCTCGGTCCAAGAGCAAGAGTGTTCAAAATAATTTTATA
CAAAAAAAAAAGTTCCGGATAGCAAACCCATCAAGAGTTCATTTTCCTTCAGTGGTACCAACCGGAGGGTG
GAAAATAGTGCAAAATACCACTCGTATTAACTAAACAAACAGCTTGTTTCCGAATCATTTGAACAAAAAAC
TGTAAAAATCGACCAAAAAACAAAAATAACGCGCCAGGTAGGGGTCGAACCTACGGCCTTCCGCTTAGGAA
ACGGACGCTCTATCCACTGAGCTACAGGCGCCTTGTTGTATGAGATGCAACGGAACCATTTTACAACAATC
GCGTAGTAGATGCATCTACGGAAGCTTATTTGGACGGAGCACAAACCCTTCTCGAAGTCTACTAGAAACAC
CGGAAGCGGCGGCGGGGACAGCACAGGGAAGGAAAAGAAGCCAAGAGGCGGCGCCGCCGATCCACCCAGAC
CGAGAGCACCTTGGCCGACGGCATGGCGCTGCTGATGGAGCCCGGGTCGGAGCCCCTGACGGAGGGCGAGA
AGGCCGACCTGGACGCCATCGCCGCCATCAAGGAGTCGGCGGCGCGCGAGTACAGGGAGGAGGGCAACCAG
TTCGTCAAGAAGGGCCGGAAGCACTACCCCGACGCCGTCGACTGCTACACCAAGGCCATCGCCCAGATGGG
CGCCCTCTCCGCCCCGAACCCCGACGCCTCCGTCCTCTTCGCCAACCGCGCGCACGTCAACCTCCTCCTCG
GCAACCACCGCCGCGCCCTCGACGACGCCCAGCAGGCCGTCCGCCTCTCCCCCTCCAACCTCAAGGTCCGC
ACGCTCGCTCGCTCTAGATTACGCCTCTCTTGCTCCAATTTCTCGGATTTGGCGAGGAAGCCGCCGTGTGA
TGTGTGACATTCGTGTAGCCAGGCGCACTACCGGGCGGCGAAGGCCGCGCTTGCTCTCGACCAGTTGCCCC
AGGCGGCGTCCTTCTGCCGGCGGGGGCTCGAGCAGGACCCCGCCAACGAGGAGCTCAAGAAATTCCTCGCG
CAGGTGGAGGCGCAGCAGCGCGAGCGGGATCTTAAAAGGGCCAAGGTTGAACAGGCCATATCCGCCGCGAA
GGTCTCTTCTGTTCCAAATTGGCAGTTGAGCATTTCCTTATTCTTTTCCTGTTTGTGTAATTGACTGTATT
AGATGCATATAGGATCTTGCTGCTGCTATAGAGAAGAGAGGGCTGAGGCTGGGGAAGGCAGCATATCAGGA
GCTGACCGGGGTAAAGAAGCCGAAGCTGGATGAGCAGGGCGTGCTCCACTGGTCAGTTCTTCTGCTCTACC
CGGAGTCATGTCGAGCGACTTTATTGAGGATTTTCCGGAGACTGATATGTTCTCGGATCACCTTGATCTCA
TATCCTTGGAAAGTTACGTGATACTTTTTCTGATAGTATGTACATGAATATGCATAGATACTTTCATCACA
AAAAGGAGGAGGAATGGTTTCTTGAATTCCTGTTATCCTTAATTATCAAACATGTTCTCAGAAAGTTCTCC
ACCTTTGCCATGGGATGAGAACCACGCTTACACAAGGGACGCTATTGAGTTGTATTGTCAGGTTTGTTTAC
ACACTTCGAATTTTAATTGAGGGTTAACCTGTAAGGCTACCTTCTGCAAAGTGCTAGCGCCCACAGATGAT
CAAATTTTCTCTATCTAAATTTCACGAGGCATGAGTCACAACCTCTTCATACAACATGAAAACAAAACATT
CATGCCCCTGTGATGTGTATATACTACACACATTGTCCTTCTGATTTATTTTTCCACTAGATGATTGTGGG
CCAAGTTTTTCGATCCAGACCTTTTTGTGATACTAAATTTTGGGGAATGCAACATAAGTTATGCTATTGC
TACTTAAGTGTTATTAGTAATTTCATTTGTCCGGTGCTAGAATGTCAAGATGGTAGCTCTAGCCTTTGTGG
CCACATTCTGAAAATTGTAGGATTATCCTTTACCAATTTTACAAGTGGCAGACTCATGTGAGAAAACTAGG
AGCTATTGAAAATTCAGATTTCAATGTGATCATTTGATCATCGTTAGCAGCAGCATCCAGTCCAGTTTTT
GAAGTTATCTTCAAATTTAACAAATCTGTAGGATGGTTGCTCCTTCATTTACAACTATTATATTATTACAG
TCGACATAACTGTCACTACTTGAGAGTTAATATATACCTTCTGCAAAGTGCTAGCACCTACAGATATCAGA
TTTTCTTCTAAATGGCATGAGGCAAGTGCCACGACCTCTTCATAGAACATTAAAACAGAACACTGATGCCT
CTGATGTGTATATGCTACAGACAATGTCTTTCTGATTTATTTTTCACTAGATGATTGTGAGACAAGTTTTT
TCGATCCATACCCTTTTGCTACTAAGTTTTGGGGGATGCAACATAAGTTATGTTATTGCTACACTGATGTA
GTTAAGTGTTGTTGTTGGTAAATGGTTTATCTGGCAATAGAATGTCGAGATGATAGCTCTAACCTCTGTGG
CAATATTCTGTAGCATTATCCTTTACCAATTTTAACAGTGTCGGACTCATGTGAGAAAACTCGGAGTTGTT
GACAATTAAGATTTCAGTACTATCATGTTGATCATCATTAGCATTATCCAGTCCAGTTTTGCAAGTTATCT
```

FIG. 13A (con't)

```
TGAAGTTTCACAAATCTGTAGGATTTTTGCTTTTTCATTCACAATTAGGATTACAGTCAACATACCATTGT
CAGTACTTTGACACAGCTTTAGGATAGAAAAACTTTCTAGTTTCATTTCGTTGCCTTGCTGGCTAACTGGT
ATTTCCATTTGATACACTAGGCTGGTGATGGCACGCCGTTCTCCAAAAGTGAAATGTTAAAATATCTTCTG
GAAGGCACTGTCGACTCAGGGTCACTCCCAGAAAGCCTTGATGGGGAAGATGGAGAACATGATACTGTGAA
GGGCAGCACAGCTATATCACCAAGTATGTAAAACATATTCCTTAGGTTATTTCTCTAAATTTACATGATGT
ACAGTAAAAAGACAGCACGATGTGAACTGTGATTCTGTCAATTTCAGTATGTAATACTCCCTCCGTTCCTA
AATATAAGTCTTTTAAGAGATTCTACTATAGACTACATACGGAGCAAAAAGAGTGAACTTATACTCTAAAA
GGTGTCTATATACATCCGAATGTAGTCTCCATAGTGGAATCTCTAAAAAGACTTATATGTAGGAACCGAGG
GAGTATATCCAATCTGCCATTAGCAGAACTACATTTACTGCAACATGCTATAATGCTGTTATGCTGCGCTG
ATAAGTAGTTTCCATTTCAATGTGTGCAGGCCAGGGTAAGTGGATCAAAGTAAGAGAAGGGAAAACTCTTC
AGGAAGCGCTGCAGCATAAAGACTACATCATCCCGGCAGTACCTGGTCCGTTCTTCAACCTGTGTATACTT
TGCATTCGTGCGTATAGAATGCTTGTCATTGTTCAGCGCAAATAAGAGCTTCCATTAATTCCTGCGTGCAG
TGTTCTTTGTGGTTTCAAGGAAATCCGCCTTCCATTCGAAGTTCAAGGCTGGGAATTGGTCTTTGCCGTAG
AGCTGCCGTGTAGTAGTTCAGTT         (SEQ ID NO: 21)
```

FIG. 13B

```
AGAGCTCGGGGCTGGGCGGTTCGGTAAGAGAGGGAGAAGAACAAGGTCAGGGCCTTCTGGATCGCTAGGAG
GGGGATAGAGAGATTTTTCAGGCGAAATTGGTGCGGGACTGTTAAATGGGGATGACATAGATTAAGAGAA
AGAAGAAGATGAATATGACACATGGACCCGCGTAGTTAGCGACATTAGCGTGTGATCCCGCTCAGGATTTT
CCTTTTCACTATGCGCCAAACATGTATTTAGCAGAAATCAACAGGAATAGACCGGGATTAAAGAGTATAGG
GTGACAGTTTCAGAGATTTATAAGTCAGGGTTTAACTCGAAGTGAGAGTACGAATTCAAGGTTTATTTCAT
ACTTTAGTGGTGCTTGCAATCCTCATGACAACTAAATTTGCCAATGTGGTACAAATTAGTTCATGTATTTA
ATTAACATATCTTGTGCACTCACCAATGTGGTTTCTCAATTGTTCACTTTGTTTCATATCTACTTTATGGC
ATGAAAATTTTGATGTCATTGTAAAAAAGAACTCTAGCCGAAGATAGAGATGCAACTCTTCAATCTTAAGG
AGTAAGGGTGTTGTGAGAACCGGGTGCTAACTCAATGGCCTGAGTTTGTAGTGGCAAAGCCATGCACTCTC
TTCGAGTCTATACAGTAGACTCCGTTGGGGTGCGATCCGTGTTAAATTGCACAAATATCTCATCACATATt
TACATAACATCCGGTTAAGTTTTTTGCCAATGTTCAGGACTAAGGCTGCTAAAGACAAATTTGAATAAAAAC
CATGAACAAGTAGCAGTTTACTGGTTAGAACGCCAATTTTTTGGCTTCAGCCCCGAGGTGTATGGATGTTG
AAAAACAAGTTTGACTGAAAACAGCTCGGTCCAAGGCCAAGAGTGTTCAAAATAATTTTATACAAAAAAAA
AAGTTCCGGATAGCAAACCCATCAAGAGTTCATTTTCCTTCAGTGGTACCAACCGGAGGGTGGAAAATAGT
GCAAAATACCACTCGTATTAACTAAACAAACAGCTTGTTTCCGAATCATTTGAACAAAAAACTGTAAAAAT
CGACCAAAAAACAAAAATAACGCGCCAGGTAGGGGTCGAACCTACGGCCTTCCGCTTAGGAAACGGACGCT
CTATCCACTGAGCTACAGGCGCCTTGTTGTATGAGATGCAACGGAACCATTTTACAACAATCGCGTAGTAG
ATGCATCTACGGAAGCTTATTTGGACGGAGCACAAACCCTTCTCGAAGTCTACTAGAAACACCGGAAGCGG
CGGCGGGGACAGCACAGGGAAGGAAAAGAAGCCAAGAGGCGGCGCCGCCGATCCACCCAGACCGAGAGCAC
CTTGGCCGACGGCATGGCGCTGCTGATGGAGCCCGGGTCGGAGCCCCTGACGGAGGGCGAGAAGGCCGACC
TGGACGCCATCGCCGCCATCAAGGAGTCGGCGGCGCGCGAGTACAGGGAGGAGGGCAACCAGTTCGTCAAG
AAGGGCCGGAAGCACTACCCCGACGCCGTCGACTGCTACACCAAGGCCATCGCCCAGATGGGCGCCCTCTC
CGCCCCGAACCCCGACGCCTCCGTCCTCTTCGCCAACCGCGCGCACGTCAACCTCCTCCTCGGCAACCACC
GCCGCGCCCTCGACGACGCCCAGCAGGCCGTCCGCCTCTCCCCTCCAACCTCAAGGTCCGCACGCTCGCT
CGCTCTAGATTACGCCTCTCTTGCTCCAATTTCTCGGATTTGGCGAGGAAGCCGCCGTGTGATGTGTGACA
TTCGTGTAGCCAGGCGCACTACCGGGCGGCGAAGGCCGCGCTTGCTCTCGACCAGTTGCCCAGGCGGCGT
CCTTCTGCCGGCGGGGCTCGAGCAGGACCCCGCCAACGAGGAGCTCAAGAAATTCCTCGCGCAGGTGGAG
GCGCAGCAGCGCGAGCGGGATCTTAAAAGGGCCAAGGTTGAACAGGCCATATCCGCCGCGAAGGTCTCTTC
TGTTCCAAATTGGCAGTTGAGCATTTCCTTATTCTTTTCCTGTTTGTGTAATTGACTGTATTAGATGCATA
TAGGATCTTGCTGCTGCTATAGAGAAGAGAGGgCTGAGGCTGGGGAAGGCAGCATATCAGGAGCTGACCGG
GGTAAAGAAGCCGAAGCTGGATGAGCAGGGCGTGCTCCACTGGTCAGTTCTTCTGCTCTACCCGGAGTCAT
GTCGAGCGACTTTATTGAGGATTTTCCGGAGACTGATATGTTCTCGGATCACCTTGATCTCATATCCTTGG
AAAGTTACGTGATACTTTTTCTGATAGTATGTACATGAATATGCATAGATACTTTCATCACAAAAAGGAGG
AGGAATGGTTTCTTGAATTCCTGTTATCCTTAATTATCAAACATGTTCTCAGAAAGTTCTCCACCTTTGCC
```

FIG. 13B (con't)

```
ATGGGATGAGAACCACGCTTACACAAGGGACGCTATTGAGTTGTATTGTCAGGTTTGTTTACACACTTCGA
ATTTTAATTGAGGGTTAACCTGTAAGGCTACCTTCTGCAAAGTGCTAGCGCCCACAGATGATCAAATTTTC
TCTATCTAAATTTCACGAGGCATGAGTCACAACCTCTTCATACAACATGAAAACAAAACATTCATGCCCCT
GTGATGTGTATATACTACACACATTGTCCTTCTGATTTATTTTTCCACTAGATGATTGTGGGCCAAGTTTT
TTCGATCCAGACCTTTTTGTGATACTAAATTTTGGGGAATGCAACATAAGTTATGCTATTGCTACTTAAGT
GTTATTAGTAATTTCATTTGTCCGGTGCTAGAATGTCAAGATGGTAGCTCTAGCCTTTGTGGCCACATTCT
GAAAATTGTAGGATTATCCTTTACCAATTTTACAAGTGGCAGACTCATGTGAGAAAACTAGGAGCTATTGA
AAATTCAGATTTCAATGTGATCATTTTGATCATCGTTAGCAGCAGCATCCAGTCCAGTTTTTGAAGTTATC
TTCAAATTTAACAAATCTGTAGGATGGTTGCTCCTTCATTTACAACTATTATATTATTACAGTCGACATAA
CTGTCACTACTTGAGAGTTAATATATACCTTCTGCAAAGTGCTAGCACCTACAGATATCAGATTTTCTTCT
AAATGGCATGAGGCAAGTGCCACGACCTCtTCATAGAACAtTAAAACAGAACACTGATGCCTCTGATGTGT
ATATGCTACAGACAATGTCTTTCTGATTTATTTTTCACTAGATGATTGTGAGACAAGTTTTTTCGATCCAT
ACCCTTTTGCTACTAAGTTTTGGGGGATGCAACATAAGTTATGTTATTGCTACACTGATGTAGTTAAGTGT
TGTTGTTGGTAAATGGTTTATCTGGCAATAGAATGTCGAGATGATAGCTCTAACCTCTGTGGCAATATTCT
GTAGCATTATCCTTTACCAATTTTAACAGTGTCGGACTCATGTGAGAAAACTCGGAGTTGTTGACAATTAA
GATTTCAGTACTATCATGTTGATCATCATTAGCATTATCCAGTCCAGTTTTGCAAGTTATCTTGAAGTTTC
ACAAATCTGTAGGATTTTGCTTTTTCATTCACAATTAGGATTACAGTCAACATACCATTGTCAGTACTTT
GACACAGCTTTAGGATAGAAAAACTTTCTAGTTTCATTTCGTTGCCTTGCTGGCTAACTGGTATTTCCATT
TGATACACTAGGCTGGTGATGGCACGCCGTTCTCCAAAAGTGAAATGTTAAAATATCTTCTGGAAGGCACT
GTCGACTCAGGGTCACTCCCAGAAAGCCTTGATGGGGAAGATGGAGAACATGATACTGTGAAGGGCAGCAC
AGCTATATCACCAAGTATGTAAAACATATTCCTTAGGTTATTTCTCTAAATTTACATGATGTACAGTAAAA
AGACAGCACGATGTGAACTGTGATTCTGTCAATTTCAGTATGTAATACTCCCTCCGTTCCTAAATATAAGT
CTTTTAAGAGATTCTACTATAGACTACATACGGAGCAAAAAGAGTGAACTTATACTCTAAAAGGTGTCTAT
ATACATCCGAATGTAGTCTCCATAGTGGAATCTCTAAAAAGACTTATATGTAGGAACCGAGGGAGTATATC
CAATCTGCCATTAGCAGAACTACATTTACTGCAACATGCTATAATGCTGTTATGCTGCGCTGATAAGTAGT
TTCCATTTCAATGTGTGCAGGCCAGGGTAAGTGGATCAAaGTAAGAGAAGGGAAAACTCTTCAGGAAGCGC
TGCAGCATAAAGACTACATCATCCCGGCAGTACCTGGTCCGTTCTTCAACCTGTGTATACTTTGCATTCGT
GCGTATAGAATGCTTGTCATTGTTCAGCGCAAATAAGAGCTTCCATTAATTCCTGCGTGCAGTGTTCTTTG
TGGTTTCAAGGAAATCCGCCTTCCATTCGAAGTTCAAGGCTGGGAATTGGTCTTTGCCGTAGAGCTGCCGT
GTAGTAGTTCAGTT       (SEQ ID NO: 22)
```

FIG. 14A

TGGCGAGCGGCGTCGGGCCGGAGGCGCGACGATGAAGGTGGTGGCCGCGGTGGACGCGAGCGAGGAGAGCC
TGCACGCGCTGTCGTGGGCGCTCGACAACGTCGTCCGGCCCCACCCCGGCGCGTCCCTCGTCGTCGTCCAC
GTCCAGCCGCGCGCCGACCACTTCGCCTACCCTGTCGCCGGGCACGGTACCGCCTGTCCTGTACAACAAGC
TAGCTCACACGCACACACACGTACGTACGCTCACGCTCACTGACGGAACTCGTTTGCGTGTGCATACGGAG
GCAGGCCTACAGTACGTCCCGCCCACGGCGGTGGACTCCGTGAGGAAGACGCACGAAGAGAACTCCCGGCG
AGTCGTGTCCGTCGCGCTCGACGTGTGCAGGCAGAAGCAGGTGAGCGCCACGGCGGCGGTGGTGGAGGGCG
ACGCCAAGGAGGCCATCTGCCGCGCCGTGGAGGACATGCACGCCGACCTCCTCGTCCTCGGCAGCCGCGGC
CTGGGCATGATCAAGAGGTACGCGCATGCCAATGAGATCACCACGCGTGAGCATCTTCGATAACAGATTGT
GATTCTGGGTGCAGTTCGACTACTTCACTGGCAGAGCCAAAAATACTAAAGCACAGCTTAGCTTTCTTCAG
TGTTCAAGCGACTTGAATTGCAAACATATGGAAATCCTTAAATTTCAAAATTTCAATGCTTGATTTGGTTG
GGGTTTGCCAGGTCCAGGCAGTAGTGCAACGCCTGGACGACACATGAGAGCCCTGGCAGCAAGCTACCGTG
ATGGGCTCTCCCCCATAAAAAATAAATTTAATATCGTTGTGGACACATGGTCCACATATCAGATATTAAAC
TGATAAGAACAGATACTACACTTGATCTTAGCCAAAAGGCCGAGAAAGGTATGAGTTGGAACATTGAGCTG
GTCTTGTTTTATAGCCATCTTTCCCCAGGGTTTCTCCTCCGTCCGGGATGTGGTACTAAACCTGCTACTG
ACCTCTCTTCTATGCTCCGGCAATGCCACCCGCTGCTCGGTTGGGCCCAAACCGAGAGCCCGTAGCAGGCC
TTATCGAGTACGTCATGGGCTTTTCTGTTCCTGTTCCTTTTACCATTCTATATCTTGTAGTTTGCCTCCTG
TTGGGCTTGTCCCTATGGGCCTCCCCTTCTTATCCAGGCACATATTGAAATGCATGGCTGGCAAGAGGTGC
AATAGCTCGTTAAACTTGCCTCCTTAAACAGTAGTACATTTAAGAGAATCCAATGGGTAAAGAAAACACAG
TTGTTTCTTAGTTTTTCATGTTTATTTACTATGAGAGCAAGCCTTTATCACCGAGACAATAGTCATGTTGC
TTGCAGAGTTACAAGCATATGCATAATAAAACTCCATGGATCATCAAGCCACGCCTTGACCCTGTGCTTGT
GCTGGTGGTGTGTTGCAGGGCGTTGCTGGGCAGCGTGAGCGACTACCTCGCCCATCACGCCTCCTGCCCCG
TTCTCATCGTGAAGCCGCCCAGCAAGGCGCACCACAAGTGAAGCTCCAACTCTGCTGCCAGTGTCGACTGA
ATGTCTCGAGTGCCTCGTGCTTCCAATAAAGATGTGATCGAGCTCATGTGCAGTACTCTATGAACATCCTA
GAATGTAGGGAATAAACTGTTGTTTGGCCGCAAGCACTTGCTGAAATTTTTAATCTTGGTTAGTGCAGTTG
TTCCGATGCATTACATTGCCATGGACGTAGTGTTCTTTCTTCCTTGAAGTACAGAGTGCGGTGATGCTGCT
GAAAAACAGGCACATCTCGAAGAGTTCGGTTCGCCAAACACATGACCAGTACAAGACCTATTGATCACAAA
TACTCCATAATTCGCTCTAAAAAACGTATTCAGAATTCCTATTCATAATGCAGAGCATGAATGACCGTCGA
AGCATGTTCTGTTTCTAAGCAAGCATGCTTTTGTTTTAAAATGGAGACAAAAGTTTTGCCTCGTCTATTTA
ATGAAGAAGAGGGTAGAGTTCTGTATTACAAGGCCGCGAGGCCCACCCGCAATAAACATGGAATTACTCTC
CTGATAGAATGTTTCCCAAAATAACAAAATTGCATCTGCCAAGACCCAAAGCTTGGTCTAGTCTTTGATGG
CCTTGAGCAAGATGGTCTTCGGCTTGCTCTATTCTCGAAACACACGGGCATTTCTCTCGTTTCAAATGGTC
CAACTAATGAGCATTGTAAGCGACGCCATTGCTTTACAGTTGACCTTGTTGTTGCGGAAAGATTGACCCAC
CAATCTTTGTTGGGGCTCTTAAGGCGCCAAGAGGAGGTTCAAAGTT          (SEQ ID NO: 23)

FIG. 14B

TGGCGAGCGGCGTCGGGCCGGAGGCGCGACGATGAAGGTGGTGGCCGCGGTGGACGCGAGCGAGGAGAGCC
TGCACGCGCTGTCGTGGGCGCTCGACAACGTCGTCCGGCCCCACCCCGGCGCGTCCCTCGTCGTCGTCCAC
GTCCAGCCGCGCGCCGACCACTTCGCCTACCCTGTCGCCGGGCACGGTACCGCCTGTCCTGTACAACAAGC
TAGCTCACACGCACACACACGTACGTACGCTCACGCTCACTGACGGAACTCGTTTGCGTGTGCATACGGAG
GCAGGCCTACAGTACGTCCCGCCCACGGCGGTGGACTCCGTGAGGAAGACGCACGAAGAGAACTCCCGGCG
AGTCGTGTCCGTCGCGCTCGACGTGTGCAGGCAGAAGCAGGTGAGCGCCACGGCGGCGGTGGTGGAGGGCG
ACGCCAAGGAGGCCATCTGCCGCGCCGTGGAGGACATGCACGCCGACCTCCTCGTCCTCGGCAGCCGCGGC
CTGGGCATGATCAAGAGGTACGCGCATGCCAATGAGATCACCACGCGTGAGCATCTTCGATAACAGATTGT
GATTCTGGGTGCAGTTCGACTACTTCACTGGCAGAGCCAAAAATACTAAAGCACAGCTTAGCTTTCTTCAG
TGTTCAAGCGACTTGAATTGCAAACATATGGAAATCCTTAAATTTCAAAATTTCAATGCTTGATTTGGTTG
GGGTTTGCCAGGTCCAGGCAGTAGTGCAACGCCTGGACGACACATGAGAGCCCTGGCAGCAAGCTACCGTG
ATGGGCTCTCCCCCATAAAAAATAAATTTAATATCGTTGTGGACACATGGTCCACATATCAGATATTAAAC
TGATAAGAACAGATACTACACTTGATCTTAGCCAAAAGGCCGAGAAAGGTATGAGTTGGAACATTGAGCTG
GTCTCGTTTTATAGCCATCTTTCCCCAGGGTTTCTCCTCCGTCCGCGATGTGGTACTAAACCTGCTACTG

FIG. 14B (con't)

```
CCCTCTCTTCTATGCTCCGGCAATGCCACCCGCTGCTCGGTTGGGCCCAAACCGAGAGCCCGTAGCAGGCC
TTACCGAGTCACGTCATGGGCTTTTCTGTTCCTGTTCCTTTTTCCATTCTCTCTCTTGCAGCTTGCCTCCT
CTTCTGCTTTTCCCTTTGTGCCTTCCCTTCTTATCCTGGTAGCATATTGAAATGCATGGCTGGAAGATGTG
CAATAGCTAGTTAACTTGCCTCCTTAAACAGTAGTACATTTAAGAAAATCCAATGGCTAAAGAAAACACAG
TTGTTTTTTAGTTTTTCATGTTTATTTACTATGAGAGCAAGCCTTTATCACCGAGACAATAGTCATGTTGC
TTGCAGAGTTACAAGCATATGCATAATAAAACTCCATGGATCATCAAGCCACGCCTTGACCCTGTGCTTGT
GCTGGTGGTGTGTTGCAGGGCGTTGCTGGGCAGCGTGAGCGACTACCTCGCCCATCACGCCTCCTGCCCCG
TTCTCATCGTGAAGCCGCCCAGCAAGGCGCACCACAAGTGAAGCTCCAACTCTGCTGCCACTGTCGACTGA
ATGTCTCGAGTGCCTCGTGCTTCCAATAAAGATGTGATCGAGCTCATGTGCAGTACTCTATGAACATCCTA
GAATGTAGGGAATAAACTGTTGTTTGGCCGCAAGCACTTGCTGAAATTTTTAATCTTGGTTAGTGCAGTTG
TTCCGATGCATTACATTGCCATGGACGTAGTGTTCTTTCTTCCTTGAAGTACAGAGTGCGGTGATGCTGCT
GAAAAACAGGCACATCTCGAAGAGTTCGGTTCGCCAAACACATGACCAGTACAAGACCTATTGATCACAAA
TACTCCATAATTCGCTCTAAAAAACGTATTCAGAATTCCTATTCATAATGCAGAGCATGAATGACCGTCGA
AGCATGTTCTGTTTCTAAGCAAGCATGCTTTTGTTTTAAAATGGAGACAAAAGTTTTGCCTCGTCTATTTA
ATGAAGAAGAGGGTAGAGTTCTGTATTACAAGGCCGCGAGGCCCACCCGCAATAAACATGGAATTACTCTC
CTGATAGAATGTTTCCCAAAATAACAAAATTGCATCTGCCAAGACCCAAAGCTTGGTCTAGTCTTTGATGG
CCTTGAGCAAGATGGTCTTCGGCTTGCTCTATTCTCGAAACACACGGGCATTTCTCTCGTTTCAAATGGTC
CAACTAATGAGCATTGTAAGCGACGCCATTGCTTTACAGTTGACCTTGTTGTTGCGGAAAGATTGACCCAC
CAATCTTTGTTGGGGCTCTTAAGGCGCCAAGAGGAGGTTCAAAGTT        (SEQ ID NO: 24)
```

FIG. 15A

A.
GCTTCTCCTGGAAGCTGCCGCGGACGTGGGTCAGGTCGGTCGACCAGCTGCCCATGAATTACGGCGACAAG
CTCTACGACCCGCTCTTCCCCTTCGGCTTCGGCCTCACCACCAAGCCGGCGGCGGATAGCAGGTAGCTAGG
AGTCTGAGTTTCTTTTCCTGCCCTAGTTAGTGTGCGATTAATTAGTGAGTCCGTGAGTAGTGAGAATCGGA
AATAAATGAGGAGGATATGGTTTTGATTGCGTCGCCCTGTAACTGTAAGTTCGCTACGAACATCCGATGAA
CTTGAAATCAATCTATATATAGTGCTGTCGGAATTCAGTCTATCTTAATTCTCGACTTCTCGAGTCGGTT
(SEQ ID NO: 25)

FIG. 15B

GCTTCTCCTGGAAGCTGCCGCGGACGTGGGTCAGGTCGGTCGACCAGCTGCCCATGAATTACGGCGACAAG
CTCTACGACCCGCTCTTCCCCTTCGGCTTCGGCCTCACCACCAAGCCGGCGGCGGATAGCAGCTAGCTAGG
AGTCTGAGTTTCTTTTCCTGCCCTAGTTAGTGTGCGATTAATTAGTGAGTCCGTGAGTAGTGAGAATCGGA
AATAAATGAGGAGGATATGGTTTTGATTGCGTCGCCCTGTAACTGTAAGTTCGCTACGAACATCCGATGAA
CTTGAAATCAATCTATATATAGTGCTGTCGGAATTCAGTCTATCTTAATTCTCGACTTCTCGAGTCGGTT
(SEQ ID NO: 26)

FIG. 16A

CAAACAGCCGTGACACACAAGAGGTACACTTTCTGAAAACTTCCGTCAATAACTACTTATTTTGGGTGGTG
ATTTCATGAAGAGGCCATGGCCCACCAGGGCTAATGTTAATACTTTGTATGTTCCTTTAAATAATGATGAT
GATGTATCTTGCTTTTTTAAGGACACATATTTTAAATATGGTTTATCAGGTGCCTTCCCCAGTTAATAAAA
CAGTGGAACCTATAAATTT
(SEQ ID NO: 27)

FIG. 16B

CAAACAGCCGTGACACACAAGAGGTACACTTTCTGAAAACTTCCGTCAATAACTACTTATTTTGGGTGGTG
ATTTCATGAAGAGGCGAATGTTAATACTTTGTATGTTCCTTTAGATAATGATGATGATGTAGCTTGCTTTT
TTAAGGACGCATATTTTAGATATGGTTTATCAAGTGCCTTCCCCAGTTAATATAACAGTGGAACCTAGAAA
TTTGTTTCTCCATTATTGTCATGCG
(SEQ ID NO: 28)

| Plant ID# | VIG1 | PCS | CHRS | AGLG | VRN-A1 | Pheno | CYS | IHY | GT | STR | KIN | CBP | USPC3 | MET | EX1 | AMT | CDO708 | BC1F2:3 A | BC1F2:3 B | BC1F2:3 H | BC1F3 A | BC1F3 B | BC1F3 H | Parents |
|---|---|---|---|---|---|---|---|---|---|---|---|---|---|---|---|---|---|---|---|---|---|---|---|---|
| D1052 | H | H | XB | B | B | B | B | B | B | B | B | B | B | B | B | B | B | 182 | 203 | 194 | | 193 | - | |
| P55 | A | A | X | H | H | H | H | H | H | H | H | H | H | H | H | H | H | | | | 159 | 193 | - | |
| D695 | H | H | H | H | H | H | H | XA | A | XB | A | A | A | A | A | A | A | 174 | 203 | 193 | | | | |
| T657 | H | H | H | H | H | H | H | H | H | XB | B | B | B | B | B | B | B | 157 | 191 | 172 | 143 | 212 | | |
| B562 | H | H | H | H | H | H | H | H | H | XH | B | B | B | B | B | B | B | 144 | 170 | 152 | | | | |
| D594 | B | B | B | B | B | B | B | B | B | XH | H | H | H | H | H | H | H | 187 | 199 | 200 | | | | |
| D731 | B | B | B | B | B | B | B | B | B | XH | H | H | H | H | H | H | H | 178 | 179 | 175 | | | | |
| D1061 | A | A | A | A | A | A | A | A | A | H | H | H | H | H | H | H | H | 159 | 163 | 157 | 168 | 206 | - | |
| L447 | H | H | H | H | H | H | H | H | H | A | A | A | A | A | A | A | A | 158 | 181 | 161 | | | | |
| A210 | A | A | A | A | A | A | A | A | A | A | A | XH | XH | H | H | H | H | 108 | 124 | 113 | | | | |
| T485 | A | A | A | A | A | A | A | A | B | B | B | B | B | H | H | H | H | 160 | 157 | 167 | | | | |
| T1013 | A | A | A | A | A | A | A | A | A | A | A | A | A | A | A | A | A | 160 | 163 | 150 | | | | |
| CAP7 | B | B | B | B | B | B | B | B | B | B | B | B | B | B | XB | XB | H | | 189 | | | | | |
| T722 | A | A | A | A | A | A | A | A | A | A | A | A | A | A | XA | A | B | 133 | 138 | 140 | | | | |
| CAP6 | A | A | A | A | A | A | A | A | A | A | A | A | A | B | BB | B | A | 145 | | | | | | |
| Jagger | A | A | A | A | A | A | A | A | A | A | A | A | A | A | | B | B | | | | | | | 155 |
| 2174 | B | B | B | B | B | B | B | B | B | B | B | B | B | B | | B | B | 158.3 | 174 | 165 | | | | 171 |

Fig. 17

FIG. 21A 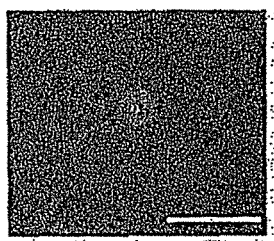 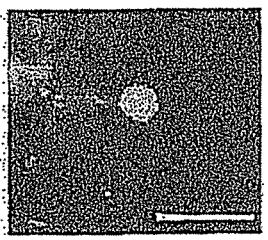 FIG. 21B
FIG. 21C 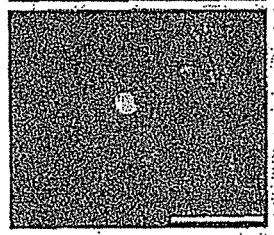 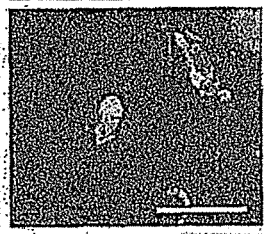 FIG. 21D
FIG. 21E  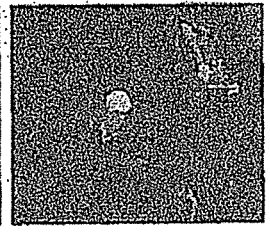 FIG. 21F Fig. 23A
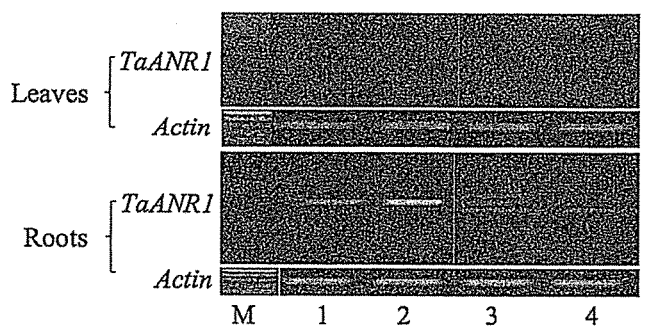
Fig. 23B
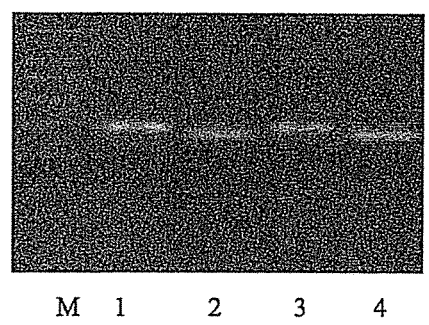
Fig. 23C
```
                Intron 5                                                              Exon 6
TaANR-A1a GTACTACAACATTTACCAGCCTGAAACGTATGAAATATTTCAACAAACTGACTATTCATTTATTTGCAGGGGAGTCTTGTCCACCAAG
          ||||||||||||||||||||||||||||||||||||||||||||||||||||||||||||                    ||||||
TaANR-A1b GTACTACAACATTTACCAGCCTGAAACGTATGAAATATTTCAACAAACTGACTATTCAT--------------------ACCAAG
```
Fig. 23D
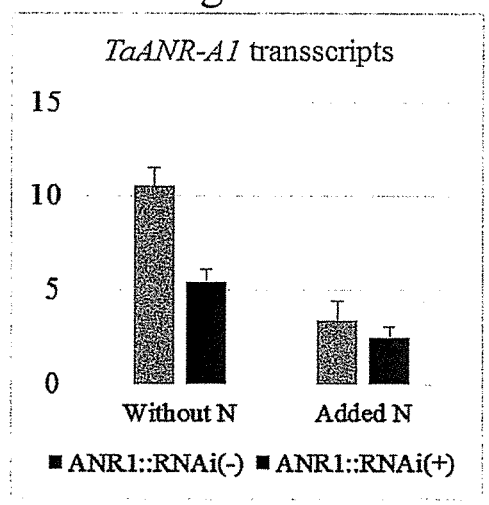
Fig. 23E
ANR1::RNAi(+)  ANR1::RNAi(-)

FIG. 24

MGRGKVQLKRIENKINRQVTFSKRRSGLLKKAHEISVLCDAEVGLIIFSTKGKLYEFSTESCMDKILERY
ERYSYAEKVLVSSESEIQGNWCHEYRKLKAKVETIQKCQKHLMGEDLESLNLKELQQLEQQLESSLKHIR
SRKNQLMHESISELQKKERSLQEENKVLQKELVEKQKAHAAQQDQTQPQTSSSSSSFMLRDAPPAANTSI
HPAATGERAEDAAVQPQAPPRTGLPPWMVSHING (SEQ ID NO: 29)

FIG. 25A

MGRGKIVIRRIDNSTSRQVTFSKRRNGIFKKAKELGILCDAEVGLVIFSSTGRLYEYASSSMKSVIDRYG
RAKEEQQLVANPNSELKSWQREAASLRQQLHNLQENHRQLMGQDLSGMGVKELQALENQLEISLRCIRTK
KDQILIDEIHELNHKGSLVHQENMELYKKINLIRQENVELQKKLSETEAVTEVNRNSRTPYNFAVVEDAN
VSVDLELNSPQQQNDVEHTAPPKLGLQLHP (SEQ ID NO: 30)

FIG. 25B

ATGGGGCGCGGCAAGATAGTGATCCGGCGGATCGACAACTCCACGAGCCGGCAGGTGACGTTCTCGAAGC
GGAGGAACGGGATCTTCAAGAAGGCCGAGGAGCTGGGTATTCTCTGCGATGCCGAGGTCGGTCTCGTCAT
CTTCTCCAGCACCGGCCGCCTCTATGAGTACGCCAGCTCCAGCATGAAGTCAGTGATAGATCGATATGGC
CGAGCCAAGGAGGAGCAGCAACTTGTTGCAAACCCCAACTCGGAGCTTAAGTTCTGGCAAAGGGAGGCAG
CAAGCTTGAGACAACAACTGCACAACTTGCAAGAAAATCATCGGCAGTTGATGGGACAAGATCTTTCTGG
AATGGGTGTCAAGGAACTGCAGGCTCTAGAAAATCAACTGGAAATAAGTCTGCGTTGCATCCGGACAAAA
AAGGACCAAATCTTGATTGATGAGATTCATGAACTGAATCACAAGGGGAGTCTTGTCCACCAAGAAAACA
TGGAATTATACAAAAAGATTAACCTAATTCGTCAGGAAAATGTTGAGTTACAGAAAAAGCTCTCTGAGAC
GGAGGCAGTGACTGAAGTTAACCGAAATTCAAGAACTCCATACAATTTTGCAGTTGTTGAAGATGCCAAT
GTTTCTGTTGATCTTGAACTCAATTCCCCGCAGCAACAAAATGATGTTGAGCATACTGCGCCCCCTAAAC
TAGGATTGCAACTACATCCATGA (SEQ ID NO: 31)

FIG. 25C

MGRGKIVIRRIDNSTSRQVTFSKRRNGIFKKAKELGILCDAEVGLVIFSSTGRLYEYASSSMKS
VIDRYGRAKEEQQLVANPNSELKSWQREAASLRQQLHNLQENHRQLMGQDLSGMGVKELQALEN
QLEISLRCIRTKKDQILIDEIHELNHKLSETEAVTEVNRNSRTPYNFAVVEDANVSVDLELNSP
QQQNDVEHTAPPKLGLQLHP (SEQ ID NO: 34)

FIG. 25D

ATGGGGCGCGGCAAGATAGTGATCCGGCGGATCGACAACTCCACGAGCCGGCAGGTGACGTTCT
CGAAGCGGAGGAACGGGATCTTCAAGAAGGCCGAGGAGCTGGGTATTCTCTGCGATGCCGAGGT
CGGTCTCGTCATCTTCTCCAGCACCGGCCGCCTCTATGAGTACGCCAGCTCCAGCATGAAGTCA
GTGATAGATCGATATGGCCGAGCCAAGGAGGAGCAGCAACTTGTTGCAAACCCCAACTCGGAGC
TTAAGTTCTGGCAAAGGGAGGCAGCAAGCTTGAGACAACAACTGCACAACTTGCAAGAAAATCA
TCGGCAGTTGATGGGACAAGATCTTTCTGGAATGGGTGTCAAGGAACTGCAGGCTCTAGAAAAT
CAACTGGAAATAAGTCTGCGTTGCATCCGGACAAAAAAGGACCAAATCTTGATTGATGAGATTC
ATGAACTGAATCACAAGCTCTCTGAGACGGAGGCAGTGACTGAAGTTAACCGAAATTCAAGAAC
TCCATACAATTTTGCAGTTGTTGAAGATGCCAATGTTTCTGTTGATCTTGAACTCAATTCCCCG
CAGCAACAAAATGATGTTGAGCATACTGCGCCCCCTAAACTAGGATTGCAACTACATCCATGA
(SEQ ID NO: 35)

FIG. 26A

MESDCQFLLAPPPRMYAAPGDDGQFLQQQQQQLSGGGAGERKRRFTEEQVRSLESTFHTRRAKLDPREKA
ELARELGLQPRQVAIWFQNKRARWRSKQPEQDFAELRGHYDALRARVESLKQEKLTLAAQLEELKKKLDE
RQDQSASCGGSCAVADVDDKRDNVSSCVAAKDESAAPAADVSDGSTPGWYEYDDHLVYGVDLHEPFCATQ
ELWETSWPLVEWNAVA (SEQ ID NO: 32)

FIG. 26B

ATGGAGAGCGACTGCCAGTTCCTGCTGGCGCCGCCGCCGCGCATGTACGCCGCGCCGGGGGACGACGGCC
AGTTCCTTCAGCAGCAGCAGCAGCAGCTGAGCGGCGGCGGCGCCGGGGAGAGGAAGCGGCGGTTCACGGA
GGAGCAGGTGCGGTCGCTGGAGAGCACGTTCCACACGCGGCGCGCCAAGCTGGACCCCCGGGAGAAGGCG
GAGCTGGCGCGCGAGCTGGGGCTGCAGCCGCGCCAGGTGGCCATCTGGTTCCAGAACAAGCGCGCCCGGT
GGCGCTCCAAGCAGCCGGAGCAGGACTTCGCGGAGCTGCGCGGCCATTACGACGCCCTCCGCGCCCGCGT
CGAGTCGCTCAAGCAGGAAAAGCTCACTCTCGCCGCGCAGCTGGAAGAGCTGAAGAAGAAGCTGGACGAG
CGGCAAGACCAGAGCGCTAGCTGCGGCGGCTCTTGCGCCGTCGCCGACGTAGACGACAAGAGGGATAACG
TTAGCAGCTGCGTCGCGGCGAAGGATGAGAGCGCGGCGCCGGCGGCAGACGTGTCGGACGGCTCAACTCC
GGGCTGGTACGAGTATGACGACCACCTGGTGTATGGGGTTGACCTGCACGAGCCGTTCTGCGCCACTCAG
GAGCTGTGGGAGACGTCATGGCCGCTGGTGGAGTGGAACGCAGTGGCATGA (SEQ ID NO: 33)

SEQUENCE LISTING

```
<160> NUMBER OF SEQ ID NOS: 35

<210> SEQ ID NO 1
<211> LENGTH: 369
<212> TYPE: DNA
<213> ORGANISM: Triticum aestivum

<400> SEQUENCE: 1
aaaccttgga cctaaccctc tgtagaaacc tttccatcca tcttcagcga tcaatcttct      60
aactacctca ctggcttttg gcttgttttg attaacctag atgaaaaaac agaaaaaaaa     120
tattaatgtg gctgatataa aaccataatt cgcaggatgc atgtacagtt aagaaataga     180 aaaaaatgc aaattctgat gacataaaga aaacatcagc tgcacggagc attttcttaa      240
agcatcacca gaaaattga acactggggg ttgaacgcta cagtctagaa gtgtgattgt      300
aattaactaa aagtctacac tcgacactat caacacagat aaaacatgta atgttaagaa     360
agttgtgaa                                                              369

<210> SEQ ID NO 2
<211> LENGTH: 370
<212> TYPE: DNA
<213> ORGANISM: Triticum aestivum
```

<400> SEQUENCE: 2

```
aaaccttgga cctaaccctc tgtagaaacc tttccatcca tcttcagcaa tcaatcttct    60
aactacctca ctggcttttg gcttgttttg attaacctag atgaaaaaac agaaaaaaaa   120
tattaatgtg gctgatataa aaccataatt cgcaggatgc atgtacagtt aagaaataga   180
aaaaaaatgc aaattcttga tgacataaag aaaacatcag ctgcacggag cattttctta   240
aagcatcacc agaaaaattg aacactgggg gttgaacgct acagtctaga agtgtgattg   300
taattaacta aaagtctaca ctcgacacta tcaacacaga taaaacatgt aatgttaaga   360
aagttgtgaa                                                          370
```

<210> SEQ ID NO 3
<211> LENGTH: 534
<212> TYPE: DNA
<213> ORGANISM: Triticum aestivum

<400> SEQUENCE: 3

```
tgcagcatcc tccttccaga ttagtgtagg tcttgctggg actaccaata agacggttaa    60
gatgccgaaa aacttcaccc ttagggcccc aggtccgggg tacacatgtg ggcgtgctct   120
tgttggcagg cctaccaagt attactcgtc agacgggcgc agggtaaccc aagctctcag   180
taagttgccc acttattgct cttcactgct tgctctatat tgctttaata ctttgcgcaa   240
atgcattagc aagctacact aattgagcta aacacatctt agtaccactt ttgtacgttt   300
ctgctcctta attgtgaatg aatttttatgt tataatatgt gtaggattag tgaaagactg   360
aaaggagtga aaccattgaa atcggaagtg attcattttc gagaggagat gagttcatca   420
cctaggatcg atgttagctc atatttattt gaaaataagc caccactaag cctgataata   480
tcttaactag ttttgttcac ttgcaaataa tggatttcaa atgcaggaaa catc         534
```

<210> SEQ ID NO 4
<211> LENGTH: 534
<212> TYPE: DNA
<213> ORGANISM: Triticum aestivum

<400> SEQUENCE: 4

```
tgcagcatcc tccttccaga ttagtgtagg tcttgctggg actaccaata agacggttaa    60
gatgccgaaa aacttcaccc ttagggcccc aggtccgggg tacacatgtg ggcgtgctct   120
tgttggcagg cctaccaagt attactcgtc agacgggcgc agggtaaccc aagctctcag   180
taagttgccc acttattgct cttcactgct tgctctatat tgctttaata ctttgcgcaa   240
atgcattagc aagctacact aattgagcta aacacatctt agtaccactt ttgtacgttt   300
ctgctcctta attgtgaatg aatttttatgt tataatatgt gtaggattag tgaaagactg   360
aaaggagtga aaccattgaa atcggaagtg attcattttc gagaggagat gagttcatca   420
cctaggatca atgttagctc atatttattt gaaaataagc caccactaag cctgataata   480
tcttaactag ttttgttcac ttgcaaataa tggatttcaa atgcaggaaa catc         534
```

<210> SEQ ID NO 5
<211> LENGTH: 1841
<212> TYPE: DNA
<213> ORGANISM: Triticum aestivum

<400> SEQUENCE: 5

```
cgagatgccg acgctgacga agctgtacag catgaaggag gccgccctcc acaacacccc    60
cgacgactgc tggatcgtcg tcgacggcaa ggtagcgcct ccctcatacc cctcgccgcc   120
```

```
gatctggctt cagcaatact gcccctaaca tcggtaggta ggtaggtagg gtctagggtg    180
tatggacgcg tttcgttgtt gctagttggg cttcgacccc cgcccttagc ctgttcgacc    240
gaatgcctgg gagatcccgc gctcgctttg ttagtgagaa ggctgcagga atcgaaaccg    300
aacgtctctg cgagtggcgt ggcctgctag tcacctcgtg gggcagttgt gctggggtat    360
cctctgttga aggcaaccac agcagatgcc tctgttgagg ctttgaatc aaatagaatt    420 tgtgtcagca gagagtagat acgcattaca atactacctg gcaaatatgt tccactactc    480
tgattctgtg gcgagctcat gccctgttga tgaatacaat gcagatttat gatgtgaccg    540
cgtatttgga tgaccatcct gggggtgctg atgtgctgct tgccgtgact ggtactactt    600
ctcagttctc acctcttgtt ttcatgttct tgttcagcac attttagttt ctcataggct    660
gtctgctcat acatgataat ctgtttcaag gtatggatgg caccgaggaa tttgaagatg    720
cgggccacag caaggatgcc aaggagttga tgaaagatta cttcattggg gagttggact    780
tggacgaaac acctgacatg cctgagatgg aggttttcag gaaagagcag gacaaggact    840
tcgccagcaa gctggcggct tacgctgtgc agtactgggc cattccggta gcagcagttg    900
ggatatcagc cgtgcttgct atattgtatg ctcgaaggaa gtgatgatcg gttataggtt    960
gattgaagga ccattttggg gtaaccaaca catttatagc tggttatgga tggagagatt   1020
atgtacttct gtccaaaggg gaagacacat tgctgtattg agcccttagg tacttgagtc   1080
aaatatttgt ccacaaaatt ggtggtacta ttttgtcaat atgtcattca atggatagat   1140
tcatttcaag acctgaacca tgtgtgtgat gtaaaccctc ttacgccttg aggcagctgc   1200
tggcgcagat ttcttccgtg ccattattgc ttctattttt gttattttcg tgggatgtgc   1260
cacggtactg ctatttctga atattgtgat ttttcaatcc ctcacttgct cctgaataac   1320
cctgaagact tttgtgtaac ttgttctttt gtaactttca agatgcaaat tgggatttgt   1380 tggccccctcc ttttgagtcg acatttgttg aaagcttccc gtgcaagcat ttcatccata   1440
tattttccta ttcgtttttc ttcccccttgt gtcacctcac aaggtgtaga tagttgggca   1500
gtagacttca gaaagatagc aggtagcttt tgccgccccc tctcttgata tttctaaact   1560
ggggttgctt cgccatcact acgtaatact agttgaagaa attttatcat gtgctactgc   1620
tgtgcttagt aacctagcac ctgggttcga cacagcctct tggcattgca ttgtgcagat   1680
aaggcttgcc tcaatgcctt gtataatcct tccccaggtg tcacctggaa atgtacacct   1740
tacctgatag tattatgcag gggtatcact tggaattgat ggtgttgctt gaaggcagag   1800
caaaaaccaa catgtggaag gtggtgctga gcttctcaac c                       1841
```

<210> SEQ ID NO 6
<211> LENGTH: 1841
<212> TYPE: DNA
<213> ORGANISM: Triticum aestivum

<400> SEQUENCE: 6

```
cgagatgccg acgctgacga agctgtacag catgaaggag gccgccctcc acaacacccc    60
cgacgactgc tggatcgtcg tcgacggcaa ggtagcgcct ccctcatacc cctcgccgcc   120
gatctggctt cagcaatact gcccctaaca tcggtaggta ggtaggtagg gtctagggtg   180
tatggacgcg tttcgttgtt gctagttggg cttcgacccc cgcccttagc ctgttcgacc   240
gaatgcctgg gagatcccgc gctcgctttg ttagtgagaa ggctgcagga atcgaaaccg   300
aacgtctctg cgagtggcgt ggcctgctag tcacctcgtg gggcagttgt gctggggtat   360
```

```
cctctgttga aggcaaccac agcagatgcc tctgttgagg ctttgaatc aaatagaatt    420 tgtgtcagca gagagtagat acgcattaca atactacctg gcaaatatgt tccactactc    480
tgattctgtg gcgagctcat gccctgttga tgaatacaat gcagatttat gatgtgaccg    540
cgtatttgga tgaccatcct gggggtgctg atgtgctgct tgccgtgact ggtactactt    600
ctcagttctc acctcttgtt ttcatgttct tgttcagcac attttagttt ctcataggct    660
gtctgctcat acatgataat ctgtttcaag gtatggatgg caccgaggaa tttgaagatg    720
cgggccacag caaggatgcc aaggagttga tgaaagatta cttcattggg gagttggact    780
tggacgaaac acctgacatg cctgagatgg aggttttcag gaaagagcag gacaaggact    840
tcgccagcaa gctggcggct tacgctgtgc agtactgggc cattccggta gcagcagttg    900
ggatatcagc cgtgcttgct atattgtatg ctcgaaggaa gtgatgatcg gttataggtt    960
gattgaagga ccattttggg gtaaccaaca catttatagc tggttatgga tggagagatt   1020
atgtacttct gtccaaaggg gaagacacat tgctgtattg agcccttagg tacttgagtc   1080
aaatatttgt ccacaaaatt ggtggtacta ttttatcaat atgtcattca atggatagat   1140
tcatttcaag acctgaacca tgtgtgtgat gtaaaccctc ttacgccttg aggcagctgc   1200
tggcgcagat ttcttccgtg ccattattgc ttctatttt gttatttcg tgggatgtgc    1260 cacggtactg ctatttctga atattgtgat ttttcaatcc ctcacttgct cctgaataac   1320
cctgaagact tttgtgtaac ttgttctttt gtaactttca agatgcaaat tgggatttgt   1380
tggcccctcc ttttgagtcg acatttgttg aaagcttccc gtgcaagcat ttcgtccata   1440
tattttccta ttcgtttttc ttccccttgt gtcacctcac aaggtgtaga tagttgggca   1500
gtagacttca gaaagatagc aggtagcttt tgccgccccc tctcttgata tttctaaact   1560
ggggttgctt cgccatcact acgtaatact agttgaagaa attttatcat gtgctactgc   1620
tgtgcttagt aacctagcac ctgggttcga cacagcctct tggcattgca ttgtgcagat   1680
aaggcttgcc tcaatgcctt gtataatcct tccccaggtg tcacctggaa atgtacacct   1740
tacctgatag tattatgcag gggtatcact tggaattgat ggtgttgctt gaaggcagag   1800
caaaaaccaa catgtggaag gtggtgctga gcttctcaac c                      1841
```

<210> SEQ ID NO 7
<211> LENGTH: 5612
<212> TYPE: DNA
<213> ORGANISM: Triticum aestivum

<400> SEQUENCE: 7

```
gaggtcggag gtcggagatg ggtcgcggca aggtggtgct gcagcggatc gagaacaaga     60
tcagccgcca ggtgacgttc gccaagcgcc gcaacggcct gctcaagaag gcctacgagc    120 tctcccctcct ctgcgacgcc gaggtcgcgc tcgtcctctt ctcccacgct ggccgcctct    180
accagttctc ctcctcctcc aagtaattac tccttccgat ctcccccagt gccgtaccat    240
atcgatccct ccatttcctt ttctctttgt ggttttgccg agtcgatcct tttgatttgc    300
tctccccgtt caaacatttt gtccatacgc gacgttcgat ctgaattttc ttgcgtctta    360
gggcgtccgt gcatgaactt atgggggggt ggtccgtac gttcttcccc tcttgtttgc    420
tgttctgttg gccactgtgt caaagaggc tagcaagaaa caaacaaagg aaaaagtgat    480
gagctcaccc gcagcagcag atcgacggac atactatgca gtaggagtat atgtcatgcg    540
tatgtttgtc tcattcacag tagaggatta aaaggggtt ttaatctaaa aaaacaaga     600 agaaaagatg ttttttatttg atgtacgcct gaccacacct gtattgagga tacatgtatg    660
```

```
cacataatta gagctttgat cacctgctga gattaatttg caccaatatg gcatgcatcc    720
ttgtgaaact catacgggca ctaattgttt ttctacaaat tttatctagc tttgtcttat    780
ggtctgggta gtatgatgat ccacttctga gaattaattt gaattatgta attttaaata    840
cttttctgca gacccaagtt caatctattt tttttctcaa aacaaaggtt cagtctaatt    900
tgacaccttt aaggcgtagg attgaattat atatgcttgt ttaatgttat ttgtcaaaga    960
actaagaaag gatatatacc gctttcagtt aactgaattg cattaatttt ctagtcaaag   1020
taccgaaata atactattga aaaaaatgaa acagttaagt gctttaattc aactgtggcc   1080
ttacatgatg tgacagggca agtgctgcat catatgtact aggtacaaat gaagtgctat   1140
ttgtacttcc ttggagcaaa agaaaacaag taataaacta gctaatgtta ggttcgtacc   1200 tactcccctcc gtcccataat gtaagacctt ttttaacacg gtcttatatt atgggatgaa   1260
aggagtacgc aataatttaa gcagctctat agggtagcat tacctaatga tatcagaact   1320
ttatgtatgt tcgagtcaaa tatagctagg ttttaatctg tcaaaattat aaagccactg   1380
agtttgctca aaaagtttgt aaaagcgctg atacatgaaa tgtgaaacca gacttggtaa   1440
aattgcatgc taatattttg tagggccaat catgattact acttgtcagt tctatacaaa   1500
catgccactg gtggctagct taaactttgt agcaattttg gctgaaatag ctttttttggt   1560 gaaaattaac aactgtactt ctcacagtag tagctcaata acattctta cagtggcata   1620 gttctcccaa aagtttaatt agtcaaagga acagatatg tcttctttt tatataatgg   1680 aaagttctttt ttaggtacat cgtcaagtct tcactagatt gtgatgttta cacaacttttg   1740 aagccatgtg tcaatggcta taaagtgacc aaaaattagc tcaaaagact aagacaacat   1800 atagaattttg ttagaagttg aacatacaga aagtttatta tgcgagagac cttcattgtc   1860
caataattat cgaattctgt catgtaaata gtgatactta gtttctaatc cctcccccctc   1920 ccccagtgaa tctgaatttta tgttatttac ctatgcgtgt acttgcacaa cttaatctcg   1980
aattttcaac tcatcgcagc atgcttaaga ccctcgagaa gtaccagagg tacattttcg   2040
cttcccaaga tgctgccgtg ccgactaccg atgagatgca ggtctgaggc ttttattccc   2100
aatgcgcata ttatgaagat tctacaaatt ttcctcagat acaacatctt tgaattttta   2160
actagcaggt tatcagagaa atttgttttc cttcgtagaa caatgtatct ataatgccct   2220
aaataacata tataaattga ttttttgtgaa gagataaaac attcagtcat acatttaaaa   2280
tatttcattc tgtatgacgt acgttatatg aagcattgcc tattcgtaaa tgttacctag   2340
ttcacacatg attgctaaaa ggtatttctc tgctggtaaa ggtgttatat ttccgtgttt   2400
agaacatgga tttctgttgc ttgtcatata ggcagtgaac taattatttt gtttgacttt   2460
tttatgtaaa attactgcct tgtaaacatg cccacatggt ttgaagcaaa agataaacct   2520
ttgataaatt tttagcagtt acaaaatatt aaatgggaat gtaagttcat ggcaattaga   2580
atgttggaaa gtacagctag agcattggcc cagtgcattt catgcatacg cgcagcataa   2640
ttcacgtacg tggctatcta tgtgaaatac agcatcgagt aactgggcac tggggagacc   2700
tatatctgcg catgttcctt gaattatcgc taatgtacat gcattttgtg gttggttata   2760
acttataagt agactaacag cttggttggc caccacatgc agtattgtag cagatagcag   2820
cttcagactg attggccata tgccatatac ctgctgatga gtttattaca acagtggaat   2880
gtattaaaat tgataaatac aatatggcta tatgttatat ggtataaatg tggtagttgt   2940
ttattaaaaa ggcatggggt aaaatgttca atttatgttt agtagagcct aagctatggt   3000
```

```
acgccttctt catggtcacg gtcatatttt ccaaatgaca tgtccaaaag aatagatttg    3060
gacttactag atcctttact attcatgcga gaatttattg tttatgagga ttcacacaca    3120
gagagttgcc agtatgtaat ttttaggatt catggtacaa tttaatcata atcttaattg    3180
ctagaacgtg tactaatttc tttagaagat ggcaagtggg aacctataaa cacacgaagc    3240
aagaaccata tgaactcaac acaagcaatc aactaagcca tagcaaagcg caaacaagag    3300
aacattgata gatgattggt ttccctaacg ctagatcgta gtgtagatga acaatccaag    3360
tgctagaagt tgcgagagag tgacaatatg actcgtttga tctcttgatg ttgtgtagaa    3420
agggagccgc agttgggttc atcttctttt ttccgataaa cttgggttca tcttcatagt    3480
catgattatg gcatgctcat gtcaaatctt atgacatata gtaaaacaaa ggtcttctgc    3540
gcacaataag gatatcgaag tataacaaaa ggttcacacg aattgctcta ggatttttca    3600
gtgatgtggt actccaagtt tttattctag gaagtattcc tagatttatg gtataagttg    3660
gtatatatta actcttcagt cataatcatc tccaaggtga tactttgacc atttgttttt    3720 ttcttcttt ttgcgactga actatcaatt tctataaaaa atatgttgat acacataaaa    3780
cattttactc attatggaat tatgttctgc gataattcaa atatctgtgt caaatgtttg    3840
taattttatt tttattttta ctgataatca gattaagagt gcttgctgtt ttttttttg    3900 aaatgaccta tactatgtga ctcatatgaa ggggtactcc tagcttgtaa tcttacaaag    3960
tcgtccggga tttatgttta aaattttaa atattacctc ttgtgtcata atgtaggttg    4020
tctccagcac gtgatacttt gacaatcagt ttccataaca atatgctggt tcaaatgaaa    4080
catggtacac tttatagatt atgtttcacg acaacgtaaa ttttgtttca cgttttgtaa    4140 gtttctttt ttatgatg aaaccaagaa tgtttgacgg acacaacttt ggaattgtcc    4200
tacaatgtta ctcacatgaa gtatttgatt tttgcgggac aaaaaggcat ttttcttaag    4260 ctttattt tgcaggacaa aatggcattt ttcttaagtt tacttgattt agcattttcc    4320
ccatatctcc ttctttacac taactgcaga atacactaac tgcagaacaa ctatctggag    4380
tatatggagc tgaagtcaag agttgaggtt ttacaacgct cacaaaggtg atgtttctat    4440
attcctctca gataattgct cattaatttc agcaggttac cgcaacattt gctatgtttg    4500
ctaaagtaag tactgttgat ggtgccacag gaatctccta ggcgaggatt tggctccact    4560
gagtacaatc gagcttgaac agcttgaggg tcaagtaggc aagaccttga ggcaaataag    4620
gtcaagaaag gtaaactaca tagcaataaa aaaagttaag agtataagta gaaattaggt    4680
taatctgcta aaatccattc gtcttatcga gcaacgcttg ctgctagttt cactaactag    4740
tgtccatgat ttaacctgta ccacagactc aagtactgct ggatgaaatg tgcgacctga    4800
agagaaaggt agcactaaaa atactttcca tttctgttgc taaatgatgg acgatgtcct    4860
attccgtagc ttcaagcaca atcttgtttt gcaggagcaa atattgcagg atgcaaatat    4920
gaccctgaaa agaaaggtaa catgacccaa atcatttttc ctagctagaa aggtctgcat    4980
ttgtacgcac gtagctaggg agggaccatc ctcaaggaga agctgtctca tttcacttgg    5040
gccagtgaca agtgattgga aagttgatga ctcggcaagc ccactagtag ttagttagta    5100 ggcagggac ccctgttgg caccacagta taaacacagg tggctttcag gtaccaccaa    5160
ttgcagctac ctgccgtgtt tatgtgtgtt tgtgcactgc aagcattctt cttcttcctg    5220
gctttcagaa aatcactctt cttgttttta ccctctactg aaaacggctt catccattgg    5280
tgtatgtaat gctcttgatc actcccgttt cacttcagct gggcgagatc gagctggagg    5340
cgacacctga tcccccgcag cagccgcagc agcagcagat gtggcagggc gaccggggcg    5400
```

-continued

| | |
|---|---|
| tgccgcccca cacgcctccg cagccagagc acttcttcca ggccctagaa cgctatcctt | 5460 |
| ccctgcagcc agtgtaagac ttctaactct tttttccctt ttcctgctgc taaactcatg | 5520 |
| gcacagagac taatgatcac cgacgttcgt ctctgcagat ttcgtggcat ggatgtgaac | 5580 |
| cagccgccgc ctgcatggat ggcatagcta cg | 5612 |

<210> SEQ ID NO 8
<211> LENGTH: 5611
<212> TYPE: DNA
<213> ORGANISM: Triticum aestivum

<400> SEQUENCE: 8

| | |
|---|---|
| gaggtcggag gtcggagatg ggtcgcggca aggtggtgct gcagcggatc gagaacaaga | 60 |
| tcagccgcca ggtgacgttc gccaagcgcc gcaacggcct gctcaagaag gcctacgagc | 120 |
| tctccctcct ctgcgacgcc gaggtcgcgc tcgtcctctt ctcccacgct ggccgcctct | 180 |
| accagttctc ctcctcctcc aagtaattac tccttccgat ctcccccagt gccgtaccat | 240 |
| atcgatccct ccatttcctt ttctctttgt ggttttgccg agtcgatcct tttgatttgc | 300 |
| tctccccgtt caaacatttt gtccatacgc gacgttcgat ctgaattttc ttgcgtctta | 360 |
| gggcgtccgt gcatgaactt atgggggggct gggtccgtac gttctttccc tcttgtttgc | 420 |
| tgttctgttg gccactgtgt caaaagaggc tagcaagaaa caaacaaagg aaaaagtgat | 480 |
| gagctcaccc gcagcagcag atcgacggac atactatgca gtaggagtat atgtcatgcg | 540 |
| tatgtttgtc tcattcacgg tagaggatta aaaaggggtt ttaatctaaa aaaaacaaga | 600 |
| agaaaagatg ttttttatttg atgtacgcct gaccacacct gtattgagga tacatgtatg | 660 |
| cacataatta gagctttgat cacctgctga gattaatttg caccaatatg gcatgcatcc | 720 |
| ttgtgaaact catacgggca ctaattgttt ttctacaaat tttatctagc tttgtcttat | 780 |
| ggtctgggta gtatgatgat ccacttctga gaattaattt gaattatgta atttaaata | 840 |
| cttttctgca gacccaagtt caatctattt tttttctcaa aacaaaggtt cagtctaatt | 900 |
| tgacaccttt aaggcgtagg attgaattat atatgcttgt ttaatgttat ttgtcaaaga | 960 |
| actaagaaag gatatatacc gctttgagtt aactgaattg cattaatttt ctagtcaaag | 1020 |
| taccgaaata atactattga acaaaatgaa acagttaagt gctttaattc aactgtggcc | 1080 |
| ttacatgatg tgacagggca agtgctgcat catatgtact aggtacaaat gaagtgctat | 1140 |
| ttgtacttcc ttggagcaaa agaaaacaag taataaacta gctaatgtta ggttcgtacc | 1200 |
| tactccctcc gtcccataat gtaagacctt ttttaacacg gtcttatatt atgggatgaa | 1260 |
| aggagtacgc aataatttaa gcagctctat agggtagcat tacctaatga tatcagaact | 1320 |
| ttatgtatgt tcgagtcaaa tatagctagg ttttaatctg tcaaaattat aaagccactg | 1380 |
| agtttgctca aaaagtttgt aaaagcgctg atacatgaaa tgtgaaacca gacttggtaa | 1440 |
| aattgcatgc taatattttg tagggccaat catgattact acttgtcagt tctatacaaa | 1500 |
| catgccactg gtggctagct taaactttgt agcaattttg gctgaaatag ctttttttggt | 1560 |
| gaaaattaac aactgtactt ctcacagtag tagctcaata aacattctta cagtggcata | 1620 |
| gttctcccaa aagtttaatt agtcaaagga aacagatatg tcttcttttt tatataatgg | 1680 |
| aaagttcttt ttaggtacat cgtcaagtct tcactagatt gtgatgttta cacaactttg | 1740 |
| aagccatgtg tcaatggcta taagtgacc aaaaattagc tcataagact aagacaacat | 1800 |
| atagaatttg ttagaagttg aacatacaga aagtttatta tgcgagagac cttcattgtc | 1860 |

```
caataattat cgaattctgt catgtaaata gtgatactta gtttctaatc cctcccccctc    1920 cccagtgaat ctgaatttat gttatttacc tatgcgtgta cttgcacaac ttaatctcga    1980
attttcaact catcgcagca tgcttaagac cctcgagaag taccagaggt acattttcgc    2040
ttcccaagat gctgccgtgc cgactaccga tgagatgcag gtctgaggct tttattccca    2100
atgcgcatat tatgaagatt ctacaaattt tcctcagata caacatcttt gaattttttaa   2160 ctagcaggtt atcagagaaa tttgttttcc ttcgtagaac aatgtatcta taatgcccta    2220
aataacatat ataaattgat ttttgtgaag agataaaaca ttcagtcata catttaaaat    2280
atttcattct gtatgacgta cgttatatga agcattgcct attcgtaaat gttacctagt    2340
tcacacatga ttgctaaaag gtatttctct gctggtaaag gtgttatatt tccgtgttta    2400
gaacatggat ttctgttgct tgtcatatag gcagtgaact aattattttg tttgactttt    2460
ttatgtaaaa ttactgcctt gtaaacatgc ccacatggtt tgaagcaaaa gataaacctt    2520
tgataaattt ttagcagtta caaaatatta aatgggaatg taagttcatg caattagaa     2580 tgttggaaag tacagctaga gcattggccc agtgcattc atgcatacgc gcagcataat    2640
tcacgtacgt ggctatctat gtgaaataca gcatcgagta actgggcact ggggagacct    2700
atatctgcgc atgttccttg aattatcgct aatgtacatg catttgtgg ttggttataa     2760 cttataagta gactaacagc ttggttggcc accacatgca gtattgtagc agatagcagc    2820
ttcagactga ttggccatat gccatatacc tgctgatgag tttattacaa cagtggaatg    2880
tattaaaatt gataaataca atatggctat atgttatatg gtataaatgt ggtagttgtt    2940
tattaaaaag gcatggggta aaatgttcaa tttatgttta gtagagccta agctatggta    3000
cgccttcttc atggtcacgg tcatattttc caaatgacat gtccaaaaga atagatttgg    3060
acttactaga tcctttacta ttcatgcgag aatttattgt ttacgaggat tcacacacag    3120
agagttgcca gtatgtaatt tttaggattc atggtacaat ttaatcataa tcttaattgc    3180
tagaacgtgt actaatttct ttagaagatg gcaagtggga acctataaac acacgaagca    3240
agaaccatat gaactcaaca caagcaatca actaagccat agcaaagcgc aaacaagaga    3300
acattgatag atgattggtt tccctaacgc tagatcgtag tgtagatgaa caatccaagt    3360
gctagaagtt gcgagagagt gacaatatga ctcgtttgat ctcttgatgt tgtgtagaaa    3420
gggagccgca gttgggttca tcttcttttt tccgataaac ttgggttcat cttcatggtc    3480
atgattatgg catgctcatg tcaaaccttca tgacatatag taaaacaaag gtcttctgcg    3540
cacaataagg atatcgaagt ataacaaaag gttcacatga attgctctag gattttttcag    3600 tgatgtggta ctccaagttt ttattctagg aagtattcct agatttatgg tataagttgg    3660
tatatattaa ctcttcagtc ataatcatct ccaaggtgat actttgacca tttgtttttt    3720
ttcttctttt tgcgactgaa ctatcaattt ctataaaaaa tatgttgata cacataaaac    3780
attttactca ttatggaatt atgttctgcg ataattcaaa tatctgtgtc aaatgtttgt    3840
aattttattt ttattttttac tgataatcag attaagagtg cttgctgttt tttttttga    3900 aatgacctat actatgtgac tcatatgaag gggtactcct agcttgtaat cttacaaagt    3960
cgtccgggat ttatgtttaa aattttttaaa tattacctct tgtgtcataa tgtaggttgt   4020
ctccagcacg tgatactttg acaatcagtt tccataacaa tatgctggtt caaatgaaac    4080
atggtacact ttatagatta tgtttcacga caacgtaaat tttgtttcac gtttttgtaag   4140 tttctttttt tttatgatga aaccaagaat gtttgacgga cacaactttg gaattgtcct    4200
acaatgttac tcacatgaag tatttgattt ttgcgggaca aaaaggcatt tttcttaagc    4260
```

```
tttatttt   gcaggacaaa   atggcatttt   tcttaagttt   acttgattta   gcattttccc      4320
catatctcct   tctttacact   aactgcagaa   tacactaact   gcagaacaac   tatctggagt      4380
atatggagct   gaaggcaaga   gttgaggttt   tacaacgctc   acaaaggtga   tgtttctata      4440
ttcctctcag   ataattgctc   attaatttca   gcaggttacc   gcaacatttg   ctatgtttgc      4500
taaagtaagt   actgttgatg   gtgccacagg   aatctcctag   gcgaggattt   ggctccactg      4560
agtacaatcg   agcttgaaca   gcttgagggt   caagtaggca   agaccttgag   gcaaataagg      4620
tcaagaaagg   taaactacat   agcaataaaa   aaagttaaga   gtataagtag   aaattaggtt      4680
aatctgctaa   aatccattcg   tcttatcgag   caacgcttgc   tgctagtttc   actaactagt      4740
gtccatgatt   taacctgtac   cacagactca   agtactgctg   atgaaatgt   gcgacctgaa      4800
gagaaaggta   gcactaaaaa   tactttccat   ttctgttgct   aaatgatgga   cgatgtccta      4860
ttccgtagct   tcaagcacaa   tcttgttttg   caggagcaaa   tattgcagga   tgcaaatatg      4920
accctgaaaa   gaaggtaac   atgacccaaa   tcattttttcc   tagctagaaa   ggtctgcatt      4980
tgtacgcacg   tagctaggga   gggaccatcc   tcaaggagaa   gctgtctcat   ttcacttggg      5040
ccagtgacaa   gtgattggaa   agttgatgac   tcggcaagcc   cactagtagt   tagttagtag      5100
gcagggacc   cctggttggc   accacagtat   aaacacaggt   ggctttcagg   taccaccaat      5160
tgcagctacc   tgccgtgttt   atgtgtgttt   gtgcactgca   agcattcttc   ttcttcctgg      5220
ctttcagaaa   atcactcttc   ttgtttttac   cctctactga   aaacggcttc   atccattggt      5280
gtatgtaatg   ctcttgatca   ctcccgtttc   acttcagctg   ggcgagatcg   agctggaggc      5340
gacacctgat   ccccccgcagc   agccgcagca   gcagcagatg   tggcagggcg   accggggcgt      5400
gccgccccac   acgcctccgc   agccagagca   cttcttccag   gccctagaac   gctatccttc      5460
cctgcagcca   gtgtaagact   tctaactctt   ttttttccttt   tcctgctgct   aaactcatgg      5520
cacagagact   aatgatcacc   gacgttcgtc   tctgcagatt   tcgtggcatg   gatgtgaacc      5580
agccgccgcc   tgcatggatg   gcatagctac   g                                          5611
```

<210> SEQ ID NO 9
<211> LENGTH: 11922
<212> TYPE: DNA
<213> ORGANISM: Triticum aestivum

<400> SEQUENCE: 9

```
gaaaggaaaa   attctgctcg   ttttttttgct   ctgtggtgtg   tgtttgtggc   gagagaaaat        60
gatttgggga   aagcaaaatc   cggagattcg   cacgtacgat   cgttcgacac   gtcgacgccc       120
ggcgggcccg   gggtgggggca   tcgtgtggct   gcaggaccgc   ggggcccgc   aaagcgggcc        180
gggccaatgg   gtgctcgaca   gcggctatgc   tccagaccag   cccggtattg   cataccgcgc       240
tcggggccag   atcccttttaa   aaaccctcc   cccctgccg   gaatcctcgt   tttggcctgg       300
ccatcctccc   tctcctcccc   tctcttccac   ctcacgtcct   cacccaacca   cctgatagcc       360
atggctccgc   cgcctcgcct   ccgcctgcgc   cagtcggagt   agccgtcgcg   gtctgccggt       420
gttggagggt   aggggcgtag   ggttggcccg   gttctcgagc   ggagatgggg   cggggggaagg       480
tgcagctgaa   gcggatcgag   aacaagatca   accggcaggt   gaccttctcc   aagcgccgct       540
cggggcttct   caagaaggcg   cacgagatct   ccgtgctctg   cgacgccgag   gtcggcctca       600
tcatcttctc   caccaaggga   aagctctacg   agttctccac   cgagtcatgg   taaattaagc       660
acgcgctgtc   tttaaatttg   ttccccaata   cgccttcgat   ttcgatttcc   tgcgcaccgt       720
```

```
tctggtcctg cgagacgacc cggccgaccc cagggccttc tccatttccg cgctgctgtt    780
tggtagattc cgtttgcccg ctcgctgttt ccatccgatt ctgccgtggc tgcttgctcg    840
tttttcttag aatcgatggg ggagctggcg ttccgcgcgg ccgcgatttc ttgctatggg    900
gggtagggcg cgcgatgggt cgccgggcta ttttatgctc cgccagcgcc gggaaggttg    960
ttcatctggc gtattttggg gaaattttgg tcccggacgc gccaggtggc accccaagtg   1020
gaagggttaa gacggtaatc tcttgatatt tctatcgggc tggggttatt tacgtaaaaa   1080
atatatatgg ggttaaagtg acatcgcaat ttagcatgct acctcatctt ctcatttgga   1140
atcttaacta gacgctacaa taccttgttg tctccctcat caaatctgtg cttgctgctt   1200
gaacaaatga acctcgtcat ctcggttatt tccagaattt tgttccacag gctttgctat   1260
cattcatatt ggtagctccg gccatgcggc cattttgttg cttgcttgga gatactgtct   1320
acggcacgca cggagaaaag agtcacttga ccagctaatg catggaatta ttgtctgcag   1380
ctgatgaaac tccggcatga agagtcaaac caaaaagtag agagttcctt ccaaatataa   1440
aataagagtt tctgcatact tttttcccct ttcaaccatc atagtttgcc cgtgatattt   1500
gttggtgctg gcgatggttc ttcacaaagt aaaggagtca ataaaatcac ggagactgat   1560
ccattatttc ccccacacgc tgacattagt ccatgttagt ttcccatttc tgtctgcttc   1620
cataattccc gtccggcgaa gtactagatc agcctccacg gtttgaaagt aagatatatc   1680
ataccgtcga aaggatcgct actgcttagt aaatatccat tgttgtttgt aatcttgctg   1740
agaaagcaac attaccatca gcttcatggc aaggacctgt atgttgaggt gctaaatctc   1800
ttctagtttt gtaccactga gggtatgcgc ggcgctaacg gaaaagggta ggtaaagttt   1860
tattggcttg ccttcagctt ccttggttgt ttgacgcata ggtgcttgca tgcatgtatc   1920
aagctggtca cgtgatgaaa acgcgtaaga atcaaagtcg gttaaattaa gatataaata   1980
gatgcagtca tattttaagc tagtgctgca ctgtgaactt cagtatctca gatcaaagta   2040
ctgaataaaa ttaccccctg tttccgtgct gttcatttgg aaaagactgc catgaacatc   2100
cgaattggta accatgcatt aatcagcttg ccggctttat tttcttctct gtcgttcctt   2160
gtcatttggt ttgctttgcc tacctctgca cgataggcac gtgtaagtag ctcacgggga   2220
caagtaactg ctatgctttg tctagagcct atgagacagc acgctgatgc accacgatat   2280
tccatggttt aggatcggaa ctaaaatctt gagatcttac aatattctaa aaaggcatct   2340
atagcctgca tataaccgac tcaggcacaa aatcagcatt gatcgagcag gcatcatatg   2400
catacactaa aatgcagcta atgatgtagc ctgctgattt tctggacctg gcttggataa   2460
tggttaatgt acccaattgt tattcactct atatcctcca tctccttatc ggtcgattaa   2520
tttaccacac atagcaaagg tccaaagctg acattgcaac caactttact catctctaga   2580
ctagtaaaca cgaagtaagc tgttagggac tgtgtgatgg gtctatgtta catgcatttg   2640
ttgtcggtct agtacttaac caagtctggg aaccagttat cctctacacc tattgtgtcc   2700
ctaaacctat atacttgaga gtaaaacaga agttattcct aggaatatct gactaagcta   2760
tgggatagtc aacttccatt tttgctcctg ccacatcttt acttagtcca caaacgacat   2820
atagatgatc agctagaacc gttatttaga gtttatatct gctcattaca tgtattaatt   2880
ccatgaaata gaagaaaaac tgaataggca cacaatatag ttgaagctcg gcagatgact   2940
tcataagtgt catatctatt aaccatttca catattgtta catttttgct gcagtgatat   3000
tttgttagct cccagttaca agttaactaa tatatgagag tcctgggcac gtacatgtaa   3060
gcagatccta tcgactttcg cgtatccgct gatggaatca cacctcagga tttcatggca   3120
```

```
tagtcttgat atgtcacgaa ctggttgtta ctttatttat ttattttaca ttgtgtttgc    3180
ccacccagat gatagaaatg ttatgtattt aaaatgtaat ctcacagtca ttgttgttgg    3240
tatcgactgt atgccaaaaa gggttttacc atgaagtcta ttaatgaata attatttatg    3300
ttacaacttg attgctttac attagttaaa attagttatt ttgtacccttt gtgcccccct    3360 tcttgttcaa ccatttatct taccaaacta tgcatcaaca aacatgcaca gtcactattc    3420
ataaatttca tattctcaaa atttaaatat taagaacaaa agttatgttt ctacttttttc    3480 caactgacaa ttctctgaac tcaaattttta taattttgaaa ttttaatatt aacattttat    3540
tttaaaactt tttgaattttc tttttttatta taaaaaagtt tggatggcat aaatttatgt    3600
atgaactatt atgaaaccac aagcaataac gaaagtgtgt ttttaagcaa aaccttatga    3660
cccatcactc aaatagtttg cgtttgattt tcaaattgac gcgcattaaa gacatataca    3720
tgcagtcttc atatcacatg tgtgcttttc ctgcttaagg tagtaggact atctcttttt    3780
tgagaaacac cgattacaac gtagatgcac acacaagtgc acattaccac cacacgtaca    3840
cactcacaca atgtttagta aggactaaaa ttgtggagct tcaagatctc tggaacgtca    3900
ggaatgtcgc ctcccacgga acgaataatc cgcacagtgt gtcaaaccat tggttcgatc    3960
ttccttggtg ggctgtgagt caaggtacta aaaaagcggt aggcgctaat ctgaattttg    4020
cctatgccta gtgcaatgac cgcctaggcg cacttatgcc ttcgtatgac aaagaaggag    4080
attttacaac aatgaaatca atggtgcgga gcctagaggg aggtatcggt ggtgagttgg    4140
agtgagaaat ccctcctctg attcaacctt tcttgacaac atagcccaaa caagaccgtc    4200 catttttcttt gcatcccccct tttcccgtct cttttgtatcg ttaggtctct ttcattcgtc    4260
atttgtatgt agcgataatg gtggtgtctg cagcttcttc cctgcattcg cttctccttt    4320
cctaccgtcg ccggaaaaag atctcatcgg tcatggagaa catagtcggg cgcctaaacc    4380
ttggcctatg gcaaaagtga ggcggtagtc tgcttagcgc ctaagtggct tcttttcatt    4440 gtccttttttt ccatgttggg agtacaaccg cactcctaac ccactaatca tagattggtt    4500
atcatctagt actttctgta ccactttttat cttacaaacg cgagggtatt gtggtggaga    4560
gccatgtatt acaactttga taatcaaaat tcaaaattca agtctctgaa gatcctttga    4620
aaaatgtgtt ttgtcaaggg caaaaaatat atctttgttt gccataccaa gatactccct    4680
ccgtaaagaa atataagagc gtttaggtca ctacttgagt gatctgaacg ctcttatatt    4740
tgtttaccag ggagtacaaa agaccatatt cttgcactaa ttttttactag tggttatgcc    4800 cgggcatatg agggtcggga aggaaggcgc aagggacatc tagtaaaaat tagtgagaga    4860
ataaccgcaa gggacattgt gcactaatgt ttaccaggga gtacaaaaga ccacattgtg    4920
cccgggcata tgagggtcgg gaaggaaggc gcaagggaca tctataagat ggctaagatc    4980
gtgaggaagg cgagggatgt caaacaagtc aaatgcatca aggatagagc agatcaactc    5040
ctggtgaagc acaaggagat caagcataga tgacaggagt actccgacaa gctattcaat    5100
ggagagatga atctaggggt ctgagattag ggaggcttta caaagaataa tgttataggga    5160 gtcattgggc accacttaag agtaatggca agcgtgacca aaaatcagtt tgttttcatg    5220
cctgagaggt tgatcatgga agtcattttc ttggtatgaa aacttatgga gaaatacagg    5280
gagcaaaaag aagacttgca tatgatgttc attgacttga aaaagtcctg caataagata    5340
ctgcaaaatg tcatgtggtg gtccttggag aaacacaaag tcccaataaa gtacattact    5400
ctcatcaagg acatgtacaa tgatctcatg acaagtgttc aaaaaagtga tggcgacact    5460
```

```
gatgaccttc cgcataaaat aggacagcac caagggtcaa cttcgagccc ttatctttt    5520 gccttgatga tggatgaggt cacaaggat atgcaaggag atattccatg gtgtattctc    5580
tttactattg atgtggtgct agtcaatgat agtagctcga ggcataatgg aaagttagag    5640
ctatggagac aaactttgga tcaaagtttt taggcttagt agaactaaaa ttgagtacat    5700
gaggtgcggt ttcagtgcta cttggcacga ggaggttagc ctcaatgggt aggtggtacc    5760
tcagaagggc accttttgat atttgggatc agtgttggaa aaggatgccg atattgatga    5820
agatgtgagc cattaaatca aagtcggatg gaggaaatga tgccaagttt ctggtgttct    5880
ctcttgacaa gatagtgcca cgaaagctaa aaggcaggtt cgataggacg gcgccccgca    5940
atgtatggcg ctgagtattg gccgactaaa atgagacata ttcaacaatt gggtgtagca    6000
gaaatgcgca tcttgagatg gatgtgtggt cacccaagaa aggatcgagt ccaaaatgat    6060
gatatacatg tagagtcggg gtagcaccga ttgaagggaa gcttgtcgaa catcgtctga    6120
gatggcttgg atatatacaa agtaggcctt tagaaacttt cgtgcatagc aggcggttaa    6180
tacatgctaa taatgtaaga gaggttgggc tagaccaaac ttgacatgga aggagtccgt    6240
gaagagagat ctgaagcact aaagtatcac acggaactag tcatggacag gggtgtgtgg    6300
aagttagcta tccacacgcc agaaccatta cttggttttg agatcttatg gatttcagct    6360
ctaccctatc aacttatttt gggactaaac gctttgttgt tgtatctctt gccttggtct    6420
tagcaactta ccatgtgcat gtcttttctc aaaaaggaaa attgaatgcc aagtatttcc    6480
tgaagttgta cattgtacaa tttgatgtcc ttgctccacg gtacatcaga tttcccatct    6540
catgatgatg caacaactag gtcttagagc aactctagca gagtcttcat ggcttccgtc    6600
gctatatttc ttttatctcg ctccatacac aggtctcgtg gcctccatat ttggaggttg    6660
gagaggtcca gtaaggagct cgccccaaaa ccaaccgcta aagttttaag cttcctcctc    6720
gcgcctcctg tcggatttga agcaacccgc gccctcggat tcttatggcg gtccattgga    6780
tgaccgccat gcggcatcat cttcttgctt gcatgtgagc agactggagg tgtgcgagta    6840
ggtcgctgca gcatttctca tagggaggcg cgcccttcga ctacccgcca ttagctgcca    6900
cccgcgtccc caagtgcctc cctaatggcg cctgcggtgg cctgtaaaag gccggcgccc    6960
tccgctctct agcttcaatg ctatcttcga cgcctcttat tccaatctca cacgcctcca    7020
atccaccatc cccttttgtcg tccacagcgc atccagagga gctccctctc gccttcaatt    7080
tttggcataa ggtggaggag tagcccgcgg atcctttgcc ccccttagg gaccagacgg    7140 acctagtcct ggagggggc tgcgcagagc aacttgtagc acccaagatt ctatcccgat    7200
cacgtgatga attcatgatc ggagcagaat cgcatttcga gcgcatagcg aggtggatat    7260
cattacaaca taccatgcac taaatagatg agaataccag ataaaggttt acactcgcca    7320
caagctacaa catgaataca tcaatacaca acaatcatca tacaggagag caggatccga    7380
ctatggatga aatcaaacaa aaagaagaac gacatctacc ctgctaatcc cgggctcctg    7440
aactggaacc catcctatga tcgacgaaga agcagaagaa gaactccaaa agcaaacatg    7500
catcgctctc acgtcaagca ttgctttatc tatacctgca cctgttgtag taatctatga    7560
gccatgggga cccagcaatc tcattaccaa gggtagcaaa actagcaaag attaatgggt    7620
atggaagggt taagtggtga ggaggctgga agcattaagc atttgtatgg tggctaactt    7680
acgagtacaa gagtaagaag agtaaactac acatagcggt cgcaaactat taatgatcaa    7740
gaagtgatcc tgaactactt atgagtcagt cataaccccca ccgtgttcac ttcccgaact    7800
ccttggaaaa gagacgatca cgtaacgcac gcggttggtg tatttttaatt gggttcagtg    7860
```

```
tcaagttctc taaaatcgga tattataaat ttttaagtcg ccacataacc gcgggcacgg   7920
cttccgaaaa gatttagccc tgcaggggtg caccaagtag tccattataa attaccacat   7980
gcatccgatg gaacatcctc acaccatgat aacacgatgc ttacaataag gaaccccggt   8040
ggacaagcca ctcgtcaaag gcaaaactaa accagcaaga ccacccggtg tgtcgtcacc   8100
ccgataagag ccgcgcctat tttctagggt tgcctaaccc ttgggatccc ttggaccacc   8160
ttactatgtg catgttttct tttcacacgg gcatttatct gctttggcat caaagctttc   8220
atttgaaaat ttgctactac cacctatatt tgtactgaca ataccttttgc atggacccac   8280 acattaggtt ttaaaatggt tctcacattc gtgttgtctt acttatctag gcatggctct   8340
tgcccagata attgttgttg gtcacaccct tctatattat cggtttgtga gtctagctga   8400
ttggatacgt gagttgttgc acactcttga actgattttg acttgatgac cattgtaacc   8460
atttgcgggt tataggctag cacatagttc aacactataa ctaattgttg gttcattcct   8520
actataggtt ataggtagc gtttgacaat tttccatgtg ttgtgggtac ttgtgacaat   8580
tgaggacacg atgtttgtgg tgacagagaa cacgttgacc tccacaaata gttaggatgc   8640
tgggtaaagc ctacgggaaa acagggagaa ggtataggag gagaataaca tgagtagtaa   8700
aaaagttaat gacttaaata caacatcaag gaacgtttct taaactgaag ctctagcact   8760
atagttaaat aatttgaatc tggcagaaat tatactaacc ttgcctagca caattccacc   8820
cctaaacttc tgttttgcaa atttcgttaa gtctatagac agaagaaaag ggtcactcta   8880
ttttcccaac aaaacttgaa caacaccaga accttaattt gaagtcagtt tcgtgctctt   8940
tctatcattt acacgtcaca gtgaaatgct ttgcaaacta tttgaccaga tgctgtatac   9000
cacatttgaa tctcatttgc atatactgac atgaaacaac gcattacaga aaagcttctg   9060
atatgtcaaa atgtatcata tatcaattct tgagattgtg catatactgg acattaatct   9120
tgtttacatg tacttccaat gactagatat ttctttctct tatgcagtat ggacaaaatt   9180
cttgaacggt atgagcgcta ttcttatgca gaaaaggttc tcgtttcaag tgaatctgaa   9240
attcaggtaa aaatgaaaaa caagcggttt gctttccttt agctatgaaa taaattgttg   9300
ccgatatcag atgttctgaa attttatttgt aggccactat attttgaatg atttccatgc   9360
gctatgaagt taattgactt gcaactatgg attgttggtc tatttgattc tcttgtaacc   9420
tattatcagt ttttcttcga tgaatgctta ggcatggtcg aataatgtaa ccaaatacca   9480
cttgaccaat ttactttcat ggctactgaa ctagactagc gtgctgattc gtacatactg   9540
cctttggaag aactacaaaa atgtgatctg actttaagag ttactaaatt agtacgtagt   9600
aaactgcaat gcatggccag atcagcaatt ctggattagc cggctgagtt tttgaagggc   9660
ttagcaacaa aaattgacaa gcttatatat tataatggct ttaaaatact tgtgtgcatc   9720
agtgaaaatc acaatatttt gattgcaata acaaaatgct atcctagatt attaagactt   9780
gttactagat tggtcattga tcttaagttc ttaggataaa ctgttgaatc tccagtcctt   9840
cggattgtat tatgctacta atggccatta aggatagccc catgacatta gttctcatct   9900 ccaattttc tgtattgttt gcgatattgc tgcagtttct tattacagct tgtctaaggc   9960
taaccatcta ggataaaaag tagatcctgc agacttagaa gatccagtta ggctcaatat  10020 tcttatttt gtaactcgga actccaggac ctcgcttcaa ttttttggcc aattttttgca  10080 caaaccaagt tgtagctcca actgagggat ccaaccagtt ctatctgatt gctgacaaac  10140
agattcagca tgtacgtatg acgaggacta tttaaacatg taattactaa cccaaaaaat  10200
```

```
attccaaatt ttatttaaat atttacctcc gctgcagcat ttttaatatt acgaaatatg    10260
atttttacat ctgatagtaa cacttgttgc agtgacataa ttgatttgaa gttatgaaaa    10320
ttcaagttca ctgcacagaa caatccttcc tgatttatgc ccccggggta aaggaggagg    10380
gttgtgatag gcttggcgag ccaacgtaaa aactcagcca ctcttatgga gatgaaaccc    10440
aaaagccaaa gagctagcta tggacagggg tgcgtggaag cttgctatcc atgtgccaga    10500
gccatgagtt ggttgcgaga tcttatgggt ttcacctcta gcctacccca acttgtttgg    10560
gactaaaggc tttgttgttg ttgttggtgg tggtggtgtc aatgttgtta aagtctcttt    10620
gttcatttct gaactaactt agcctatttg tagcatttct gtcattgttc cttcctgtcc    10680
cacccaaagt tagcaatgcg attgttattt gtttgtgcag ggaaactggt gtcacgaata    10740
taggaaactg aaggcgaagg ttgagacaat acagaaatgt caaaagtaat ttgtaacgat    10800
tttggttgat tgccagtata ttgtatacac tctgaagata aatgggactg aatttctaca    10860
tcctgcatct gcaggcatct catgggagag gatcttgaat cttgaatct caaggagttg    10920 cagcaactgg agcagcagct ggaaagctca ctgaaacata tcagatccag gaaggtactg    10980
atttaaatga tttgatacag cagcacaata tataaaaaaa caagaaaaac acttgcagag    11040
aagttcagca aagtatatct gaaatcagat tctagactga gatgttcaaa atatgtatat    11100 gcatttagt catatgctct tcatagttaa aaaaatgact aattttttc atttttgta     11160 cttgcagaac caacttatgc acgaatccat ttctgagctt cagaagaagg taagctgtca    11220
accttgcata ccttattcgg tattcgaact ggtcaacttg tcatgaagcc ttagcttgtt    11280
tcaagatttg tgacattata acatgtatgc aagtaactgg tctacatgca cgtaacctca    11340
ttacatcgtt cttgctgcag gagaggtcac tgcaggagga gaataaagtt ctccagaagg    11400
aagtaagccc gttatatcac cttatggtcc aaccggtcta aattgttccg tatagcaaat    11460
tttattgaca gaggtccgtg tcccttcccc acagctcgtg gagaagcaga aggcccatgc    11520
ggcgcagcaa gatcaaactc agcctcaaac cagctcttca tcttcttcct tcatgctgag    11580
ggatgctccc cctgccgcaa ataccaggtg atgatgtaca tcacaagtct aatcttattc    11640
agagttcaag taaccatctt ttgaattggt cgggttgttc cttgcagccc acttttggtc    11700
tctatgcagt tctgtcgggc cacatttaag taacataata ctaatatgct tgtgttcgct    11760
ttggttgtgc agcattcatc cagcggcaac aggcagagg gcagaggatg cggcagtgca    11820
gccgcaggcc ccaccccgga cggggcttcc accgtggatg gtgagccaca tcaacgggtg    11880
aagggcatcc agcccataca ggcgtactat tcagtagagg gt                      11922
```

<210> SEQ ID NO 10
<211> LENGTH: 11921
<212> TYPE: DNA
<213> ORGANISM: Triticum aestivum

<400> SEQUENCE: 10

```
gaaaggaaaa attctgctcg ttttttttgct ctgtggtgtg tgtttgtggc gagagaaaat      60
gatttgggga aagcaaaatc cggagattcg cacgtacgat cgttcgacac gtcgacgccc     120
ggcgggcccg gggtggggca tcgtgtggct gcaggaccgc ggggcccgc aaagcgggcc     180 gggccaatgg gtgctcgaca gcggctatgc tccagaccag cccggtattg catacccgcgc    240 tcggggccag atccctttaa aaaccctcc ccccctgccg gaatcctcgt tttggcctgg     300
ccatcctccc tctcctcccc tctcttccac ctcacgtcct caccaacca cctgatagcc     360 atggctccgc cgcctcgcct ccgcctgcgc cagtcggagt agccgtcgcg gtctgccggt     420
```

```
gttggagggt aggggcgtag ggttggcccg gttctcgagc ggagatgggg cgggggaagg      480
tgcagctgaa gcggatcgag aacaagatca accggcaggt gaccttctcc aagcgccgct      540
cggggcttct caagaaggcg cacgagatct ccgtgctctg cgacgccgag gtcggcctca      600
tcatcttctc caccaaggga aagctctacg agttctccac cgagtcatgg taaattaagc      660
acgcgctgtc tttaaatttg ttccccaata cgccttcgat ttcgatttcc tgcgcaccgt      720
tctggtcctg cgagacgacc cggccgaccc cagggccttc tccatttccg cgctgctgtt      780
tggtagattc cgtttgcccg ctcgctgttt ccatccgatt ctgccgtggc tgcttgctcg      840
tttttcttag aatcgatggg ggagctggcg ttccgcgcgg ccgcgatttc ttgctatggg      900
gggtagggcg cgcgatgggt cgccgggcta ttttatgctc cgccagcgcc gggaaggttg      960
ttcatctggc gtattttggg gaaattttgg tcccggacgc gccaggtggc accccaagtg     1020
gaagggttaa gacggtaatc tcttgatatt tctatcgggc tggggttatt tacgtaaaaa     1080
atatatatgg ggtaaagtg acatcgcaat ttagcatgct acctcatctt ctcatttgga     1140
atcttaacta gacgctacaa taccttgttg tctccctcat caaatctgtg cttgctgctt     1200
gaacaaatga acctcgtcat ctcggttatt tccagaattt tgttccacag gctttgctat     1260
cattcatatt ggtagctccg gccatgcggc cattttgttg cttgcttgga gatactgtct     1320
acggcacgca cggagaaaag agtcacttga ccagctaatg catggaatta ttgtctgcag     1380
ctgatgaaac tccggcatga agagtcaaac caaaaagtag agagttcctt ccaaatataa     1440
aataagagtt tctgcatact tttttttccct ttcaaccatc atagtttgcc cgtgatattt     1500
gttggtgctg gcgatggttc ttcacaaagt aaaggagtca ataaaatcac ggagactgat     1560
ccatatttcc cccacacgct gacattagtc catgttagtt tcccatttct gtctgcttcc     1620
ataattcccg tccggcgaag tactagatca gcctccacgg tttgaaagta agaaatatca     1680
taccgtcgaa aggatcgcta ctgcttagta aatatccatt gttgtttgta atcttgctga     1740
gaaagcaaca ttaccatcag cttcatggca aggacctgta tgttgaggtg ctaaatctct     1800
tctagttttg taccactgag ggtatgcgcg gcgctaacgg aaaagggtaa gtaaagtttt     1860
attggcttgc cttcagcttc cttggttgtt tgacgcatag gtgcttgcat gcatgtatca     1920
agctggtcac gtgatgaaaa cgcgtaagaa tcaaagtcgg ttaaattaag atataaatag     1980
atgcagtcat attttaagct agtgctgcac tgtgaacttc agtatctcag atcaaagtac     2040
tgaataaaat taccccctgt ttccgtgctg ttcatttgga aaagactgcc atgaacatcc     2100
gaattggtaa ccatgcatta atcagcttgc cggctttatt ttcttctctg tcgttccttg     2160
tcatttggtt tgctttgcct acctctgcac gataggcacg tgtaagtagc tcacggggac     2220
aagtaactgc tatgctttgt ctagagccta tgagacagca cgctgatgca ccacgatatt     2280
ccatggttta ggatcggaac taaaatcttg agatcttaca atattctaaa aaggcatcta     2340
tagcctgcat ataaccgact caggcacaaa atcagcattg atcgagcagg catcatatgc     2400
atacactaaa atgcagctaa tgatgtagcc tgctgatttt ctggacctgg cttggataat     2460
ggttaatgta cccaattgtt attcactcta tatcctccat ctccttatcg gtcgattaat     2520
ttaccacaca tagcaaaggt ccaaagctga cattgcaacc aactttactc atctctagac     2580
tagtaaacac gaagtaagct gttagggact gtgtgatggg tctatgttac atgcatttgt     2640
tgtcggtcta gtacttaacc aagtctggga accagttatc ctctacacct attgtgtccc     2700
taaacctata tacttgagag taaaacagaa gttattccta ggaatatctg actaagctat     2760
```

```
gggatagtca acttccattt ttgctcctgc cacatcttta cttagtccac aaacgacata    2820
tagatgatca gctagaaccg ttatttagag tttatatctg ctcattacat gtattaattc    2880
catgaaatag aagaaaaact gaataggcac acaatatagt tgaagctcgg cagatgactt    2940
cataagtgtc atatctatta accatttgac atattgttac attttttgctg cagtgatatt    3000 ttgttagctc ccagttacaa gttaactaat atatggagat cctgggcacg tacatgtaag    3060
cagatcctat cgactttcgt ggatccgctg atggaatcac acctcaggat ttcatggcat    3120
agtcttgata tgtcacgaac tggttgttac tttatttatt tattttacat tgtgtttgcc    3180
cacccagatg atagaaatgt tatgtattta aaatataatc tcacagtcat tgttgttggt    3240
atggaccgta tgccaaaaag ggttttacca tgaagtctat taatgaataa ttatttatgt    3300
tacaacttga ttgctttaca ttagttaaaa ttagttattt tgtacctttg tgccccccctt    3360 cttgttcaac catttatctt accaaactat gcatcaacaa acatgcacag tcactattca    3420
taaatttcat attctcaaaa tttaaatatt aagaacaaaa gttatgtttc tactttttcc    3480
aactgacaat tctctgaact caaatttttat aatttgaaat tttaatatta acattttatt    3540
ttaaaacttt ttgaatttct tttttattat aaaaaagttt ggatggcata aatttatgta    3600
tgaactatta tgaaaccaca agcaataacg aaagtgtgtt tttaagcaaa accttatgac    3660
ccatcactca aatagtttgc gtttgatttt caaattgacg cgcattaaag acatatacat    3720
gcagtcttca tatcacatgt gtgctttttcc tgcttaaggt agtaggacta tctctttttt    3780
gagaaacacc gattacaacg tagatgcaca cacaagtgca cattaccacc acacgtacac    3840
actcacacaa tgtttagtaa ggactaaaat tgtggagctt caagatctct ggaacgtcag    3900
gaatgtcgcc tcccacggaa cgaataatcc gcacagtgtg tcaaaccatt ggttcgatct    3960
tccttggtgg gctgtgagtc aaggtactaa aaaagcggta ggcgctaatc tgaattttgc    4020
ctatgcctag tgcaatgacc gcctaggcgc acttatgcct tcgtatgaca agaaggaga    4080 ttttacaaca atgaaatcaa tggtgcggag cctagaggga ggtatcggtg gtgagttgga    4140
gtgagaaatc cctcctctga ttcaaccttt cttgacaaca tagcccaaac aagaccgtcc    4200
attttctttg catccccctt ttcccgtctc tttgtatcgt taggtctctt tcattcgtca    4260
tttgtatgta gcgataatgg tggtgtctgc agcttcttcc ctgcattcgc ttctcctttc    4320
ctaccgtcgc cggaaaaaga tctcatcggt catggagaac atagtcgggc gcctaaacct    4380
tggcctatgg caaaagtgag gcggtagtct gcttagcgcc taagtggctc cttttcattg    4440
tccttttttc catgttggga gtacaaccgc actcctaacc cactaaccat agattggtta    4500
tcatctagta ctttctgtac cacgtttatc ttacaaacgc gagggtattg tggtggagag    4560
ccatgtatta caactttgat aatcaaaatt caaaattcaa gtctctgaag atcctttgaa    4620
aaatgtgttt tgtcaagggc aaaaaatata tctttgtttg ccataccaag atactccctc    4680
cgtaaagaaa tataagagcg tttaggtcac tacttgagtg atctgaacgc tcttatattt    4740
gtttaccagg gagtacaaaa gaccatattc ttgcactaat ttttactagt ggttatgccc    4800 ggcatatga gggtcggaa ggaaggcgca agggacatct agtaaaaatt agtgagagaa    4860
taaccgcaag ggacattgtg cactaatgtt taccagggag tacaaaagac cacattgtgc    4920
ccgggcatat gagggtcggg aaggaaggcg caagggacat ctataagatg gctaagatcg    4980
tgaggaaggc gagggatgtc aaacaagtca aatgcatcaa ggatagagca gatcaactcc    5040
tggtgaagga caatgagatc aagcatagat gacaggagta ctccgacaag ctattcaatg    5100
gagagatgaa tctagggtgc tgagattagg gaggctttac aaagaataat gttataggag    5160
```

```
tcattgggca ccacttaaga gtaatggcaa gcgtgaccaa aaatcagttt gttttcatgc    5220
ctgagaggtt gatcatggaa gtcattttct tggtatgaaa acttatggag aaatacaggg    5280
agcaaaaaga agacttgcat atgatgttca ttgacttgaa aaagtcctgc aataagatac    5340
tgcaaaatgt catgtggtgg tccttggaga acacaaagt cccaataaag tacattactc    5400
tcatcaagga catgtacgat gatctcatga caagtgttca aaaagtgat ggcgacactg    5460 atgaccttcc gcataaaata ggacagcacc aagggtcaac ttcgagccct tatctttttg    5520
ccttgatgat ggatgaggtc acaagggata tgcaaggaga tattccatgg tgtattctct    5580
ttacgattga tgtggtgcta gtcaatgata gtagctcgag gcataatgga aagttagagc    5640
tatggagaca aactttggat caaagttttt aggcttagta gaactaaaat tgagtacatg    5700
aggtgcggtt tgagtactac ttggcacgag gaggttagcc tcaatgggta ggtggtacct    5760
cagaagggca ccttttgata tttgggatca gtgttggaaa aggatgccga tattgatgaa    5820
gatgtgagcc attaaatcaa agtcggatgg aggaaatgat gccaagtttc tggtgttctc    5880
tcttgacaag atagtgccac gaaagctaaa aggcaggttc gataggacgg cgccccgcaa    5940
tgtttggcgc tgagtattgg ccgactaaaa tgagacatat tcaacaattg ggtgtagcag    6000
aaatgcgcat cttgagatgg atgtgtggtc acccaagaaa ggatcgagtc caaaatgatg    6060
atatacatgt agagtcgggg tagcaccgat tgaagggaag cttgtcgaac atcgtctgag    6120
atggcttgga tatatacaaa gtaggccttt agaaactttc gtgcatagca ggcggttaat    6180
acatgctaat aatgtaagag aggttgggct agaccaaact tgacatggaa ggagtccgtg    6240
aagagagatc tgaagcacta agtatcaca cggaactagt catggacagg ggtgtgtgga    6300
agttagctat ccacacgcca gaaccattac ttggttttga gatcttatgg atttcagctc    6360
taccctatcc aacttatttg ggactaaacg cttttgttgtt gtatctcttg ccttggtctt    6420
agcaacttac catgtgcatg tcttttctca aaaaggaaaa ttgaatgcca agtatttcct    6480
gaagttgtac attgtacaat ttgatgtcct tgctccacgg tacatcagat ttcccatctc    6540
atgatgatgc aacaactagg tcttagagca actctagcag agtcttcatg gcttccgtcg    6600
ctatatttct tttatctcgc tccatacaca ggtctcgtgg cctccatatt tggaggttgg    6660
agaggtccag taaggagctc gccccaaaac taaccgctaa agttttaagc ttcctcctcg    6720
cgcctcctgt cggatttgaa gcaacccgcg ccctcggatt cctatggcgg tccattggat    6780
gaccgccatg cggcatcatc ttcttgcttg catgtgagca gactggaggt gtgcgagtag    6840
gtcgctgcag catttctcat agggaggcgc gcccttcgac tacccgccat agctgccac    6900 ccgcgtcccc aagtgcctcc ctaatggcgc ctgcggtggc ctgtaaaagg ccggcgccct    6960
ccgctctcta gcttcaatgc tatcttcgac gcctcttatt ccaatctcac acgcctccaa    7020
tccaccatcc cctttgtcgt ccacagcgca tccagaggag ctccctctcg ccttcaattt    7080
ttggcataag gtggaggagt agcccgcgga tccttttgccc ccctttaggg accagacgga    7140
cctagtcctg gagggggct gcgcagagca acttgtagca cccaagattc tatcccgatc    7200
acgtgatgaa ttcatgatcg gagcagaatc gcatttcgag cgcatagcga ggtggatatc    7260
attacaacat accatgcact aaatagatga gaataccaga taaggttta cactcgccac    7320 aagctacaac atgaatacat caatacacaa caatcatcat acaggagagc aggatccgac    7380
tatggatgaa atcaaacaaa aagaagaaag acatctaccc tgctaatccc gggctcctga    7440
actggaaccc atcctatgat cgacgaagaa gcagaagaag aactccaaaa gcaaacatgc    7500
```

```
atcgctctca cgtcaagcat tgctttatct atacctgcac ctgttgtagt aatctatgag    7560
ccatggggac ccagcaatct cattaccaag ggtagcaaaa ctagcaaaga ttaatgggta    7620
tggaagggtt aagtggtgag gaggctggaa gcattaagca tttgtatggt ggctaactta    7680
cgagtacaag agtaagaaga gtaaactaca catagcggtc gcaaactatt aatgatcaag    7740
aagtgatcct gaactactta tgagtcagtc ataacccacc cgtgttcact tcccgaactc    7800
cttggaaaag agacgatcac gtaacgcacg cggttggtgt attttaattg ggttcagtgt    7860
caagttctct aaaatcggat attataaatt tttaagtcgc cacataaccg cgggcacggc    7920
ttccgaaaag atttagccct gcaggggtgc accaagtagt ccattataaa ttaccacatg    7980
catcggatgg aacatcctca caccatgata acacgatgct tacaataagg aaccccggtg    8040
gacaagccac tcgtcaaagg caaaactaaa ccagcaagac cacccggtgt gtcgtcaccc    8100
cgataagagc cgcgcctatt ttctagggtt gcctaaccct tgggatccct tggaccacct    8160
tactatgtgc atgttttctt ttcacacggg catttatctg ctttggcatc aaagctttca    8220
tttgaaaatt tgctactacc acctatattt gtactgacaa taccttttgca tggacccaca    8280 cattaggttt taaaatggtt ctcacattcg tgttgtctta cttatctagg catggctctt    8340
gcccagataa ttgttgttgg tcacacccTT ctatattatc ggtttgtgag tctagctgat    8400
tggatacgtg agttgttgca cactcttgaa ctgattttga cttgatgacc attgtaacca    8460
tttgcgggtt ataggctagc acatagttca acactataac taattgttgg ttcattccta    8520
ctataggtta tagggtagcg tttgacaatt ttccatgtgt tgtgggtact tgtgacaatt    8580
gaggacacga tgtttgtggt gacagagaac acgttgacct ccacaaatag ttaggatgct    8640
gggtaaagcc tacgggaaaa cagggagaag gtataggagg agaataacat gagtagtaaa    8700
aaagttaatg acttaaatac aacatcaagg aacgtttctt aaactgaagc tctagcacta    8760
tagttaaata atttgaatct ggcagaaatt atactaacct tgcctagcac aattccaccc    8820
ctaaacttct gttttgcaaa tttcggtaag tctatagaca gaagaaaagg gtcactctat    8880
tttcccaaca aaacttgaac aacaccagaa ccttaatttg aagtcagttt cgtgctcttt    8940
ctatcattta cacgtcacag tgaaatgctt gcaaactat ttgaccagat gctgtatacc    9000
acatttgaat ctcatttgca tatactgaca tgaaacaacg cattacagaa aagcttctga    9060
tatgtcaaaa tgtatcatat atcaattctt gagattgtgc atatactgga cattaatctt    9120
gtttacatgt acttccaatg actagatatt tcttttctctt atgcagtatg gacaaaattc    9180
ttgaacggta tgagcgctat tcttatgcag aaaaggttct cgtttcaagt gaatctgaaa    9240
ttcaggtaaa aatgaaaaac aagcggtttg ctttccttta gctatgaaat aaattgttgc    9300
cgatatcaga tgttctgaaa tttatttgta ggccactata ttttgaatga tttccatgcg    9360
ctatgaagtt aattgacttg caactatgga ttgttggtct atttgattct cttgtaacct    9420
attatcagtt tttcttcgat gaatgcttag gcatggtcga ataatgtaac caaataccac    9480
ttgaccaatt tactttcatg gctactgaac tagactagcg tgctgattcg tacatactgc    9540
ctttggaaga actacaaaaa tgtgatctga ctttaagagt tactaaatta gtacgtagta    9600
aactgcaatg catggccaga tcagcaattc tggattagcc ggctgagttt ttgaagggct    9660
tagcaacaaa aattgacaag cttatatatt ataatggctt taaaatactt gtgtgcatca    9720
gtgaaaatca caatattttg attgcaataa caaaatgcta tcctagatta ttaagacttg    9780
ttactagatt ggtcattgat cttaagttct taggataaac tgttgaatct ccagtccttc    9840
ggattgtatt atgctactaa tggccattaa ggatagcccc atgacattag ttctcatctc    9900
```

```
caatttttct gtattgtttg cgatattgct gcagtttctt attacagctt gtctaaggct    9960
aaccatctag gataaaaagt agatcctgca gacttagaag atccagttag gctcaatatt   10020
cttattttg taactcggaa ctccaggacc tcgcttcaat ttttggcca atttttgcac    10080
aaaccaagtt gtagctccaa ctgagggatc caaccagttc tatctgattg ctgacaaaca   10140
gattcagcat gtacgtatga cgaggactat ttaaacatgt aattactaac ccaaaaaata   10200
ttccaaattt tatttaaata tttacctccg ctgcagcatt tttaatatta cgaaatatga   10260
tttttacatc tgatagtaac acttgttgca gtgacataat tgatttgaag ttatgaaaat   10320
tcaagttcac tgcacagaac aatccttcct gatttatgcc cccggggtaa aggaggaggg   10380
ttgtgatagg cttggcgagc caacgtaaaa actcagccac tcttatggag atgaaaccca   10440
aaagccaaag agctagctat ggacaggggg gcgtggaagc ttgctatcca tgtgccagag   10500
ccatgagttg gttgcgagat cttatgggtt tcacctctag cctaccccaa cttgtttggg   10560
actaaagtct tgttgttgt tgttggtggt ggtggtgtca atgttgttaa agtctctttg   10620
ttcatttctg aactaactta gcctatttgt agcatttctg tcattgttcc ttcctgtccc   10680
acccaaagtt agtaatgcga ttgttatttg tttgtgcagg gaaactggtg tcacgaatat   10740
aggaaactga aggcgaaggt tgagacaata cagaaatgtc aaaagtaatt tgtaacgatt   10800
ttggttgatt gccagtatat tgtatacact ctgaagataa atgggactga atttctacat   10860
cctgcatctg caggcatctc atgggagagg attttgaatc tttgaatctc aaggagttgc   10920
agcaactgga gcagcagctg gaaagctcac tgaaacatat cagatccagg aaggtactga   10980
tttaaatgat ttgatacagc agcacaatat ataaaaaaac aagaaaaaca cttgcagaga   11040
agttcagcaa agtatatctg aaatcagatt ctagactgag atgttcaaaa tatgtatatg   11100
cattttagtc atatgctctt catagttaaa aaaaatgact aatttttttc attttttgta   11160
cttgcagaac caacttatgc acgaatccat ttctgagctt cagaagaagg taagctgtca   11220
accttgcata ccttattcgg tattcgaact ggtcaacttg tcatgaagcc ttagcttgtt   11280
tcaagatttg tgacattata acatgtatgc aagtaactgg tctacatgca cgtaacctca   11340
ttacatcgtt cttgctgcag gagaggtcac tgcaggagga gaataaagtt ctccagaagg   11400
aagtaagccc gttatatcac ctttggtcca accggtctaa attgttccgt atagcaaatt   11460
ttattgacag aggtccgtgt cccttcccca cagctcgtgg agaagcagaa ggcccatgtg   11520
gcgcagcaag atcaaactca gcctcaaacc agctcttcat cttcttcctt catgctgagg   11580
gatgctcccc ctgccgcaaa taccaggtga tgatgtacat cacaagtcta atcttattca   11640
gagttcaagt aaccatcttt tgaattggtc gggttgttcc ttgcagccca cttttggtct   11700
ctatgcagtt ctgtcgggcc acatttaagt aacataatac taatatgctt gtgttcgctt   11760
tggttgtgca gcattcatcc agcggcaaca ggcgagaggg cagaggatgc ggcagtgcag   11820
ccgcaggccc caccccggac ggggcttcca ccgtggatgt tgagccacat caacgggtga   11880
agggcatcca gcccatacag gcgtactatt cagtagaggg t                       11921
```

<210> SEQ ID NO 11
<211> LENGTH: 1309
<212> TYPE: DNA
<213> ORGANISM: Triticum aestivum

<400> SEQUENCE: 11

```
cattcccaca ggccacagct agccatgtct cggtccacgt taatcatcct cgctctcctc      60
```

```
gccgtgagca gcgccgtcgc tgctccccgt gctctcgcgg cacgggagct cgccggcaac      120
gatgccatcg ccgtcgacgc tgccatggtg ttgaggcacg agaagtggat ggcggagcac      180
gggcgcacgt acgcggacga ggaggagaag gcgcggcggc tggaggtatt cctcgccaac      240
gccaagttca tcgactcgtt taacgccctc accgtcagca gcggggagca tggactggag      300
ggccatgggc gccgtcaccg gcgtcaagga ccaaggctct tgcggtacgt acaatcaaca      360
cgacaacact ggcacgcacg ctactgcaga tgcatacaaa ttaagctgca gaacattgca      420
agcaccggaa catttaccac ctggatcaag ctttttttaga cttctaaaaa tgttaaaaaa      480
gaacttgcaa gtggcaacac gcgcgtagga aaagtaaaaa attgacgtga gattgtaccg      540
ggatgactag agtctacaaa caagtcatgc gtgcactttt cggtcaaccc agacagcaag      600
aggagtcagc gttcacttta cttcaatgat tggagtatca ttcttaattt tccattttgg      660
acatgtccta agcttaattg cctctgtttc atcatttaat caaataactt gggtgacatg      720
catatgcagg ctgctgctgg gcgttctcgg cggtggcggc ggtggaaggg ctgaccaaga      780
tccgcacggg gcggcttatg tcactgtcgg agcagcagct ggtggactgc gacgtgaacg      840
gcgacgacga gggctgcgcc ggcggcctca tggacaacgc cttcgagtac atggtccgcc      900
gcggcggcct caccacggag tcgtcctacc cgtaccgcgg cacggacggg tcgtgccgcc      960
gctcggcctc ggccgcgtcc atccgtgggt acgaggacgt gccggccaac aacgaggcgg     1020
cgctgatggc ggtcgtggcg caccagcccg tgtccgtggc catcaacggc ggcgacagtg     1080
tgttccggtt ctacgacagc ggcgtgctgg gcgggtccgg ctgcggcacg gagctcaacc     1140
acgccatcac ggcggtcggg tacggcacgg cgagcgacgg cagcaagtac tggatcatga     1200
agaactcgtg gggcacgtcg tggggcgagc gcggctacgt caggatccgc gcggggagc     1260 gcggcgaggg cgtctgcggc ctcgcccagc tcgcgtcctc cctgtctag              1309

<210> SEQ ID NO 12
<211> LENGTH: 1314
<212> TYPE: DNA
<213> ORGANISM: Triticum aestivum

<400> SEQUENCE: 12
cattcccaca ggccacagct agccatgtct cggtccacgt taatcatcct cgctctcctc       60
gccgtgagca gcgccgtcgc cgctccccgt gctctcgcgg cacgggagct cgccggcaac      120
gatgccatcg ccgtcgacgc tgccatggtg tcgaggcacg agaagtggat ggcggagcac      180
gggcgcacgt acgccgacga ggaggagaag gcgcggcggc tggaggtatt cctcgccaac      240
gccaagttca tcgactcgtt tagcgccctc accgtcagca gcggggagca tggactggag      300
ggccatgggc gccgtcaccg gcgtcaagga ccaaggctct tgcggtacgt acaatcaaca      360
cgacaacact ggcacgcacg ctactgcaga tgcatacaaa ttaagctgca gaacattgca      420
agcaccggaa catttaccac ctggatcaag ctttttttaga cttctaaaaa tgttaaaaaa      480
gaacttgcaa gtggcaacac gcgcgtagga aaagtaaaaa attgacgtga gattgtaccg      540
ggatgaccag agtctacaaa caagtcatgc gtgcactttt cggtcaaccc agacagcaag      600
aggagtcagc gttcacttta cttcaatgat tggagtatca ttcttaattt tccatttcgg      660
acatgtccta agcttaattg cctccgtttc atcatgtact aatccaataa ctttgggtga      720
catgcatatg caggctgttg ctgggcgttc tcggcggtgg cggcggtgga agggctgacc      780
aagatccgca cggggcggtt ggtgtcgctg tcggagcagc agctggtgga ctgcgacgtg      840
aacggcgacg acgagggctg cgccggcggc ctcatggaca acgccttcga gtacatggtc      900
```

| cgccgcggcg gcctcaccac ggagtcgtcc tacccgtacc gcggcacgga cgggtcgtgc | 960 |
| cgccgctcgg cctcggccgc gtccatccgg gggtacgagg acgtgccggc caacaacgag | 1020 |
| gccgcgctga tggcggccgt ggcgcaccag cccgtgtccg tggccatcaa cggcggcgac | 1080 |
| agcgtgttcc ggttctacga cagcggcgtg ctgggcgggt ccggctgcgg cacggagctc | 1140 |
| aaccacgcca tcacggcggt cgggtacggc acggcgagcg acggcagcaa atactggatc | 1200 |
| atgaagaact cgtggggcgc gtcgtgggge gagcgcggct acgtcaggat ccgccgcggc | 1260 |
| gtgcgcggcg agggcgtctg cggcctcgcc cagctcgcgt cctaccctgt ctag | 1314 |

<210> SEQ ID NO 13
<211> LENGTH: 907
<212> TYPE: DNA
<213> ORGANISM: Triticum aestivum

<400> SEQUENCE: 13

| atcaagtggg aagcgccatc caaattagcc gagctcgcac actactgccg cgtcagctct | 60 |
| tgcggggaag acgagccgcg ccggagtgac gtcgtacggc ttcccgttcc cctctcggtt | 120 |
| tcccgacgcc tctcttggct cacccgcccg cccgccgccg cctgccact tcctccgcgc | 180 |
| gtgaaagccc accgcctatt ccccttccct tcgctctccg acgccgggcg ccaccccggc | 240 |
| ggatcgagcg ggcgggcggt tagttagttg cgcatcgctg ttgcttgctt cttctaccgt | 300 |
| ttggcgcagg gaggaggagc gtgggggtaa catcgctgtc ccactccac ccgggtgctg | 360 |
| cccctcctg tttcccttctc actcactgcg tgtgcttatc cgcgccgggc gaatccaatc | 420 |
| ccccactctc ccccgtcctt ctccagaaaa gtcgcggctt tcccccgcc cctcatgat | 480 |
| tcccgtcgat tcctcctccg cccatttgcc cctccgcgtc gcagaatccc ccgcgccacc | 540 |
| gctgctgacc gtcgcgccgt aggggaggg gcaggagcga ggagcctagc tcggggtgg | 600 |
| tcgtggtggc gaccgcggc gagatgtcgt cgtcgcggtc caacaaccgg ccggcgtgct | 660 |
| cgcggggag ctcggcgcgc tccaagcaca gcgagcgggt ggtggcgcag acgcccgtgg | 720 |
| acgcgcgcct gcacgccgag ttcgagggct cgcagcgcca cttcgactat tcctcctcgg | 780 |
| tcagcgcgct caaccgctcc ggggccagca ccagctccgc cgtctccgcc tacctccaga | 840 |
| acatgcagcg gggccgctac atccagcct tcggctgcct gctcgcgatc cacccggagt | 900 |
| ccttcgc | 907 |

<210> SEQ ID NO 14
<211> LENGTH: 907
<212> TYPE: DNA
<213> ORGANISM: Triticum aestivum

<400> SEQUENCE: 14

| atcaagtggg aagcgccatc caaattagcc gagctcgcac actactgccg cgtcagctct | 60 |
| tgcggggaag acgagccgcg ccggagtgac gtcgtacggc ttcccgttcc cctctcggtt | 120 |
| tcccgacgcc tctcttggct cacccgcccg cccgccgccg cctgccact tcctccgcgc | 180 |
| gtgaaagccc accgcctatt ccccttccct tcgctctccg acgccgggcg ccaccccggc | 240 |
| ggatcgagcg ggcgggcggt tagttagctg cgcatcgctg ttgcttgctt cttctaccgt | 300 |
| ttggcgcagg gaggaggagc gtgggggtaa catcgctgtc ccactccac ccgggtgctg | 360 |
| cccctcctg tttcccttctc actcactgcg tgtgcttatc cgcgccgggc gaatccaatc | 420 |
| ccccactctc ccccgtcctt ctccagaaaa gtcgcggctt tcccccgcc cctcatgat | 480 |

```
tcccgtcgat tcctcctccg cccatttgcc cctccgcgtc gcagaatccc ccgcgccacc        540
gctgctgacc gtcgcgccgt aggggagggg gcaggagcga ggagcctagc tcggggtgg         600 tcgtggtggc gaccggcggc gagatgtcgt cgtcgcggtc caacaaccgg ccggcgtgct        660 cgcggggag ctcggcgcgc tccaagcaca gcgagcgggt ggtggcgcag acgcccgtgg         720
acgcgcgcct gcacgccgag ttcgagggct cgcagcgcca cttcgactat tcctcctcgg        780
tcagcgcgct caaccgctcc ggggccagca ccagctccgc cgtctccgcc tacctccaga        840
acatgcagcg gggccgctac atccagccct tcggctgcct gctcgcgatc cacccggagt       900
ccttcgc                                                                907
```

```
<210> SEQ ID NO 15
<211> LENGTH: 949
<212> TYPE: DNA
<213> ORGANISM: Triticum aestivum

<400> SEQUENCE: 15
ctgatctgct tgcagcaacc cgggtacgac atcatagcgc agttcatgat cggctacgcg         60
ctacccggca agcccatcgc caacctgctc ttcaagatct acggccggat cagcaccgtg        120
cacgcgctct ccttcctcgc cgacctcaag ctcggccact acatgaagat cccgccacgc        180
tgcatgtaca ccgcccaggt acgtgacaga gatcgatctc tcagccccca caatgcacta        240
gatgctcatc actcgctgaa ctaaccggcg tgcgcttggc cggtgcagct ggtgggcacg        300
gtggtcgccg gcgtggtgaa cctggcggtg gcgtggtgga tgctggacag catcgacaac        360
atctgcgacg tggaggcgct gcacccggac agccctggga cgtgccccaa gtaccgggtc        420
accttcgacg cgtcggtgat ctggggcctc atcgggccgg ggcgcctctt cggccagcac        480
gggttgtacc ggaacctggt gtggctgttc gtggtcggcg ccgtgctgcc ggtgccggtg        540
tggctgctga gccgggcgtt cccggagaag aagtggatcg cgctcgtcaa cgtgcccgtc        600
atctcctacg gcttcgccgg gatgccgccg gccacgccca caacatcgc cagctggctc         660 gtcaccggca ccgtcttcaa cttcttcgtc ttcaggtacc gcaaggggtg gtggcagaag        720
tacaactacg tgctatcggc ggcgctcgac gccggcaccg ccttcatggg ggtgctcatc        780
ttcttcgcgc tccagaacgc gcaccacgac ctcaagtggt ggggcaccga ggtcgaccac        840
tgcccgctcg ccacctgccc caccgcgccc ggcatcgtcg tcaagggctg cccggtcttc        900
tgagcactga gctcgccgga gcatcatcgg acactgcccg ccatgtatg                   949
```

```
<210> SEQ ID NO 16
<211> LENGTH: 948
<212> TYPE: DNA
<213> ORGANISM: Triticum aestivum

<400> SEQUENCE: 16
ctgatctgct tgcagcaacc cgggtacgac atcatagcgc agttcatgat cggctacgcg         60
ctacccggca agcccatcgc caacatgctc ttcaagatct acggccggat cagcaccgtg        120
cacgcgctct ccttcctcgc cgacctcaag ctcggccact acatgaagat cccgccacgc        180
tgcatgtaca ccgcccaggt acgtgacaga gatcgatctc tcagccccca caatgcacta        240
gatgctcatc actcgctgaa ctaaccggcg tgcgcttggc cggtgcagct ggtgggcacg        300
gtggtcgccg gcgtggtgaa cctggcggtg gcgtggtgga tgctggacag catcgacaac        360
atctgcgacg tggaggcgct gcacccggac agccctggga cgtgccccaa gtaccgggtc        420
accttcgacg cgtcggtgat ctggggcctc atcgggccgg ggcgcctctt cggccagcac        480
```

```
gggttgtacc ggaacctggt gtggctgttc gtggtcggcg ccgtgctgcc ggtgccggtg      540
tggctgctga gccgggcgtt cccggagaag aagtggatcg cgctcgtcaa cgtgcccgtc      600
atctcctacg gcttcgccgg gatgccgccg gccacgccca ccaacatcgc cagctggctc      660
gtcaccggca ccgtcttcaa cttcttcgtc ttcaggtacc gcaaggggtg gtggcagaag      720
tacaactacg tgctatcggc ggcgctcgac gccggcaccg ccttcatggg ggtgctcatc      780
ttcttcgcgc tccagaacgc gcaccacgac ctcaagtggt ggggcaccga ggtcgaccac      840
tgcccgctcg ccacctgccc gaccgcgccc ggcatcgtcg tcaagggctg cccggtcttc      900
tgagcactga gctcgccgga gcatcatcgg acactgcccg ccatgtag                   948

<210> SEQ ID NO 17
<211> LENGTH: 884
<212> TYPE: DNA
<213> ORGANISM: Triticum aestivum

<400> SEQUENCE: 17
gttctcacat tcgtggttg tttgtcctgg gactttcatt ctgcagttgg ttttctctgg       60
acatgcctct ggaggctct tgaaatacaa tcccgaaaca aaggagacaa cagtccttca      120
ccgcaacctc cagtttccca acggagtgag cttaagcaag gatggctcgt tcttcgtctt      180
ctgtgaagga tctcgtggaa ggtctataca ctcttccctc catttggttc aggatttcat      240
acatgtatac ttgaaattag tcactgatta ttgtgtcctt atccaaacag gttgagcaga      300
tactggctga aaggtgagaa ggcaggcacc gtcgatctct tcgccatcct gcctgggttc      360
ccggacaacg tgaggaccaa cgacaagggc gaattctggg tggccatcca ttgccgacgc      420
agcgcatacg cccggctctt gagtcgccgc gtccagctca gaaagttctt gctcagcctc      480
ccgatccccg ccaagtatca ctacctgatg caaatcggcg gcaatctgca cgcgctcatc      540
atcaagtaca gccctgaagg cgaggtgctt gacatcttgg aggacactaa agggcaggtg      600
gtgagagctg tgagcgaagt ggaggagaag gatggcaagc tctggatagg atctgttctc      660
atgcccttca ttgccgtctt tgactacgcc aaggaatcct aagccgccct tttgccggga      720
tacatgggta agagagtatg aaatccacga acgccgttgc acactattgc ttcatccaaa      780
taaatctagt gttggaagca acctagaatt gcttgatgtt tcagccttt cctagtagca      840 actgtaactc actgacattt tagtttgtcc ctgggatctt tcaa                      884

<210> SEQ ID NO 18
<211> LENGTH: 886
<212> TYPE: DNA
<213> ORGANISM: Triticum aestivum

<400> SEQUENCE: 18
cggcagcact tttcatgatg tttgtcctgg gactttcatt atgcagtggg ttttctctgg       60
agatgcctct ggaggctct tgaaatacaa tcccgaaaca aaggagacaa cagtccttca      120
ccgcaacctc cagtttccca acggagtgag cttaagcaag gatggctcgt tcttcgtctt      180
ctgtgaagga tctcgtggaa ggtctataca ctcttccctc catttggttc agaatttcat      240
acatgtatac ttgaaattag tcactgatta ttgtgtcctt atccaaacag gttgagcaga      300
tactggctga aaggtgagaa ggcaggcacc gtcgatctct tcgccatcct gcctgggttc      360
ccggacaacg tgaggaccaa cgacaagggc gaattctggg tggcaatcca ttgccgacgc      420
agcgcatacg cccggctctt gagtcgccgc gtccagctca gaaagttctt gctcagcctc      480
```

| | |
|---|---|
| ccgatcccg ccaagtatca ctacctgatg caaatcggcg gcaatctgca cgcgctcatc | 540 |
| atcaagtaca gccctgaagg cgaggtgctt gacatcttgg aggacactaa agggcaggtg | 600 |
| gtgagagctg tgagcgaagt ggaggagaag gatggcaagc tctggatagg atctgttctc | 660 |
| atgcccttca ttgccgtctt tgactacgcc aaggaatcct aagccgccct tttgccggga | 720 |
| tacatgggta agagagtatg aaatccacga acgccgttgc acactattgc ttcatccaaa | 780 |
| ataaatctag tgttggaagc aacctagaat tgcttgatgt ttcagccttt tcctagtagc | 840 |
| aactgtaact cactgacatt ttagtttgtc cctggggatc tttcaa | 886 |

<210> SEQ ID NO 19
<211> LENGTH: 9611
<212> TYPE: DNA
<213> ORGANISM: Triticum aestivum

<400> SEQUENCE: 19

| | |
|---|---|
| cgcgccaggc cgccgcccac acttcccgcc gagcctaaaa gatgcaagaa gagagagggg | 60 |
| agaggctaga gggtgatgga ggggctcacc gcaccaataa caatggatag cgctgctgcg | 120 |
| gtggatttcc ctctggctga atttgtcccc caccccaccc gctcaccac actcgcgtga | 180 |
| attgatttgc gccattcgcc gttgccgtct gtttttaatc tttttcaagc gggtgcaggt | 240 |
| gagctcgggc ccgactgagg gccttttga ttcataggat tgcaaaaaca caggaatagg | 300 |
| aaaaacgcag gattgaaatg gcatgtccat tggatcccta taggatttga gtttgtttga | 360 |
| ttgtgttaag ggaaaaacaa aggattttt ttcaagaggt ttgagtggat gctagaattt | 420 |
| ctgtgaaatg tagtacaaat gaacccttag aaaaaaatac aggattcaat cctacgaatc | 480 |
| aaacgatcaa cgtagaaaaa attcctaagg attctaatcc ttcaaagatc ttatgaaaat | 540 |
| cctttgaatc aaagagacct tgaagttgtg gagctcaaaa tttatagtat tcctctagaa | 600 |
| gaagctcgaa attacttcta tactgattaa ctgatgtgtg tgcaaaaaga aagaactga | 660 |
| ttaaccgatg aaacaaccag tgtttggtac acttctgcgg gggtgaattg gtgagctgga | 720 |
| cagggcccac ccgcagcaaa ttgcttctat tatggtggcc gcctcctctc ctctccctgg | 780 |
| ccagatccca aatttgaaat cgcccaacgt ctccagactc ctctccgctc cccatttcaa | 840 |
| aacctccaat ctcgtcctct ccccaccccc acccaccgcc gccggccccgc cgcgccgctg | 900 |
| ctctgcccag atcccgcccg ccgcaagccc atccctgcct ccgtcgcagc cgcagcggta | 960 |
| cccgcagccg cagccgcgat gctgtcggac ggtggcgacg acgacagctc cgcccccgcg | 1020 |
| cggttcgagc tgcaggagga cccctccttc tggaaggaca caacgtgca ggtagtgatt | 1080 |
| cttctcgccc ccctcgccgg gagctcccgc gcctccgcct cctcgattct cccctggcag | 1140 |
| cggcgtcccg atctagtttc gcccgcgcc gcgcgctgcg ccgttggatc atttcgtcga | 1200 |
| gcacctaggt tcgtcaggtc cggtccgcgc taaccgctcc gccccgcagg tcgtgattcg | 1260 |
| tgtccggccg ctcagcagca gcgagatatc ggtgcagggg gacaagaggt gcgtcaggca | 1320 |
| ggacagcggc cagagcatta cctggacctg ccacccggag tccggttca cctttgatct | 1380 |
| agtcgccgat gagcacatca cgcaggtata ctccttgttc ctgttcgccc gttcctttac | 1440 |
| ttgttccgca gatgtgtaaa tactcttgtg cttgtgctgt ataggagagt cttttcaagg | 1500 |
| ttgctggggt gcccatggtg gagaactgca tggctggcta taacagctgc atgtttgcct | 1560 |
| atgggcaggt gagctacagc ctccacctcc acctgctgtt gcagtgtgct tactctcttt | 1620 |
| tatttgcact ttgaatcatt gagcttacaa aagtatcctg tttcttagac cggtagtggc | 1680 |
| aagacccaca cgatgcttgg ggacatagaa aatggcacac ggggaaacaa tgagaactgt | 1740 |

```
ggtatgacgc ctcgagtgtt tgagcatctc ttcctaagaa tccagaaggc aagctctgat    1800
gatatgttga ttctgatgcc taattttgtg ctgtagatgg tgtactgttt ctgaggtaaa    1860
cttttcaatt gctgtttgca ggaaaaggaa atacgaagag atgaaaagct cagttttact    1920
tgcaagtgct cattcctgga gatatataat gagcagattc tggatttgct caatccaaat    1980
gcaacaaact tacaggtaat tcactgaaat ctagtgtctg cgtataccta tttggtggtt    2040
gcatctttgt cgtgacactg ttgggaaaag tttacaaagt ttgcatctaa cttacagcta    2100
tgcttttctt ttacagttaa gggaggatgc gaaaagggt atgcatgttg agaatctgac    2160
tgaacatgag gtttctaatg cccgagaagc actgcaacaa cttatcgagg tcagtgtccc    2220
aaaaacagcg tagtaggcct gattttggca gtacctgtgt cgatgattgc agaatgatta    2280
atataacatg cctacatcaa ttttgctcaa ggttcttcgc acaaacagtc aaatacacac    2340
atataaacta agtgtataaa tataaacatg cttttttcaa tctccaattc cttgtctcct    2400
tgacttctct tttgatcgtt ttagcaactg tcactgacaa ttacagccac ttacttttca    2460
aaactatata cttaaacatt acacaataca gttttctttt gatgcagtat gaatagaaat    2520 ccgtaaaatat gaattttaaa taggaaaaac aattagcata ttatacttta ctgacaagat    2580
ggagtgactg aactatttag aacatggact gcagttaagc tgatcagatc catcattttc    2640
gcatggcatg ttacactagt ttttccttta tctctaggga ttgcagcaag ttttttccctc    2700 cctttattag tcacattatt atctgtgtta gtttcactaa atcactagct aaattctgca    2760
ttttctcttc aggggcagc aaacagaaag gtggcatcta ccaatatgaa ccgagcaagt    2820
agccgttctc atagtgtatt cacttgtctt atagagagca aggtatagtt tttgtgtaat    2880
aggaagcaaa acattcttgc cttaactttc aaagatattg ctagaccagc atatatttgt    2940 ccctaccta atgcatgcat atgtattgat gcacttaatc ttctaactga actatcaacc    3000
ttacagtggg aatctcaagg tatcaagcat catcgatttt ctcatcttaa ccttgttgac    3060
cttgctggct cagagaggta agttccacat gtaaccttgc tttttttgt tacgtatgat    3120 cttgtatttc agagccacca caaatatacc tgttatgctt ctcaagtctc ctattcttgc    3180
aactgaacgt ggatgatgtg tgatgtgcag gcaaagagt tcaggtgcag aaggggaacg    3240
cttgaaggaa gcttcgaaca tcaacaagtc actctcaacc ttagggttag ttgtggagct    3300
tcaattcttt acctcagata atactaaact gttcatagct tgacttgatt cagtttaatc    3360
atttcactgt ttccctatgg gattgttaca gacatgttat taccagcctt attgctgtgt    3420
caaacaaaaa gtcacagcat gttccctacc gagattcaaa attgacattt ctgctgcagg    3480
taatatgcac agctgaagtg gtagatttct cacgttatgt ttttgacatc tctgatgtta    3540
actttgttta tttatacatt ttcatctctt tccaggactc acttggaggt aactccaaga    3600
ccactataat tgcaaatata agcccatcta gctggtagac ttctaaacac gatttctttt    3660
tccttttctg caaaaggctt gctatagtta catgcatctt actgatattt taatttgtat    3720
ttctagctgt gcagctgaga cattgagcac attaaaattc gcgcaacggg ctaagcacat    3780
acggaataat gtatgtcatg aacatgtctt attgacttgt ttttaatatg caaaacaata    3840
actaattgtt gttttttgtag ctattataa atgaggatgc ctctggtgat gtgctgagca    3900
tgcgtttaga gatccaacat ctcaaggtat agatgatgaa tttcaattc ggtttaatga    3960 aaaatattct gtgcactgga ttgcaataag ttccaggtta acatgttct tctaattatg    4020 gtccttgtg ctatgattga cgtttgttgt taattaacag tggcctgtgc ctgatatttt    4080
```

```
ttgttgcaga gcgttaatat gttttgttgt acacaatcta atgctttgct attaccacag    4140
aaagagctta gtcgcctgca aggacaatct ggatttacta acaatggatt tgtctgcgag    4200 tccccctagcg cattcaaatg ggatcaagct aatggcacat tcagtccact tatgtttgat    4260
aagagagcta cacaggtatt catatactgt tttgtctata tcgaacatta tccatgtact    4320
ggttctgttt gttgaactta tgttttttaac cgtatgctta ctttctcttt ctcgtgttgt    4380
gttcagagga gagattatga tattacactt gccgctgcat ttaggaggga gcaggaaaaa    4440
gaagcaaagc taaaggcagc aattgctgca aagcagattg ccgaagagct ggtatgcatc    4500
tctcttcact acattagatt tgtagatac tctagaacac tttgtcacta aaaaagcaaa    4560
tatatgccag tatagtattt ttttttctta atgtcaattt gttgttgcac cacaggtgac    4620
tcaaagatca gaagaggtga aagtttcag gatgaggctt cgctttcgtg aagatcgaat    4680
caagagattg gagcaagttg catcggggaa gttatccgct gaagcacatc tcttgcaaga    4740
aaaggaagac ctcatgaagg aaattgaagc tctacggaac caactagaac gaaatccaga    4800
aattacaaga tttgctatgg aaaatctaca actgaaggag gagattcgaa ggttagcttc    4860
ggtatccaat cacttcagtt gccccccttt tctactgcct acactaatat agttggtagc    4920
ttgatgcctt tttttttgaa cttgtaggtt gcagtcattt gttgatgaag gagaattgga    4980
aagaatgcat cagcagataa atgttttaga acatcaggta tccacttttg tgaaggggaa    5040
tttttcagtg ataaattttt tttgtactaa aatgaacttt tttttactct tataattttc    5100
ttaacatcct gaacttactt agtttgtttt cctttagctc ctagaagcac ttgactggaa    5160
acttatgaat gagaaggatc ctgttaacaa ggtatgctat ataatttgta gacttcaatc    5220
ctgtttagtg aaaatatatg caaaactttt gaattttctt tagctagctg ttacaaatac    5280
ttgcatggca ttatatctct ttacctacca ttttgcttag acgatatccc ataatgactt    5340
ctacaggacc tctcactatt tggggaggaa gctggtgatg agaaaaacga gtttcttctt    5400
gtgcaggttg gtattgtaga actatatttg gcatatcgtc tgatgatatc ttcacagatc    5460
tttaaaaaca acctgtaaat taatcataag tgtacattgt tgatcaactc cgatacggag    5520
gaggtagctg acttaataag tatcctattc tgattcattt ttttctgtaa catcagtttg    5580
taatgttgtt atacaggcta tccaaaatga gagagaaatc gagtcactac gtaaaaattt    5640
gagcgtctgt cttcaagcaa aagagaaact cgagaggtat atcactattt cttgtctgtg    5700
tattctgtta ttgcatgcta tggttgtgtg gtatgatgag aaaggaatat cactatttct    5760
tgtctgtgta ttctgttatt gcatgctatg gttgtgtggt atgatgagaa aggaatatta    5820
atgtcatcag cttttgcaat cataattagt tccttaaatt tacagtattt acttcaggcc    5880
ccatggtaac acaactctca catatgtaaa accccttggtg ccccacaaac aagattagag    5940
gtgtatagta tctagaagta aaaaaacact tgttgttag tgtttcaagt cactgtaact    6000
gcagaaattg ttgtgctgtt tttgcgcgct acatttcaag acctaccatt tggttcttgg    6060
tgttcttctt gttgttgttt tttattctcc ttaggaacga agcctataat agttggtggg    6120
aggtcaccca ggtttgagtt ccctcaacc tgaatctggg tgcttatctc tccatcactg    6180
aaaagtttct tagttccttc caggcaatct agtattttt tctgcttggt agtactgtgc    6240
atatcgaatg gataatatgc ttagaatagt tggtgggagg tcacccaggt tttgagatat    6300 caattatttta gtggttggag ttaatgatgc atttgtgcaa gttcaagaaa aggtgtgctt    6360
ctcagaaggg gtgatggcta gcgtaggtgt agatcaacca caacaactca tctgtgctgc    6420 attttgttttg atttacttgc atatgatatc ccaagaatta taaaaaggcc ctaaagagta    6480
```

```
tggcaagtca tttctaaatc atcttggttt gcaagcttca ctgatggttt tcactgcata    6540
ctattttgtg tgtccggaat tatgttcctt ttttttgctt tgtcttgtcc agagatttat    6600
gtggttcatt tctcacattg gatgttgtgc aggcgtgttg atgatttgac tgtggagttg    6660
gaggtagcga agaaatgcga ccatgagaac aaagaattta aggctgcaca gcaccaggaa    6720
cagtccgtct tgcttgatgc tcagacagaa cttaagacat tggtagatgc aatagcaact    6780
gcaagtcaaa gagaagcaga agctcatgaa actgcaattg ggttggccaa agagaatgag    6840
aaattgagaa cagagcttac gaccctgatc gaggataaca agagactggt tgatctctat    6900
gaacaggcta ttgtcaacat tgaggtgaaa caacatggaa attatccttc cattcctcaa    6960
actgaagatt cgaatgagca gcagagcagc catccttcta atggagggaa tagcctgctg    7020
gatgaccaac cagagggtgc atatggttca cgtagtgatg ctgtagaaga gcctatgata    7080
gtggatgaaa actgcagcca caaggatgac ccttcgagat ctgaattttc agaactgcag    7140
cttcaactgg aagagatgca tgaagaaaat gataaactta tgagtttgta tgagaaagca    7200
atgcaagaaa gggatgaatt taaaaggaaa ttttctgagc aaagcaatca tgaaaccaca    7260
gaagacgttc agttcagaga tgctgaaatg gatgaagcaa tggataccat gcaaagcaat    7320
cctgaaacta cagaagacat tcagttcaga gatgctgaaa tggatagtat gctaagcaat    7380
cttgaaagtt cagaagacat tcagttcaga gatgctgaaa ccgatgctga gggtttccaa    7440
ggagagcatg tacatgactc tccaattgta gctttcaaag aagcgatgca gcttgtccgt    7500
gtcaagctgg agcatgtcca agacaagctt gtgactgccc aggatgcagt gcaatatttc    7560
aagctacttg aaatggctag caccaaggca gaagaacttt catcaagcat tcagctctgc    7620
tgtctagatg tccagaaaga gcaggaagac atcaacgccc tcaagtccgc actgtcaata    7680
tcacacgaga gagaaaacgc tttggaaggc aagttttttct cgcctgtggc atcatgccgg    7740
gacttgcatt tgaaaaccga agcccttgcc gggtccaagt ttggcgtcaa tgttcaatca    7800
atgaataaaa agatggagca gttgagtagg ttgagaactc gcaaaaccga gatttccgct    7860
gcacgtgcag aggcacgcag gtctgaaacc gagctgagaa acaaaatcga tggccttaaa    7920
cagaaatacc gttccttcga ggcccaaagg aaggagacag aaagggttct cttcgccatc    7980
gacaacctgg agtgccccgc gactccgttg cagaagccca tgaatttcgg caaggcgtcg    8040
gagctgctga agtccgagga ggagaggaca agctcttgt ctgaactgaa gaagttccgc    8100
gagcagctta gcgtggtgca gaaggagatc aagagcatga ggaactgcga cgacatcgac    8160
ggtgagatgt cgcgccttga atcggagatg gagggctgct tcctctccct gctgaaagcc    8220
gagaccgaga agtttgtgcg ggatcacacc ttggccgaag tctgggaggt tcagcagaag    8280
gacttgccga gcctactggt cgactaccag gacagcgttt tccatgtgaa gctggaggag    8340
gagcagatca gggtgtgcga ggcgtcgttg cagcaccaga cgacgtccct ggacgagatg    8400
aactcgaagc tgagccaggc gatgcgggac ctcggcgagc ttctggttgc cagaggtttg    8460
gacgcctcca cgccgcacgt ctccgacaag gtgaaggggg acctcgacgc catcgaggcc    8520
catgtcgccg aggccaggca gctcttgctc gtcgacaacc aataagattt gctgcgaacc    8580
aaagcaaacc ggttctcgcc attgacagac aggctggtct gtctccgcct tcattttgta    8640
caaattcttt gtaacggaac gttggttctc tcgggtgctg ttatctgtga ttcgattctg    8700
tagtttggat ggatgggtgg atgtaggtcc tgaagtggac tgtaataact gttctgcgcg    8760
gcctcttgtt ctgttctctg gtggtctggc atcgaagctt cttccagaag gccgttgcta    8820
```

```
agctatgcaa ctatagattc acctccttct ggtatgcact tggccgtgca agacagcaat    8880
gattggacaa tgtcgatttc aagagggctt gactattttg ttgtttatca taatctgtgg    8940
cagcgagcgt ggttgcgtgt gttcgtgaag aaaagaatgc cggtgtttca gttcatcgca    9000
ggaggttgca ggccgagaaa cttgttttcc attattgtac tactacattt ggtgttaact    9060
tgggctgtgt cgtggcggtt gagaaatgtg ttctgcaggt ccttgagggc attagggcag    9120
gtacaacggt gtccagtcag ctgtctggaa ggggtgacag ctaggatttt agatgatgtg    9180
gaggagagag aacaaagaaa gagaaacaac ccgtctgtag aataaccaac gatctgcagc    9240
ccttaaaatc cggtggatac agatggcctt ctaccgttgt atgggtgcc gtctgcaaag     9300
ttgtttgtaa ctgcctcctt tgtccctgga ttagtcttcc actcatcaat atttgacagt    9360
aaaatagacg gtctaatgta tagggtgtct taatctctgt atatacgtga tgtggagcat    9420
cgttacagac aacgagttgt ctgaactaat gtaaatgccc tcatgctcca tgctgccgcc    9480
aggttcggtt gtttggattg cttctggaag ctccttgagc tattttttgtc tcttcagggt    9540
tgcttctttg cctctttgtg tccacttgtt tggttggact gctcggctcg cctatttggt    9600
cgttgttttt c                                                         9611
```

<210> SEQ ID NO 20
<211> LENGTH: 9622
<212> TYPE: DNA
<213> ORGANISM: Triticum aestivum

<400> SEQUENCE: 20

```
cgcgccaggc cgccgcccac acttcccgcc gagcctaaaa gatgcaagaa gagagagggg      60
agaggctaga gggtgatgga ggggctcacc gcaccaataa caatggatag cgctgctgcg     120
gtggatttcc ctctggctga atttgtcccc caccccaccc gctcaccac actcgcgtga     180
attgatttgc gccattcgcc gttgccgtct gttttaatc ttttttcaagc gggtgcaggt    240
gagctcgggc ccgactgagg gccttttga ttcataggat tgcaaaaaca caggaatagg     300
aaaaacgcag gattgaaatg gcatgtccat ggatcccta taggatttga gtttgtttga     360
ttgtgttaag ggaaaaacaa aggatttttt ttcaagaggt ttgagtggat gctagaattt    420
ctgtgaaatg tagtacaaat gaacccttag aaaaaaatac aggattcaat cctacgaatc    480
aaacgatcaa cgtagaaaaa attcctaagg attctaatcc ttcaaagatc ttatgaaaat    540
cctttgaatc aaagagacct tgaagttgtg gagctcaaaa tttatagtat tcctctagaa    600
gaagctcgaa attacttcta tactgattaa ctgatgtgtg tgcaaaaaga aaagaactga    660
ttaaccgatg aaacaaccag tgtttggtac acttctgcgg gggtgaattg gtgagctgga    720
cagggcccac ccgcagcaaa ttgcttctat tatggtggcc gctcctctc ctctccctgg    780
ccagatccca aatttgaaat cgcccaacgt ctccagactc ctctccgctc cccatttcaa    840
aacctccaat ctcgtcctct ccccacccc acccaccgcc gccggcccgc cgcgccgctg    900
ctctgcccag atcccgcccg ccgcaagccc atccctgcct ccgtcgcagc cgcagcggta   960
cccgcagccg cagccgcgat gctgtcggac ggtggcgacg acgacagctc cgcccccgcg  1020
cggttcgagc tgcaggagga cccctccttc tggaaggaca caacgtgca ggtagtgatt    1080
cttctcgccc cctcgccgg gagctcccgc gcctccgcct cctcgattct cccctggcag   1140
cggcgtcccg atctagtttc gccgcgggcc gcgcgctgcg ccgttggatc atttcgtcga   1200
gcacctaggt tcgtcaggtc cggtccgcgc taaccgctcc gccccgcagg tcgtgattcg   1260
tgtccggccg ctcagcagca gcgagatatc ggtgcagggg gacaagaggt gcgtcaggca   1320
```

```
ggacagcggc cagagcatta cctggacctg ccacccggag tcccggttca cctttgatct    1380
agtcgccgat gagcacatca cgcaggtata ctccttgttc ctgttcgccc gttcctttac    1440
ttgttccgca gatgtgtaaa tactcttgtg cttgtgctgt ataggagagt cttttcaagg    1500
ttgctggggt gcccatggtg gagaactgca tggctggcta aacagctgc atgtttgcct     1560 atgggcaggt gagctacagc ctccacctcc acctgctgtt gcagtgtgct tactctcttt    1620
tatttgcact ttgaatcatt gagcttacaa agtatcctg tttcttagac cggtagtggc     1680
aagacccaca cgatgcttgg ggacatagaa atggcacac ggggaaacaa tgagaactgt     1740
ggtatgacgc ctcgagtgtt tgagcatctc ttcctaagaa tccagaaggc aagctctgat    1800
gatatgttga ttctgatgcc taattttgtg ctgtagatgg tgtactgttt ctgaggtaaa    1860
cttttcaatt gctgtttgca ggaaaaggaa atacgaagag atgaaaagct cagttttact    1920
tgcaagtgct cattcctgga gatatataat gagcagattc tggatttgct caatccaaat    1980
gcaacaaact tacaggtaat tcactgaaat ctagtgtctg cgtataccta tttggtggtt    2040
gcatctttgt cgtgacactg ttgggaaaag tttacaaagt ttgcatctaa cttacagcta    2100
tgcttttctt ttacagttaa gggaggatgc gaaaaggggt atgcatgttg agaatctgac    2160
tgaacatgag gtttctaatg cccgagaagc actgcaacaa cttatcgagg tcagtgtccc    2220
aaaaacagcg tagtaggcct gattttggca gtacctgtgt cgatgattgc agaatgatta    2280
atataacatg cctacatcaa ttttgctcaa ggttcttcgc acaaacagtc aaatacacac    2340
atataaacta agtgtataaa tataaacatg cttttttcaa tctccaattc cttgtctcct    2400
tgacttctct tttgatcgtt ttagcaactg tcactgacaa ttacagccac ttacttttca    2460
aaactatata cttaaacatt acacaataca gttttctttt gatgcagtat gaatagaaat    2520
ccgtaaatat gaattttaaa taggaaaaac aattagcata ttatacttta ctgacaagat    2580
ggagtgactg aactatttag aacatggact gcagttaagc tgatcagatc catcattttc    2640
gcatggcatg ttacactagt ttttcctta tctctaggga ttgcagcaag ttttttccctc     2700 cctttattag tcacattatt atctgtgtta gtttcactaa atcactagct aaattctgca    2760
ttttctcttc aggggcagc aaacagaaag gtggcatcta ccaatatgaa ccgagcaagt      2820
agccgttctc atagtgtatt cacttgtctt atagagagca aggtatagtt tttgtgtaat    2880
aggaagcaaa acattcttgc cttaactttc aaagatattg ctagaccagc atatatttgt    2940
ccctacctta atgcatgcat atgtattgat gcacttaatc ttctaactga actatcaacc    3000
ttacagtggg aatctcaagg tatcaagcat catcgatttt ctcatcttaa ccttgttgac    3060
cttgctggct cagagaggta agttccacat gtaaccttgc ttttttttgt tacgtatgat    3120
cttgtatttc agagccacca caaatatacc tgttatgctt ctcaagtctc ctattcttgc    3180
aactgaacgt ggatgatgtg tgatgtgcag gcaaagagt tcaggtgcag aaggggaacg      3240
cttgaaggaa gcttcgaaca tcaacaagtc actctcaacc ttagggttag ttgtggagct    3300
tcaattcttt acctcagata atactaaact gttcatagct tgacttgatt cagtttaatc    3360
atttcactgt ttccctatgg gattgttaca gacatgttat taccagcctt attgctgtgt    3420
caaacaaaaa gtcacagcat gttccctacc gagattcaaa attgacattt ctgctgcagg    3480
taatatgcac agctgaagtg gtagatttct cacgttatgt ttttgacatc tctgatgtta    3540
actttgttta tttatacatt ttcatctctt tccaggactc acttggaggt aactccaaga    3600
ccactataat tgcaaatata agcccatcta gctggtagac ttctaaacac gatttctttt    3660
```

```
tcctttctg caaaaggctt gctatagtta catgcatctt actgatattt taatttgtat   3720
ttctagctgt gcagctgaga cattgagcac attaaaattc gcgcaacggg ctaagcacat   3780
acggaataat gtatgtcatg aacatgtctt attgacttgt ttttaatatg caaaacaata   3840
actaattgtt gttttgtag gctattataa atgaggatgc ctctggtgat gtgctgagca   3900
tgcgtttaga gatccaacat ctcaaggtat agatgatgaa tttcaatttc ggtttaatga   3960
aaaatattct gtgcactgga ttgcaataag ttccaggtta acatgtttct tctaattatg   4020
gtcctttgtg ctatgattga cgtttgttgt taattaacag tggcctgtgc ctgatatttt   4080
ttgttgcaga gcgttaatat gttttgttgt acacaatcta atgctttgct attaccacag   4140
aaagagctta gtcgcctgca aggacaatct ggatttacta acaatggatt tgtctgcgag   4200
tcccctagcg cattcaaatg ggatcaagct aatggcacat tcagtccact tatgtttgat   4260
aagagagcta cacaggtatt catatactgt tttgtctata tcgaacatta tccatgtact   4320
ggttctgttt gttgaactta tgttttaac cgtatgctta ctttctcttt ctcgtgttgt   4380
gttcagagga gagattatga tattcacttt gccgctgcat ttaggaggga gcaggaaaaa   4440
gaagcaaagc taaaggcagc aattgctgca aagcagattg ccgaagagct ggtatgcatc   4500
tctcttcact acattagatt ttgtagatac tctagaacac tttgtcacta aaaaagcaaa   4560
tatatgccag tatagtattt tttttctta atgtcaattt gttgttgcac cacaggtgac   4620
tcaaagatca gaagaggtga aagtttcag gatgaggctt cgctttcgtg aagatcgaat   4680
caagagattg gagcaagttg catcggggaa gttatccgct gaagcacatc tcttgcaaga   4740
aaaggaagac ctcatgaagg aaattgaagc tctacgaaac caactagaac gaaatccaga   4800
aattacaaga tttgctatgg aaaatctaca actgaaggag gagattcgaa ggttagcttc   4860
ggtatccaat cacttcagtt gccccccttt tctactgcct acactaatat agttggtagc   4920
ttgatgcctt ttttttgaa cttgtaggtt gcagtcattt gttgatgaag gagaattgga   4980
aagaatgcat cagcagataa atgtttaga acatcaggta tccacttttg tgaaggggaa   5040
ttttcagtg ataaatttt tttgtactaa aatgaacttt tttttactct tataatttc   5100
ttaacatcct gaacttactt agtttgttt cctttagctc ctagaagcac ttgactggaa   5160
acttatgaat gagaaggatc ctgttaacaa ggtatgctat ataatttgta gacttcaatc   5220
ctgtttagtg aaaatatatg caaaacttt gaattttctt tagctagctg ttacaaatac   5280
ttgcatggca ttatatctct ttacctacca ttttgcttag acgatatccc ataatgactt   5340
ctacaggacc tctcactatt tggggaggaa gctggtgatg agaaaaacga gtttcttctt   5400
gtgcaggttg gtattgtaga actatatttg gcatatcgtc tgatgatatc ttcacagatc   5460
ttttaaaaca acctgtaaat taatcataag tgtacattgt tgatcaactc cgatacggag   5520
gaggtagctg acttaataag tatcctattc tgattcattt ttttctgtaa catcagtttg   5580
taatgttgtt atacaggcta tccaaaatga gagagaaatc gagtcactac gtaaaaattt   5640
gagcgtctgt cttcaagcaa aagagaaact cgagaggtat atcactattt cttgtctgtg   5700
tattctgtta ttgcatgcta tggttgtgtg gtatgatgag aaaggaatat cactatttct   5760
tgtctgtgta ttctgttatt gcatgctatg gttgtgtggt atgatgagaa aggaatatta   5820
atgtcatcag cttttgcaat cataattagt tccttaaatt tacagtatt acttcaggcc   5880
ccatggtaac acaactctca catatgtaaa acccttggtg ccccacaaac aagattagag   5940
gtgtatagta tctagaagta aaaaacact ttgttgttag tgtttcaagt cactgtaact   6000
gcagaaattg ttgtgctgtt tttgcgcgct acattcaag acctaccatt tggttcttgg   6060
```

```
tgttcttctt gttgttgttt tttattctcc ttaggaacga agcctataat agttggtggg    6120
aggtcaccca ggtttgagtt cccctcaacc tgaatctggg tgcttatctc tccatcactg    6180
aaaagtttct tagttccttc caggcaatct agtattttt tctgcttggt agtactgtgc    6240
atatcgaatg gataatatgc ttagaatagt tggtgggagg tcacccaggt tttgagatat    6300
caattattta gtggttggag ttaatgatgc atttgtgcaa gttcaagaaa aggtgtgctt    6360
ctcagaaggg gtgatggcta gcgtaggtgt agatcaacca caacaactca tctgtgctgc    6420
attttgtttg atttacttgc atatgatatc ccaagaatta taaaaaggcc ctaaagagta    6480
tggcaagtca tttctaaatc atcttggttt gcaagcttca ctgatggttt tcactgcata    6540
ctattttgtg tgtccggaat tatgttcctt ttttttgctt tgtcttgtcc agagatttat    6600
gtggttcatt tctcacattg gatgttgtgc aggcgtgttg atgatttgac tgtggagttg    6660
gaggtagcga agaaatgcga ccatgagaac aaagaattta aggctgcaca gcaccaggaa    6720
cagtccgtct tgcttgatgc tcagacagaa cttaagacat tggtagatgc aatagcaact    6780
gcaagtcaaa gagaagcaga agctcatgaa actgcaattg ggttggccaa agagaatgag    6840
aaattgagaa cagagcttac gaccctgatc gaggataaca agagactggt tgatctctat    6900
gaacaggcta ttgtcaacat tgaggtgaaa caacatggaa attatccttc cattcctcaa    6960
actgaagatt cgaatgagca gcagagcagc catccttcta atggagggaa tagcctgctg    7020
gatgaccaac cagagggtgc atatggttca cgtagtgatg ctgtagaaga gcctatgata    7080
gtggatgaaa actgcagcca caaggatgac ccttcgagat ctgaattttc agaactgcag    7140
cttcaactgg aagagatgca tgaagaaaat gataaactta tgagtttgta tgagaaagca    7200
atgcaagaaa gggatgaatt taaaaggaaa ttttctgagc aaagcaatca tgaaaccaca    7260
gaagacgttc agttcagaga tgctgaaatg gatgaagcaa tggataccat gcaaagcaat    7320
cctgaaacta cagaagacat tcagttcaga gatgctgaaa tggatagtat gctaagcaat    7380
cttgaaagtt cagaagacat tcagttcaga gatgctgaaa ccgatgctga gggtttccaa    7440
ggagagcatg tacatgactc tccaattgta gctttcaaag aagcgatgca gcttgtccgt    7500
gtcaagctgg agcatgtcca agacaagctt gtgactgccc aggatgcagt gcaatatttc    7560
aagctacttg aaatggctag caccaaggca gaagaacttt catcaagcat tcagctctgc    7620
tgtctagatg tccagaaaga gcaggaagac atcaacgccc tcaagtccgc actgtcaata    7680
tcacacgaga gagaaaacgc tttggaaggc aagttttct cgcctgtggc atcatgccgg    7740
gacttgcatt tgaaaaccga agcccttgcc gggtccaagt ttggcgtcaa tgttcaatca    7800
atgaataaaa agatggagca gttgagtagg ttgagaactc gcaaaaccga gatttccgct    7860
gcacgtgcag aggcacgcag gtctgaaacc gagctgagaa acaaaatcga tggccttaaa    7920
cagaaatacc gttccttcga ggcccaaagg aaggagacag aaagggttct cttcgccatc    7980
gacaacctgg agtgccccgc gactccgttg cagaagccca tgaatttcgg caaggcgtcg    8040
gagctgctga agtccgagga ggagaggaca aagctcttgt ctgaactgaa gaagttccgc    8100
gagcagctta gcgtggtgca gaaggagatc aagagcatga ggaactgcga cgacatcgac    8160
ggtgagatgt cgcgccttga atcggagatg gagggctgct tcctctccct gctggaagcc    8220
gagaccgaga gtttgtgcg ggatcacacc ttggccgaag tctgggaggt tcagcagaag    8280
gacttgccga gcctactggt cgactaccag gacagcgttt tccatgtgaa gctggaggag    8340
gagcagatca gggtgtgcga ggcgtcgttg cagcaccaga cgacgtccct ggacgagatg    8400
```

```
aactcgaagc tgagccaggc gatgcgggac ctcggcgagc ttctggttgc cagaggtttg      8460
gacgcctcca cgccgcacgt ctccgacaag gtgaaggggg acctcgacgc catcgaggcc      8520
catgtcgccg aggccaggca gctcttgctc gtcgacaacc aataagattt gctgcgaacc      8580
aaagcaaacc ggttctcgcc attgacagac aggctggtct gtctccgcct tcattttgta      8640
caaattcttt gtaacggaac gttggttctc tcgggtgctg ttatctgtga ttcgattctg      8700
tagtttggat ggatgggtgg atgtaggtcc tgaagtggac tgtaataact gttctgcgcg      8760
gcctcttgtt ctgttctctg tggtctggca atcgaagctt cttccagaag gccgttgcta      8820
agctatgcaa ctatagattc acctccttct ggtatgcact tggccgtgca agacagcaat      8880
gattggacaa tgtcgatttc aagagggctt gactattttg ttgtttatca taatctgtgg      8940
cagcgagcgt ggttgcgtgt gttcgtgaag aaaagaatgc cggtgtttca gttcatcgca      9000
ggaggttgca ggccgagaaa cttgtttttcc attattgtac tactacattt ggtgttaact      9060
tgggctgtgt cgtggcggtt gagaaatgtg ttctgcaggt ccttgagggc attagggcag      9120
gtacaacggt gtccagtcag ctgtctgaa ggggtgacac taggatttt agatgatgtg      9180 gaggagagag aacaaagaaa gagaaacaac ccgtctgtag aataaccaac gatctgcagc      9240
ccttaaaatc cggtggatac agatggcctt ctaccgttgt atggggtgcc gtctgcaaag      9300
ttgtttgtaa ctgcctcctt tgtccctgga ttagtcttcc actcatcaat atttgagagt      9360
gctatagaca gtaaaataga cggtctaatg tatagggtgt cttaatctct gtctatacgt      9420
gacgtggagc atcgttacag acaacgagtt gtctgaacta atgtacatgc cctcatgctc      9480
catgctgccg cccggttcgg ttgtttggat tgcttctgga agctccttga gctatttttg      9540
tctcttcagg gttgcttctt tgcctctttg tgtccacttg tttggttgga ctgctcggct      9600
cgcctatttg gtcgttgttt tc                                               9622

<210> SEQ ID NO 21
<211> LENGTH: 4496
<212> TYPE: DNA
<213> ORGANISM: Triticum aestivum

<400> SEQUENCE: 21
agagctcggg gctgggcggt tcggtaagag agggagaaga acaaggtcag ggccttctgg        60
atcgctagga gggggataga gagatttttc aggcgaaatt ggtgcgggac tgttaaaatg       120
gggatgacat agattaagag aaagaagaag atgaatatga cacatggacc cgcgtagtta       180
gcgacattag cgtgtgatcc cgctcaggat tttccttttc actatgcgcc aaacatgtat       240
ttagcagaaa tcaacaggaa tagaccggga ttaaagagta taggggtgaca gtttcagaga       300 tttataagtc agggtttaac tcgaagtgag agtacgaatt caaggtttat ttcatacttt       360
agtggtgctt gcaatcctca tgacaactaa atttgccaat gtggtacaaa ttagttcatg       420
tatttaatta acatatcttg tgcactcacc aatgtggttt ctcaattgtt cactttgttt       480
catatctact ttatggcatg aaaattttga tgtcattgta aaaagaact ctagccgaag        540 atagagatgc aactcttcaa tcttaaggag taagggtgtt gtgagaaccg ggtgaaccgg       600
gtgctaactc aatggcctga gtttgtagtg gcaaagccat gcactctctt cgagtctata       660
cagtagactc cgttggggtg cgatccgtgt taaattgcac aaatatctca tcacatattt       720
acataacatc cggttaagtt ttttgccaat gttcaggact aaggctgcta aagcaatttt       780
gaataaaaac catgaacaag tagcagtta ctggttagaa cgccaatttt ttggcttcag        840
ccccgaggtg tatggatgtt gaaaaacaag tttgactgaa aacagctcgg tccaagagca       900
```

```
agagtgttca aaataatttt atacaaaaaa aaaagttccg gatagcaaac ccatcaagag    960
ttcattttcc ttcagtggta ccaaccggag ggtggaaaat agtgcaaaat accactcgta   1020
ttaactaaac aaacagcttg tttccgaatc atttgaacaa aaaactgtaa aaatcgacca   1080
aaaaacaaaa ataacgcgcc aggtaggggt cgaacctacg gccttccgct taggaaacgg   1140
acgctctatc cactgagcta caggcgcctt gttgtatgag atgcaacgga accattttac   1200
aacaatcgcg tagtagatgc atctacgaaa gcttatttgg acggagcaca aacccttctc   1260
gaagtctact agaaacaccg gaagcggcgg cggggacagc acagggaagg aaaagaagcc   1320
aagaggcggc gccgccgatc cacccagacc gagagcacct tggccgacgg catggcgctg   1380
ctgatggagc ccgggtcgga gcccctgacg gagggcgaga aggccgacct ggacgccatc   1440
gccgccatca aggagtcggc ggcgcgcgag tacaggagg agggcaacca gttcgtcaag   1500
aagggccgga agcactaccc cgacgccgtc gactgctaca ccaaggccat cgcccagatg   1560
ggcgccctct ccgccccgaa ccccgacgcc tccgtcctct tcgccaaccg cgcgcacgtc   1620
aacctcctcc tcggcaacca ccgccgcgcc ctcgacgacg cccagcaggc cgtccgcctc   1680
tccccctcca acctcaaggt ccgcacgctc gctcgctcta gattacgcct ctcttgctcc   1740
aatttctcgg atttggcgag gaagccgccg tgtgatgtgt gacattcgtg tagccaggcg   1800
cactaccggg cggcgaaggc cgcgcttgct ctcgaccagt tgccccaggc ggcgtccttc   1860
tgccggcggg ggctcgagca ggaccccgcc aacgaggagc tcaagaaatt cctcgcgcag   1920
gtggaggcgc agcagcgcga gcgggatctt aaaagggcca aggttgaaca ggccatatcc   1980
gccgcgaagg tctcttctgt tccaaattgg cagttgagca tttccttatt cttttcctgt   2040
ttgtgtaatt gactgtatta gatgcatata ggatcttgct gctgctatag agaagagagg   2100
gctgaggctg gggaaggcag catatcagga gctgaccggg gtaaagaagc cgaagctgga   2160
tgagcagggc gtgctccact ggtcagttct tctgctctac ccggagtcat gtcgagcgac   2220
tttattgagg attttccgga gactgatatg ttctcggatc accttgatct catatccttg   2280
gaaagttacg tgatactttt tctgatagta tgtacatgaa tatgcataga tactttcatc   2340
acaaaaagga ggaggaatgg tttcttgaat tcctgttatc cttaattatc aaacatgttc   2400
tcagaaagtt ctccaccttt gccatgggat gagaaccacg cttacacaag ggacgctatt   2460
gagttgtatt gtcaggtttg tttacacact tcgaatttta attgagggtt aacctgtaag   2520
gctaccttct gcaaagtgct agcgcccaca gatgatcaaa ttttctctat ctaaatttca   2580
cgaggcatga gtcacaacct cttcatacaa catgaaaaca aaacattcat gcccctgtga   2640
tgtgtatata ctacacacat tgtccttctg atttattttt ccactagatg attgtgggcc   2700
aagttttttc gatccagacc tttttgtgat actaaatttt ggggaatgca acataagtta   2760
tgctattgct acttaagtgt tattagtaat ttcatttgtc cggtgctaga atgtcaagat   2820
ggtagctcta gcctttgtgg ccacattctg aaaattgtag gattatcctt taccaatttt   2880
acaagtggca gactcatgtg agaaaactag gagctattga aaattcagat ttcaatgtga   2940
tcattttgat catcgttagc agcagcatcc agtccagttt ttgaagttat cttcaaattt   3000
aacaaatctg taggatggtt gctccttcat ttacaactat tatattatta cagtcgacat   3060
aactgtcact acttgagagt taatatatac cttctgcaaa gtgctagcac ctacagatat   3120
cagatttcct tctaaatggc atgaggcaag tgccacgacc tcttcataga acattaaaac   3180
agaacactga tgcctctgat gtgtatatgc tacagacaat gtctttctga tttattttc    3240
```

-continued

```
actagatgat tgtgagacaa gttttttcga tccatacccct tttgctacta agttttgggg    3300
gatgcaacat aagttatgtt attgctacac tgatgtagtt aagtgttgtt gttggtaaat    3360
ggtttatctg gcaatagaat gtcgagatga tagctctaac ctctgtggca atattctgta    3420
gcattatcct ttaccaattt taacagtgtc ggactcatgt gagaaaactc ggagttgttg    3480
acaattaaga tttcagtact atcatgttga tcatcattag cattatccag tccagttttg    3540
caagttatct tgaagtttca caaatctgta ggattttgc ttttcattc acaattagga    3600 ttacagtcaa cataccattg tcagtacttt gacacagctt taggatagaa aaactttcta    3660
gtttcatttc gttgccttgc tggctaactg gtatttccat ttgatacact aggctggtga    3720
tggcacgccg ttctccaaaa gtgaaatgtt aaaatatctt ctggaaggca ctgtcgactc    3780
agggtcactc ccagaaagcc ttgatgggga agatggagaa catgatactg tgaagggcag    3840
cacagctata tcaccaagta tgtaaaacat attccttagg ttatttctct aaatttacat    3900
gatgtacagt aaaaagacag cacgatgtga actgtgattc tgtcaatttc agtatgtaat    3960
actccctccg ttcctaaaata taagtctttt aagagattct actatagact acatacggag    4020
caaaaagagt gaacttatac tctaaaaggt gtctatatac atccgaatgt agtctccata    4080
gtggaatctc taaaaagact tatatgtagg aaccgaggga gtatatccaa tctgccatta    4140
gcagaactac atttactgca acatgctata atgctgttat gctgcgctga taagtagttt    4200
ccatttcaat gtgtgcaggc cagggtaagt ggatcaaagt aagagaaggg aaaactcttc    4260
aggaagcgct gcagcataaa gactacatca tcccggcagt acctggtccg ttcttcaacc    4320
tgtgtatact ttgcattcgt gcgtatagaa tgcttgtcat tgttcagcgc aaataagagc    4380
ttccattaat tcctgcgtgc agtgttcttt gtggtttcaa ggaaatccgc cttccattcg    4440
aagttcaagg ctgggaattg gtctttgccg tagagctgcc gtgtagtagt tcagtt         4496
```

<210> SEQ ID NO 22
<211> LENGTH: 4487
<212> TYPE: DNA
<213> ORGANISM: Triticum aestivum

<400> SEQUENCE: 22

```
agagctcggg gctgggcggt tcggtaagag agggagaaga acaaggtcag ggccttctgg     60
atcgctagga gggggataga gagatttttc aggcgaaatt ggtgcgggac tgttaaaatg    120
gggatgacat agattaagag aaagaagaag atgaatatga cacatggacc cgcgtagtta    180
gcgacattag cgtgtgatcc cgctcaggat tttccttttc actatgcgcc aaacatgtat    240
ttagcagaaa tcaacaggaa tagaccggga ttaaagagta tagggtgaca gtttcagaga    300
tttataagtc agggtttaac tcgaagtgag agtacgaatt caaggtttat ttcatacttt    360
agtggtgctt gcaatcctca tgacaactaa atttgccaat gtggtacaaa ttagttcatg    420
tatttaatta acatatcttg tgcactcacc aatgtggttt ctcaattgtt cactttgttt    480
catatctact ttatggcatg aaaatttga tgtcattgta aaaagaact ctagccgaag    540 atagagatgc aactcttcaa tcttaaggag taagggtgtt gtgagaaccg ggtgctaact    600
caatggcctg agtttgtagt ggcaaagcca tgcactctct tcgagtctat acagtagact    660
ccgttggggt gcgatccgtg ttaaattgca caaatatctc atcacatatt tacataacat    720
ccggttaagt ttttttgccaa tgttcaggac taaggctgct aaagacaatt tgaataaaaa    780
ccatgaacaa gtagcagttt actggttaga acgccaattt tttggcttca gccccgaggt    840
gtatggatgt tgaaaaacaa gtttgactga aaacagctcg gtccaagagc aagagtgttc    900
```

```
aaaataattt tatacaaaaa aaaaagttcc ggatagcaaa cccatcaaga gttcattttc    960
cttcagtggt accaaccgga gggtggaaaa tagtgcaaaa taccactcgt attaactaaa   1020
caaacagctt gtttccgaat catttgaaca aaaaactgta aaaatcgacc aaaaaacaaa   1080
aataacgcgc caggtagggg tcgaacctac ggccttccgc ttaggaaacg gacgctctat   1140
ccactgagct acaggcgcct tgttgtatga gatgcaacgg aaccatttta caacaatcgc   1200
gtagtagatg catctacgga agcttatttg gacggagcac aaacccttct cgaagtctac   1260
tagaaacacc ggaagcggcg gcggggacag cacaggaag gaaagaagc caagaggcgg    1320 cgccgccgat ccacccagac cgagagcacc ttggccgacg gcatggcgct gctgatggag   1380
cccgggtcgg agcccctgac ggagggcgag aaggccgacc tggacgccat cgccgccatc   1440
aaggagtcgg cggcgcgcga gtacaggag gagggcaacc agttcgtcaa gaagggccgg    1500
aagcactacc ccgacgccgt cgactgctac accaaggcca tcgcccagat gggcgccctc   1560
tccgccccga accccgacgc ctccgtcctc ttcgccaacc gcgcgcacgt caacctcctc   1620
ctcggcaacc accgccgcgc cctcgacgac gcccagcagg ccgtccgcct ctccccctcc   1680
aacctcaagg tccgcacgct cgctcgctct agattacgcc tctcttgctc caatttctcg   1740
gatttggcga ggaagccgcc gtgtgatgtg tgacattcgt gtagccaggc gcactaccgg   1800
gcggcgaagg ccgcgcttgc tctcgaccag ttgccccagg cggcgtcctt ctgccggcgg   1860
gggctcgagc aggaccccgc caacgaggag ctcaagaaat tcctcgcgca ggtggaggcg   1920
cagcagcgcg agcgggatct taaaagggcc aaggttgaac aggccatatc cgccgcgaag   1980
gtctcttctg ttccaaattg gcagttgagc atttccttat tcttttcctg tttgtgtaat   2040
tgactgtatt agatgcatat aggatcttgc tgctgctata gagaagagag ggctgaggct   2100
ggggaaggca gcatatcagg agctgaccgg ggtaaagaag ccgaagctgg atgagcaggg   2160
cgtgctccac tggtcagttc ttctgctcta cccggagtca tgtcgagcga ctttattgag   2220
gattttccgg agactgatat gttctcggat caccttgatc tcatatcctt ggaaagttac   2280
gtgatacttt ttctgatagt atgtacatga atatgcatag atactttcat cacaaaaagg   2340
aggaggaatg gtttcttgaa ttcctgttat ccttaattat caaacatgtt ctcagaaagt   2400
tctccacctt tgccatggga tgagaaccac gcttacacaa gggacgctat tgagttgtat   2460
tgtcaggttt gtttacacac ttcgaatttt aattgagggt taacctgtaa ggctaccttc   2520
tgcaaagtgc tagcgcccac agatgatcaa atttttctcta tctaaatttc acgaggcatg   2580
agtcacaacc tcttcataca acatgaaaac aaaacattca tgcccctgtg atgtgtatat   2640
actacacaca ttgtccttct gatttatttt tccactagat gattgtgggc caagtttttt   2700
cgatccagac cttttttgtga tactaaattt tggggaatgc aacataagtt atgctattgc   2760
tacttaagtg ttattagtaa tttcatttgt ccggtgctag aatgtcaaga tggtagctct   2820
agcctttgtg gccacattct gaaaattgta ggattatcct ttaccaattt tacaagtggc   2880
agactcatgt gagaaaacta ggagctattg aaaattcaga tttcaatgtg atcattttga   2940
tcatcgttag cagcagcatc cagtccagtt tttgaagtta tcttcaaatt taacaaatct   3000
gtaggatggt tgctccttca tttacaacta ttatattatt acagtcgaca taactgtcac   3060
tacttgagag ttaatatata ccttctgcaa agtgctagca cctacagata tcagattttc   3120
ttctaaatgg catgaggcaa gtgccacgac ctcttcatag aacattaaaa cagaacactg   3180
atgcctctga tgtgtatatg ctacagacaa tgtctttctg atttattttt cactagatga   3240
```

```
ttgtgagaca agtttttcg atccataccc ttttgctact aagttttggg ggatgcaaca      3300
taagttatgt tattgctaca ctgatgtagt taagtgttgt tgttggtaaa tggtttatct      3360
ggcaatagaa tgtcgagatg atagctctaa cctctgtggc aatattctgt agcattatcc      3420
tttaccaatt ttaacagtgt cggactcatg tgagaaaact cggagttgtt gacaattaag      3480
atttcagtac tatcatgttg atcatcatta gcattatcca gtccagtttt gcaagttatc      3540
ttgaagtttc acaaatctgt aggattttg ctttttcatt cacaattagg attacagtca      3600
acataccatt gtcagtactt tgacacagct ttaggataga aaaactttct agtttcattt      3660
cgttgccttg ctggctaact ggtatttcca tttgatacac taggctggtg atggcacgcc      3720
gttctccaaa agtgaaatgt taaaatatct tctggaaggc actgtcgact cagggtcact      3780
cccagaaagc cttgatgggg aagatggaga acatgatact gtgaagggca gcacagctat      3840
atcaccaagt atgtaaaaca tattccttag gttatttctc taaatttaca tgatgtacag      3900
taaaaagaca gcacgatgtg aactgtgatt ctgtcaattt cagtatgtaa tactccctcc      3960
gttcctaaat ataagtcttt taagagattc tactatagac tacatacgga gcaaaaagag      4020
tgaacttata ctctaaaagg tgtctatata catccgaatg tagtctccat agtggaatct      4080
ctaaaaagac ttatatgtag gaaccgaggg agtatatcca atctgccatt agcagaacta      4140
catttactgc aacatgctat aatgctgtta tgctgcgctg ataagtagtt tccatttcaa      4200
tgtgtgcagg ccagggtaag tggatcaaag taagagaagg gaaaactctt caggaagcgc      4260
tgcagcataa agactacatc atcccggcag tacctggtcc gttcttcaac ctgtgtatac      4320
tttgcattcg tgcgtataga atgcttgtca ttgttcagcg caaataagag cttccattaa      4380
ttcctgcgtg cagtgttctt tgtggtttca aggaaatccg ccttccattc gaagttcaag      4440
gctgggaatt ggtctttgcc gtagagctgc cgtgtagtag ttcagtt                    4487
```

<210> SEQ ID NO 23
<211> LENGTH: 2318
<212> TYPE: DNA
<213> ORGANISM: Triticum aestivum

<400> SEQUENCE: 23

```
tggcgagcgg cgtcgggccg gaggcgcgac gatgaaggtg gtggccgcgg tggacgcgag        60
cgaggagagc ctgcacgcgc tgtcgtgggc gctcgacaac gtcgtccggc ccacccccgg       120
cgcgtccctc gtcgtcgtcc acgtccagcc gcgcgccgac cacttcgcct accctgtcgc       180
cgggcacggt accgcctgtc ctgtacaaca agctagctca cacgcacaca cacgtacgta       240
cgctcacgct cactgacgga actcgtttgc gtgtgcatac ggaggcaggc ctacagtacg       300
tcccgcccac ggcggtggac tccgtgagga agacgcacga agagaactcc cggcgagtcg       360
tgtccgtcgc gctcgacgtg tgcaggcaga agcaggtgag cgccacggcg gcggtggtgg       420
agggcgacgc caaggaggcc atctgccgcg ccgtggagga catgcacgcc gacctcctcg       480
tcctcggcag ccgcggcctg ggcatgatca agaggtacgc gcatgccaat gagatcacca       540
cgcgtgagca tcttcgataa cagattgtga ttctgggtgc agttcgacta cttcactggc       600
agagccaaaa atactaaagc acagcttagc tttcttcagt gttcaagcga cttgaattgc       660
aaacatatgg aaatccttaa atttcaaaat ttcaatgctt gatttggttg gggtttgcca       720
ggtccaggca gtagtgcaac gcctggacga cacatgagag ccctggcagc aagctaccgt       780
gatgggctct ccccataaaa aataaatttt aatatcgttg tggacacatg gtccacatat       840
cagatattaa actgataaga acagatacta cacttgatct tagccaaaag gccgagaaag       900
```

```
gtatgagttg gaacattgag ctgggtcttg ttttatagcc atctttcccc agggtttctc    960
ctccgtccgg gatgtggtac taaacctgct actgacctct cttctatgct ccggcaatgc   1020
cacccgctgc tcggttgggc ccaaaccgag agcccgtagc aggccttatc gagtacgtca   1080
tgggcttttc tgttcctgtt ccttttacca ttctatatct tgtagtttgc ctcctgttgg   1140
gcttgtccct atgggcctcc ccttcttatc caggcacata ttgaaatgca tggctggcaa   1200
gaggtgcaat agctcgttaa acttgcctcc ttaaacagta gtacatttaa gagaatccaa   1260
tgggtaaaga aaacacagtt gtttcttagt ttttcatgtt tatttactat gagagcaagc   1320
ctttatcacc gagacaatag tcatgttgct tgcagagtta caagcatatg cataataaaa   1380
ctccatggat catcaagcca cgccttgacc ctgtgcttgt gctggtggtg tgttgcaggg   1440
cgttgctggg cagcgtgagc gactacctcg cccatcacgc ctcctgcccc gttctcatcg   1500
tgaagccgcc cagcaaggcg caccacaagt gaagctccaa ctctgctgcc agtgtcgact   1560
gaatgtctcg agtgcctcgt gcttccaata aagatgtgat cgagctcatg tgcagtactc   1620
tatgaacatc ctagaatgta gggaataaac tgttgtttgg ccgcaagcac ttgctgaaat   1680
ttttaatctt ggttagtgca gttgttccga tgcattacat tgccatggac gtagtgttct   1740
ttcttccttg aagtacagag tgcggtgatg ctgctgaaaa acaggcacat ctcgaagagt   1800
tcggttcgcc aaaacacatga ccagtacaag acctattgat cacaaatact ccataattcg   1860
ctctaaaaaa cgtattcaga attcctattc ataatgcaga gcatgaatga ccgtcgaagc   1920
atgttctgtt tctaagcaag catgcttttg ttttaaaatg gagacaaaag ttttgcctcg   1980
tctatttaat gaagaagagg gtagagttct gtattacaag gccgcgaggc ccacccgcaa   2040
taaacatgga attactctcc tgatagaatg tttcccaaaa taacaaaatt gcatctgcca   2100
agacccaaag cttggtctag tcttttgatgg ccttgagcaa gatggtcttc ggcttgctct   2160
attctcgaaa cacacgggca tttctctcgt ttcaaatggt ccaactaatg agcattgtaa   2220
gcgacgccat tgctttacag ttgaccttgt tgttgcggaa agattgaccc accaatcttt   2280
gttggggctc ttaaggcgcc aagaggaggt tcaaagtt                           2318
```

<210> SEQ ID NO 24
<211> LENGTH: 2318
<212> TYPE: DNA
<213> ORGANISM: Triticum aestivum

<400> SEQUENCE: 24

```
tggcgagcgg cgtcgggccg gaggcgcgac gatgaaggtg gtggccgcgg tggacgcgag    60
cgaggagagc ctgcacgcgc tgtcgtgggc gctcgacaac gtcgtccggc cccaccccgg   120
cgcgtcccte gtcgtcgtcc acgtccagcc gcgcgccgac cacttcgcct accctgtcgc   180
cgggcacggt accgcctgtc ctgtacaaca agctagctca cacgcacaca cacgtacgta   240
cgctcacgct cactgacgga actcgtttgc gtgtgcatac ggaggcaggc ctacagtacg   300
tcccgcccac ggcggtggac tccgtgagga agacgcacga agagaactcc cggcgagtcg   360
tgtccgtcgc gctcgacgtg tgcaggcaga agcaggtgag cgccacggcg gcggtggtgg   420
agggcgacgc caaggaggcc atctgccgcg ccgtggagga catgcacgcc gacctcctcg   480
tcctcggcag ccgcggcctg ggcatgatca agaggtacgc gcatgccaat gagatcacca   540
cgcgtgagca tcttcgataa cagattgtga ttctgggtgc agttcgacta cttcactggc   600
agagccaaaa atactaaagc acagcttagc tttcttcagt gttcaagcga cttgaattgc   660
```

```
aaacatatgg aaatccttaa atttcaaaat ttcaatgctt gatttggttg gggtttgcca     720
ggtccaggca gtagtgcaac gcctggacga cacatgagag ccctggcagc aagctaccgt     780
gatgggctct cccccataaa aaataaattt aatatcgttg tggacacatg gtccacatat     840
cagatattaa actgataaga acagatacta cacttgatct tagccaaaag gccgagaaag     900
gtatgagttg gaacattgag ctgggtctcg ttttatagcc atctttcccc agggtttctc     960
ctccgtccgc gatgtggtac taaacctgct actgccctct cttctatgct ccggcaatgc    1020
cacccgctgc tcggttgggc ccaaaccgag agcccgtagc aggccttacc gagtcacgtc    1080
atgggctttt ctgttcctgt tccttttttcc attctctctc ttgcagcttg cctcctcttc    1140
tgcttttccc tttgtgcctt cccttcttat cctggtagca tattgaaatg catggctgga    1200
agatgtgcaa tagctagtta acttgcctcc ttaaacagta gtacatttaa gaaaatccaa    1260
tggctaaaga aaacacagtt gttttttagt ttttcatgtt tatttactat gagagcaagc    1320
ctttatcacc gagacaatag tcatgttgct tgcagagtta caagcatatg cataataaaa    1380
ctccatggat catcaagcca cgccttgacc ctgtgcttgt gctggtggtg tgttgcaggg    1440
cgttgctggg cagcgtgagc gactacctcg cccatcacgc ctcctgcccc gttctcatcg    1500
tgaagccgcc cagcaaggcg caccacaagt gaagctccaa ctctgctgcc actgtcgact    1560
gaatgtctcg agtgcctcgt gcttccaata aagatgtgat cgagctcatg tgcagtactc    1620
tatgaacatc ctagaatgta gggaataaac tgttgtttgg ccgcaagcac ttgctgaaat    1680
ttttaatctt ggttagtgca gttgttccga tgcattacat tgccatggac gtagtgttct    1740
ttcttccttg aagtacagag tgcggtgatg ctgctgaaaa acaggcacat ctcgaagagt    1800
tcggttcgcc aaacacatga ccagtacaag acctattgat cacaaatact ccataattcg    1860
ctctaaaaaa cgtattcaga attcctattc ataatgcaga gcatgaatga ccgtcgaagc    1920
atgttctgtt tctaagcaag catgcttttg ttttaaaatg gagacaaaag ttttgcctcg    1980
tctatttaat gaagaagagg gtagagttct gtattacaag gccgcgaggc ccacccgcaa    2040
taaacatgga attactctcc tgatagaatg tttcccaaaa taacaaaatt gcatctgcca    2100
agacccaaag cttggtctag tctttgatgg ccttgagcaa gatggtcttc ggcttgctct    2160
attctcgaaa cacacgggca tttctctcgt ttcaaatggt ccaactaatg agcattgtaa    2220
gcgacgccat tgctttacag ttgaccttgt tgttgcggaa agattgaccc accaatcttt    2280
gttgggcctc ttaaggcgcc aagaggaggt tcaaagtt                             2318
```

<210> SEQ ID NO 25
<211> LENGTH: 354
<212> TYPE: DNA
<213> ORGANISM: Triticum aestivum

<400> SEQUENCE: 25

```
gcttctcctg gaagctgccg cggacgtggg tcaggtcggt cgaccagctg cccatgaatt      60
acggcgacaa gctctacgac ccgctcttcc ccttcggctt cggcctcacc accaagccgg     120
cggcggatag caggtagcta ggagtctgag tttcttttcc tgccctagtt agtgtgcgat     180
taattagtga gtccgtgagt agtgagaatc ggaaataaat gaggaggata tggttttgat     240
tgcgtcgccc tgtaactgta agttcgctac gaacatccga tgaacttgaa atcaatctat     300
atatagtgct gtcggaattc agtctatctt aattctcgac ttctcgagtc ggtt            354
```

<210> SEQ ID NO 26
<211> LENGTH: 354

```
<212> TYPE: DNA
<213> ORGANISM: Triticum aestivum

<400> SEQUENCE: 26
gcttctcctg gaagctgccg cggacgtggg tcaggtcggt cgaccagctg cccatgaatt      60
acggcgacaa gctctacgac ccgctcttcc ccttcggctt cggcctcacc accaagccgg     120
cggcggatag cagctagcta ggagtctgag tttcttttcc tgccctagtt agtgtgcgat     180
taattagtga gtccgtgagt agtgagaatc ggaaataaat gaggaggata tggttttgat     240
tgcgtcgccc tgtaactgta agttcgctac gaacatccga tgaacttgaa atcaatctat     300
atatagtgct gtcggaattc agtctatctt aattctcgac ttctcgagtc ggtt           354

<210> SEQ ID NO 27
<211> LENGTH: 232
<212> TYPE: DNA
<213> ORGANISM: Triticum aestivum

<400> SEQUENCE: 27
caaacagccg tgacacacaa gaggtacact ttctgaaaac ttccgtcaat aactacttat      60
tttgggtggt gatttcatga agaggccatg gcccaccagg gctaatgtta atactttgta     120
tgttccttta ataatgatg atgatgtatc ttgctttttt aaggacacat attttaaata      180
tggtttatca ggtgccttcc ccagttaata aaacagtgga acctataaat tt             232

<210> SEQ ID NO 28
<211> LENGTH: 238
<212> TYPE: DNA
<213> ORGANISM: Triticum aestivum

<400> SEQUENCE: 28
caaacagccg tgacacacaa gaggtacact ttctgaaaac ttccgtcaat aactacttat      60
tttgggtggt gatttcatga agaggcgaat gttaatactt tgtatgttcc tttagataat     120
gatgatgatg tagcttgctt ttttaaggac gcatatttta gatatggttt atcaagtgcc     180
ttccccagtt aatataacag tggaacctag aaatttgttt ctccattatt gtcatgcg       238

<210> SEQ ID NO 29
<211> LENGTH: 244
<212> TYPE: PRT
<213> ORGANISM: Triticum aestivum

<400> SEQUENCE: 29

Met Gly Arg Gly Lys Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
```

```
                115                 120                 125
Glu Gln Gln Leu Glu Ser Ser Leu Lys His Ile Arg Ser Arg Lys Asn
            130                 135                 140
Gln Leu Met His Glu Ser Ile Ser Glu Leu Gln Lys Lys Glu Arg Ser
145                 150                 155                 160
Leu Gln Glu Glu Asn Lys Val Leu Gln Lys Glu Leu Val Glu Lys Gln
                165                 170                 175
Lys Ala His Ala Ala Gln Gln Asp Gln Thr Gln Pro Gln Thr Ser Ser
            180                 185                 190
Ser Ser Ser Ser Phe Met Leu Arg Asp Ala Pro Ala Ala Asn Thr
            195                 200                 205
Ser Ile His Pro Ala Ala Thr Gly Glu Arg Ala Glu Asp Ala Ala Val
            210                 215                 220
Gln Pro Gln Ala Pro Pro Arg Thr Gly Leu Pro Pro Trp Met Val Ser
225                 230                 235                 240
His Ile Asn Gly

<210> SEQ ID NO 30
<211> LENGTH: 240
<212> TYPE: PRT
<213> ORGANISM: Triticum aestivum

<400> SEQUENCE: 30

Met Gly Arg Gly Lys Ile Val Ile Arg Arg Ile Asp Asn Ser Thr Ser
1               5                   10                  15
Arg Gln Val Thr Phe Ser Lys Arg Arg Asn Gly Ile Phe Lys Lys Ala
                20                  25                  30
Lys Glu Leu Gly Ile Leu Cys Asp Ala Glu Val Gly Leu Val Ile Phe
            35                  40                  45
Ser Ser Thr Gly Arg Leu Tyr Glu Tyr Ala Ser Ser Ser Met Lys Ser
        50                  55                  60
Val Ile Asp Arg Tyr Gly Arg Ala Lys Glu Glu Gln Gln Leu Val Ala
65                  70                  75                  80
Asn Pro Asn Ser Glu Leu Lys Ser Trp Gln Arg Glu Ala Ala Ser Leu
                85                  90                  95
Arg Gln Gln Leu His Asn Leu Gln Glu Asn His Arg Gln Leu Met Gly
                100                 105                 110
Gln Asp Leu Ser Gly Met Gly Val Lys Glu Leu Gln Ala Leu Glu Asn
            115                 120                 125
Gln Leu Glu Ile Ser Leu Arg Cys Ile Arg Thr Lys Lys Asp Gln Ile
            130                 135                 140
Leu Ile Asp Glu Ile His Glu Leu Asn His Lys Gly Ser Leu Val His
145                 150                 155                 160
Gln Glu Asn Met Glu Leu Tyr Lys Lys Ile Asn Leu Ile Arg Gln Glu
                165                 170                 175
Asn Val Glu Leu Gln Lys Lys Leu Ser Glu Thr Glu Ala Val Thr Glu
            180                 185                 190
Val Asn Arg Asn Ser Arg Thr Pro Tyr Asn Phe Ala Val Val Glu Asp
            195                 200                 205
Ala Asn Val Ser Val Asp Leu Glu Leu Asn Ser Pro Gln Gln Gln Asn
            210                 215                 220
Asp Val Glu His Thr Ala Pro Pro Lys Leu Gly Leu Gln Leu His Pro
225                 230                 235                 240
```

<210> SEQ ID NO 31
<211> LENGTH: 723
<212> TYPE: DNA
<213> ORGANISM: Triticum aestivum

<400> SEQUENCE: 31

```
atggggcgcg gcaagatagt gatccggcgg atcgacaact ccacgagccg gcaggtgacg      60
ttctcgaagc ggaggaacgg gatcttcaag aaggccgagg agctgggtat tctctgcgat     120
gccgaggtcg gtctcgtcat cttctccagc accggccgcc tctatgagta cgccagctcc     180
agcatgaagt cagtgataga tcgatatggc cgagccaagg aggagcagca acttgttgca     240
aacccaact cggagcttaa gttctggcaa agggaggcag caagcttgag acaacaactg     300
cacaacttgc aagaaaatca tcggcagttg atgggacaag atctttctgg aatgggtgtc     360
aaggaactgc aggctctaga aaatcaactg gaaataagtc tgcgttgcat ccggacaaaa     420
aaggaccaaa tcttgattga tgagattcat gaactgaatc acaagggag tcttgtccac     480
caagaaaaca tggaattata caaaaagatt aacctaattc gtcaggaaaa tgttgagtta     540
cagaaaaagc tctctgagac ggaggcagtg actgaagtta accgaaattc aagaactcca     600
tacaattttg cagttgttga agatgccaat gtttctgttg atcttgaact caattccccg     660
cagcaacaaa atgatgttga gcatactgcg cccctaaac taggattgca actacatcca     720
tga                                                                   723
```

<210> SEQ ID NO 32
<211> LENGTH: 226
<212> TYPE: PRT
<213> ORGANISM: Triticum aestivum

<400> SEQUENCE: 32

```
Met Glu Ser Asp Cys Gln Phe Leu Leu Ala Pro Pro Arg Met Tyr
 1               5                  10                  15

Ala Ala Pro Gly Asp Asp Gly Gln Phe Leu Gln Gln Gln Gln Gln
                20                  25                  30

Leu Ser Gly Gly Gly Ala Gly Glu Arg Lys Arg Arg Phe Thr Glu Glu
            35                  40                  45

Gln Val Arg Ser Leu Glu Ser Thr Phe His Thr Arg Arg Ala Lys Leu
        50                  55                  60

Asp Pro Arg Glu Lys Ala Glu Leu Ala Arg Glu Leu Gly Leu Gln Pro
 65                 70                  75                  80

Arg Gln Val Ala Ile Trp Phe Gln Asn Lys Arg Ala Arg Trp Arg Ser
                85                  90                  95

Lys Gln Pro Glu Gln Asp Phe Ala Glu Leu Arg Gly His Tyr Asp Ala
            100                 105                 110

Leu Arg Ala Arg Val Glu Ser Leu Lys Gln Glu Lys Leu Thr Leu Ala
        115                 120                 125

Ala Gln Leu Glu Glu Leu Lys Lys Lys Leu Asp Glu Arg Gln Asp Gln
    130                 135                 140

Ser Ala Ser Cys Gly Gly Ser Cys Ala Val Ala Asp Val Asp Asp Lys
145                 150                 155                 160

Arg Asp Asn Val Ser Ser Cys Val Ala Lys Asp Glu Ser Ala Ala
                165                 170                 175

Pro Ala Ala Asp Val Ser Asp Gly Ser Thr Pro Gly Trp Tyr Glu Tyr
            180                 185                 190

Asp Asp His Leu Val Tyr Gly Val Asp Leu His Glu Pro Phe Cys Ala
        195                 200                 205
```

```
Thr Gln Glu Leu Trp Glu Thr Ser Trp Pro Leu Val Glu Trp Asn Ala
    210                 215                 220

Val Ala
225

<210> SEQ ID NO 33
<211> LENGTH: 681
<212> TYPE: DNA
<213> ORGANISM: Triticum aestivum

<400> SEQUENCE: 33
atggagagcg actgccagtt cctgctggcg ccgccgccgc gcatgtacgc cgcgccgggg      60
gacgacggcc agttccttca gcagcagcag cagcagctga gcggcggcgg cgccggggag     120
aggaagcggc ggttcacgga ggagcaggtg cggtcgctgg agagcacgtt ccacacgcgg     180
cgcgccaagc tggaccccc g ggagaaggcg agctggcgc gcgagctggg gctgcagccg     240
cgccaggtgg ccatctggtt ccagaacaag cgcgcccgt ggcgctccaa gcagccggag     300
caggacttcg cggagctgcg cggccattac gacgccctcc gcgcccgcgt cgagtcgctc     360
aagcaggaaa agctcactct cgccgcgcag ctggaagagc tgaagaagaa gctggacgag     420
cggcaagacc agagcgctag ctgcggcggc tcttgcgccg tcgccgacgt agacgacaag     480
agggataacg ttagcagctg cgtcgcggcg aaggatgaga gcgcggcgcc ggcggcagac     540
gtgtcggacg gctcaactcc gggctggtac gagtatgacg accacctggt gtatggggtt     600
gacctgcacg agccgttctg cgccactcag gagctgtggg agacgtcatg gccgctggtg     660
gagtggaacg cagtggcatg a                                               681

<210> SEQ ID NO 34
<211> LENGTH: 212
<212> TYPE: PRT
<213> ORGANISM: Triticum aestivum

<400> SEQUENCE: 34

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
                20                  25                  30

Lys Glu Leu Gly Ile Leu Cys Asp Ala Glu Val Gly Leu Val Ile Phe
            35                  40                  45

Ser Ser Thr Gly Arg Leu Tyr Glu Tyr Ala Ser Ser Ser Met Lys Ser
        50                  55                  60

Val Ile Asp Arg Tyr Gly Arg Ala Lys Glu Glu Gln Gln Leu Val Ala
65                  70                  75                  80

Asn Pro Asn Ser Glu Leu Lys Ser Trp Gln Arg Glu Ala Ala Ser Leu
                85                  90                  95

Arg Gln Gln Leu His Asn Leu Gln Glu Asn His Arg Gln Leu Met Gly
            100                 105                 110

Gln Asp Leu Ser Gly Met Gly Val Lys Glu Leu Gln Ala Leu Glu Asn
        115                 120                 125

Gln Leu Glu Ile Ser Leu Arg Cys Ile Arg Thr Lys Lys Asp Gln Ile
    130                 135                 140

Leu Ile Asp Glu Ile His Glu Leu Asn His Lys Leu Ser Glu Thr Glu
145                 150                 155                 160

Ala Val Thr Glu Val Asn Arg Asn Ser Arg Thr Pro Tyr Asn Phe Ala
                165                 170                 175
```

-continued

```
Val Val Glu Asp Ala Asn Val Ser Val Asp Leu Glu Leu Asn Ser Pro
            180                 185                 190

Gln Gln Gln Asn Asp Val Glu His Thr Ala Pro Pro Lys Leu Gly Leu
        195                 200                 205

Gln Leu His Pro
    210

<210> SEQ ID NO 35
<211> LENGTH: 639
<212> TYPE: DNA
<213> ORGANISM: Triticum aestivum

<400> SEQUENCE: 35 atgggggcgcg gcaagatagt gatccggcgg atcgacaact ccacgagccg gcaggtgacg      60
ttctcgaagc ggaggaacgg gatcttcaag aaggccgagg agctgggtat tctctgcgat     120
gccgaggtcg gtctcgtcat cttctccagc accggccgcc tctatgagta cgccagctcc     180
agcatgaagt cagtgataga tcgatatggc cgagccaagg aggagcagca acttgttgca     240
aaccccaact cggagcttaa gttctggcaa agggaggcag caagcttgag acaacaactg     300
cacaacttgc aagaaaatca tcggcagttg atgggacaag atctttctgg aatgggtgtc     360
aaggaactgc aggctctaga aaatcaactg gaaataagtc tgcgttgcat ccggacaaaa     420
aaggaccaaa tcttgattga tgagattcat gaactgaatc acaagctctc tgagacggag     480
gcagtgactg aagttaaccg aaattcaaga actccataca attttgcagt tgttgaagat     540
gccaatgttt ctgttgatct tgaactcaat tccccgcagc aacaaaatga tgttgagcat     600
actgcgcccc ctaaactagg attgcaacta catccatga                            639
```

ENHANCEMENT OF NITROGEN USE EFFICIENCY IN WHEAT AND OTHER PLANTS

CROSS REFERENCE TO RELATED APPLICATIONS

This application is a continuation-in-part of co-pending application Ser. No. 13/892,403, filed May 13, 2013 entitled: "ENHANCEMENT OF NITROGEN USE EFFICIENCY IN WHEAT AND OTHER PLANTS", which is a continuation of abandoned application Ser. No. 13/841,201, filed Mar. 15, 2013, entitled "ENHANCEMENT OF NITROGEN USE EFFICIENCY IN WHEAT AND OTHER PLANTS", which application is a continuation-in-part of co-pending U.S. application Ser. No. 13/157,057 filed on Jun. 9, 2011 entitled, "ENHANCEMENT OF NITROGEN USE EFFICIENCY IN WHEAT AND OTHER PLANTS", which application claims the priority of U.S. Provisional Patent Application No. 61/352,979 entitled, "ENHANCEMENT OF NITROGEN USE EFFICIENCY IN WHEAT AND OTHER PLANTS," filed Jun. 9, 2010, and U.S. Provisional Patent Application No. 61/367,671 entitled, "ENHANCEMENT OF NITROGEN USE EFFICIENCY IN WHEAT AND OTHER PLANTS," filed Jul. 26, 2010, the contents of all five are hereby incorporated by reference.

FIELD OF THE INVENTION

The invention generally relates to the enhancement of the efficiency of nitrogen use in plants. In particular, the invention provides genes responsible for efficient use of nitrogen in plants, methods of using the genes to genetically engineer plants so that they use nitrogen more efficiently, and transgenic plants that are genetically engineered to contain and express such genes and thereby utilize nitrogen more efficiently. Identification of the genes also aids in carrying out suitable crosses for plant breeding in order to enhance the desired phenotype of efficient nitrogen utilization by progeny plants

BACKGROUND OF THE INVENTION

Nitrogen is One of the Most Important Nutrients in Crop Production.

Nitrogen (N) is an essential nutrient for growth and development and a major constituent of proteins, nucleic acids, and secondary metabolites in plants (Scheible 2004; Moose and Below 2009). Wheat is highly responsive to N fertilization, with significant amounts of supplemental N required to achieve maximal grain yields. A sevenfold increase in N fertilizer usage has been associated with a twofold increase in food production over the last four decades (Hirel et al. 2007; Shrawat et al. 2008). A further threefold increase in N input has been projected to meet food demands for main crops including wheat, rice and maize (Shrawat et al. 2008; Tilman et al. 2002), due to a projected increase in world population to 9 billion by 2050 (McMichael 2001). An estimated 12.5 million tons of N were applied to agriculture production in 2007 in the United States, and additional N fertilizer is needed to account for N removal in consumed forage in dual purpose wheat planted in the southern Great Plains (MacKown and Carver 2007).

Nitrogen Use Efficiency is One of the Most Effective Approaches to Sustainable Agriculture.

Although large amounts of N are applied to soils, only part of the N is taken up and utilized by plants in the year of application. For example, nitrogen use efficiency (NUE) in wheat is only about 30-35% (Raun and Johnson 1999; Tilman et al. 2002), and the remaining 65-70% (assuming fertilizer-soil equilibrium) is lost by gaseous plant emission, soil denitrification, surface runoff, volatilization, and leaching, which contributes to atmospheric greenhouse gases and environment pollution (Shrawat et al. 2008). Therefore, enhancing NUE is an ideal strategy to increase grain yield without increasing—and possibly even when decreasing—fertilizer use, decreasing investment costs, and minimizing ecological and environmental risks (Hirel et al. 2007).

NUE in cereal crops refers to the ratio of grain yield to N supplied by soil and fertilizer, which is dissected into two components: N uptake efficiency (NupE) and N utilization efficiency (NutE) (Hirel et al. 2007; Laperche et al. 2007; Moll et al. 1982; Raun and Johnson 1999). NupE is defined as the ratio of N supplied (from both natural soil levels and applied N fertilizer) to N in total shoots and biomass, and is used to describe the ability of the plant to absorb and assimilate N from the soil, which mainly occurs in vegetative roots and leaves. On the other hand, NutE is defined as the ratio of grain yield to the acquired N, which is used to indicate sink capacity to utilize N by recycling of assimilated N taking place during seed set and filling (Hirel et al. 2007). A genotype with high NUE is expected to have a high level in both NupE and NutE.

QTL (Quantitative Trait Loci) for NUE have been Mapped by Genome-Wide Markers.

A first step in understanding biological process underlying a complex trait is to discover quantitative trait loci (QTL) associated with the variation in the trait. Twenty-one QTL have previously been characterized to describe N uptake in winter wheat grown in the field (An et al. 2006). It is reported that wheat cultivars differ in their NUE (Boman et al. 1995; Cox et al. 1985; Gouis and Pluchard 1996; Van Sanford and MacKown 1987), and as many as 126 genes are predicted to be associated with N utilization and grain yield components in a spring wheat population (Habash et al. 2007; Quarrie et al. 2005). However, only a small part of the total phenotypic variation is explained by each QTL (<30%), which has limited further molecular manipulation of these mapped QTL.

SUMMARY OF THE INVENTION

An embodiment is based on the identification, in the plant genome, of genes that are associated with nitrogen utilization efficiency (NUE), and the discovery of at least one variant of the one or more genes that, when present in a plant, causes the plant to exhibit increased or elevated NUE. The increase in NUE is manifested phenotypically, for example, as increased grain yield in cereal plants. A major QTL associated with increased NUE was identified as located in chromosome 5A in hexaploid bread wheat. This QTL locus has been denominated QNue.osu-5A, and the gene of the invention is located at the QNue.osu-5A locus. Isolated and cloned forms of the gene were used to produce genetically engineered plants which validated the function of the gene. The VRN1$^N$ gene from wheat cultivar Jagger is herein disclosed as the TaNUE1 gene (SEQ ID NO: 9).

This embodiment provides plant cultivars comprising at least one VRN1$^N$ gene from the wheat cultivar Jagger. In some aspects, the plant cultivar is a wheat cultivar. In some aspects, the plant cultivar is not a Jagger cultivar, but may be a cross between Jagger and another cultivar. In other aspects, the plant cultivar is not a Jagger cultivar. In additional aspects, the plant cultivar further comprises plant gene ANR1 from wheat cultivar Jagger (SEQ ID NO: 31) or from wheat cultivar 2174 (SEQ ID NO: 35).

One variation also provides methods of increasing one or more traits associated with nitrogen use efficiency (NUE) in a plant. The methods comprise the step of genetically engineering the plant to contain and express or over-express VRN1$^N$ from wheat cultivar Jagger (SEQ ID NO: 9). In some aspects, the one or more traits associated with NUE are selected from the group consisting of heading date, chlorophyll content, grain yield, harvest index, nitrogen concentration in grain, spike number per plant, grain number per spike, biomass per plant, and a ratio of grain yield to N supplied.

Further aspects of the invention provide methods of providing a plant cultivar that exhibits increased nitrogen use efficiency (NUE). The methods comprise the steps of i) crossing a plant cultivar comprising the VRN1$^N$ allele from wheat cultivar Jagger with a plant cultivar that does not comprise the VRN1$^N$ allele from wheat cultivar Jagger; ii) testing F1 generation plants produced by said step of crossing for the presence of the VRN1$^N$ allele from wheat cultivar Jagger; and iii) selecting, as a plant cultivar that exhibits increased NUE, a plant which tests positive for the presence of the VRN1$^N$ allele from wheat cultivar Jagger.

Yet further aspects of the invention include the plant gene ANR1 from wheat cultivar Jagger (SEQ ID NO: 31) and the plant gene ANR1 from wheat cultivar 2174 (SEQ ID NO: 35). The plant gene ANR1 encodes a protein that interacts physically with the protein encoded by VRN1$^N$. Plant cultivars comprising at least one plant gene ANR1 from wheat cultivar Jagger and/or from wheat cultivar 2174 are also compassed. In some aspects, the plant cultivar is a wheat cultivar. In other aspects, plant cultivar is not a Jagger cultivar or is not a 2174 cultivar. In additional aspects, the plant cultivar further comprises plant gene VRN1$^N$ from wheat cultivar Jagger. Methods of making such cultivars, either by genetic modification or by selective breeding, are also encompassed.

BRIEF DESCRIPTION OF THE DRAWINGS

FIG. 3A and FIG. 3B: FIG. 3A: Sequence of *Triticum aestivum* gene Gene 1 from A, Jagger cultivar (SEQ ID NO: 1) and FIG. 3B: 2174 cultivar (SEQ ID NO: 2).

FIG. 4A and FIG. 4B: FIG. 4A: Sequence of *T. aestivum* gene PCS from A, Jagger cultivar (SEQ ID NO: 3) and FIG. 4B: 2174 cultivar (SEQ ID NO: 4).

FIG. 5A and FIG. 5B: FIG. 5A: Sequence of *T. aestivum* gene CYB5 from A, Jagger cultivar (SEQ ID NO: 5) and FIG. 5B: 2174 cultivar (SEQ ID NO: 6).

FIG. 6A and FIG. 6B: FIG. 6A: Sequence of *T. aestivum* gene AGLG1 from A, Jagger cultivar (SEQ ID NO: 7) and FIG. 6B: 2174 cultivar (SEQ ID NO: 8).

FIG. 7A and FIG. 7B: FIG. 7A: Sequence of *T. aestivum* gene VRN1 from A, Jagger cultivar (SEQ ID NO: 9) and FIG. 7B: 2174 cultivar (SEQ ID NO: 10).

FIG. 8A and FIG. 8B: FIG. 8A: Sequence of *T. aestivum* gene CYS from A, Jagger cultivar (SEQ ID NO: 11) and FIG. 8B: 2174 cultivar (SEQ ID NO: 12).

FIG. 9A and FIG. 9B: FIG. 9A: Sequence of *T. aestivum* gene PHY from A, Jagger cultivar (SEQ ID NO: 13) and FIG. 9B: 2174 cultivar (SEQ ID NO: 14).

FIG. 10A and FIG. 10B: FIG. 10A: Sequence of *T. aestivum* gene GT1 from A, Jagger cultivar (SEQ ID NO: 15) and FIG. 10B: 2174 cultivar (SEQ ID NO: 16).

FIG. 11A and FIG. 11B: FIG. 11A: Sequence of *T. aestivum* gene STR from A, Jagger cultivar (SEQ ID NO: 17) and FIG. 11B: 2174 cultivar (SEQ ID NO: 18).

FIG. 12A and FIG. 12B: FIG. 12A: Sequence of *T. aestivum* gene KIN from A, Jagger cultivar (SEQ ID NO: 19) and FIG. 12B: 2174 cultivar (SEQ ID NO: 20).

FIG. 13A and FIG. 13B: FIG. 13A: Sequence of *T. aestivum* gene CBP1b from A, Jagger cultivar (SEQ ID NO: 21) and FIG. 13B: 2174 cultivar (SEQ ID NO: 22).

FIG. 14A and FIG. 14B: FIG. 14A: Sequence of *T. aestivum* gene USP from A, Jagger cultivar (SEQ ID NO: 23) and FIG. 14B: 2174 cultivar (SEQ ID NO: 24).

FIG. 15A and FIG. 15B: FIG. 15A: Sequence of *T. aestivum* gene EX from A, Jagger cultivar (SEQ ID NO: 25) and FIG. 15B: 2174 cultivar (SEQ ID NO: 26).

FIG. 16A and FIG. 16B: FIG. 16A: Sequence of *T. aestivum* gene CDO708 from A, Jagger cultivar (SEQ ID NO: 27) and FIG. 16B: 2174 cultivar (SEQ ID NO: 28).

FIG. 17: Recombinant lines that were tested for genetic effects of QNue.osu-5A on heading date in N-deficient soil. Results are shown in tabular form. Three critical recombinant lines, D1032, P55 and D695, indicate that TaNUE1 is in the targeted gene between PCS1 and CYS1.

FIG. 18A: Genetic map of the location of the indicated traits.

FIG. 18B: Final physical map of TaNUE1. TaNUE1 was located between two flanking markers PCS1 and CYS1, in the region where only three candidate genes, CYB5, AGLG1, and VRN1, were present.

FIG. 19A: spikes per plant; FIG. 19B: grains per spike; FIG. 19C: weight (g) per 1000 grains; FIG. 19D: grain yield; FIG. 19E: biomass; FIG. 19F: harvest index.

FIG. 20A: ANR1 and VRN1 proteins and FIG. 20B: ANR1 and AGLG1 proteins. ANR1, VRN1a, AGLG1a were from Jagger, whereas VRN1b and AGLG1b were from 2174. M: protein molecular weight markers.

FIG. 21A-FIG. 21F: In vivo protein interactions between ANR1 and VRN1. FIG. 21A: The subcellular location of TaANR1-YFP protein expressed by pEG101 in the nucleus (N) of living cells in tobacco leaves. FIG. 21B: TaANR1-YFP-pEG101 cell nucleus was stained with 4', 6-diamidino-2-phenylindole (DAPI). FIG. 21C: VRN1-pEG201-YN and ANR1-pEG202-YC proteins were expressed in the nucleus (N) of living cells. FIG. 21D: The interacting proteins were stained with DAPI. FIG. 21E: The image (A) was taken with a bright filter (BF) to indicate the background of the leaves. FIG. 21F. The overlay images align the location of YFP with the DAPI-stained nucleus.

FIG. 22A: Regulation of VRN-A1$^N$ transcripts by N in normal wheat grown in different soils. FIG. 22B: Regulation of heading date by N in normal wheat grown in different soils. FIG. 22C: Regulation of VRN-A1$^N$ transcripts by RNAi in transgenic wheat grown in yellow soil. FIG. 22D: Regulation of heading date by RNAi in transgenic wheat grown in yellow soil.

FIG. 23A-FIG. 23E: ANR1 natural mutant and transgenic plant. FIG. 23A: Variation of ANR1 transcripts between Jagger and 2174. FIG. 23B: A PCR marker for ANR1 between the Jagger and 2174 alleles. For FIG. 23A and FIG. 23B: lanes 1 and 2 are independent samples from Jagger; lanes 3 and 4 are two independent samples from 2174; and M=molecular weight markers. FIG. 23C: A diagram of indel locations and sequences in ANR1 between the Jagger and 2174 alleles. FIG. 23D: Regulation of ANR1 transcripts by N and RNAi in transgenic wheat. FIG. 23E: Comparison of typical transgenic plant carrying ANR1::RNAi and a non-transgenic plant.

FIG. 24: Amino acid sequence of the VRN1 protein from the Jaggar cultivar (SEQ ID NO: 29).

FIG. 25A-FIG. 25D: FIG. 25A: amino acid sequence of ANR1 protein (SEQ ID NO: 30) from Jagger; FIG. 25B: nucleotide sequence of ANR1 gene (SEQ ID NO: 31) from Jagger; FIG. 25C: amino acid sequence of ANR1 protein (SEQ ID NO: 34) from 2174; and FIG. 25D: nucleotide sequence of ANR1 gene (SEQ ID NO: 35) from 2174.

FIG. 26A and FIG. 26B: FIG. 26A: amino acid sequence of HOX1 gene protein (SEQ ID NO: 32) from Jagger; and FIG. 26B: nucleotide sequence of HOX1 gene (SEQ ID NO: 33) from Jagger.

DETAILED DESCRIPTION OF THE PREFERRED EMBODIMENTS

Figure 1:
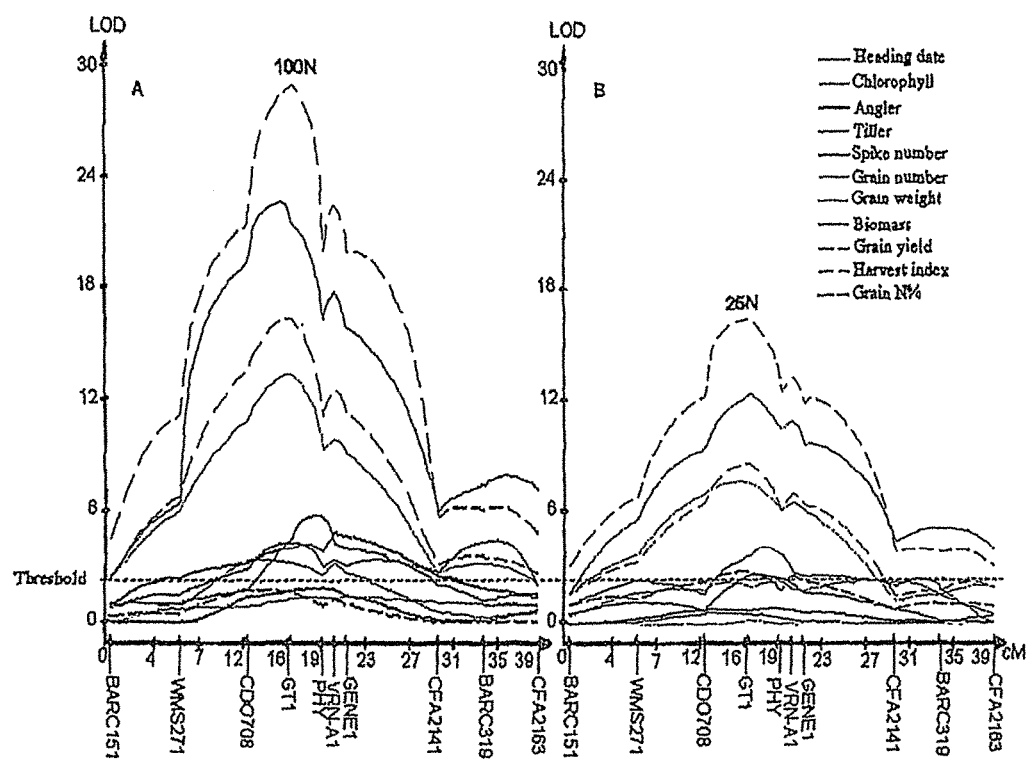
FIG. 1: QNue.osu-5A. A major QTL responsible for multiple phenotypic traits that vary in response to variations in N amounts was mapped by testing in Jagger×2174 population. Plants were grown in N-deficient soil with normal levels of other essential nutrients. The N-stressed plants were then supplied with 100-mg N/pot (A) and 25-mg N/pot (B).

Wheat genetics experiments have allowed the identification of a major QTL QNue.osu-5A associated with high NUE in plants in a population of recombinant inbred lines generated from two winter wheat cultivars, Jagger and 2174. The genes included within the QTL are located on wheat chromosome 5A at locus QNue.osu-5A, in the genomic region between the two flanking genes GENE1 and CDO708 (see FIG. 2). 44 genes (encoding proteins) in the collinear region in rice, were analyzed, including: 1) OSJNBa0069E14.12 (hypothetical protein), 2) OSJNBa0069E14.13 (dehydrogenase), 3) OSJNBa0069E14.3 (growth inhibitory protein ING1), 4) OSJNBa0069E14.14 (antifreeze glycoprotein precursor), 5) SRPK4 (Serine/Threonine rich protein kinase), 6) OSJNBa0069E14.15 (reductase), 7) OSJNBa0069E14.10 (unknown protein), 8) OSJNBa0069E14.4 (hydrogenase), 9) OSJNBa0069E14.16 (helicase), 10) OSJNBa0069E14.5 (arginine-rich protein), 11) OSJNBa0069E14.17 (ammonium transporter), 12) OSJNBa0069E14.6 (beta-D-glucan exohydrolase), 13) OSJNBa0069E14.7 (exoglucanase precursor), 14) OSJNBa0069E14.20 (hypothetical protein), 15) OSJNBa0069E14.21 (circumsporozoite protein-like protein), 16) OSJNBa0069E14.22 (hypothetical protein), 17) OSJNBa0069E14.8 (EX, exohydrolase), 18) OSJNBa0069E14.24 (hypothetical protein), 19) OSJNBa0069E14.23 (tousled-like protein kinase), 20) OSJNBa0047E24.24 (expressed protein), 21) OSJNBa0047E24.26 (USP, expressed protein), 22) OSJNBa0047E24.27 (CBP, putative stress-related protein), 23) OSJNBa0047E24.25 (KIN, kinesin-like protein), 24) OSJNBa0047E24.22 (STR, strictosidine synthase), 25) OSJNBa0047E24.21 (transcriptional adaptor), 26) OSJNBa0047E24.20 (hypothetical protein), 27) OSJNBa0047E24.19 (expressed protein), 28) OSJNBa0047E24.18 (expressed protein), 29) OSJNBa0047E24.17 (GT: glutathione transporter, oligopeptide transporter protein), 30) OSJNBa0047E24.15 (hypothetical protein), 31) OSJNBa0047E24.14 (transposase) (wheat orthologue, if present), 32) OSJNBa0047E24.13 (ribosomal protein L6), 33) OSJNBa0047E24.10 (hypothetical protein), 34) OSJNBa0047E24.9 (phytochrome C), 35) OSJNBa0047E24.8 (DNA topoisomerase), 36) OSJNBa0047E24.7 (potassium channel protein), 37) OSJNBa0047E24.5 (cysteine protease), 38) OSJNBa0047E24.2 (VRN-A1, AP1-like MADS box protein), 39) OSJNBa0047E24.1 (AGLG1, MADS-box transcriptional factor), 40) EAY91897 (CYB5, Cytochrome b5-like), 40) 3615.7 (AAM22488.1, putative phytochelatin synthetase), 40) 3615.5 (AAG45493.1, DUF1618), 42) 3615.4 (ABC transporter), 43) 3615.3 (serine/threonine kinase), 44) 3615.2 (cleavage stimulation factor subunit 1). 45) 3615.1 (putative mitochondrial carrier protein).

In particular, the following genes were identified as associated with increased NUE: CYB5; AGLG1 (OSJNBa0047E24.1); VRN1 (OSJNBa0047E24.2) by experiments on critical RILs that have crossovers at QNue.osu-5A, as shown FIG. 17.

More particularly, the VRN1 gene from Jagger cultivar (SEQ ID NO: 9) has been identified as a TaNUE1 responsible for NUE in plants. VRN1 is hereafter referred to as VRN1$^N$ for its reaction to N.

Generally, the invention encompasses the VRN1$^N$ gene from Jagger cultivar (SEQ ID NO: 9) which encodes the VRN1 protein (FIG. 24, SEQ ID NO: 29), as well as sequences which encode proteins or polypeptides that are at least about 50%, 55%, 60%, 65%, 70%, 75%, 80%, 85%, 90%, 95% or even more (e.g. 96, 97, 98, 99 or 100%) identical or similar to VRN1. By "identical" or "identity" we mean that the primary sequence of amino acids in the protein/polypeptide is the same when the sequences are aligned (excluding regions where deletions or insertions have occurred). By "similar" or "similarity" we mean that the primary sequence of amino acids in the protein/polypeptides, when rice and wheat translation products are aligned, is either identical (the amino acids at corresponding positions are the same) or are contains only conservative substitutions, e.g. the amino acids at both positions is negatively charged, positively charged, aliphatic, etc. Those of skill in the art are familiar with methods for determining levels of identity and similarity (e.g. by using software programs that are designed to provide this information) and are also familiar with interpreting the results and significance of such analyses. As is the case for determining identity, regions of insertions or deletions may be excluded from such analyses, or may be "weighted" so as to taken into account in a final analysis, or more than one value for identity or similarity may be provided, e.g. a value may be provided only for regions where no insertions or deletions have taken place. Further, those of skill in the art will recognize that the genes encoding the proteins/polypeptides may or may not have high levels of identical sequences when compared to one another, due to the redundancy of the genetic code (i.e. several different codons may encode the same amino acid). Thus, the level of identity (which may also be referred to as "homology") between the gene sequence of the VRN1$^N$ gene may be the same as described above for the proteins/polypeptides, but may also be lower, e.g. 10%, 15%, 20%, 25%, 30%, 35%, 40%, 45%, 50% or more, and so on, as described above.

VRN1$^N$ or variants thereof cause increased NUE in plants which contain and express VRN1$^N$ and/or its variants, resulting in advantageous traits such as early heading and increased grain yield in cereal crops, when compared to plants containing only wild type genes.

Generally, the present invention encompasses NUE-associated nucleic acid sequences (which may be genes), methods for their use, and plants which contain the sequences, the plants having been produced either by cross-breeding or by genetic engineering. By "NUE-associated nucleic acid sequences" we mean sequences which have been identified as impacting (influencing, governing, controlling, responsible for, etc.) the efficiency of nitrogen utilization by a plant, e.g. VRN1$^N$ from cultivar Jaggar. The sequences may be associated with one or both of N uptake efficiency (NupE) and N utilization efficiency (NutE), or with other factors which have an impact on N utilization by the plant.

In some embodiments, the NUE-associated nucleic acid sequence is a gene which encodes a protein. Generally, the protein is involved in nitrogen uptake and sequestration in the plant, or with utilization of nitrogen that has been taken up, or both. The nucleic acid sequences for VRN1$^N$ are presented in FIG. 7A and FIG. 7B. For convenience, a NUE-associated gene may be referred to herein and in the Examples section below as "TaNUE1", i.e. the gene has been named (or renamed) to accord to its newly-recognized functions and capabilities. A series of such genes may be referred to as TaNUE1-1, TaNUE1-2, etc. In some aspects, TaNUE1 is the VRN1$^N$ gene from the Jaggar cultivar.

Generally, the enhanced or increased NUE caused by a TaNUE1 of the invention is at a level that is at least about 5%, 10%, 15%, 20%, 25%, 30%, 35%, 40%, 45%, 50%, 55%, 60%, 65%, 70%, 75%, 80%, 85%, 90%, 95%, 100% or even higher than the level of NUE that is displayed by a control plant (e.g. a wild type plant, or a reference plant that has not been genetically engineered to contain and express or overexpress the variant), or even 2, 3, 4, 5, 6, 7, 8, 9, or 10-fold or more higher. Such increases are determined by measuring at least one detectable parameter, e.g. an objective criteria or trait associated with increased with increased NUE. Examples of such criteria or traits include but are not limited to: heading date; chlorophyll content of plant, e.g. in the leaves; angler degree of leaves; tillers per plant; spikes per plant; biomass; harvest index; grains per spike, grain weight, grain yield, content of nitrogen and other nutrients in grains and plant tissues, etc.

One embodiment also provides genetically engineered plants that have been genetically modified, using molecular biology techniques, to contain and express at least one VRN1$^N$ gene (e.g. from Jaggar) and/or at least one ANR1 gene (e.g. from Jaggar or 2174), or variants thereof as described herein. In other words, plants comprising multiple copies of the genes described herein are also encompassed. For example, the plant may comprise a "native" gene and one or more copies of the same gene, or a function conservative variant thereof, or one or more copies of a different gene (or genes), that have been introduced by genetic engineering or selective breeding. A function conservative variant has the same or substantially the same level of an activity of interest (e.g. increasing NUE) as the parent molecule, e.g. at least about 50, 60. 70. 80 or 90% or more, of the activity of the parent molecule.

The genetically engineered plants of the invention are transformed using any of the many methods that are known in the art. Exemplary methods include but are not limited to: particle bombardment using small metal particles, e.g. gold or tungsten, coated with DNA and which are shot into young plant cells or plant embryos; electroporation, whereby transient holes are made in plant cell membranes using an electric shock, thereby allowing DNA to enter, etc.

One variation of the invention also encompasses nucleic acid sequences that are not identical to those provided herein, but which are at least about 90, 91, 92, 93, 94, 95, 96, 97, 98, or 99% homologous to those sequences. The sequences may be the result of point mutations and may or may not change the encoded amino acid. Other variations of the sequences include those which result from various deletions or insertions, so long as the resulting encoded amino acid sequence has substantially the same activity with respect to plant NUE as the amino acid sequence encoded by the nucleotide sequences disclosed herein. Generally, the activity level is at least about 50, 60, 70, 80, or 90% or even greater, than that of the original encoded amino acid sequence, and may even be greater than that of the original, parent sequence. Further possible changes include but are not limited to: the insertion or removal of restriction enzyme cleavage sites, incorporation of sequences which assist in manipulation of the sequence or the amino acid sequence encoded thereby (e.g. the inclusion of sequences encoding a Histidine tag, or sequences which function as a label of the nucleotides); etc. Such nucleic acid sequences may be single or double stranded. In addition, homologous or base-paired sequences such as cDNA, mRNA, DNA-RNA hybrids, etc. that correspond to or are based on the sequences disclosed herein are also encompassed.

The amino acid sequences of an embodiment may also vary somewhat from those that are encoded by the nucleotide sequences disclosed herein. For example, various conserved amino acid substitutions may be present, as may certain deletions (typically at the amino or carboxy termini), or even non-conserved amino acid substitutions may occur, so long as the changes do not significantly attenuate the NUE activity of the amino acid sequence. The variations may be due to, for example, natural variations in sequence among different species or cultivars, the addition of a leader sequence to promote secretion, the addition of a sequence to promote translocation of the sequence within the cell, the addition of tagging sequences which facilitate tracking or isolation of polypeptides, the addition or elimination of glycosylation sites, sequences which improve or decrease solubility of a polypeptide, etc. Generally, the altered sequences will exhibit identity (similarity) to the sequences disclosed herein of at least about 50, 55, 60, 65, 70, 75, 80, 85, 90, 95, or higher. Such variations can be tolerated and are encompassed by the present invention so long as the resulting sequence displays or retains at least about 75%, preferably 80, 85, 90%, or at least about 95% or more of the activity of the sequences disclosed herein. In some cases, such changes may cause an increase in activity. All such variations of the sequences disclosed herein are encompassed by the present invention.

In other embodiments of the invention, plants containing and expressing the NUE-associated VRN1$^N$ are produced by purposeful, directed plant breeding techniques, and are not necessarily genetically engineered. Those of skill in the art are familiar with methods used to select, cross and cultivate suitable plants, and to identify plant progeny of interest which display a desired trait, such as a trait that is indicative of increased NUE. Further, the presence of one or more nucleic acid sequences of the invention in such progeny plants can be confirmed by known methods of gene sequencing, or identification and characterization of mRNA or an amino acid sequence that is encoded by the gene.

The invention also encompasses transgenic (genetically modified) plants which contain and express or overexpress VRN1$^N$, as well as method of making such plants. Exemplary plants that can be genetically modified as described herein include but are not limited to: grasses, e.g. members of the monocot families Poaceae or Gramineae which may also be known as cereals, grains or cereal grains, examples of which include but are not limited to wheat, rice, maize (corn), triticale, oats, barley, rye, spelt, sorghum, millet, fonio, and others; members of the Polygonacea family such as buckwheat; members of the Amaranthaceae family such as quinoa and various amaranths. In addition, one of skill in the art will recognize that the genetically engineered plants of the invention may also include: vegetable plants (e.g. carrots, tomatoes, onions, squash, beets, lettuce, peppers, cabbage, potatoes, etc.); various legumes or beans such as peas, soybeans, peanuts, etc.; herbs; various ornamental plants; plants which produce berries; plants which produce materials for use in various manufactures such as cotton, flax, etc.; various species of trees and shrubs; plants or other organisms which are used to generate biofuel (e.g. switchgrass, *Brachypodium distachyon*, hemp, sunflowers, soy, rapeseed, photosynthetic algae, etc.). Any plant or organism which utilizes nitrogen may benefit from being genetically engineered to contain and express the NUE-associated nucleic acid sequences described herein.

Progeny of the genetically engineered and selectively bred plants described herein are also encompassed, as are all parts or portions of the plants, e.g. seeds stalks, leaves, roots, etc., and all stages of the life cycle of the plant, e.g. embryos, cuttings, grafts, etc.

Experimental evidence provided herein (see the Examples below) demonstrates that $VRN1^N$ is TaNUE1 at QNue.osu-5A in bread wheat. In addition, direct interaction of the $VRN1^N$ protein with ANR1, and regulation of $VRN1^N$ and ANR1 by N in normal and transgenic wheat plants, further suggests that the gene ANR1 may also be involved in NUE. Thus, further aspects of the invention include transgenic plants and methods of making the plants which include one or more copies of ANR1, optionally with $VRN1^N$ in the same plant. Further experiments described below showed that the protein encoded by the HOX1 gene, HOX1, is also involved in plant development (e.g. due to its interaction with $VRN1^N$). Thus, further aspects of the invention include transgenic plants and methods of making the plants which include one or more copies of HOX1, optionally with $VRN1^N$ and/or ANR1 in the same plant. For example, in winter wheat, the VRN1-HOX1 interaction has a significantly stronger effect on e.g. flowering time than the VRN1-ANR1 interaction.

In some aspects, the genes described herein are used as molecular markers, e.g. for gene pyramiding to produce novel wheat cultivars with desirable traits, such as high NUE. Gene pyramiding is a method aimed at assembling multiple desirable genes (markers) from multiple parents into a single genotype. This technique can be applied to enhance NUE, for example, using two or more of the genes described herein, e.g. $VRN1^N$ and/or ANR1 (e.g. from cultivars such as Jagger and 2174, and variants thereof) by selecting for two genes at a time. Selection can be performed, e.g. by designing and using oligonucleotide primers specific for the genes described herein (e.g. $VRN1^N$, ANR1, etc.), and such primers are also encompassed by the invention. The design of primers to amplify a sequence of interest is known in the art, e.g. primers with sequences that are base pair with a portion of a sequence of interest. One advantage of using markers is that this allows selection of additional QTL-allele-linked markers that have the same phenotypic effect. Once identified, several marker genes can be incorporated into a plant, e.g. by genetic engineering or by selective breeding, in order to promote a particular desirable phenotype, e.g. highly efficient use of nitrogen.

The following Examples serve to illustrate various embodiments of the invention but should not be construed so as to limit the invention in any way.

EXAMPLES

Example 1. Discovery of a Major QTL for NUE

Construction of a Genetic Map for Winter Wheat

A total of 365 markers were mapped in the Jagger×2174 population of 96 recombinant inbred lines (RILs) generated from a cross between two locally adapted winter wheat cultivars Jagger and 2174. This high density of genetic map has been used successfully to locate QTLs for complex traits related to developmental process for stem elongation and winter dormancy release (Chen et al. 2009), heading date and physiological maturity (Chen et al. 2010), resistance to powdery mildew (Chen et al. 2009), resistance to leaf rust (Cao et al. 2010), resistance to stripe rust (Fang et al. 2011). This genetic map has now been used to locate a major QTL for NUE in this study.

Discovery of a Major QTL for NUE

Three sets of populations of 96 recombinant inbred lines (RILs) and their parental lines were tested for segregation for responses to nitrogen (N). The experiments were performed in pots in a greenhouse, where conditions were controlled for temperature, photoperiod, and moisture conditions in order to reduce interactions between genetic and environmental factors on N utilization.

The first set population was grown in a commercial growth media, and only the heading date was recorded for the purpose of comparison with another two sets of populations that were tested for the responses to N fertilizer. The second and third sets of population plants were first grown in soil with N-deficiency but with an adequate supply of other nutrients. The initial plant available nutrient levels of the soil were, nitrate N (2.4 $mgKg^{-1}$), P (42.2 $mgKg^{-1}$), K (115.5 $mgKg^{-1}$), $SO_4$ (6.4 $mgKg^{-1}$), Ca (420.7 $mgKg^{-1}$), Mg (81.9 $mgKg^{-1}$), Fe (28.7 $mgKg^{-1}$), Zn (0.9 $mgKg^{-1}$), B (0.14 $mgKg^{-1}$), Cu (0.3 $mgKg^{-1}$), and organic matter content (OM: 0.69%). The soil had a low organic matter content (0.39%) and moderate pH value (5.83).

The parental lines and second and third sets of populations showed no significant difference in morphological trait at young seedlings when grown in N-deficient soil, indicating that these two cultivars have similar tolerance to N stress. After they were fertilized with 100 mg N/pot (=54.06 mg N/kg soil, 100N) and 25 mg N/pot (=13.51 mg N/kg soil, 25N) respectively, these population plants showed significant segregation in agronomic and physiological traits.

Eleven traits were characterized for two populations supplied with different N levels of soils. When the phenotypic traits were analyzed with the genetic map, it was found that a major QTL was associated with variation in all of the traits studied (FIG. 1). This major QTL locus was located in chromosome 5A, where the vernalization gene $VRN1^N$ resides. Hence, this QTL locus was designated QNue.osu-5A.

Genetic effects of QNue.osu-5A on each of the traits are summarized in Table 1. Overall, the following conclusion can be made: 1) QNue.osu-5A was associated with strong responses to N fertilizers at both N levels supplied to the soil; 2) most of the phenotypes characterized in the preliminary experiments showed larger segregation in the population treated with 100N than 25N; 3) fertilizer N level variation resulted in various effects on different phenotypes characterized in this study.

Heading date is a most sensitive trait to N fertilizer. At the 100N fertilizer level, QNue.osu-5A explained as much as 68.2% of the total phenotypic variation, and at the 25N fertilizer level, it explained 51% of the total phenotypic variation. In the commercial growth medium, it accounted for 20.6% of the total phenotypic variation (data not shown).

Chlorophyll content of the leaf is a trait that is directly affected by N level. 20.7% of the total phenotypic variation in 100N population could be explained by QNue.osu-5A, but no significant genetic effect in 25N population was detected at this QTL.

Grain yield is the most important trait for utilization of N fertilizers. Grain yield of this experiment had a typical response to N fertilization. Plant grain yield of the 100N population was 0.601 g/plant, increased 121% in comparison to 0.272 g/plant for the 25N population. Significantly, about 55.3% and 38.5% of the total variation in grain yield in 100N and 25N populations were respectively explained by QNue.osu-5A.

The N content of wheat grains also showed a direct link to the QTL at QNue.osu-5A, which had a LOD score value of 3.3 and 1.9 explaining 15.4% and 8.8% to the total phenotypic variation in 25N and 100N populations, respectively.

It is noteworthy that these data were obtained from the population plants grown under controlled temperature and light conditions through the life cycle. Moreover, these plants are a winter type but they were not vernalized at all, because the two parental lines had different vernalization requirements. The major aim of this experiment was to find a major QTL for NUE under controlled conditions, from which a starting point could be opened to enter the NUE gene network for further studies on how the complex trait is regulated under varying environments.

TABLE 1

Genetic effects of ONue.osu-5A on 11 traits related to N utilization and yield
Analysis of sequences of collinear region of rice genome

| | 100N | | 25N | |
|---|---|---|---|---|
| Traits | LOD | R2 (%) | LOD | R2 (%) |
| Heading date | 22.8 | 68.2 | 14.6 | 51.0 |
| Chlorophyll % in leaf | 4.2 | 19.4 | NS | NS |
| Angler degree of 2nd leaf | 1.9 | 8.8 | NS | NS |
| Tillers per plant | 5.8 | 25.4 | 3.1 | 13.9 |
| Spikes per plant | 4.3 | 18.6 | 4.8 | 22.7 |
| Grains per spike | 13.5 | 47.4 | 9.1 | 36.4 |
| Grain weight | 3.5 | 15.9 | NS | NS |
| Grain yield | 16.5 | 55.3 | 10.2 | 38.5 |
| Biomass | 1.4 | 6.4 | 2.6 | 13.2 |
| Harvest index | 29.1 | 74.9 | 19.4 | 60.9 |
| N% in grains | 1.8 | 8.8 | 3.3 | 15.4 |

Figure 2:
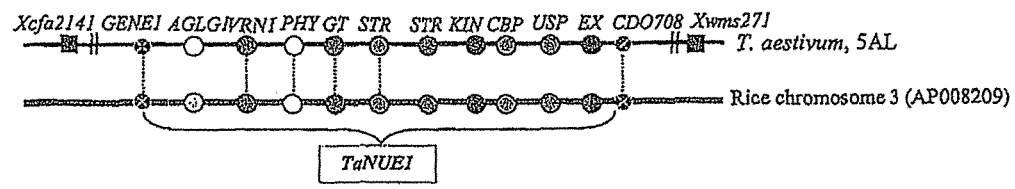
FIG. 2: Candidate genes for TaNUE1 on QNue.osu-5A according to genomic sequences of collinear region in rice. Genes that are mapped between Gene1 and CDO708 are candidate genes for TaNUE1.

Sequences of regions collinear to QNue.osu-5A in rice (GenBank accession number AP008209) were analyzed. QNue.osu-5A is located in the region encompassing the VRN1 locus and is conserved among diploid wheat *T. monococcum*, rice and other cereal crops (Yan et al. 2003). Several genes have been successfully mapped in genome A of bread wheat (FIG. 1 and FIG. 2).

The gene responsible for QNue.osu-5A is designated TaNUE1, the first gene for NUE in *Triticum aestivum*. Cloning and characterization of TaNUE1 will be an entry point for construction of the gene network for NUE in wheat.

Example 2. Narrowing Down the Genomic Region Encompassing TaNUE1

As described above. TaNUE1 at the QTL locus QNue.osu-5A on wheat chromosome 5A was previously identified as one among 44 orthologous genes (encoding proteins) in the 344-kb collinear region on chromosome 3 in rice. To further elucidate the identity of TaNUE1, RIL23 carrying the Jagger QNue.osu-5A allele was backcrossed with the parental line 2174 and a total of 6,410 $BC_1F_3$ plants derived from $BC_1F_2$ plants heterozygous at QNue.osu-5A were generated. PCR markers for GENE1 and CDO708 that flanked the gene responsible for QNue.osu-5A (original FIG. 2) were used to genotype the 6,410 individual plants and 106 crossovers were found between GENE1 and CDO708. Progeny plants of seven critical recombinant plants were tested for their reactions to N.

Based on progeny tests of 15 recombinant lines (FIG. 17), TaNUE1 was delimited between GENE1 and CDO708.

Figures 18A, 18B:
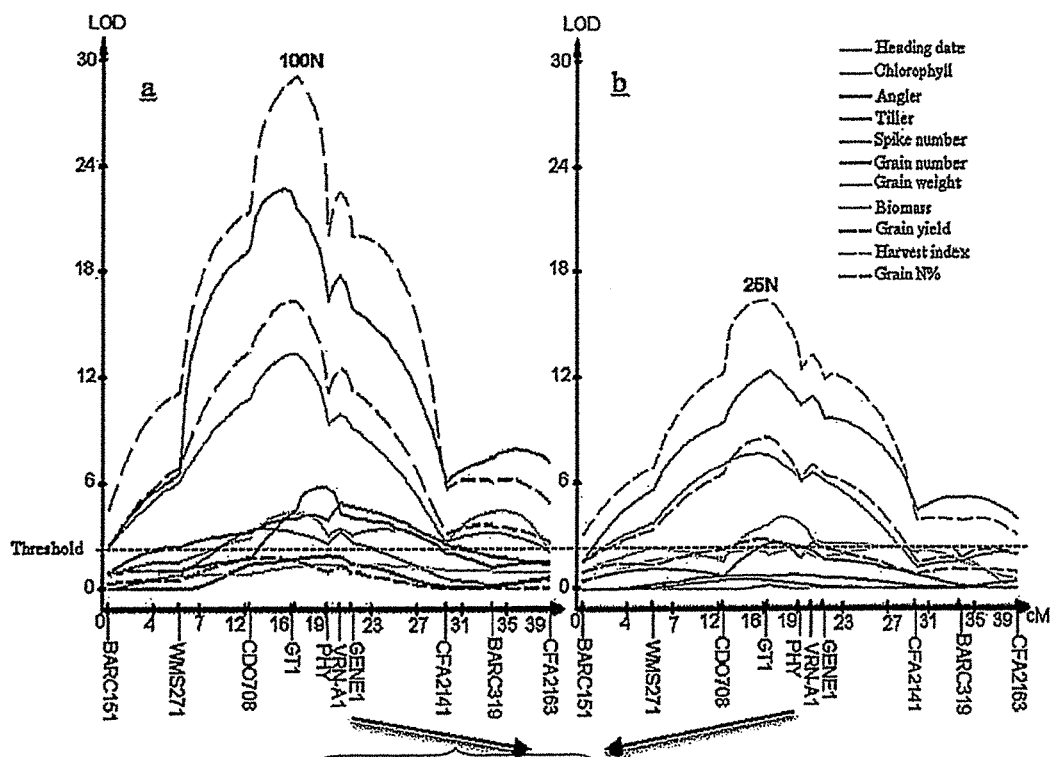
FIG. 18A and FIG. 18B: Genetic and physical maps of TaNUE1.

Heading date is one of several phenotypes associated with nitrogen use efficiency in winter wheat. Progeny plants generated from 15 of the 106 recombinant $BC_1F_{2:3}$ lines were tested for the segregation of heading date, and crossovers in these plants were distributed along the targeted region (nor shown). As the original RILs were tested to map QNue.osu-5A, the progeny plants were grown in the same type of N-deficient soil, fertilized with 100 mg N/pot (=54.06 mg N/kg soil, 100N) 12 weeks after planting, and not vernalized. The integration of phenotypes and genotypes of these recombinant lines showed that the gene for the segregation of heading date was located in the region between two gene markers for PCS1 and CYS1 (shown in tabular form in FIG. 18). Those plants carrying the Jagger allele (158.3 days) headed up significantly earlier than those plants carrying the 2174 allele (174 days). The averaged difference between the two alleles in the 15 recombinant lines was similar to the difference between the two parental lines (16 days). The Jagger allele for early heading showed a dominant effect over the 2174 allele for late heading in the heterozygous $BC_1F_{2:3}$ population, and the acceleration of heading date by the Jagger allele was confirmed in three $BC_1F_3$ populations (FIG. 17).

When the seven critical recombinant plants were grown in commercial soils with sufficient N and vernalized with 3 weeks, the Jagger allele for early heading was dominant over the 2174 allele for late heading, and the average difference between the two alleles was 25 days. Further comparison of the heading date in the N experiments and the three week vernalization experiments showed that the segregation pattern in heading date was similar in each of the populations (Table 2). These results suggested that the genes for N and low temperatures were located in the same region, where only three genes were encompassed including CYB5, AGLG1 and $VRN1^N$.

TABLE 2

Comparison of the effect of QNue.osu-5A on flowering time in different soils

| Plant ID | Yellow soil | | | Commercial soil | | |
|---|---|---|---|---|---|---|
| | A | B | H | A | B | H |
| D1032 | 182 | 203 | 194 | 148 | 147 | 149 |
| P55 | 159 | 193 | — | 93 | 122 | — |
| D695 | 174 | 203 | 193 | 92 | 139 | 98 |
| D731 | 178 | 179 | 175 | 133 | 141 | 142 |
| D1061 | 159 | 163 | 157 | 90 | 94 | 94 |
| L447 | 168 | 206 | — | 86 | 147 | — |
| T657 | 143 | 201 | — | 89 | 159 | — |
| Jagger | 155 | | | 84 | | |
| 2174 | | 177 | | | 122 | |

Phenotypic Effects of TaNUE1 in the Field

Seven critical recombinant lines, each having a crossover at QNue.osu-5A, were tested in the field for effects of TaNUE1 on productivity. The experiments were performed at OSU Perkins Research Station near Stillwater for two years, in a field where no N fertilizer had been used for two consecutive seasons. Forage was grown in the field to level soil fertility for all lines tested. Plots were arranged in a completely randomized design with three replications for the recombinant lines and parents.

Figure 19A:
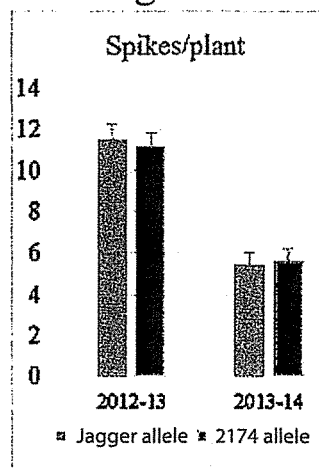
FIG. 19A-FIG. 19F: Genetic effects of VRN1 in seven critical recombinant lines tested in the field. The experiments were conducted at OSU Perkins Research Station.
Figure 19B:
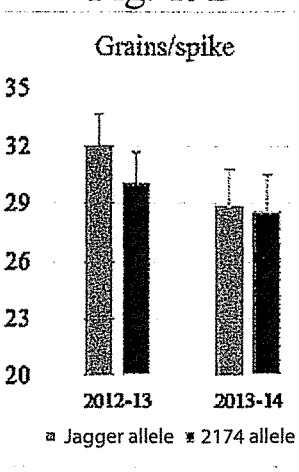
Figure 19C:
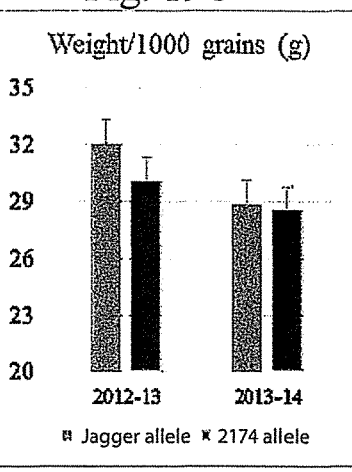
Figure 19D:
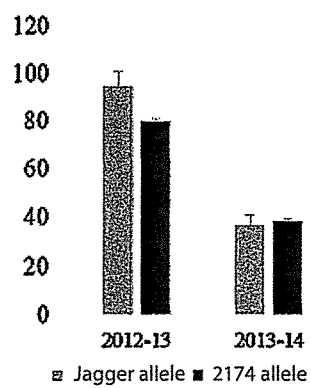
Figure 19E:
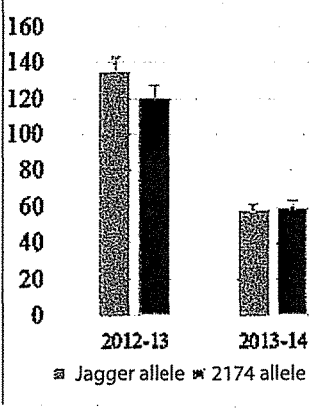
Figure 19F:
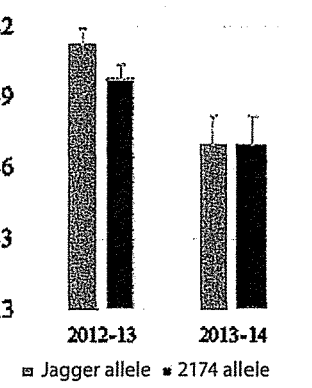

When the seven critical recombinant lines were tested and the basal fertility in the soil was 15 lbs. per acre for $NO_3^-$—N, spike number per plant (FIG. 19A), grain number per spike (FIG. 19B), and weight per thousand grains (FIG. 19C) all were relatively increased. As a result, grain yield was increased by 18.1% (FIG. 19D). The significant increase of grain yield was due to increases of both biomass (12.7%, FIG. 19E) and harvest index (4%, FIG. 19F). These results indicated that the N resources available in the soil were more efficiently utilized throughout the whole life cycle in those lines carrying the Jagger allele than those lines carrying the 2174 allele at QNue.osu-5A.

When the seven critical recombinant lines were further tested and the basal fertility in the soil was decreased to 10.3 lbs. per acre for $NO_3^-$—N, plant productivity was dramatically decreased, and no significant difference was observed between the two alleles in any of the grain yield components or in grain or biomass productivity (FIG. 19A-F). The observation was consistent with the previous results that the LOD value of QNue.osu-5A was significantly decreased when RILs having diverse genetic backgrounds were tested in 25 mg N/pot compared with 100 mg N/pot. These results confirmed that the TaNUE1 is a gene within the targeted region between the two gene markers, PCS1 and CYS1. Three candidate genes were included in this region CYB5, AGLG1 or $VRN1^N$.

Example 3 Identification of Candidate Genes for TaNUE1

Allelic Variation in Candidate Genes for TaNUE1

Only three genes, CYB5, AGLG1, and $VRN1^N$, were identified as candidate genes for TaNUE1. A comparison of allelic variation in these three candidates showed no difference in the gene region from the start codon to the stop codon of CYB5, but a SNP resided in its downstream region at the 3' end, permitting development of a PCR marker for mapping. There was also one SNP in the AGLG1 gene region which resulted in a point mutation in the AGLG1 protein: serine (Ser) in Jagger and alanine (Ala) in 2174. There were two SNPs in $VRN1^N$ which resulted in two point mutations in the VRN1 protein. One SNP occurred in exon 4, producing a leucine (Leu) at position 117 in the VRN1a protein encoded by the Jagger allele but a phenylalanine (Phe) at the same position in VRN1b encoded by the 2174 allele. This $Leu^{117}/Phe^{117}$ substitution occurred within the conserved K-box which is located at positions from 89 to 174. The second SNP occurred in exon 7, producing an alanine (Ala) at position 180 in VRN1a but a valine (Val) at the same position in VRN1b, and the $Ala^{180}/Val^{118}$ substitution occurred in the divergent C-terminus of the protein.

No gene related to NUE has previously been found or cloned in wheat or any other crop. AtANR1, a $NO_3^-$-inducible Arabidopsis gene, is a MADS-box gene and plays a key role in regulating lateral root growth in response to changes in the external $NO_3^-$ supply in Arabidopsis (Zhang and Forde 1998). The plant MADS-box proteins may form protein complexes, in which one MADS-box protein may positively or negatively regulate the expression of another MADS-box gene in a direct interaction manner (Riechmann and Meyerowitz 1997; Jack 2004). In Arabidopsis, another several MADS-box genes, e.g. AGL14, AGL16, AGL19, SOC1 and AGL21, have been reported to respond to N fertilizers (Gan et al. 2005). Both VRN-A1 and AGLG1 belong to the MADS-box gene family. Based on genetic association, allelic variation and predicted protein function, both AGLG1 and VRN1 were viable candidates for TaNUE1. Therefore, further properties of these proteins were investigated.

A Direct Interaction of VRN1 Protein with ANR1

Figure 20A:
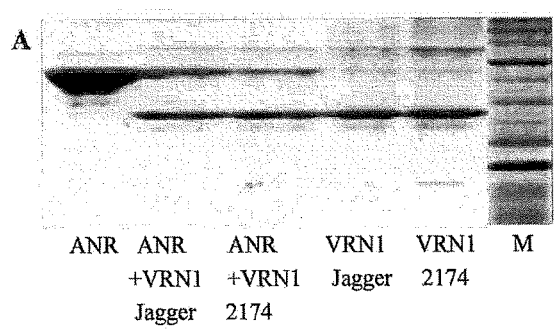
FIG. 20A and FIG. 20B: In vitro protein interactions of ANR1 with VRN1 and AGLG1.
Figure 20B:
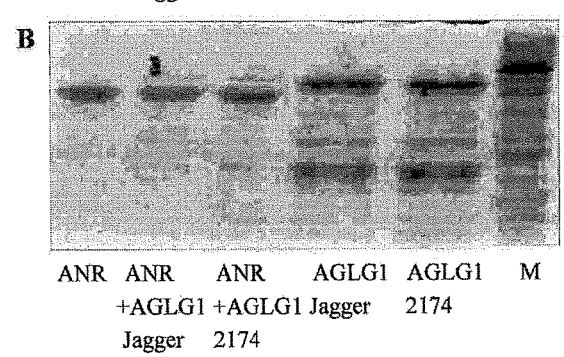

In order to test if there is cross-talk (interaction) between the wheat orthologous protein of AtANR1 and $VRN1^N$ or AGLG1, specific primers were designed to amplify cDNA of ANR1 from Jagger, and ANR1, $VRN1^N$ and AGLG1 proteins were expressed in E. coli. ANR1 and VRN1 proteins showed strong interactions in vitro (FIG. 20A), but no interaction was observed between ANR1 and AGLG1 proteins (FIG. 20B). The in vitro interaction result suggested than $VRN1^N$ rather than AGLG1 was TaNUE1. ANR1 was cloned using the pEG101-YFP vector and the construct was transformed into tobacco leaves. As shown in FIG. 21A-FIG. 21B, enriched yellow fluorescent signals of ANR1-yellow fluorescent protein (YFP) were detected predominantly in the nucleus, which was the same pattern observed for VRN1 (Li et al., 2013), suggesting that $VRN1^N$ and ANR1 may have in vivo interaction in plants. Next, $VRN1^N$ was cloned into the pEG201-YN vector and ANR1 was cloned into the pEG202-YC vector, and in vivo protein interactions were analyzed by bimolecular fluorescence complementation (BiFC). When $VRN1^N$-YN and ANR1-YC were simultaneously expressed in the same cell, yellow fluorescence was observed in the nucleus (FIG. 21C-FIG. 21F). The results confirmed that $VRN1^N$ and ANR1 proteins exhibit direct binding in plants, and thus they may function in the same N metabolism pathway.

Figure 22A:
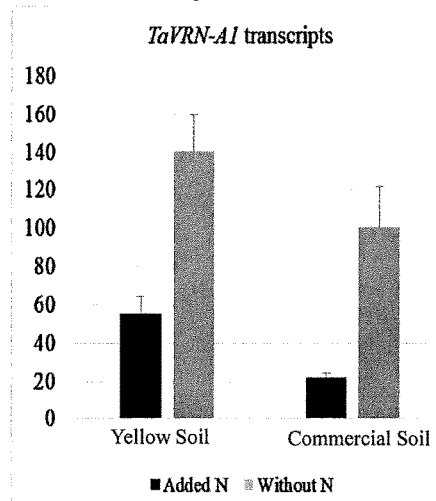
FIG. 22A-FIG. 22D: Regulation of VRN1$^N$ in normal wheat and transgenic wheat plants.
Figure 22B:
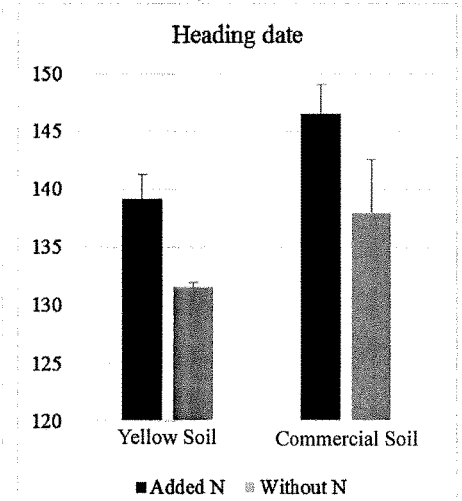

Example 4. Regulation of $VRN1^N$ Transcripts by N in Normal Wheat and Transgenic Wheat Plants RT-PCR was used to test whether the transcripts of $VRN1^N$ were regulated by nitrogen. The parental Jagger and three RILs carrying the Jagger $VRN1^N$ allele were tested in the same type of yellow soil that was used to discover QNue.osu-5A. Commercial soil was used as a control. In both of the soils tested, the $VRN1^N$ transcripts in fertilized plants were lower than in non-fertilized plants, indicating the $VRN1^N$ transcripts were down-regulated by N (FIG. 22A). The higher $VRN1^N$ transcriptional level was associated with earlier heading, and the heading date of the fertilized plants was delayed (FIG. 22B).

Figure 22C:
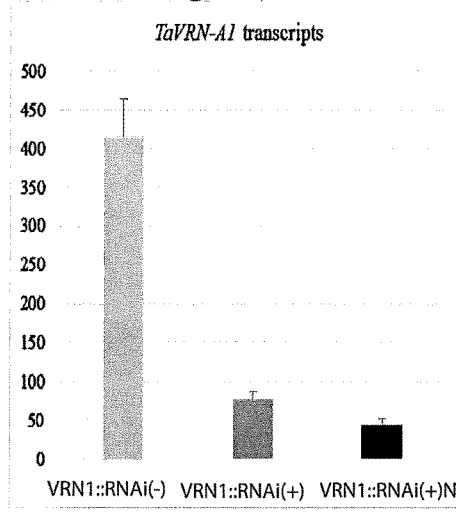
Figure 22D:
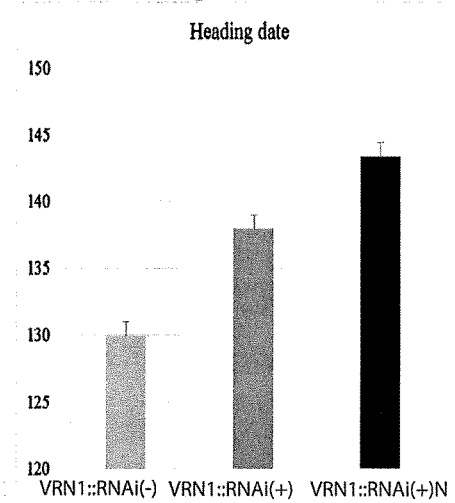

RNAi was used to interfere with expression of VRN1$^N$ in Jagger as a host plant. Two individual transgenic plants were successfully generated. T$_1$ populations were tested in yellow soil (as above). VRN1$^N$ transcript levels were dramatically reduced in positive plants compared with non-transgenic plants, and fertilization of the positive plants with N decreased VRN1$^N$ transcript levels even further, in comparison to non-fertilized positive plants. (FIG. 22C). The heading date of non-transgenic plants was 130 days, which was delayed to 138 days in the positive transgenic plants, and to 143.4 days in positive transgenic plants fertilized with N (FIG. 22D). These results provided direct evidence that VRN1$^N$ functioned in the N metabolism and flowering pathways.

Example 5 Regulation of ANR1 by N

Genetic Effects of a Natural Mutant of ANR1

The functional characterization of the ANR1 gene in normal wheat and transgenic plants provided further evidence that ANR1 and VRN1$^N$ function in the same N metabolism pathway. When conserved primers for homologous ANR1 genes were designed to test expression profiles, ANR1 transcripts were found not in leaves but predominantly in roots in Jagger, but PCR products with different sizes were observed in the root cDNA samples of cultivar 2174. In order to determine if the variable cDNA products were caused by an exon skipping event or by a deletion event at the gDNA level, we cloned the ANR1 cDNA from 2174 (FIG. 23A). Further sequencing results indicated that an 84 bp-exon 6 was missing in the PCR products of one homologous ANR1 gene from 2174. By sequence comparison, we found that the smaller ANR1 cDNA product in the 2174 allele was caused by a 23-bp deletion event involving an AG splice site at the 5' end of intron 5 in 2174 (FIG. 23C). The 23-bp deletion included 10 bp in intron 5 and 13 bp in exon 6. The absence of the AG splice site results in the loss of the full exon 6 of 84 bp in the cDNA products.

Based on the polymorphism of 23 bp indel, a PCR marker for ANR1 was developed (FIG. 23B). ANR1 was mapped to chromosome 2A in bread wheat. When the phenotypic data used to map QNue.osu-5A were analyzed for the genetic effects of ANR1 in the RIL population, the 2174 allele for the 23 bp deletion in the non-functional ANR1b gene was associated with early heading, whereas the Jagger allele for the functional ANR1a gene was associated with late heading, with a difference of 3.7 days between the two alleles. The result suggested that the functional Jagger ANR1a gene may be a repressor for flowering in wheat.

Regulation of ANR1 Transcripts by N in Normal Wheat and Transgenic Wheat Plants

RNAi was used to interfere with ANR1 expression using Jagger as the host plant. Three individual transgenic plants were successfully generated, and their T$_1$ populations were tested in the yellow soil type used to discover QNue.osu-5A. Like VRN1''. ANR1 transcript levels were down-regulated in positive plants compared with non-transgenic plants, and VRN1'' transcript levels were further down-regulated by N in the positive plants compared with non-fertilized positive plants (FIG. 23D). Unlike VRN1$^N$, ANR1 showed a repressive effect on flowering in transgenic plants, with a difference of 2.5 days for positive plants compared with non-transgenic plants. The heading date of non-transgenic plants was 2.5 days earlier days, compared with non-transgenic plants. A typical positive plant carrying ANR1::RNAi also showed reduced plant size compared with a non-transgenic plant (FIG. 23E). These results provided direct evidence that ANR1 functioned in the N metabolism and flowering pathways.

Example 5. Significance and Impact

Wheat is one of the most important economic crops worldwide. The United States produces approximately 11% of the world supply and nearly 35% of world exports. Between now and the year 2050, the human population of around 6 billion people is expected to increase to 9 billion. Therefore, the challenge for the next decades will be to accommodate the needs of the expanding world population by developing a highly productive agriculture.

Application of N fertilizers is the most direct and efficient approach to increase wheat production, and thus the addition of excess amounts of N is usually considered as a type of yield insurance, particularly in developed countries. While the purchase of this "insurance" cannot be totally avoided, it is important to search for genotypes that are able to absorb and accumulate high concentrations of N more efficiently. On the other hand, in developing countries which lack natural resources and cannot afford the cost of fertilizers, N is often the most yield limiting nutrient. To develop wheat varieties carrying high NUE genes is a viable strategy to increase economic income in wheat production worldwide.

Strategies for optimized use of N via soil and fertilization management in wheat have been developed and promoted by universities and scientists, laying a foundation for a complementary study of better use of N via genetic improvement. Over the past century, genetics, through the pyramiding of favorable alleles in a single genotype, has proven to be far and away the most powerful tool for improving stress tolerance and yield potential. Novel genomic and computational tools will hasten the progress of gene discovery and accelerate plant improvement to enhance yields. In the previous Examples, we have described how the gene network for genetic improvements of NUE and grain yield is established in wheat.

A simple definition of NUE is crop yield/N supplied, but NUE is a complex trait and many genes could be involved in biological processes for this trait. A key focus is on the starting point to enter the gene network for the complex process by cloning a large QTL for NUE. We have mapped the large QTL in the wheat genome itself, and candidate genes are identified by comparative genomics with the cereal model species rice. Gene function is tested by comparison with orthologous genes characterized in the model plant *Arabidopsis*. This streamlined approach facilitates cloning and characterization of agronomically important genes in wheat breeding and transgenic wheat.

NUE genes have extensive use in agriculture, environment, and industry. First, increased cereal yields are needed to feed a growing world population. Cereal crops have not yet fulfilled their promise with respect to increasing yields via N-fixation, and thus high amounts of supplemental N are required for high cereal yields to attain significant economic income. Currently, most crop plants utilize only 30-35% of added N fertilizer. If even a 1% increase in NUE is obtained in the world, then grains yield would markedly increase by million tons without additional cost, or the same yield could be obtained with a multi-million dollar decrease in fertilizer costs. Second, the inefficient use of large amounts of N fertilizers in agriculture causes significant and potentially irreversible environmental damage, which will lead to a diminished capacity for sustained productivity and deteriorated ecosystems. This consideration makes it essential to attempt to increase yield by other approaches not currently available such as enhancing NUE in an economically and environmentally sustainable fashion. Sustainability of agricultural production refers to our ability to meet current needs for natural resources, products or manufactured goods while preserving the capacity of future generations to meet their needs. Finally, knowledge and genes which improve NUE in wheat can be applied in the production of other crops. For example, biomass from plants such as switchgrass has been proposed to produce ethanol to replace fossil energy. Switchgrass can grow in nutrient poor soils, and a genotype that has a larger capacity to produce biomass with a minimal amount of N fertilizer in marginal lands (e.g. switchgrass that is genetically engineered to contain and express one or more genes related to NUE) is another interesting economic and environmental challenge.

QNue.osu-5A explains a large part of the total phenotypic variation in several N utilization traits. For instance, it accounted for 38.5% and 55.3% of the total variation in grain yield, when the population of plants was initially grown in N-deficient soil and then fertilized with two different levels of N. The gene TaNUE1 could be allelic to the genetic locus that accounted for 13.6% and 22.5% of the total phenotypic variation respectively in leaf GS activity and flowering time in the Chinese Spring×SQ1 population (Habash et al. 2007). However, the presently identified gene population has a larger segregation and the gene(s) is/are cloned from locally adapted winter wheat cultivars. These advantages provide a unique opportunity for the cloning, characterization, and manipulation of TaNUE1 for production of wheat throughout the world.

In summary, experimental evidence provided herein demonstrates that $VRN1^N$ is TaNUE1 at QNue.osu-5A in bread wheat, as shown by genetic association of $VRN1^N$ and TaNUE1, direct interaction of $VRN1^N$ and ANR1, and regulation of $VRN1^N$ and ANR1 by N in normal and transgenic wheat plants. When N fertilizer was utilized, both $VRN1^N$ and ANR1 were down-regulated. HOX1 can be used to promote development, due to its interaction with $VRN1^N$. Therefore, $VRN1^N$ competes with HOX1 in the vernalization pathway and ANR1 in the N metabolism pathway. Molecular markers for these genes developed herein can be used for pyramiding these N genes/alleles in novel wheat cultivars.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

REFERENCES

An D, Su J, Liu Q, Zhu Y, Tong Y, Li J, Jing R, Li B, Li Z (2006) Mapping QTLs for nitrogen uptake in relation to the early growth of wheat (*Triticum aestivum* L.). Plant and Soil 284:73-84

Boman R K, Westerman R L, Raun W R, Jojola M E (1995) Time of nitrogen application: Effects on winter wheat and residual soil nitrate. Soil Science Society of America Journal 59:1364-1369

Broothaerts W, Mitchell H J, Weir B, Kaines S, Smith L M, Yang W, Mayer J E, Roa-Rodríguez C, Jefferson R A (2005) Gene transfer to plants by diverse species of bacteria. Nature 433: Cao S, Carver B F, Zhu X, Fang T, Chen Y, Hunger P M, Yan L (2010) A single-nucleotide poly-morphism that accounts for allelic variation in the Lr34 gene and leaf rust reaction in hard winter wheat. Theoretical and Applied Genetics. 121:385-392. DOI: 10.1007/s00122-010-1317-6.

Chen Y, Carver B F, Wang S, Zhang F, Yan L. 2009 Genetic loci associated with stem elongation and dormancy release in winter wheat. Theoretical and Applied Genetics 118: 881-889. Chen Y, Hunger R M, Carver B F, Zhang H, Yan L (2009) Genetic characterization of powdery mildew resistance in U.S. hard winter wheat. Molecular Breeding. 24:141-152

Chen Y, Carver B F, Wang S, Cao S, Yan L (2010) Genetic regulation of developmental phases in winter wheat. Molecular Breeding. 26: 573-582. DOI. 10.1007/s11032-010-9392-6.

Cox M C, Qualset C O, Rains D W (1985) Genetic variation for nitrogen assimilation and translocation in wheat: III. Nitrogen translocation in relation to grain yield and protein. Crop Science 26:737-740.

Fang T, Campbell K G, Li Z, Chen X, Wan A, Liu S, Liu Z J, Cao S, Chen Y, Bowden R L, Carver B F, Yan L (2011). Stripe rust resistance in the wheat cultivar Jagger is due to Yr17 and a novel resistance gene. Crop Science (in press). Gelvin S B (2005) *Agrobacterium*-mediated plant transformation: the biology behind the "gene-jockeying" tool. Microbiol Mol Biol Rev 67: 16-37.

Gan Y B, Filleur S, Rahman A, Gotensparre S. Forde B G (2005) Nutritional regulation of ANR1 and other root-expressed MADS-box genes in *Arabidopsis thaliana*. Planta 222: 730-742.

Gouis J, Pluchard P (1996) Genetic variation for nitrogen use efficiency in winter wheat (*Triticum aestivum* L.). Euphytica 92:221-224.

Habash D, Bernard S, Schondelmaier J, Weyen J, Quarrie S (2007) The genetics of nitrogen use in hexaploid wheat: N utilisation, development and yield. Theoretical and Applied Genetics 114:403-419.

Hirel B, Le Gouis J, Ney B, Gallais A (2007) The challenge of improving nitrogen use efficiency in crop plants: towards a more central role for genetic variability and quantitative genetics within integrated approaches. Journal of Experimental Botany 58:2369-2387.

Jack T (2004) Molecular and genetic mechanisms of floral control. Plant Cell 16:S1-S17.

Laperche A, Brancourt-Hulmel M, Heumez E, Gardet O, Hanocq E, Devienne-Barret F, Le Gouis J (2007) Using genotype×nitrogen interaction variables to evaluate the QTL involved in wheat tolerance to nitrogen constraints. Theoretical and Applied Genetics 115:399-415.

Li G, Yu M, Fang T, Cao S, Carver B F, Yan L (2013) Vernalization requirement duration in winter wheat is controlled by TaVRN-A1 at the protein level. The Plant Journal. 76:742-753

MacKown C T, Carver B F (2007) Nitrogen use and biomass distribution in culms of winter wheat populations selected from grain-only and dual-purpose systems. Crop Science 47:350-358.

Mandel, M. A., Gustafsonbrown, C., Savidge, B., and Yanofsky, M. F. (1992). Molecular characterization of the *Arabidopsis* floral homeotic gene Apetala1. Nature 360, 273-277.

McMichael A J (2001) International and Public Health Group Symposium on 'Nutritional challenges in the new millennium' Impact of climatic and other environmental changes on food production and population health in the coming decades. Proceedings of the Nutrition Society 60:195-201.

Messenguy F, Dubois E. (2003) Role of MADS box proteins and their cofactors in combinatorial control of gene expression and cell development. Gene. 316:1-21

Moll R H, Kamprath E J, Jackson W A (1982) Analysis and interpretation of factors which contribute to efficiency of nitrogen utilization. Agronomy Journal 74:562-564.

Moose S, Below F E (2009) Biotechnology Approaches to Improving Maize Nitrogen Use Efficiency. Molecular Genetic Approaches to Maize Improvement, pp 65-77.

Murai, K., Miyamae, M., Kato, H., Takumi, S., and Ogihara, Y. (2003). WAP1, a wheat APETALA1 homolog, plays a central role in the phase transition from vegetative to reproductive growth. Plant Cell Physiol. 44, 1255-1265.

Ng, M., and Yanofsky, M. F. (2001). Function and evolution of the plant MADS-box gene family. Nature Rev. Genet. 2: 186-195.

Parenicova L, de Folter S, Kieffer M, Horner D S, Favalli C, Busscher J, Cook H E, Ingram R M, Kater M M, Davies B, Angenent G C, Colombo L (2003) Molecular and phylogenetic analyses of the complete MADS-box transcription factor family in *Arabidopsis*: New openings to the MADS world. Plant Cell 15:1538-1551.

Riechmann J L, Meyerowitz E M (1997) MADS domain proteins in plant development. Biol Chem 378:1079-1101.

Quarrie S A, Steed A, Calestani C, Semikhodskii A, Lebreton C, Chinoy C, Steele N, Pljevljakusic D, Waterman E, Weyen J, Schondelmaier J, Habash D Z, Farmer P, Saker L, Clarkson D T, Abugalieva A, Yessimbekova M, Turuspekov Y, Abugalieva S, Tuberosa R, Sanguineti M C, Hollington P A, Aragués R, Royo A, Dodig D (2005) A high-density genetic map of hexaploid wheat (*Triticum aestivum* L.) from the cross Chinese Spring×SQ1 and its use to compare QTLs for grain yield across a range of environments. Theoretical and Applied Genetics 110:865-880.

Raun W R, Johnson G V (1999) Improving nitrogen use efficiency for cereal production. Agronomy Journal 91:357-363.

Scheible W-R, Morcuende R, Czechowski T, Fritz C, Osuna D, Palacios-Rojas N, Schindelasch D, Thimm O, Udvardi M K, Stitt M (2004) Genome-wide reprogramming of primary and secondary metabolism, protein synthesis, cellular growth processes, and the regulatory infrastructure of *Arabidopsis* in response to nitrogen. Plant Physiology 136:2483-2499.

Shrawat A K, Carroll R T, DePauw M, Taylor G J, Good A G (2008) Genetic engineering of improved nitrogen use efficiency in rice by the tissue-specific expression of alanine aminotransferase. Plant Biotechnology Journal, 6:722-732.

Tilman D, Cassman K G, Matson P A, Naylor R, Polasky S (2002) Agricultural sustainability and intensive production practices. Nature 418:671-677.

Van Sanford D A, MacKown C T (1987) Cultivar differences in nitrogen remobilization during grain fill in soft red winter wheat. Crop Science 27:295-300.

Yan L, Fu D, Li C, Blechl A, Tranquilli G, Bonafede M, Sanchez A, Valarik M, Yasuda S, Dubcovsky J (2006) From the Cover: The wheat and barley vernalization gene VRN3 is an orthologue of FT. Proceedings of the National Academy of Sciences 103:19581-19586.

Yan L, Loukoianov A, Tranquilli G, Blechl A, Khan I A, Ramakrishna W, San Miguel P, Bennetzen J L, Echenique V, Lijavetzky D, Dubcovsky J (2004) The wheat VRN2 gene is a flowering repressor down-regulated by vernalization. Science 303:1640-1644. Yan L, Loukoianov A, Tranquilli G, Helguera M, Fahima T, Dubcovsky J (2003) Positional cloning of wheat vernalization gene VRN1. Proceedings of the National Academy of Sciences USA 100:6263-6268.

Zhang H M, Forde B G (1998) An *Arabidopsis* MADS box gene that controls nutrient-induced changes in root architecture. Science 279:407-409.

---

What is claimed is:

1. A method of producing a plant in which one or more traits associated with nitrogen use efficiency (NUE) are improved, comprising the steps of
genetically engineering said plant to contain and express at least one plant gene TaNUE1 from locus Qnue.osu-5A which is responsible for nitrogen use efficiency (NUE), wherein said at least one plant gene is or includes VRN1$^N$ from wheat cultivar Jagger having the amino acid sequence as set forth in SEQ ID NO: 9, or having an amino acid sequence that is at least 95% identical to SEQ ID NO: 9,
testing the plant for one or more traits associated with NUE, and
selecting the plant if the one or more traits are increased in the plant, compared to plants that have not been genetically engineered to contain and express the at least one plant gene TaNUE1 from locus Qnue.osu-5A which is responsible for NUE.

2. The method of claim 1, wherein said one or more traits associated with NUE is selected from the group consisting of heading date, chlorophyll content, grain yield, harvest index, nitrogen concentration in grain, spike number per plant, grain number per spike, biomass per plant, and a ratio of grain yield to N supplied.

3. A method of providing a plant cultivar that exhibits increased nitrogen use efficiency (NUE) comprising
crossing a plant cultivar comprising a VRN1$^N$ allele from wheat cultivar Jagger with a plant cultivar that does not comprise the VRN1$^N$ allele from wheat cultivar Jagger;
testing an F1 generation plants produced by said step of crossing for the presence of the VRN1$^N$ allele from wheat cultivar Jagger;
testing the F1 generation plants for one or more traits associated with NUE; and
selecting a plant which tests positive for the presence of the VRN1$^N$ allele from wheat cultivar Jagger and which exhibits an increase in one or more traits associated with NUE.

4. The method of claim 3, wherein said one or more traits associated with NUE is selected from the group consisting of heading date, chlorophyll content, grain yield, harvest index, nitrogen concentration in grain, spike number per plant, grain number per spike, biomass per plant, and a ratio of grain yield to N supplied.

5. A method of providing a plant cultivar that exhibits increased NUE, comprising
crossing a plant cultivar comprising a ANR1 allele from wheat cultivar Jagger with a plant cultivar that does not comprise the ANR1 allele from wheat cultivar Jagger;
testing an F1 generation plants produced by said step of crossing for the presence of the ANR1 allele from wheat cultivar Jagger;
testing the F1 generation plants for an increase in one or more traits associated with NUE; and
selecting a plant which tests positive for the presence of the VRN1$^N$ allele from wheat cultivar Jagger and which exhibits an increase in one or more traits associated with NUE.

* * * * *